US012708654B2

(12) United States Patent
Vollmer et al.

(10) Patent No.: US 12,708,654 B2
(45) Date of Patent: Aug. 18, 2026

(54) VIRUS PARTICLES FOR THERAPEUTIC PURPOSES

(71) Applicant: Abalos Therapeutics GmbH, Dusseldorf (DE)

(72) Inventors: Jorg Vollmer, Dusseldorf (DE); Marcus Kostka, Dusseldorf (DE); Philipp Lang, Dusseldorf (DE); Haifeng Xu, Dusseldorf (DE)

(73) Assignee: Abalos Therapeutics GmbH, Dusseldorf (DE)

( * ) Notice: Subject to any disclaimer, the term of this patent is extended or adjusted under 35 U.S.C. 154(b) by 1212 days.

(21) Appl. No.: 17/680,960

(22) Filed: Feb. 25, 2022

(65) Prior Publication Data

US 2022/0273741 A1 Sep. 1, 2022

(30) Foreign Application Priority Data

Feb. 26, 2021 (EP) .................................... 21159746

(51) Int. Cl.
*A61K 35/768* (2015.01)
*A61P 35/00* (2006.01)

(52) U.S. Cl.
CPC ............ *A61K 35/768* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 12,129,281 | B2 * | 10/2024 | Lang | A61P 35/00 |
| 2008/0124308 | A1 * | 5/2008 | Laer | A61P 43/00 424/93.2 |
| 2018/0344830 | A1 * | 12/2018 | Schmidt | A61K 39/00116 |

FOREIGN PATENT DOCUMENTS

| | | | |
|---|---|---|---|
| WO | 2016166285 | A1 | 10/2016 |
| WO | 2020053324 | A1 | 3/2020 |
| WO | WO/20/053324 | * | 3/2020 |

OTHER PUBLICATIONS

Flatz et al., Recovery of an arenavirus entirely from RNA polymerase III-driven cDNA, 2006, PNAS, vol. 103, No. 12, pp. 4663-4668.*

International Search Report and Written Opinion issued in PCT/EP2022/054766 dated Dec. 7, 2022 (12 pages).

Sommerstein et al., Arenavirus Glycan Shield Promotes Neutralizing Antibody Evasion and Protracted Infection. PLoS Pathog. Nov. 20, 2015;11(11):e1005276.

Schnell et al., Lymphocytic choriomeningitis virus infection in FVB mouse produces hemorrhagic disease. PLoS Pathog. Dec. 2012;8(12):e1003073.

Riviere et al., Genetic Mapping of Lymphocytic Choriomeningitis Virus Pathogenicity: Virulence in Guinea Pigs Is Associated with the L RNA Segment. J Virol. Sep. 1985;55(3):704-709.

Riviere et al., The use of lymphocytic choriomeningitis virus reassortants to map viral genes causing virulence. Med Microbiol Immunol. 1986;175(2-3):191-192.

Platz et al., Recovery of an arenavirus entirely from RNA polymerase I/II-driven cDNA. Proc Natl Acad Sci U S A. Mar. 21, 2006;103(12):4663-4668.

Oldstone et al., Lymphocytic choriomeningitis virus Clone 13 infection causes either persistence or acute death dependent on IFN-1, cytotoxic T lymphocytes (CTLs), and host genetics. Proc Natl Acad Sci U S A. Aug. 14, 2018;115 (33):E7814-E7823.

Mazur et al., Combined inhibition of BET family proteins and histone deacetylases as a potential epigenetics-based therapy for pancreatic ductal adenocarcinoma. Nat Med. Oct. 2015;21(10):1163-1171.

Matloubian et al., Genetic Basis of Viral Persistence: Single Amino Acid Change in the Viral Glycoprotein Affects Ability of Lymphocytic Choriomeningitis Virus to Persist in Adult Mice. J Exp Med. Oct. 1, 1990;172(4):1043-1048.

Maleki Vareki, High and low mutational burden tumors versus immunologically hot and cold tumors and response to immune checkpoint inhibitors. J Immunother Cancer. Dec. 27, 2018;6(1):157.

Lang et al., Genes determining the course of virus persistence in the liver: lessons from murine infection with lymphocytic choriomeningitis virus. Cell Physiol Biochem. 2010;26(3):263-272.

Kalkavan et al., Spatiotemporally restricted arenavirus replication induces immune surveillance and type I interferon-dependent tumour regression. Nat Commun. Mar. 1, 2017;8:14447.

Gajewski et al., Cancer Immunotherapy Targets Based on Understanding the T Cell-Inflamed Versus Non-T Cell-Inflamed Tumor Microenvironment. Adv Exp Med Biol. 2017;1036:19-31.

Baccala et al., Type I interferon is a therapeutic target for virus-induced lethal vascular damage. Proc Natl Acad Sci U S A. Jun. 17, 2014;111(24):8925-8930.

* cited by examiner

*Primary Examiner* — Benjamin P Blumel
(74) *Attorney, Agent, or Firm* — Michael A. Whittaker

(57) ABSTRACT

The invention relates to a virus particle comprising a lymphocytic choriomeningitis virus (LCMV) S segment and an LCMV L segment, wherein the S segment comprises an open reading frame encoding a glycoprotein derived from LCMV strain WE, and wherein the L segment comprises an open reading frame encoding an L protein derived from LCMV strain Clone13. The invention also relates to related host cells, methods of producing such virus particles, pharmaceutical compositions comprising such virus particles, and medical uses of such virus particles.

10 Claims, 80 Drawing Sheets

Specification includes a Sequence Listing.

Weight

Thrombocytes
C57BL/6J
BALB/c
FVB/N
Weight (% of d0)
Platelets (count/µL)
Time (d)
WE
Cl13
Arm
WE-Cl13(L)

B16-Ova (melanoma) tumor model

MC38 (colon) tumor model

Tumor draining lymph node

Tumor

| Ctrl. vs. | Day 7 | Day 9 | Day 11 |
| --- | --- | --- | --- |
| WE | * | ** | ** |
| WE-Cl13(L) | ns | ** | ** |
| P52-Cl13(L) | ns | ** | ns |

B16-Ova (melanoma) tumor model (day 7)

Figure 38

A. Lymphocytic choriomeningitis virus (LCMV) strain WE

```
Lymphocytic choriomeningitis virus (LCMV) strain WE-DUE
Source: 1-3376 Segment = S
LCMV WE S-Segment
GCGCACCGGGGATCCTAGGCTTTTTGGATTGCGCTTTCCTTTAGGACAATTGGGTGCTGGATTCT
ATCCAATAAAAGGATGGGTCAGATTGTGACAATGTTTGAGGCTTTGCCTCACATCATTGATGAGG
TCATCAACATTGTCATTATTGTGCTCATTATAATCACGAGCATCAAAGCTGTGTACAATTTCGCC
ACCTGTGGGATATTAGCACTGGTCAGCTTCCTTTTTTTGGCTGGTAGGTCCTGTGGCATGTACGG
CCTTAATGGTCCCGACATCTATAAAGGGGTTTACCAGTTCAAATCAGTGGAGTTTGATATGTCTC
ACTTAAATCTGACGATGCCCAATGCGTGCTCAGCCAACAACTCTCATCACTACATCAGTATGGGA
AGCTCTGGACTGGAGCTAACTTTCACTAACGACTCCATCCTTAATCACAATTTTTGCAACTTAAC
CTCCGCTTTCAACAAAAAGACTTTTGACCATACACTCATGAGTATAGTCTCGAGTCTGCACCTCA
GTATTAGAGGGAATTCCAACCACAAAGCAGTGTCTTGTGATTTTAACAATGGCATCACCATTCAA
TACAACTTGTCATTTTCGGACCCACAGAGCGCTATAAGCCAGTGTAGGACTTTCAGAGGTAGAGT
CTTGGACATGTTTAGAACTGCCTTTGGAGGAAAATACATGAGAAGTGGCTGGGGCTGGGCAGGTT
CAGATGGCAAGACCACTTGGTGCAGCCAAACAAGCTATCAGTACCTAATCATACAAAACAGGACT
TGGGAAAACCACTGTAGATATGCAGGCCCTTTTGGGATGTCTAGAATCCTCTTTGCTCAGGAAAA
GACAAAGTTTCTCACTAGGAGACTTGCAGGCACATTCACCTGGACCCTGTCAGACTCCTCAGGAG
TAGAAAATCCAGGTGGTTATTGCCTGACCAAATGGATGATCCTTGCTGCAGAGCTCAAATGTTTT
GGGAATACAGCTGTTGCAAAATGTAATGTCAATCATGATGAAGAGTTCTGTGACATGCTACGACT
AATTGATTACAACAAGGCCGCCCTGAGTAAGTTCAAGCAAGATGTAGAGTCTGCCTTGCATGTAT
TCAAAACAACAGTAAATTCTCTGATTTCCGATCAGCTGTTGATGAGGAATCATCTAAGAGATCTA
ATGGGGGTACCATACTGTAATTACTCAAAGTTCTGGTATCTGGAACATGCTAAGACTGGTGAGAC
TAGTGTACCCAAGTGCTGGCTTGTCACTAATGGCTCCTACTTGAATGAGACCCACTTTAGTGATC
AAATCGAACAAGAAGCAGATAACATGATCACAGAGATGTTGAGGAAGGACTACATAAAAAGACAA
GGGAGTACTCCTTTAGCCTTAATGGATCTTTTGATGTTTTCAACATCAGCATATCTAATCAGCAT
CTTTCTGCATCTTGTGAAGATACCAACACATAGACACATAAAGGGCGGTTCATGTCCAAAGCCAC
ACCGCTTGACCAACAAGGGGATCTGTAGTTGTGGTGCATTCAAGGTGCCTGGTGTAAAAACTATC
TGGAAAAGACGCTGATCAGCAGCGCCTCCCTGACTCTCCACCTCGAAAGAGGTGGAGAGTCAGGG
AGGCCCAGTGGGTCTTAGAGTGTCACAACATTGGGTCCTCTGAAGATTAAATCATGTGGCAGGAT
GTTGTGAACGGTTTTTAGATCAGGGAGTCTTGCCTTGGAAGCACTCTCAAAAATGATGCAGTCCA
TGAGTGCACAGTGTGGGGTGATCTCTTTCTTCTTTTTGTCTCTCACTACCCCAGTGTGCATTTTG
CATAGCCAGCCATATTTGTCCCACACTTTATCTTCATATTCTCTTGAGGCCTCCTTGGTCATCTC
AACATCAATGAGTTTTATGTCCCTTCTATTTTGTGAGTCCAGAAGCTTTCTGATGTCATCAGAAC
CTTGACAGCTCAAAACCATCCCTTGTGGGAGAGCACCTATAACTGATGAGGTCAGCCCAGGCTGT
GCATTGAAGAGATCAGCAAGATCCATGCCGTGTGAATACTTTGAGTCCTGCTTGAATTGCTTCTG
GTCCGTAGGTTCCCTGTAAAAATGTATGAATTGCCCATTTTGTGGTTGGAATATTGCTATCTCCA
CTGGATCATTGAACCTGCCCTCAATGTCAATCCATGTGGGAGCATTGGGATCAATCCCTCCCATC
AAGTCTTTCAACAGCATTGTCTGACTGTAACTCAAGCCCACCTGAGGTGGGCCTGCTGCTCCAGG
CACTGGCCTAGATGAGTTGGCAACAAGTTTTTCATTTGTGAGATCAATTGTTGTGTTCTCCCATG
CTCTCCCCACAACTGACGTTCTACAGGCTATGTATGGCCATCCTTCACCTGAAAGACAGACTTTA
TAAAGGATGTTTTCATAGGGATTTCTATCTCCAACTTGATCTGAGACAAACATGTTGAGTTTCTT
CTTGGCCCCGAGGACTGCTTTTAGGAGATCCTCACTGTTGCTCGGTTTGATCAAGATAGATTCCA
GCATGTTCCCTCCATCTAGCAGAGCTGCCCCCGCTTTCACAGCTGCACCAAGACTGAAATTATAA
CCAGAGATATTGATACTAGATTGCTGTTCAGTAATGACCCCCAGAACTGGGTGTTTATCCTTTAG
CCTTTCAAGATCACTGAGATTCGGGTATTTGACTGTGTAAAGTAAGCCAAGGTCTGTGAGTGCCT
GCACAACATCATTGAGTGGGGTCTGTGACTGTTTTGCCATGCAAGCCATTGTCAGGCTTGGCATT
GTGCCGAACTGATTGTTCAGAAGTGATGAGTCCTTCACATCCCAAACCCTTACTACACCACTTGC
```

Figure 38 (cont'd)

ACCCTGCTGAGGTCTTCTCATCCCAACCATTTGCAGTATTTGGGATCTTTGATCAAGTTGTTGTG
CTGTCAAATTTCCCATGTAGACTCCAGAAGCTTGAGGCCTCTCAGTTCTCATAATTTTGGCCTTC
AGCTTCTCAAGATCAGCTGCAAGGGTCATCAATTCCTCTGCACTAAGTCTTCCCACTTTCAGAAC
ATTTTTCTTTGATGTAGACTTCAGATCAACAAGAGAATGCACAGTCTGGTTAAGACTCCTGAGTC
TCTGCAAGTCTTTATCATCCCTCCTTTCCTTTCTCATGATCCTCTGAACGTTGCTGACTTCAGAA
AAGTCCAACCCATTTAGAAGACTGGTTGCGTCCTTGATGACGGCAGCCTTTACATCTGATGTAAA
ACTCTGCAACTCCCTCCTCAACGCCTGTGTCCACTGAAAGCTTTTGACTTCTTTGGACAAAGACA
TTTTGTCACACAATGAATTTCCAAATAAAAGCGCAATTAAATGCCTAGGATCCACTGTGCG
(SEQ ID NO: 1)

Figure 38 (cont'd)

Lymphocytic choriomeningitis virus (LCMV) strain WE-DUE
Source: 1-7236 Segment = L
LCMV WE L-Segment

GCGCACCGGGGATCCTAGGCGTTTAGTTGCGCTGCTTTATTGCACAGCTTCACTCTGCTAAACCA
TCAGGAACTGACCGATCATCAGTCATGGGCCAAGGCAAGTCCAAAGAAGAAAGGGACACCAGCAA
TACAGGCAGAGCAGAGCTTTTGCCAGACACCACCTATCTTGGTCCTCTAAATTGTAAATCATGTT
GGCAGAAATTTGACAGCTTGGTTAGATGCCATGACCACTATCTTTGCAGACACTGTCTGAATCTC
CTGCTGTCAGTTTCCGACAGATGTCCTCTCTGTAAGTATCCACTGCCAACCAAACTGAAGGTGTC
AACAGTCCCAAGCTCCCCACCTCCCTATGAGGAGTGACGCCCCAGACCTCGACACAACAGGCCAC
CCAACACAGAAAAACCACACACAAACCGGCACACACAGACACAGCAACCAGCACAAAGCGCACGA
AAACACACACACACACACACACACACACCCTCACCCACGCGCCCCCCCGCACCGCCGGGGGGGCGCC
CCCCCGGGGGGCAGCCCCCCGGGGGCCCGGGCAGGGCCCCGCGGAGATGCCGGCTAGTCGATCTC
CTCGGCCACCCGCTCCGCCAGCCAATCGTCACAGGATTTCCCCTTGAGTCTGAACCTGCCCCCAG
TTGTCTCATACATTACAGTGTTCTTTGACCTGCTGAAGCAGAGCCTACAATCTCTGAAGGTGAAC
CAATCTGGCACAAAAGATAATGGTGTCAGCATGACGGATCTGTCCATGCAGAGCTCCTGAAGAAC
TGTACTTATTTCTGACTCCATCAAGTGCTCACCAGTTCTGAATCGGTGCAGGAGGAGGCTGCCGA
GGACATCACCAATTTTTCCACAGCCCTCGAGCTCTGCCAGAAAGACCCTCATGTCCTTTGTCTCC
AATTTCACAGAGATATTCTGAACAAAGTTCCTCCCCTCAAAGAGGGCACCCTTCCTTATGGTCAG
AGGCACAGGTTCCCACTCAGGCCCTATCCTCTCAAAGTCAGTAGATTTGATCTCATTCAGAATCC
TTCTAGAACCTATTAGTTCAAGTTCTAGTGAATCACCAAGTGTCAAAGGGTCTTCCATGTAATCT
TCAAACTCTTCAGACCTAATGTCAAAGACTCCATCATTCGCTTTAAAGATGGGGTCTGTCCTCAA
CAGATTGAGACACTCATCTAATAATCTCCTGTCAACCTCACCTTTGAAGAAATGAGAGCACGATA
AGTAATCAGCTACACCTGGACTCTGTAATTGGCATTTAACCACAAAGATCAATGAAAATTTCCTC
AAGCAGTCAGTGTTGTTCTGGTTGTGTGTGAAATCCACTGTGATTGAGAACTCCAATATCCCCTC
TGTGCTGCTGAGCATGTAATCCCACAAATCTCTTAAAGATTTAAATGCTTTTGGATCTGTCAAAC
CCTGCTTAATTAACATAGCGGCATTACACACAACATCCCCCACACGATAAGAGAACCAACCAAAA
CCAAACTGCAAGTCATTCCTAAACATGGGCCTCTCTATTTTCTTGTTCACCACTTTCAAAATAAA
TGATTGGAAGGGTCCCAGTGCTTCAGCGCCATCTTCAGATGGCATCATGTCCTTATGGGGGAACC
ATGAAAAGTTACCTAAGGTCCTAGCTGTTGCAACAAACTCTCGTACAAATGATTCGAAATACACT
TGCTTCAAAAAGTTCTTGCAGACATCCCTTGTGCTGACAACAAATTCATCAACTAAACTTGAGTC
TGACCGTTGGTGAGAGTTGACGAGATCAGAAAACAGCACAGTGTAATGTTCGTCCCTCTTCCATT
TGACAACATGAGAAATGAGTGACAAAGACTCTGAGTTGATGTCAATCAGCACACAAAGGTCAAGG
AATTTAATCCTGGGACTCCATCTCATATTTTTTGAGCTCACATCAGACATGAATGGGAGCAACTG
ATCCTCAAAGATTTTGGGGTACAGTCGCCTCACAGATTGAATTACATGATTCAAACTCACTTTAT
CCTCTAGTAGTCTCGAACTCTCAGGTTTTCTTGCTACATAATCACATGGATTTAAGTGCCTAACA
GCCGAATTACTCTCGTTCTTTCCTTTCACAGGTTCTGCTAAAACCCAAACACCCAGCTCAAAAGA
GTTGCTCAATGAGATGCAAATGTAGTCCCAGAGAAGGGGCCTCAAAAGGTTGATGTGGTCACGGT
GAGCCTCTGGGTGTCTCTGCTTGTCGCAAATGTACAACATCACACCATCTTGTTTGTGAACCCTT
GTGACATGTTCATCCATGGTCAGATCTTCAAGCACCTTTCTGATATACATATTTTCCCTGTTTTT
ATTTCTCACACACCTACTTCCTAAAGTCTTACAGAGACCTATAAAGCCGGATGAGACACAACTCT
GAAAAGCTGATTTGTTGATTGCCTCTGACAACAGCTTCTGTGCACCTCTTGTGAACTTACTACAA
AGCTTATTTTGGAGTGTTTTAATCAATGAGGGGATCTTTTCCTCTTGAAAGGTCATTACTGATGG
GTAAACCACTTTTTGTCTCAGAACCATCCTCAATGGGAACATTTCATTCAGATTCAACCAATTGA
TGCTTGCCAACTCATTAAGATCATCCTCAAGACCAAGAATCTCTCCCAATTGAAGGATGGCCTCT
TTCTTTTCCCTGTTGAAGAGGTCTAGAAAAAATTCCTCGTTACATTCACCGTTCTTGAGTTTGTG
ATGTAGTCTTCTTACAAGTTTTCTCATGATCTTTGTTTCACTGGGACACAATTCTTCAATGAGTC
TTTGGATTCTATAACCTCTAGAACCATCTAACCAATCCTTTACATCAGTGTGAGTGTTTAACAAG
AATGGATCTAAAGGGAAATTAGCATATTTCAAGAGATCCAGTGTCCTCCTCTGGATACAGTTTAC
TAAAAAAACTGGAACTCCATTTGCTATAGCTTGATCAGCAATCGTATCTATTGTCTCACAAAGTT

Figure 38 (cont'd)

GATGCGGTTCTTTACACTTAACATTGTGTAGTGCCGCAGACACAAATTTCGTGAGGAGAGGGACC
TCCTCCCCCCACACATAAAATCTGGATTTGAATTCCGCTGCAAACCGCCCAACCACACTTTTTGG
ACTGATGAACTTGTTCAACAAACCACTTAAGTGAGAGTGGAATTCCAGCAAGACAAGGACTTCTT
CTGGGTCACTATCAACTAAGTCACTCAATCTCTTGTCAAATAAAGTGATCTGATCATCACTTGAT
GTATAGGCTTCTGGCCTCTCTCCAAAAATGACACCAATACAATAATTGATAAACCTTTCACTAAT
TAAACCGTAAAAATCAGAAGCATTGTGTAGGATCCCCTGTCCCATGTCAATGAGACTAGATATGT
GAGATGGCACCACCCCCATTTCAAAATACTCTCTAAAGATTCTCTCCGTAACAGTCGTTCCTGAC
CCTTTGAGAAGCTTGAGTTTTGATTTAACATATGATTTCATCATTGCATTCACAACAGGGAAAGG
GACTTCAACAAGTTTATGCATATGCCAAGTCAACAAGGTGCTAACATGATCTTTTCCAGAACGCA
CGTACTGATCATCACCCAGTTTGAGATTTTGGAGAAGCATTAAGAATAGGAATGGGCACATCATT
GGTCCCCATTTGCTGTGATCCATGCTGTAGTTTAACAACCCTTCTCTCACATTGATAGTCATTGA
CAAGATTGCATTTTCAAACTCTTTGTCATTGTTTAAACAAGATCCTGAAAAGAAACTAGAAAAGG
ATTCAAAATAATCTTCTACCAATCTTGTGAACATTTTTGTCCTCAAATCCCCAATGTAAAGCTCT
CTATTTCCCCCAACCTGCTCTTTGTATGACAATGCAAATTTTAGTCTCCCAGAGTCAGGGCCAAC
TGAAGTGTATGATGTTGGTGATTCTTCTGAGTAAAAACACAGATTCTTTAGAGCAGCACTCATGC
ATTTTGTCAATGAAAGGGCCTTACTTAGAGATTCAGAATTGCTTTCCCTTTCACTAATTCTTACA
TCTTCTTCCAATTTGTCCCAGTCAAATTTAAAATTTAAGCTCTGCCTCTGCATGTGTCTGTACTT
CCCTGAATACGCATTTGCATTCATCTGTAACAAGATCATCTTCATACATGAGAACCAATCACCCT
CTGAGAAGAACTTTCTACAGAGGTTTCTTGCCATCTCATCCAGACCACATTGTTCTTTGACAGCT
GATGTAAAATACAATGGTGACAGTTCTGTTGAACCTTCAACAGCCTCACAAATAAACCTCATGTC
GTCATTGGTGAGACAGGATGGATCAAAGTCCTCTACTAGATGAAATGAAATTTCTGATAAAATGA
CTTTCCTCAGATAAGCTCTTTTACCTGACAAAATAATCTGAAGGTGGTGTAGTCCTTTTGTGTTC
TTGAATTCTCCCTCCCCTTGCCCTTCATTAAGCCTAGTGCCTCTATTATACCGTGTTATTGTGGA
GCTGACCTTATCTTCTAAACTCCTGAAAAAACTTGTCTCCTCCTCCCCCTCGAAACACACATCTA
CCGGATCATCTTCCAATTTGTCTACTTCTGTTTTCCTGGAACCGATGACTAATCTAGAGACAAGC
TTTGAGACCTTATATTCGTAATCTGAGTGTCTCAGCTTATACTTTTGTTTCCTCATGAAGCCCTC
TGTAATTTGGCTCACAGCACTAACAAGCAATTTGTTAAAATCATACTCCAAAAGCCGTTCTCCAT
TCAGATGTTTATTGACAACCACACTTTTGTTGCTTGCGAGATCTAATGCTGTCGCACATCCAGAG
TTGGTCATGGGGTCCAGATTGTTGAGCCTTTTCTCCCCTTTTAGAATTAAGGTGCCATTGTTGAA
TGAAGATACCATCATGCTAAAGATCTCTAAATTAACACCAGGGGTTGAATGCTGACAATCAATAT
CTTTACCGGTGAACTTCTTCATTTGTTCATAAAAAACACATTCCTCTTCGGGTGTGATTGTTTCC
TTAGGGTTGACAAAGAAACCAAACTCACTCTTGGGCTCAAAGAACTTTTCAAAACATTTTATCTG
ATCTGTCAATCTATCAGGGGTCTCCTTTGTGATCAAATGACACAGGTATGACACATTCAACATAA
ACTTGAATTTTGCACTCAATAACACCTTTTCACCAGTACCAAAAATTGTCCTAATCAAAAACCGA
AGCAGCCTGTACACCACTTTCTCGGCAGGTGTGATTAGATCCTCCTTCAACTTATCCATTAATGA
GGTCGATGAAAAGTCTGAGACGATGGCCATCACTAAATACCTAATATTTTGAACCTGCTTTTGAT
TT

Figure 38 (cont'd)

CTCTTTGTTGGGTTGGTGAGCATCAGTAGGATCAATGTCCTTAGTGCAGTCTCAATGTCAATAAG
AGAATCTTTTAAGTCAGGGCATGACCTAATCCATGAAATCATTGTGTCTATCATGTTGTGCAACA
CCTCATCTGAAAAAATTGGTAAAAAGAACCTTTTTGGATCTGCGTAAAAGGAAATCAAGTGACCA
TCCGGACCTTGTATGGAATAACACCTCGATGATTCTCCAGTTTTCTGATATAGTAGATGATACTC
TTCGGAATCCAGTTTTATTATCTGGCAAAACACCTCTTTGCACTCCACCACTTGATATCTCACAG
ACCCCAGTTGGTTCTGTCTCAACCTTGCAACTGAGCTTGTTTTCATGCTGTTTGTTAGAGCCAAA
CAAACAGATGACAGTTTTCTCAAACTCTGTAAACCCCTCAATTGCTCTATGTTAGGCTGGAAAGT
GTAATCTTCAAATTTTGTGTAATGCATTACAGGATGAGTCCCGGCTCTCATAAAGTTCTCAAATT
CAGCAAATGGTATATGGCATTCTTGCACGAGGCATTCTGATAGTCCGTAATGCTCAAAACTAAGT
CCCACTGTTGATAGGCATTTCTGGATTTTTGCTATGAACTCATTTATGGATACCCTAAAAAGCTC
ATCAAGAGATGCCTTTTTGTGCACTCTTGATTTTCTTCTGTTCTTCAAAAGTCTCATGAATTCTT
CTTTGGTACTTTGAAGGCTCACAAGCCTATCATTCACACTACTGTAGCAACAACCAACCCAATGT
TTATCATTTTCCAACCCTTTGGAAATTGACTGCTTAATAAGTGAAGAAAGACATAAGACATCTAA
GTTCAGCAGCTGTCTCCTTCTAGTGTTTAATAATTTTAAACTTTTCACCTTGTTCAACATAGAGA
GTAGCCTTTCATACTCAGTGTTAGCATCGCTTCCTCTCTCATGCCCATGGGTCTCTGCTGTAATG
AACCTCATTAAGGGGCAGGATTCAACTGCCTCTTTGCTCAACATTAATATGTCATCATTATCAGT
AAGGGTTTCATAAAGTTCAGAGAATTCCTTGATTAAGCCCCCAGGGCTGACCTTTTGGAAATTCC
TTTTGAGTTTCCCATTTAACAGGTCCCTCCTAAACCTGCCAAAAAAGGAATTTATGCCAAAGACC
ACATCATCGCAACTCATGTTGGGGTTGACACCATCGTGGCACATTTTCATAATCTCATCGTTATG
AAATGATCTTGCGTCTTTCAAAATTTTCATTGAGTCCATGCCGGAACGTTTGTCAACAGTGGTCT
TAAGAGACTCACAGAGCCTGAAGTATTCAGACTCCTCAAAAACTTTCTCATCTTGACTAGAATAC
TCCAGGAGTTTAAATAGGAGGTCTCTGAACTTAAAATTCACCCATTCTGGCATGAAACTGTTATC
ATAATCACAACGACCATCCACTATTGGAACCAGTGTGATGCCTGCAACAGCAAGATCTTCTTTGA
TGCATGCTAGTTTGTTGGTGTCCTCAATGAACTTCTTTTCAAAACTAGCTGGTGTGCTTCTAACA
AAACATTCAAGAAGAATAAGGGAATTGTCAATCAACTTATAACCATCAGGGATGATGAGTGGCAG
TCCTGGACACACAATCCCAGAGTCTATTAGGATTGTTTCAACAGATTTGTCATCGTGGTTGTGTA
TGCAACCACTTTTGTCTGCACTGTCTATCTCTATACAGCGTGATAACAATTTGAGTCCCTCAATT
AGCACCATTCTGGGTTCTCTTTGTCCCAGGAAGTTGAGTTTTTGCCTTGACAGCCTCTCGTCCTG
TTCTATGTAATTTAGACACAACTCTCTCAAATCTGCAATAGTTTCATCCATTGCGCATCAAAAAG
CCTAGGATCCTCGGTGCGC
(SEQ ID NO: 2)

Figure 38 (cont'd)

Lymphocytic choriomeningitis virus (LCMV) strain WE-DUE
Source: 1-3376 Segment = S
Protein: Pre-glycoprotein polyprotein GP complex
Gene: GPC
LCMV WE GPC

ATGGGTCAGATTGTGACAATGTTTGAGGCTTTGCCTCACATCATTGATGAGGTCATCAACATTGT
CATTATTGTGCTCATTATAATCACGAGCATCAAAGCTGTGTACAATTTCGCCACCTGTGGGATAT
TAGCACTGGTCAGCTTCCTTTTTTTGGCTGGTAGGTCCTGTGGCATGTACGGCCTTAATGGTCCC
GACATCTATAAAGGGGTTTACCAGTTCAAATCAGTGGAGTTTGATATGTCTCACTTAAATCTGAC
GATGCCCAATGCGTGCTCAGCCAACAACTCTCATCACTACATCAGTATGGGAAGCTCTGGACTGG
AGCTAACTTTCACTAACGACTCCATCCTTAATCACAATTTTTGCAACTTAACCTCCGCTTTCAAC
AAAAAGACTTTTGACCATACACTCATGAGTATAGTCTCGAGTCTGCACCTCAGTATTAGAGGGAA
TTCCAACCACAAAGCAGTGTCTTGTGATTTTAACAATGGCATCACCATTCAATACAACTTGTCAT
TTTCGGACCCACAGAGCGCTATAAGCCAGTGTAGGACTTTCAGAGGTAGAGTCTTGGACATGTTT
AGAACTGCCTTTGGAGGAAAATACATGAGAAGTGGCTGGGGCTGGGCAGGTTCAGATGGCAAGAC
CACTTGGTGCAGCCAAACAAGCTATCAGTACCTAATCATACAAAACAGGACTTGGGAAAACCACT
GTAGATATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAATCCAGG
TGGTTATTGCCTGACCAAATGGATGATCCTTGCTGCAGAGCTCAAATGTTTTGGGAATACAGCTG
TTGCAAAATGTAATGTCAATCATGATGAAGAGTTCTGTGACATGCTACGACTAATTGATTACAAC
AAGGCCGCCCTGAGTAAGTTCAAGCAAGATGTAGAGTCTGCCTTGCATGTATTCAAAACAACAGT
AAATTCTCTGATTTCCGATCAGCTGTTGATGAGGAATCATCTAAGAGATCTAATGGGGGTACCAT
ACTGTAATTACTCAAAGTTCTGGTATCTGGAACATGCTAAGACTGGTGAGACTAGTGTACCCAAG
TGCTGGCTTGTCACTAATGGCTCCTACTTGAATGAGACCCACTTTAGTGATCAAATCGAACAAGA
AGCAGATAACATGATCACAGAGATGTTGAGGAAGGACTACATAAAAAGACAAGGGAGTACTCCTT
TAGCCTTAATGGATCTTTTGATGTTTTCAACATCAGCATATCTAATCAGCATCTTTCTGCATCTT
GTGAAGATACCAACACATAGACACATAAAGGGCGGTTCATGTCCAAAGCCACACCGCTTGACCAA
CAAGGGGATCTGTAGTTGTGGTGCATTCAAGGTGCCTGGTGTAAAAACTATCTGGAAAAGACGCT
GA
(SEQ ID NO: 3)

Translation =
LCMV WE GPC

MGQIVTMFEALPHIIDEVINIVIIVLIIITSIKAVYNFATCGILALVSFLFLAGRSCGMYGLNGP
DIYKGVYQFKSVEFDMSHLNLTMPNACSANNSHHYISMGSSGLELTFTNDSILNHNFCNLTSAFN
KKTFDHTLMSIVSSLHLSIRGNSNHKAVSCDFNNGITIQYNLSFSDPQSAISQCRTFRGRVLDMF
RTAFGGKYMRSGWGWAGSDGKTTWCSQTSYQYLIIQNRTWENHCRYAGPFGMSRILFAQEKTKFL
TRRLAGTFTWTLSDSSGVENPGGYCLTKWMILAAELKCFGNTAVAKCNVNHDEEFCDMLRLIDYN
KAALSKFKQDVESALHVFKTTVNSLISDQLLMRNHLRDLMGVPYCNYSKFWYLEHAKTGETSVPK
CWLVTNGSYLNETHFSDQIEQEADNMITEMLRKDYIKRQGSTPLALMDLLMFSTSAYLISIFLHL
VKIPTHRHIKGGSCPKPHRLTNKGICSCGAFKVPGVKTIWKRR
(SEQ ID NO: 4)

Figure 38 (cont'd)

Lymphocytic choriomeningitis virus (LCMV) strain WE-DUE
Source: 1-3376 Segment = S
Protein: Nucleoprotein
Gene: NP
LCMV WE NP

ATGTCTTTGTCCAAAGAAGTCAAAAGCTTTCAGTGGACACAGGCGTTGAGGAGGGAGTTGCAGAG
TTTTACATCAGATGTAAAGGCTGCCGTCATCAAGGACGCAACCAGTCTTCTAAATGGGTTGGACT
TTTCTGAAGTCAGCAACGTTCAGAGGATCATGAGAAAGGAAAGGAGGGATGATAAAGACTTGCAG
AGACTCAGGAGTCTTAACCAGACTGTGCATTCTCTTGTTGATCTGAAGTCTACATCAAAGAAAAA
TGTTCTGAAAGTGGGAAGACTTAGTGCAGAGGAATTGATGACCCTTGCAGCTGATCTTGAGAAGC
TGAAGGCCAAAATTATGAGAACTGAGAGGCCTCAAGCTTCTGGAGTCTACATGGGAAATTTGACA
GCACAACAACTTGATCAAAGATCCCAAATACTGCAAATGGTTGGGATGAGAAGACCTCAGCAGGG
TGCAAGTGGTGTAGTAAGGGTTTGGGATGTGAAGGACTCATCACTTCTGAACAATCAGTTCGGCA
CAATGCCAAGCCTGACAATGGCTTGCATGGCAAAACAGTCACAGACCCCACTCAATGATGTTGTG
CAGGCACTCACAGACCTTGGCTTACTTTACACAGTCAAATACCCGAATCTCAGTGATCTTGAAAG
GCTAAAGGATAAACACCCAGTTCTGGGGGTCATTACTGAACAGCAATCTAGTATCAATATCTCTG
GTTATAATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGGGCCAA
GAAGAAACTCAACATGTTTGTCTCAGATCAAGTTGGAGATAGAAATCCCTATGAAAACATCCTTT
ATAAAGTCTGTCTTTCAGGTGAAGGATGGCCATACATAGCCTGTAGAACGTCAGTTGTGGGGAGA
GCATGGGAGAACACAACAATTGATCTCACAAATGAAAAACTTGTTGCCAACTCATCTAGGCCAGT
GCCTGGAGCAGCAGGCCCACCTCAGGTGGGCTTGAGTTACAGTCAGACAATGCTGTTGAAAGACT
TGATGGGAGGGATTGATCCCAATGCTCCCACATGGATTGACATTGAGGGCAGGTTCAATGATCCA
GTGGAGATAGCAATATTCCAACCACAAAATGGGCAATTCATACATTTTTACAGGGAACCTACGGA
CCAGAAGCAATTCAAGCAGGACTCAAAGTATTCACACGGCATGGATCTTGCTGATCTCTTCAATG
CACAGCCTGGGCTGACCTCATCAGTTATAGGTGCTCTCCCACAAGGGATGGTTTTGAGCTGTCAA
GGTTCTGATGACATCAGAAAGCTTCTGGACTCACAAAATAGAAGGGACATAAAACTCATTGATGT
TGAGATGACCAAGGAGGCCTCAAGAGAATATGAAGATAAAGTGTGGGACAAATATGGCTGGCTAT
GCAAAATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTTCACAA
CATCCTGCCACATGATTTAATCTTCAGAGGACCCAATGTTGTGACACTCTAA
(SEQ ID NO: 5)

Translation =
LCMV WE NP

MSLSKEVKSFQWTQALRRELQSFTSDVKAAVIKDATSLLNGLDFSEVSNVQRIMRKERRDDKDLQ
RLRSLNQTVHSLVDLKSTSKKNVLKVGRLSAEELMTLAADLEKLKAKIMRTERPQASGVYMGNLT
AQQLDQRSQILQMVGMRRPQQGASGVVRVWDVKDSSLLNNQFGTMPSLTMACMAKQSQTPLNDVV
QALTDLGLLYTVKYPNLSDLERLKDKHPVLGVITEQQSSINISGYNFSLGAAVKAGAALLDGGNM
LESILIKPSNSEDLLKAVLGAKKKLNMFVSDQVGDRNPYENILYKVCLSGEGWPYIACRTSVVGR
AWENTTIDLTNEKLVANSSRPVPGAAGPPQVGLSYSQTMLLKDLMGGIDPNAPTWIDIEGRFNDP
VEIAIFQPQNGQFIHFYREPTDQKQFKQDSKYSHGMDLADLFNAQPGLTSSVIGALPQGMVLSCQ
GSDDIRKLLDSQNRRDIKLIDVEMTKEASREYEDKVWDKYGWLCKMHTGVVRDKKKKEITPHCAL
MDCIIFESASKARLPDLKTVHNILPHDLIFRGPNVVTL
(SEQ ID NO: 6)

Figure 38 (cont'd)

Lymphocytic choriomeningitis virus (LCMV) strain WE-DUE
Source: 1-7235 Segment = L
Protein: RING finger protein Z
Gene: ZP
LCMV WE ZP
ATGGGCCAAGGCAAGTCCAAAGAAGAAAGGGACACCAGCAATACAGGCAGAGCAGAGCTTTTGCC
AGACACCACCTATCTTGGTCCTCTAAATTGTAAATCATGTTGGCAGAAATTTGACAGCTTGGTTA
GATGCCATGACCACTATCTTTGCAGACACTGTCTGAATCTCCTGCTGTCAGTTTCCGACAGATGT
CCTCTCTGTAAGTATCCACTGCCAACCAAACTGAAGGTGTCAACAGTCCCAAGCTCCCCACCTCC
CTATGAGGAGTGA
(SEQ ID NO: 7)

Translation =
LCMV WE ZP
MGQGKSKEERDTSNTGRAELLPDTTYLGPLNCKSCWQKFDSLVRCHDHYLCRHCLNLLLSVSDRC
PLCKYPLPTKLKVSTVPSSPPPYEE
(SEQ ID NO: 8)

Figure 38 (cont'd)

Lymphocytic choriomeningitis virus (LCMV) strain WE-DUE
Source: 1-7235 Segment = L
Protein: RNA-directed RNA polymerase L
Gene: LCMV WE LP

ATGGATGAAACTATTGCAGATTTGAGAGAGTTGTGTCTAAATTACATAGAACAGGACGAGAGGCT
GTCAAGGCAAAAACTCAACTTCCTGGGACAAAGAGAACCCAGAATGGTGCTAATTGAGGGACTCA
AATTGTTATCACGCTGTATAGAGATAGACAGTGCAGACAAAAGTGGTTGCATACACAACCACGAT
GACAAATCTGTTGAAACAATCCTAATAGACTCTGGGATTGTGTGTCCAGGACTGCCACTCATCAT
CCCTGATGGTTATAAGTTGATTGACAATTCCCTTATTCTTCTTGAATGTTTTGTTAGAAGCACAC
CAGCTAGTTTTGAAAAGAAGTTCATTGAGGACACCAACAAACTAGCATGCATCAAAGAAGATCTT
GCTGTTGCAGGCATCACACTGGTTCCAATAGTGGATGGTCGTTGTGATTATGATAACAGTTTCAT
GCCAGAATGGGTGAATTTTAAGTTCAGAGACCTCCTATTTAAACTCCTGGAGTATTCTAGTCAAG
ATGAGAAAGTTTTTGAGGAGTCTGAATACTTCAGGCTCTGTGAGTCTCTTAAGACCACTGTTGAC
AAACGTTCCGGCATGGACTCAATGAAAATTTTGAAAGACGCAAGATCATTTCATAACGATGAGAT
TATGAAAATGTGCCACGATGGTGTCAACCCCAACATGAGTTGCGATGATGTGGTCTTTGGCATAA
ATTCCTTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAATGATGA
CATATTAATGTTGAGCAAAGAGGCAGTTGAATCCTGCCCCTTAATGAGGTTCATTACAGCAGAGA
CCCATGGGCATGAGAGAGGAAGCGATGCTAACACTGAGTATGAAAGGCTACTCTCTATGTTGAAC
AAGGTGAAAAGTTTAAAATTATTAAACACTAGAAGGAGACAGCTGCTGAACTTAGATGTCTTATG
TCTTTCTTCACTTATTAAGCAGTCAATTTCCAAAGGGTTGGAAAATGATAAACATTGGGTTGGTT
GTTGCTACAGTAGTGTGAATGATAGGCTTGTGAGCCTTCAAAGTACCAAAGAAGAATTCATGAGA
CTTTTGAAGAACAGAAGAAAATCAAGAGTGCACAAAAAGGCATCTCTTGATGAGCTTTTTAGGGT
ATCCATAAATGAGTTCATAGCAAAAATCCAGAAATGCCTATCAACAGTGGGACTTAGTTTTGAGC
ATTACGGACTATCAGAATGCCTCGTGCAAGAATGCCATATACCATTTGCTGAATTTGAGAACTTT
ATGAGAGCCGGGACTCATCCTGTAATGCATTACACAAAATTTGAAGATTACACTTTCCAGCCTAA
CATAGAGCAATTGAGGGGTTTACAGAGTTTGAGAAAACTGTCATCTGTTTGTTTGGCTCTAACAA
ACAGCATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCATCTACT
ATATCAGAAAACTGGAGAATCATCGAGGTGTTATTCCATACAAGGTCCGGATGGTCACTTGATTT
CCTTTTACGCAGATCCAAAAAGGTTCTTTTTACCAATTTTTTCAGATGAGGTGTTGCACAACATG
ATAGACACAATGATTTCATGGATTAGGTCATGCCCTGACTTAAAAGATTCTCTTATTGACATTGA
GACTGCACTAAGGACATTGATCCTACTGATGCTCACCAACCCAACAAAGAGAAATCAAAAGCAGG
TTCAAAATATTAGGTATTTAGTGATGGCCATCGTCTCAGACTTTTCATCGACCTCATTAATGGAT
AAGTTGAAGGAGGATCTAATCACACCTGCCGAGAAAGTGGTGTACAGGCTGCTTCGGTTTTTGAT
TAGGACAATTTTTGGTACTGGTGAAAAGGTGTTATTGAGTGCAAAATTCAAGTTTATGTTGAATG
TGTCATACCTGTGTCATTTGATCACAAAGGAGACCCCTGATAGATTGACAGATCAGATAAAATGT
TTTGAAAAGTTCTTTGAGCCCAAGAGTGAGTTTGGTTTCTTTGTCAACCCTAAGGAAACAATCAC
ACCCGAAGAGGAATGTGTTTTTTATGAACAAATGAAGAAGTTCACCGGTAAAGATATTGATTGTC
AGCATTCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGATGTGC
GACAGCATTAGATCTCGCAAGCAACAAAAGTGTGGTTGTCAATAAACATCTGAATGGAGAACGGC
TTTTGGAGTATGATTTTAACAAATTGCTTGTTAGTGCTGTGAGCCAAATTACAGAGGGCTTCATG
AGGAAACAAAAGTATAAGCTGAGACACTCAGATTACGAATATAAGGTCTCAAAGCTTGTCTCTAG
ATTAGTCATCGGTTCCAGGAAAACAGAAGTAGACAAATTGGAAGATGATCCGGTAGATGTGTGTT
TCGAGGGGGAGGAGGAGACAAGTTTTTTCAGGAGTTTAGAAGATAAGGTCAGCTCCACAATAACA
CGGTATAATAGAGGCACTAGGCTTAATGAAGGGCAAGGGGAGGGAGAATTCAAGAACACAAAAGG
ACTACACCACCTTCAGATTATTTTGTCAGGTAAAAGAGCTTATCTGAGGAAAGTCATTTTATCAG
AAATTTCATTTCATCTAGTAGAGGACTTTGATCCATCCTGTCTCACCAATGACGACATGAGGTTT

Figure 38 (cont'd)

ATTTGTGAGGCTGTTGAAGGTTCAACAGAACTGTCACCATTGTATTTTACATCAGCTGTCAAAGA
ACAATGTGGTCTGGATGAGATGGCAAGAAACCTCTGTAGAAAGTTCTTCTCAGAGGGTGATTGGT
TCTCATGTATGAAGATGATCTTGTTACAGATGAATGCAAATGCGTATTCAGGGAAGTACAGACAC
ATGCAGAGGCAGAGCTTAAATTTTAAATTTGACTGGGACAAATTGGAAGAAGATGTAAGAATTAG
TGAAAGGGAAAGCAATTCTGAATCTCTAAGTAAGGCCCTTTCATTGACAAAATGCATGAGTGCTG
CTCTAAAGAATCTGTGTTTTTACTCAGAAGAATCACCAACATCATACACTTCAGTTGGCCCTGAC
TCTGGGAGACTAAAATTTGCATTGTCATACAAAGAGCAGGTTGGGGGAAATAGAGAGCTTTACAT
TGGGGATTTGAGGACAAAAATGTTCACAAGATTGGTAGAAGATTATTTTGAATCCTTTTCTAGTT
TCTTTTCAGGATCTTGTTTAAACAATGACAAAGAGTTTGAAAATGCAATCTTGTCAATGACTATC
AATGTGAGAGAAGGGTTGTTAAACTACAGCATGGATCACAGCAAATGGGGACCAATGATGTGCCC
ATTCCTATTCTTAATGCTTCTCCAAAATCTCAAACTGGGTGATGATCAGTACGTGCGTTCTGGAA
AAGATCATGTTAGCACCTTGTTGACTTGGCATATGCATAAACTTGTTGAAGTCCCTTTCCCTGTT
GTGAATGCAATGATGAAATCATATGTTAAATCAAAACTCAAGCTTCTCAAAGGGTCAGGAACGAC
TGTTACGGAGAGAATCTTTAGAGAGTATTTTGAAATGGGGGTGGTGCCATCTCACATATCTAGTC
TCATTGACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGTGATGA
TCAGATCACTTTATTTGACAAGAGATTGAGTGACTTAGTTGATAGTGACCCAGAAGAAGTCCTTG
TCTTGCTGGAATTCCACTCTCACTTAAGTGGTTTGTTGAACAAGTTCATCAGTCCAAAAAGTGTG
GTTGGGCGGTTTGCAGCGGAATTCAAATCCAGATTTTATGTGTGGGGGGAGGAGGTCCCTCTCCT
CACGAAATTTGTGTCTGCGGCACTACACAATGTTAAGTGTAAAGAACCGCATCAACTTTGTGAGA
CAATAGATACGATTGCTGATCAAGCTATAGCAAATGGAGTTCCAGTTTTTTTAGTAAACTGTATC
CAGAGGAGGACACTGGATCTCTTGAAATATGCTAATTTCCCTTTAGATCCATTCTTGTTAAACAC
TCACACTGATGTAAAGGATTGGTTAGATGGTTCTAGAGGTTATAGAATCCAAAGACTCATTGAAG
AATTGTGTCCCAGTGAAACAAAGATCATGAGAAAACTTGTAAGAAGACTACATCACAAACTCAAG
AACGGTGAATGTAACGAGGAATTTTTTCTAGACCTCTTCAACAGGGAAAAGAAAGAGGCCATCCT
TCAATTGGGAGAGATTCTTGGTCTTGAGGATGATCTTAATGAGTTGGCAAGCATCAATTGGTTGA
ATCTGAATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGTAAGTT
CACAAGAGGTGCACAGAAGCTGTTGTCAGAGGCAATCAACAAATCAGCTTTTCAGAGTTGTGTCT
CATCCGGCTTTATAGGTCTCTGTAAGACTTTAGGAAGTAGGTGTGTGAGAAATAAAAACAGGGAA
AATATGTATATCAGAAAGGTGCTTGAAGATCTGACCATGGATGAACATGTCACAAGGGTTCACAA
ACAAGATGGTGTGATGTTGTACATTTGCGACAAGCAGAGACACCCAGAGGCTCACCGTGACCACA
TCAACCTTTTGAGGCCCCTTCTCTGGGACTACATTTGCATCTCATTGAGCAACTCTTTTGAGCTG
GGTGTTTGGGTTTTAGCAGAACCTGTGAAAGGAAAGAACGAGAGTAATTCGGCTGTTAGGCACTT
AAATCCATGTGATTATGTAGCAAGAAAACCTGAGAGTTCGAGACTACTAGAGGATAAAGTGAGTT
TGAATCATGTAATTCAATCTGTGAGGCGACTGTACCCCAAAATCTT

Figure 38 (cont'd)

TGAGGATCAGTTGCTCCCATTCATGTCTGATGTGAGCTCAAAAAATATGAGATGGAGTCCCAGGA
TTAAATTCCTTGACCTTTGTGTGCTGATTGACATCAACTCAGAGTCTTTGTCACTCATTTCTCAT
GTTGTCAAATGGAAGAGGGACGAACATTACACTGTGCTGTTTTCTGATCTCGTCAACTCTCACCA
ACGGTCAGACTCAAGTTTAGTTGATGAATTTGTTGTCAGCACAAGGGATGTCTGCAAGAACTTTT
TGAAGCAAGTGTATTTCGAATCATTTGTACGAGAGTTTGTTGCAACAGCTAGGACCTTAGGTAAC
TTTTCATGGTTCCCCCATAAGGACATGATGCCATCTGAAGATGGCGCTGAAGCACTGGGACCCTT
CCAATCATTTATTTTGAAAGTGGTGAACAAGAAAATAGAGAGGCCCATGTTTAGGAATGACTTGC
AGTTTGGTTTTGGTTGGTTCTCTTATCGTGTGGGGGATGTTGTGTGTAATGCCGCTATGTTAATT
AAGCAGGGTTTGACAGATCCAAAAGCATTTAAATCTTTAAGAGATTTGTGGGATTACATGCTCAG
CAGCACAGAGGGGATATTGGAGTTCTCAATCACAGTGGATTTCACACACAACCAGAACAACACTG
ACTGCTTGAGGAAATTTTCATTGATCTTTGTGGTTAAATGCCAATTACAGAGTCCAGGTGTAGCT
GATTACTTATCGTGCTCTCATTTCTTCAAAGGTGAGGTTGACAGGAGATTATTAGATGAGTGTCT
CAATCTGTTGAGGACAGACCCCATCTTTAAAGCGAATGATGGAGTCTTTGACATTAGGTCTGAAG
AGTTTGAAGATTACATGGAAGACCCTTTGACACTTGGTGATTCACTAGAACTTGAACTAATAGGT
TCTAGAAGGATTCTGAATGAGATCAAATCTACTGACTTTGAGAGGATAGGGCCTGAGTGGGAACC
TGTGCCTCTGACCATAAGGAAGGGTGCCCTCTTTGAGGGGAGGAACTTTGTTCAGAATATCTCTG
TGAAATTGGAGACAAAGGACATGAGGGTCTTTCTGGCAGAGCTCGAGGGCTGTGGAAAAAATTGGT
GATGTCCTCGGCAGCCTCCTCCTGCACCGATTCAGAACTGGTGAGCACTTGATGGAGTCAGAAAT
AAGTACAGTTCTTCAGGAGCTCTGCATGGACAGATCCGTCATGCTGACACCATTATCTTTTGTGC
CAGATTGGTTCACCTTCAGAGATTGTAGGCTCTGCTTCAGCAGGTCAAAGAACACTGTAATGTAT
GAGACAACTGGGGGCAGGTTCAGACTCAAGGGGAAATCCTGTGACGATTGGCTGGCGGAGCGGGT
GGCCGAGGAGATCGACTAG
(SEQ ID NO: 9)

Figure 38 (cont'd)

Translation =LCMV WE LP

MDETIADLRELCLNYIEQDERLSRQKLNFLGQREPRMVLIEGLKLLSRCIEIDSADKSGCIHNHD
DKSVETILIDSGIVCPGLPLIIPDGYKLIDNSLILLECFVRSTPASFEKKFIEDTNKLACIKEDL
AVAGITLVPIVDGRCDYDNSFMPEWVNFKFRDLLFKLLEYSSQDEKVFEESEYFRLCESLKTTVD
KRSGMDSMKILKDARSFHNDEIMKMCHDGVNPNMSCDDVVFGINSFFGRFRRDLLNGKLKRNFQK
VSPGGLIKEFSELYETLTDNDDILMLSKEAVESCPLMRFITAETHGHERGSDANTEYERLLSMLN
KVKSLKLLNTRRRQLLNLDVLCLSSLIKQSISKGLENDKHWVGCCYSSVNDRLVSLQSTKEEFMR
LLKNRRKSRVHKKASLDELFRVSINEFIAKIQKCLSTVGLSFEHYGLSECLVQECHIPFAEFENF
MRAGTHPVMHYTKFEDYTFQPNIEQLRGLQSLRKLSSVCLALTNSMKTSSVARLRQNQLGSVRYQ
VVECKEVFCQIIKLDSEEYHLLYQKTGESSRCYSIQGPDGHLISFYADPKRFFLPIFSDEVLHNM
IDTMISWIRSCPDLKDSLIDIETALRTLILLMLTNPTKRNQKQVQNIRYLVMAIVSDFSSTSLMD
KLKEDLITPAEKVVYRLLRFLIRTIFGTGEKVLLSAKFKFMLNVSYLCHLITKETPDRLTDQIKC
FEKFFEPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQITEGFM
RKQKYKLRHSDYEYKVSKLVSRLVIGSRKTEVDKLEDDPVDVCFEGEEETSFFRSLEDKVSSTIT
RYNRGTRLNEGQGEGEFKNTKGLHHLQIILSGKRAYLRKVILSEISFHLVEDFDPSCLTNDDMRF
ICEAVEGSTELSPLYFTSAVKEQCGLDEMARNLCRKFFSEGDWFSCMKMILLQMNANAYSGKYRH
MQRQSLNFKFDWDKLEEDVRISERESNSESLSKALSLTKCMSAALKNLCFYSEESPTSYTSVGPD
SGRLKFALSYKEQVGGNRELYIGDLRTKMFTRLVEDYFESFSSFFSGSCLNNDKEFENAILSMTI
NVREGLLNYSMDHSKWGPMMCPFLFLMLLQNLKLGDDQYVRSGKDHVSTLLTWHMHKLVEVPFPV
VNAMMKSYVKSKLKLLKGSGTTVTERIFREYFEMGVVPSHISSLIDMGQGILHNASDFYGLISER
FINYCIGVIFGERPEAYTSSDDQITLFDKRLSDLVDSDPEEVLVLLEFHSHLSGLLNKFISPKSV
VGRFAAEFKSRFYVWGEEVPLLTKFVSAALHNVKCKEPHQLCETIDTIADQAIANGVPVFLVNCI
QRRTLDLLKYANFPLDPFLLNTHTDVKDWLDGSRGYRIQRLIEELCPSETKIMRKLVRRLHHKLK
NGECNEEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVRNKNRE
NMYIRKVLEDLTMDEHVTRVHKQDGVMLYICDKQRHPEAHRDHINLLRPLLWDYICISLSNSFEL
GVWVLAEPVKGKNESNSAVRHLNPCDYVARKPESSRLLEDKVSLNHVIQSVRRLYPKIFEDQLLP
FMSDVSSKNMRWSPRIKFLDLCVLIDINSESLSLISHVVKWKRDEHYTVLFSDLVNSHQRSDSSL
VDEFVVSTRDVCKNFLKQVYFESFVREFVATARTLGNFSWFPHKDMMPSEDGAEALGPFQSFILK
VVNKKIERPMFRNDLQFGFGWFSYRVGDVVCNAAMLIKQGLTDPKAFKSLRDLWDYMLSSTEGIL
EFSITVDFTHNQNNTDCLRKFSLIFVVKCQLQSPGVADYLSCSHFFKGEVDRRLLDECLNLLRTD
PIFKANDGVFDIRSEEFEDYMEDPLTLGDSLELELIGSRRILNEIKSTDFERIGPEWEPVPLTIR
KGALFEGRNFVQNISVKLETKDMRVFLAELEGCGKIGDVLGSLLLHRFRTGEHLMESEISTVLQE
LCMDRSVMLTPLSFVPDWFTFRDCRLCFSRSKNTVMYETTGGRFRLKGKSCDDWLAERVAEEID
(SEQ ID NO: 10)

Figure 38 (cont'd)

B. Lymphocytic choriomeningitis virus (LCMV) strain P52-WE

Lymphocytic choriomeningitis virus (LCMV) strain P52-WE(L)
Source: 1-3376 Segment = S
LCMV P52-WE(L)S-Segment

GCGCACCGGGGATCCTAGGCTTTTTGGATTGCGCTTTCCTTTAGGACAATTGGGTGCTGGATTCT
ATCCAATAAAAGGATGGGTCAGATTGTGACAATGTTTGAGGCTTTGCCTCACATCATTGATGAGG
TCATCAACATTGTCATTATTGTGCTCATTATAATCACGAGCATCAAAGCTGTGTACAATTTCGCC
ACCTGTGGGATATTAGCACTGGTCAGCTTCCTTTTTTTGGCTGGTAGGTCCTGTGGCATGTACGG
CCTTAATGGTCCCGACATCTATAAAGGGGTTTACCAGTTCAAATCAGTGGAGTTTGATATGTCTC
ACTTAAATCTGACGATGCCCAATGCGTGCTCAGCCAACAACTCTCATCACTACATCAGTATGGGA
AGCTCTGGACTGGAGCTAACTTTCACTAACGACTCCATCCTTAATCACAATTTTTGCAACTTAAC
CTCCGCTTTCAACAAAAAGACTTTTGACCATACACTCATGAGTATAGTCTCGAGTCTGCACCTCA
GTATTAGAGGGAATTCCAACCACAAAGCAGTGTCTTGTGATTTTAACAATGGCATCACCATTCAA
TACAACTTGTCATTTTCGGACCCACAGAGCGCTATGAGCCAGTGTTGGACTTTCAGAGGTAGAGT
CTTGGACATGTTTAGAACTGCCTTTGGAGGAAAATACATGAGAAGTGGCTGGGGCTGGGCAGGTT
CAGATGGCAAGACCACTTGGTGCAGCCAAACAAGCTATCAGTACCTAATCATACAAAACAGGACT
TGGGAAAACCACTGTAGATATGCAGGCCCTTTTGGGATGTCTAGAATCCTCTTTGCTCAGGAAAA
GACAAAGTTTCTCACTAGGAGACTTGCAGGCACATTCACCTGGACCCTGTCAGACTCCTCAGGAG
TAGAAAATCCAGGTGGTTATTGCCTGACCAAATGGATGATCCTTGCTGCAGAGCTCAAATGTTTT
GGGAATACAGCTGTTGCAAAATGTAATGTCAATCATGATGAAGAGTTCTGTGACATGCTACGACT
AATTGATTACAACAAGGCCGCCCTGAGTAAGTTCAAGCAAGATGTAGAGTCTGCCTTGCATGTAT
TCAAAACAACAGTAAATTCTCTGATTTCCGATCAGCTGTTGATGAGGAATCATCTAAGAGATCTA
ATGGGGGTACCATACTGTAATTACTCAAAGTTCTGGTATCTGGAACATGCTAAGACTGGTGAGAC
TAGTGTACCCAAGTGCTGGCTTGTCACTAATGGCTCCTACTTGAATGAGACCCACTTTAGTGATC
AAATCGAACAAGAAGCAGATAACATGATCACAGAGATGTTGAGGAAGGACTACATAAAAAGACAA
GGGAGTACTCCTTTAGCCTTAATGGATCTTTTGATGTTTTCAACATCAGCATATCTAATCAGCAT
CTTTCTGCATCTTGTGAAGATACCAACACATAGACACATAAAGGGCGGTTCATGTCCAAAGCCAC
ACCGCTTGACCAACAAGGGGATCTGTAGTTGTGGTGCATTCAAGGTGCCTGGTGTAAAAACTATC
TGGAAAAGACGCTGATCAGCAGCGCCTCCCTGACTCTCCACCTCGAAAGAGGTGGAGAGTCAGGG
AGGCCCAGTGGGTCTTAGAGTGTCACAACATTGGGTCCTCTGAAGATTAAATCATGTGGCAGGAT
GTTGTGAACGGTTTTTAGATCAGGGAGTCTTGCCTTGGAAGCACTCTCAAAAATGATGCAGTCCA
TGAGTGCACAGTGTGGGGTGATCTCTTTCTTCTTTTTGTCTCTCACTACCCCAGTGTGCATTTTG
CATAGCCAGCCATATTTGTCCCACACTTTATCTTCATATTCTCTTGAGGCCTCCTTGGTCATCTC
AACATCAATGAGTTTTATGTCCCTTCTATTTGTGAGTCCAGAAGCTTTCTGATGTCATCAGAAC
CTTGACAGCTCAAAACCATCCCTTGTGGGAGAGCACCTATAACTGATGAGGTCAGCCCAGGCTGT
GCATTGAAGAGATCAGCAAGATCCATGCCGTGTGAATACTTTGAGTCCTGCTTGAATTGCTTCTG
GTCCGTAGGTTCCCTGTAAAAATGTATGAATTGCCCATTTTGTGGTTGGAATATTGCTATCTCCA
CTGGATCATTGAACCTGCCCTCAATGTCAATCCATGTGGGAGCATTGGGATCAATCCCTCCCATC
AAGTCTTTCAACAGCATTGTCTGACTGTAACTCAAGCCCACCTGAGGTGGGCCTGCTGCTCCAGG
CACTGGCCTAGATGAGTTGGCAACAAGTTTTTCATTTGTGAGATCAATTGTTGTGTTCTCCCATG
CTCTCCCCACAACTGACGTTCTACAGGCTATGTATGGCCATCCTTCACCTGAAAGACAGACTTTA
TAAAGGATGTTTTCATAGGGATTTCTATCTCCAACTTGATCTGAGACAAACATGTTGAGTTTCTT
CTTGGCCCCGAGGACTGCTTTTAGGAGATCCTCACTGTTGCTCGGTTTGATCAAGATAGATTCCA
GCATGTTCCCTCCATCTAGCAGAGCTGCCCCCGCTTTCACAGCTGCACCAAGACTGAAATTATAA
CCAGAGATATTGATACTAGATTGCTGTTCAGTAATGACCCCCAGAACTGGGTGTTTATCCTTTAG
CCTTTCAAGATCACTGAGATTCGGGTATTTGACTGTGTAAAGTAAGCCAAGGTCTGTGAGTGCCT
GCACAACATCATTGAGTGGGGTCTGTGACTGTTTTGCCATGCAAGCCATTGTCAGGCTTGGCATT
GTGCCGAACTGATTGTTCAGAAGTGATGAGTCCTTCACATCCCAAACCCTTACTACACCACTTGC

Figure 38 (cont'd)

ACCCTGCTGAGGTCTTCTCATCCCAACCATTTGCAGTATTTGGGATCTTTGATCAAGTTGTTGTG
CTGTCAAATTTCCCATGTAGACTCCAGAAGCTTGAGGCCTCTCAGTTCTCATAATTTTGGCCTTC
AGCTTCTCAAGATCAGCTGCAAGGGTCATCAATTCCTCTGCACTAAGTCTTCCCACTTTCAGAAC
ATTTTTCTTTGATGTAGACTTCAGATCAACAAGAGAATGCACAGTCTGGTTAAGACTCCTGAGTC
TCTGCAAGTCTTTATCATCCCTCCTTTCCTTTCTCATGATCCTCTGAACGTTGCTGACTTCAGAA
AAGTCCAACCCATTTAGAAGACTGGTTGCGTCCTTGATGACGGCAGCCTTTACATCTGATGTAAA
ACTCTGCAACTCCCTCCTCAACGCCTGTGTCCACTGAAAGCTTTTGACTTCTTTGGACAAAGACA
TTTTGTCACACAATGAATTTCCAAATAAAAGCGCAATTAAATGCCTAGGATCCACTGTGCG
(SEQ ID NO: 11)

Figure 38 (cont'd)

Lymphocytic choriomeningitis virus (LCMV) strain P52-WE(L)
Source: 1-7236 Segment = L
LCMV P52-WE(L)L-Segment

GCGCACCGGGGATCCTAGGCGTTTAGTTGCGCTGCTTTATTGCACAGCTTCACTCTGCTAAACCA
TCAGGAACTGACCGATCATCAGTCATGGGCCAAGGCAAGTCCAAAGAAGAAAGGGACACCAGCAA
TACAGGCAGAGCAGAGCTTTTGCCAGACACCACCTATCTTGGTCCTCTAAATTGTAAATCATGTT
GGCAGAAATTTGACAGCTTGGTTAGATGCCATGACCACTATCTTTGCAGACACTGTCTGAATCTC
CTGCTGTCAGTTTCCGACAGATGTCCTCTCTGTAAGTATCCACTGCCAACCAAACTGAAGGTGTC
AACAGTCCCAAGCTCCCCACCTCCCTATGAGGAGTGACGCCCCAGACCTCGACACAACAGGCCAC
CCAACACAGAAAAACCACACACAAACCGGCACACACAGACACAGCAACCAGCACAAAGCGCACGA
AAACACACACACACACACACACACACACCCTCACCCACGCGCCCCCCCGCACCGCCGGGGGGGCGCC
CCCCCGGGGGGCAGCCCCCCGGGGGCCCGGGCAGGGCCCCGCGGAGATGCCGGCTAGTCGATCTC
CTCGGCCACCCGCTCCGCCAGCCAATCGTCACAGGATTTCCCCTTGAGTCTGAACCTGCCCCCAG
TTGTCTCATACATTACAGTGTTCTTTGACCTGCTGAAGCAGAGCCTACAATCTCTGAAGGTGAAC
CAATCTGGCACAAAAGATAATGGTGTCAGCATGACGGATCTGTCCATGCAGAGCTCCTGAAGAAC
TGTACTTATTTCTGACTCCATCAAGTGCTCACCAGTTCTGAATCGGTGCAGGAGGAGGCTGCCGA
GGACATCACCAATTTTTCCACAGCCCTCGAGCTCTGCCAGAAAGACCCTCATGTCCTTTGTCTCC
AATTTCACAGAGATATTCTGAACAAAGTTCCTCCCCTCAAAGAGGGCACCCTTCCTTATGGTCAG
AGGCACAGGTTCCCACTCAGGCCCTATCCTCTCAAAGTCAGTAGATTTGATCTCATTCAGAATCC
TTCTAGAACCTATTAGTTCAAGTTCTAGTGAATCACCAAGTGTCAAAGGGTCTTCCATGTAATCT
TCAAACTCTTCAGACCTAATGTCAAAGACTCCATCATTCGCTTTAAAGATGGGGTCTGTCCTCAA
CAGATTGAGACACTCATCTAATAATCTCCTGTCAACCTCACCTTTGAAGAAATGAGAGCACGATA
AGTAATCAGCTACACCTGGACTCTGTAATTGGCATTTAACCACAAAGATCAATGAAAATTTCCTC
AAGCAGTCAGTGTTGTTCTGGTTGTGTGTGAAATCCACTGTGATTGAGAACTCCAATATCCCCTC
TGTGCTGCTGAGCATGTAATCCCACAAATCTCTTAAAGATTTAAATGCTTTTGGATCTGTCAAAC
CCTGCTTAATTAACATAGCGGCATTACACACAACATCCCCCACACGATAAGAGAACCAACCAAAA
CCAAACTGCAAGTCATTCCTAAACATGGGCCTCTCTATTTTCTTGTTCACCACTTTCAAAATAAA
TGATTGGAAGGGTCCCAGTGCTTCAGCGCCATCTTCAGATGGCATCATGTCCTTATGGGGGAACC
ATGAAAAGTTACCTAAGGTCCTAGCTGTTGCAACAAACTCTCGTACAAATGATTCGAAATACACT
TGCTTCAAAAAGTTCTTGCAGACATCCCTTGTGCTGACAACAAATTCATCAACTAAACTTGAGTC
TGACCGTTGGTGAGAGTTGACGAGATCAGAAAACAGCACAGTGTAATGTTCGTCCCTCTTCCATT
TGACAACATGAGAAATGAGTGACAAAGACTCTGAGTTGATGTCAATCAGCACACAAAGGTCAAGG
AATTTAATCCTGGGACTCCATCTCATATTTTTTGAGCTCACATCAGACATGAATGGGAGCAACTG
ATCCTCAAAGATTTTGGGGTACAGTCGCCTCACAGATTGAATTACATGATTCAAACTCACTTTAT
CCTCTAGTAGTCTCGAACTCTCAGGTTTTCTTGCTACATAATCACATGGATTTAAGTGCCTAACA
GCCGAATTACTCTCGTTCTTTCCTTTCACAGGTTCTGCTAAAACCCAAACACCCAGCTCAAAAGA
GTTGCTCAATGAGATGCAAATGTAGTCCCAGAGAAGGGGCCTCAAAAGGTTGATGTGGTCACGGT
GAGCCTCTGGGTGTCTCTGCTTGTCGCAAATGTACAACATCACACCATCTTGTTTGTGAACCCTT
GTGACATGTTCATCCATGGTCAGATCTTCAAGCACCTTTCTGATATACATATTTTCCCTGTTTTT
ATTTCTCACACACCTACTTCCTAAAGTCTTACAGAGACCTATAAAGCCGGATGAGACACAACTCT
GAAAAGCTGATTTGTTGATTGCCTCTGACAACAGCTTCTGTGCACCTCTTGTGAACTTACTACAA
AGCTTATTTTGGAGTGTTTTAATCAATGAGGGGATCTTTTCCTCTTGAAAGGTCATTACTGATGG
GTAAACCACTTTTTGTCTCAGAACCATCCTCAATGGGAACATTTCATTCAGATTCAACCAATTGA
TGCTTGCCAACTCATTAAGATCATCCTCAAGACCAAGAATCTCTCCCAATTGAAGGATGGCCTCT
TTCTTTTCCCTGTTGAAGAGGTCTAGAAAAAATTCCTCGTTACATTCACCGTTCTTGAGTTTGTG
ATGTAGTCTTCTTACAAGTTTTCTCATGATCTTTGTTTCACTGGGACACAATTCTTCAATGAGTC
TTTGGATTCTATAACCTCTAGAACCATCTAACCAATCCTTTACATCAGTGTGAGTGTTTAACAAG
AATGGATCTAAAGGGAAATTAGCATATTTCAAGAGATCCAGTGTCCTCCTCTGGATACAGTTTAC
TAAAAAAACTGGAACTCCATTTGCTATAGCTTGATCAGCAATCGTATCTATTGTCTCACAAAGTT

Figure 38 (cont'd)

GATGCGGTTCTTTACACTTAACATTGTGTAGTGCCGCAGACACAAATTTCGTGAGGAGAGGGACC
TCCTCCCCCCACACATAAAATCTGGATTTGAATTCCGCTGCAAACCGCCCAACCACACTTTTTGG
ACTGATGAACTTGTTCAACAAACCACTTAAGTGAGAGTGGAATTCCAGCAAGACAAGGACTTCTT
CTGGGTCACTATCAACTAAGTCACTCAATCTCTTGTCAAATAAAGTGATCTGATCATCACTTGAT
GTATAGGCTTCTGGCCTCTCTCCAAAAATGACACCAATACAATAATTGATAAACCTTTCACTAAT
TAAACCGTAAAAATCAGAAGCATTGTGTAGGATCCCCTGTCCCATGTCAATGAGACTAGATATGT
GAGATGGCACCACCCCCATTTCAAAATACTCTCTAAAGATTCTCTCCGTAACAGTCGTTCCTGAC
CCTTTGAGAAGCTTGAGTTTTGATTTAACATATGATTTCATCATTGCATTCACAACAGGGAAAGG
GACTTCAACAAGTTTATGCATATGCCAAGTCAACAAGGTGCTAACATGATCTTTTCCAGAACGCA
CGTACTGATCATCACCCAGTTTGAGATTTTGGAGAAGCATTAAGAATAGGAATGGGCACATCATT
GGTCCCCATTTGCTGTGATCCATGCTGTAGTTTAACAACCCTTCTCTCACATTGATAGTCATTGA
CAAGATTGCATTTTCAAACTCTTTGTCATTGTTTAAACAAGATCCTGAAAAGAAACTAGAAAAGG
ATTCAAAATAATCTTCTACCAATCTTGTGAACATTTTTGTCCTCAAATCCCCAATGTAAAGCTCT
CTATTTCCCCCAACCTGCTCTTTGTATGACAATGCAAATTTTAGTCTCCCAGAGTCAGGGCCAAC
TGAAGTGTATGATGTTGGTGATTCTTCTGAGTAAAAACACAGATTCTTTAGAGCAGCACTCATGC
ATTTTGTCAATGAAAGGGCCTTACTTAGAGATTCAGAATTGCTTTCCCTTTCACTAATTCTTACA
TCTTCTTCCAATTTGTCCCAGTCAAATTTAAAATTTAAGCTCTGCCTCTGCATGTGTCTGTACTT
CCCTGAATACGCATTTGCATTCATCTGTAACAAGATCATCTTCATACATGAGAACCAATCACCCT
CTGAGAAGAACTTTCTACAGAGGTTTCTTGCCATCTCATCCAGACCACATTGTTCTTTGACAGCT
GATGTAAAATACAATGGTGACAGTTCTGTTGAACCTTCAACAGCCTCACAAATAAACCTCATGTC
GTCATTGGTGAGACAGGATGGATCAAAGTCCTCTACTAGATGAAATGAAATTTCTGATAAAATGA
CTTTCCTCAGATAAGCTCTTTTACCTGACAAAATAATCTGAAGGTGGTGTAGTCCTTTTGTGTTC
TTGAATTCTCCCTCCCCTTGCCCTTCATTAAGCCTAGTGCCTCTATTATACCGTGTTATTGTGGA
GCTGACCTTATCTTCTAAACTCCTGAAAAAACTTGTCTCCTCCTCCCCCTCGAAACACACATCTA
CCGGATCATCTTCCAATTTGTCTACTTCTGTTTTCCTGGAACCGATGACTAATCTAGAGACAAGC
TTTGAGACCTTATATTCGTAATCTGAGTGTCTCAGCTTATACTTTTGTTTCCTCATGAAGCCCTC
TGTAATTTGGCTCACAGCACTAACAAGCAATTTGTTAAAATCATACTCCAAAAGCCGTTCTCCAT
TCAGATGTTTATTGACAACCACACTTTTGTTGCTTGCGAGATCTAATGCTGTCGCACATCCAGAG
TTGGTCATGGGGTCCAGATTGTTGAGCCTTTTCTCCCCTTTTAGAATTAAGGTGCCATTGTTGAA
TGAAGATACCATCATGCTAAAGATCTCTAAATTAACACCAGGGGTTGAATGCTGACAATCAATAT
CTTTACCGGTGAACTTCTTCATTTGTTCATAAAAAACACATTCCTCTTCGGGTGTGATTGTTTCC
TTAGGGTTGACAAAGAAACCAAACTCACTCTTGGGCTCAAAGAACTTTTCAAAACATTTTATCTG
ATCTGTCAATCTATCAGGGGTCTCCTTTGTGATCAAATGACACAGGTATGACACATTCAACATAA
ACTTGAATTTTGCACTCAATAACACCTTTTCACCAGTACCAAAAATTGTCCTAATCAAAAACCGA
AGCAGCCTGTACACCACTTTCTCGGCAGGTGTGATTAGATCCTCCTTCAACTTATCCATTAATGA
GGTCGATGAAAAGTCTGAGACGATGGCCATCACTAAATACCTAATATTTTGAACCTGCTTTTGAT
TT

Figure 38 (cont'd)

CTCTTTGTTGGGTTGGTGAGCATCAGTAGGATCAATGTCCTTAGTGCAGTCTCAATGTCAATAAG
AGAATCTTTTAAGTCAGGGCATGACCTAATCCATGAAATCATTGTGTCTATCATGTTGTGCAACA
CCTCATCTGAAAAAATTGGTAAAAAGAACCTTTTTGGATCTGCGTAAAAGGAAATCAAGTGACCA
TCCGGACCTTGTATGGAATAACACCTCGATGATTCTCCAGTTTTCTGATATAGTAGATGATACTC
TTCGGAATCCAGTTTTATTATCTGGCAAAACACCTCTTTGCACTCCACCACTTGATATCTCACAG
ACCCCAGTTGGTTCTGTCTCAACCTTGCAACTGAGCTTGTTTTCATGCTGTTTGTTAGAGCCAAA
CAAACAGATGACAGTTTTCTCAAACTCTGTAAACCCCTCAATTGCTCTATGTTAGGCTGGAAAGT
GTAATCTTCAAATTTTGTGTAATGCATTACAGGATGAGTCCCGGCTCTCATAAAGTTCTCAAATT
CAGCAAATGGTATATGGCATTCTTGCACGAGGCATTCTGATAGTCCGTAATGCTCAAAACTAAGT
CCCACTGTTGATAGGCATTTCTGGATTTTTGCTATGAACTCATTTATGGATACCCTAAAAAGCTC
ATCAAGAGATGCCTTTTTGTGCACTCTTGATTTTCTTCTGTTCTTCAAAAGTCTCATGAATTCTT
CTTTGGTACTTTGAAGGCTCACAAGCCTATCATTCACACTACTGTAGCAACAACCAACCCAATGT
TTATCATTTTCCAACCCTTTGGAAATTGACTGCTTAATAAGTGAAGAAAGACATAAGACATCTAA
GTTCAGCAGCTGTCTCCTTCTAGTGTTTAATAATTTTAAACTTTTCACCTTGTTCAACATAGAGA
GTAGCCTTTCATACTCAGTGTTAGCATCGCTTCCTCTCTCATGCCCATGGGTCTCTGCTGTAATG
AACCTCATTAAGGGGCAGGATTCAACTGCCTCTTTGCTCAACATTAATATGTCATCATTATCAGT
AAGGGTTTCATAAAGTTCAGAGAATTCCTTGATTAAGCCCCCAGGGCTGACCTTTTGGAAATTCC
TTTTGAGTTTCCCATTTAACAGGTCCCTCCTAAACCTGCCAAAAAAGGAATTTATGCCAAAGACC
ACATCATCGCAACTCATGTTGGGGTTGACACCATCGTGGCACATTTTCATAATCTCATCGTTATG
AAATGATCTTGCGTCTTTCAAAATTTTCATTGAGTCCATGCCGGAACGTTTGTCAACAGTGGTCT
TAAGAGACTCACAGAGCCTGAAGTATTCAGACTCCTCAAAAACTTTCTCATCTTGACTAGAATAC
TCCAGGAGTTTAAATAGGAGGTCTCTGAACTTAAAATTCACCCATTCTGGCATGAAACTGTTATC
ATAATCACAACGACCATCCACTATTGGAACCAGTGTGATGCCTGCAACAGCAAGATCTTCTTTGA
TGCATGCTAGTTTGTTGGTGTCCTCAATGAACTTCTTTTCAAAACTAGCTGGTGTGCTTCTAACA
AAACATTCAAGAAGAATAAGGGAATTGTCAATCAACTTATAACCATCAGGGATGATGAGTGGCAG
TCCTGGACACACAATCCCAGAGTCTATTAGGATTGTTTCAACAGATTTGTCATCGTGGTTGTGTA
TGCAACCACTTTTGTCTGCACTGTCTATCTCTATACAGCGTGATAACAATTTGAGTCCCTCAATT
AGCACCATTCTGGGTTCTCTTTGTCCCAGGAAGTTGAGTTTTTGCCTTGACAGCCTCTCGTCCTG
TTCTATGTAATTTAGACACAACTCTCTCAAATCTGCAATAGTTTCATCCATTGCGCATCAAAAAG
CCTAGGATCCTCGGTGCGC
(SEQ ID NO: 12)

Figure 38 (cont'd)

Lymphocytic choriomeningitis virus (LCMV) strain P52-WE(L)
Source: 1-3376 Segment = S
Protein: Pre-glycoprotein polyprotein GP complex
Gene: GPC
LCMV P52-WE(L)GPC

ATGGGTCAGATTGTGACAATGTTTGAGGCTTTGCCTCACATCATTGATGAGGTCATCAACATTGT
CATTATTGTGCTCATTATAATCACGAGCATCAAAGCTGTGTACAATTTCGCCACCTGTGGGATAT
TAGCACTGGTCAGCTTCCTTTTTTTGGCTGGTAGGTCCTGTGGCATGTACGGCCTTAATGGTCCC
GACATCTATAAAGGGGTTTACCAGTTCAAATCAGTGGAGTTTGATATGTCTCACTTAAATCTGAC
GATGCCCAATGCGTGCTCAGCCAACAACTCTCATCACTACATCAGTATGGGAAGCTCTGGACTGG
AGCTAACTTTCACTAACGACTCCATCCTTAATCACAATTTTTGCAACTTAACCTCCGCTTTCAAC
AAAAAGACTTTTGACCATACACTCATGAGTATAGTCTCGAGTCTGCACCTCAGTATTAGAGGGAA
TTCCAACCACAAAGCAGTGTCTTGTGATTTTAACAATGGCATCACCATTCAATACAACTTGTCAT
TTTCGGACCCACAGAGCGCTATGAGCCAGTGTTGGACTTTCAGAGGTAGAGTCTTGGACATGTTT
AGAACTGCCTTTGGAGGAAAATACATGAGAAGTGGCTGGGGCTGGGCAGGTTCAGATGGCAAGAC
CACTTGGTGCAGCCAAACAAGCTATCAGTACCTAATCATACAAAACAGGACTTGGGAAAACCACT
GTAGATATGCAGGCCCTTTTGGGATGTCTAGAATCCTCTTTGCTCAGGAAAAGACAAAGTTTCTC
ACTAGGAGACTTGCAGGCACATTCACCTGGACCCTGTCAGACTCCTCAGGAGTAGAAAATCCAGG
TGGTTATTGCCTGACCAAATGGATGATCCTTGCTGCAGAGCTCAAATGTTTTGGGAATACAGCTG
TTGCAAAATGTAATGTCAATCATGATGAAGAGTTCTGTGACATGCTACGACTAATTGATTACAAC
AAGGCCGCCCTGAGTAAGTTCAAGCAAGATGTAGAGTCTGCCTTGCATGTATTCAAAACAACAGT
AAATTCTCTGATTTCCGATCAGCTGTTGATGAGGAATCATCTAAGAGATCTAATGGGGGTACCAT
ACTGTAATTACTCAAAGTTCTGGTATCTGGAACATGCTAAGACTGGTGAGACTAGTGTACCCAAG
TGCTGGCTTGTCACTAATGGCTCCTACTTGAATGAGACCCACTTTAGTGATCAAATCGAACAAGA
AGCAGATAACATGATCACAGAGATGTTGAGGAAGGACTACATAAAAAGACAAGGGAGTACTCCTT
TAGCCTTAATGGATCTTTTGATGTTTTCAACATCAGCATATCTAATCAGCATCTTTCTGCATCTT
GTGAAGATACCAACACATAGACACATAAAGGGCGGTTCATGTCCAAAGCCACACCGCTTGACCAA
CAAGGGGATCTGTAGTTGTGGTGCATTCAAGGTGCCTGGTGTAAAAACTATCTGGAAAAGACGCT
GA
(SEQ ID NO: 13)

Translation =
LCMV P52-WE(L)GPC

MGQIVTMFEALPHIIDEVINIVIIVLIIITSIKAVYNFATCGILALVSFLFLAGRSCGMYGLNGP
DIYKGVYQFKSVEFDMSHLNLTMPNACSANNSHHYISMGSSGLELTFTNDSILNHNFCNLTSAFN
KKTFDHTLMSIVSSLHLSIRGNSNHKAVSCDFNNGITIQYNLSFSDPQSAMSQCWTFRGRVLDMF
RTAFGGKYMRSGWGWAGSDGKTTWCSQTSYQYLIIQNRTWENHCRYAGPFGMSRILFAQEKTKFL
TRRLAGTFTWTLSDSSGVENPGGYCLTKWMILAAELKCFGNTAVAKCNVNHDEEFCDMLRLIDYN
KAALSKFKQDVESALHVFKTTVNSLISDQLLMRNHLRDLMGVPYCNYSKFWYLEHAKTGETSVPK
CWLVTNGSYLNETHFSDQIEQEADNMITEMLRKDYIKRQGSTPLALMDLLMFSTSAYLISIFLHL
VKIPTHRHIKGGSCPKPHRLTNKGICSCGAFKVPGVKTIWKRR
(SEQ ID NO: 14)

Figure 38 (cont'd)

Lymphocytic choriomeningitis virus (LCMV) strain P52-WE(L)
Source: 1-3376 Segment = S
Protein: Nucleoprotein
Gene: NP
LCMV P52-WE(L)NP

ATGTCTTTGTCCAAAGAAGTCAAAAGCTTTCAGTGGACACAGGCGTTGAGGAGGGAGTTGCAGAG
TTTTACATCAGATGTAAAGGCTGCCGTCATCAAGGACGCAACCAGTCTTCTAAATGGGTTGGACT
TTTCTGAAGTCAGCAACGTTCAGAGGATCATGAGAAAGGAAAGGAGGGATGATAAAGACTTGCAG
AGACTCAGGAGTCTTAACCAGACTGTGCATTCTCTTGTTGATCTGAAGTCTACATCAAAGAAAAA
TGTTCTGAAAGTGGGAAGACTTAGTGCAGAGGAATTGATGACCCTTGCAGCTGATCTTGAGAAGC
TGAAGGCCAAAATTATGAGAACTGAGAGGCCTCAAGCTTCTGGAGTCTACATGGGAAATTTGACA
GCACAACAACTTGATCAAAGATCCCAAATACTGCAAATGGTTGGGATGAGAAGACCTCAGCAGGG
TGCAAGTGGTGTAGTAAGGGTTTGGGATGTGAAGGACTCATCACTTCTGAACAATCAGTTCGGCA
CAATGCCAAGCCTGACAATGGCTTGCATGGCAAAACAGTCACAGACCCCACTCAATGATGTTGTG
CAGGCACTCACAGACCTTGGCTTACTTTACACAGTCAAATACCCGAATCTCAGTGATCTTGAAAG
GCTAAAGGATAAACACCCAGTTCTGGGGGTCATTACTGAACAGCAATCTAGTATCAATATCTCTG
GTTATAATTTCAGTCTTGGTGCAGCTGTGAAAGCGGGGGCAGCTCTGCTAGATGGAGGGAACATG
CTGGAATCTATCTTGATCAAACCGAGCAACAGTGAGGATCTCCTAAAAGCAGTCCTCGGGGCCAA
GAAGAAACTCAACATGTTTGTCTCAGATCAAGTTGGAGATAGAAATCCCTATGAAAACATCCTTT
ATAAAGTCTGTCTTTCAGGTGAAGGATGGCCATACATAGCCTGTAGAACGTCAGTTGTGGGGAGA
GCATGGGAGAACACAACAATTGATCTCACAAATGAAAAACTTGTTGCCAACTCATCTAGGCCAGT
GCCTGGAGCAGCAGGCCCACCTCAGGTGGGCTTGAGTTACAGTCAGACAATGCTGTTGAAAGACT
TGATGGGAGGGATTGATCCCAATGCTCCCACATGGATTGACATTGAGGGCAGGTTCAATGATCCA
GTGGAGATAGCAATATTCCAACCACAAAATGGGCAATTCATACATTTTTACAGGGAACCTACGGA
CCAGAAGCAATTCAAGCAGGACTCAAAGTATTCACACGGCATGGATCTTGCTGATCTCTTCAATG
CACAGCCTGGGCTGACCTCATCAGTTATAGGTGCTCTCCCACAAGGGATGGTTTTGAGCTGTCAA
GGTTCTGATGACATCAGAAAGCTTCTGGACTCACAAAATAGAAGGGACATAAAACTCATTGATGT
TGAGATGACCAAGGAGGCCTCAAGAGAATATGAAGATAAAGTGTGGGACAAATATGGCTGGCTAT
GCAAAATGCACACTGGGGTAGTGAGAGACAAAAAGAAGAAAGAGATCACCCCACACTGTGCACTC
ATGGACTGCATCATTTTTGAGAGTGCTTCCAAGGCAAGACTCCCTGATCTAAAAACCGTTCACAA
CATCCTGCCACATGATTTAATCTTCAGAGGACCCAATGTTGTGACACTCTAA
(SEQ ID NO: 15)

Translation =
LCMV P52-WE(L)NP

MSLSKEVKSFQWTQALRRELQSFTSDVKAAVIKDATSLLNGLDFSEVSNVQRIMRKERRDDKDLQ
RLRSLNQTVHSLVDLKSTSKKNVLKVGRLSAEELMTLAADLEKLKAKIMRTERPQASGVYMGNLT
AQQLDQRSQILQMVGMRRPQQGASGVVRVWDVKDSSLLNNQFGTMPSLTMACMAKQSQTPLNDVV
QALTDLGLLYTVKYPNLSDLERLKDKHPVLGVITEQQSSINISGYNFSLGAAVKAGAALLDGGNM
LESILIKPSNSEDLLKAVLGAKKKLNMFVSDQVGDRNPYENILYKVCLSGEGWPYIACRTSVVGR
AWENTTIDLTNEKLVANSSRPVPGAAGPPQVGLSYSQTMLLKDLMGGIDPNAPTWIDIEGRFNDP
VEIAIFQPQNGQFIHFYREPTDQKQFKQDSKYSHGMDLADLFNAQPGLTSSVIGALPQGMVLSCQ
GSDDIRKLLDSQNRRDIKLIDVEMTKEASREYEDKVWDKYGWLCKMHTGVVRDKKKKEITPHCAL
MDCIIFESASKARLPDLKTVHNILPHDLIFRGPNVVTL
(SEQ ID NO: 16)

Figure 38 (cont'd)

Lymphocytic choriomeningitis virus (LCMV) strain P52-WE(L)
Source: 1-7235 Segment = L
Protein: RING finger protein Z
Gene: ZP
LCMV P52-WE(L) ZP

ATGGGCCAAGGCAAGTCCAAAGAAGAAAGGGACACCAGCAATACAGGCAGAGCAGAGCTTTTGCC
AGACACCACCTATCTTGGTCCTCTAAATTGTAAATCATGTTGGCAGAAATTTGACAGCTTGGTTA
GATGCCATGACCACTATCTTTGCAGACACTGTCTGAATCTCCTGCTGTCAGTTTCCGACAGATGT
CCTCTCTGTAAGTATCCACTGCCAACCAAACTGAAGGTGTCAACAGTCCCAAGCTCCCCACCTCC
CTATGAGGAGTGA
(SEQ ID NO: 17)

Translation =
LCMV P52-WE(L) ZP

MGQGKSKEERDTSNTGRAELLPDTTYLGPLNCKSCWQKFDSLVRCHDHYLCRHCLNLLLSVSDRC
PLCKYPLPTKLKVSTVPSSPPPYEE
(SEQ ID NO: 18)

Figure 38 (cont'd)

Lymphocytic choriomeningitis virus (LCMV) strain P52-WE(L)
Source: 1-7235 Segment = L
Protein: RNA-directed RNA polymerase L
Gene: LCMV P52-WE(L) LP

ATGGATGAAACTATTGCAGATTTGAGAGAGTTGTGTCTAAATTACATAGAACAGGACGAGAGGCT
GTCAAGGCAAAAACTCAACTTCCTGGGACAAAGAGAACCCAGAATGGTGCTAATTGAGGGACTCA
AATTGTTATCACGCTGTATAGAGATAGACAGTGCAGACAAAAGTGGTTGCATACACAACCACGAT
GACAAATCTGTTGAAACAATCCTAATAGACTCTGGGATTGTGTGTCCAGGACTGCCACTCATCAT
CCCTGATGGTTATAAGTTGATTGACAATTCCCTTATTCTTCTTGAATGTTTTGTTAGAAGCACAC
CAGCTAGTTTTGAAAAGAAGTTCATTGAGGACACCAACAAACTAGCATGCATCAAAGAAGATCTT
GCTGTTGCAGGCATCACACTGGTTCCAATAGTGGATGGTCGTTGTGATTATGATAACAGTTTCAT
GCCAGAATGGGTGAATTTTAAGTTCAGAGACCTCCTATTTAAACTCCTGGAGTATTCTAGTCAAG
ATGAGAAAGTTTTTGAGGAGTCTGAATACTTCAGGCTCTGTGAGTCTCTTAAGACCACTGTTGAC
AAACGTTCCGGCATGGACTCAATGAAAATTTTGAAAGACGCAAGATCATTTCATAACGATGAGAT
TATGAAAATGTGCCACGATGGTGTCAACCCCAACATGAGTTGCGATGATGTGGTCTTTGGCATAA
ATTCCTTTTTTGGCAGGTTTAGGAGGGACCTGTTAAATGGGAAACTCAAAAGGAATTTCCAAAAG
GTCAGCCCTGGGGGCTTAATCAAGGAATTCTCTGAACTTTATGAAACCCTTACTGATAATGATGA
CATATTAATGTTGAGCAAAGAGGCAGTTGAATCCTGCCCCTTAATGAGGTTCATTACAGCAGAGA
CCCATGGGCATGAGAGAGGAAGCGATGCTAACACTGAGTATGAAAGGCTACTCTCTATGTTGAAC
AAGGTGAAAAGTTTAAAATTATTAAACACTAGAAGGAGACAGCTGCTGAACTTAGATGTCTTATG
TCTTTCTTCACTTATTAAGCAGTCAATTTCCAAAGGGTTGGAAAATGATAAACATTGGGTTGGTT
GTTGCTACAGTAGTGTGAATGATAGGCTTGTGAGCCTTCAAAGTACCAAAGAAGAATTCATGAGA
CTTTTGAAGAACAGAAGAAAATCAAGAGTGCACAAAAAGGCATCTCTTGATGAGCTTTTTAGGGT
ATCCATAAATGAGTTCATAGCAAAAATCCAGAAATGCCTATCAACAGTGGGACTTAGTTTTGAGC
ATTACGGACTATCAGAATGCCTCGTGCAAGAATGCCATATACCATTTGCTGAATTTGAGAACTTT
ATGAGAGCCGGGACTCATCCTGTAATGCATTACACAAAATTTGAAGATTACACTTTCCAGCCTAA
CATAGAGCAATTGAGGGGTTTACAGAGTTTGAGAAAACTGTCATCTGTTTGTTTGGCTCTAACAA
ACAGCATGAAAACAAGCTCAGTTGCAAGGTTGAGACAGAACCAACTGGGGTCTGTGAGATATCAA
GTGGTGGAGTGCAAAGAGGTGTTTTGCCAGATAATAAAACTGGATTCCGAAGAGTATCATCTACT
ATATCAGAAAACTGGAGAATCATCGAGGTGTTATTCCATACAAGGTCCGGATGGTCACTTGATTT
CCTTTTACGCAGATCCAAAAAGGTTCTTTTTACCAATTTTTTCAGATGAGGTGTTGCACAACATG
ATAGACACAATGATTTCATGGATTAGGTCATGCCCTGACTTAAAAGATTCTCTTATTGACATTGA
GACTGCACTAAGGACATTGATCCTACTGATGCTCACCAACCCAACAAAGAGAAATCAAAAGCAGG
TTCAAAATATTAGGTATTTAGTGATGGCCATCGTCTCAGACTTTTCATCGACCTCATTAATGGAT
AAGTTGAAGGAGGATCTAATCACACCTGCCGAGAAAGTGGTGTACAGGCTGCTTCGGTTTTTGAT
TAGGACAATTTTTGGTACTGGTGAAAAGGTGTTATTGAGTGCAAAATTCAAGTTTATGTTGAATG
TGTCATACCTGTGTCATTTGATCACAAAGGAGACCCCTGATAGATTGACAGATCAGATAAAATGT
TTTGAAAAGTTCTTTGAGCCCAAGAGTGAGTTTGGTTTCTTTGTCAACCCTAAGGAAACAATCAC
ACCCGAAGAGGAATGTGTTTTTTATGAACAAATGAAGAAGTTCACCGGTAAAGATATTGATTGTC
AGCATTCAACCCCTGGTGTTAATTTAGAGATCTTTAGCATGATGGTATCTTCATTCAACAATGGC
ACCTTAATTCTAAAAGGGGAGAAAAGGCTCAACAATCTGGACCCCATGACCAACTCTGGATGTGC
GACAGCATTAGATCTCGCAAGCAACAAAAGTGTGGTTGTCAATAAACATCTGAATGGAGAACGGC
TTTTGGAGTATGATTTTAACAAATTGCTTGTTAGTGCTGTGAGCCAAATTACAGAGGGCTTCATG
AGGAAACAAAAGTATAAGCTGAGACACTCAGATTACGAATATAAGGTCTCAAAGCTTGTCTCTAG
ATTAGTCATCGGTTCCAGGAAAACAGAAGTAGACAAATTGGAAGATGATCCGGTAGATGTGTGTT
TCGAGGGGGAGGAGGAGACAAGTTTTTTCAGGAGTTTAGAAGATAAGGTCAGCTCCACAATAACA
CGGTATAATAGAGGCACTAGGCTTAATGAAGGGCAAGGGGAGGGAGAATTCAAGAACACAAAAGG
ACTACACCACCTTCAGATTATTTTGTCAGGTAAAAGAGCTTATCTGAGGAAAGTCATTTTATCAG
AAATTTCATTTCATCTAGTAGAGGACTTTGATCCATCCTGTCTCACCAATGACGACATGAGGTTT

Figure 38 (cont'd)

ATTTGTGAGGCTGTTGAAGGTTCAACAGAACTGTCACCATTGTATTTTACATCAGCTGTCAAAGA
ACAATGTGGTCTGGATGAGATGGCAAGAAACCTCTGTAGAAAGTTCTTCTCAGAGGGTGATTGGT
TCTCATGTATGAAGATGATCTTGTTACAGATGAATGCAAATGCGTATTCAGGGAAGTACAGACAC
ATGCAGAGGCAGAGCTTAAATTTTAAATTTGACTGGGACAAATTGGAAGAAGATGTAAGAATTAG
TGAAAGGGAAAGCAATTCTGAATCTCTAAGTAAGGCCCTTTCATTGACAAAATGCATGAGTGCTG
CTCTAAAGAATCTGTGTTTTTACTCAGAAGAATCACCAACATCATACACTTCAGTTGGCCCTGAC
TCTGGGAGACTAAAATTTGCATTGTCATACAAAGAGCAGGTTGGGGGAAATAGAGAGCTTTACAT
TGGGGATTTGAGGACAAAAATGTTCACAAGATTGGTAGAAGATTATTTTGAATCCTTTTCTAGTT
TCTTTTCAGGATCTTGTTTAAACAATGACAAAGAGTTTGAAAATGCAATCTTGTCAATGACTATC
AATGTGAGAGAAGGGTTGTTAAACTACAGCATGGATCACAGCAAATGGGGACCAATGATGTGCCC
ATTCCTATTCTTAATGCTTCTCCAAAATCTCAAACTGGGTGATGATCAGTACGTGCGTTCTGGAA
AAGATCATGTTAGCACCTTGTTGACTTGGCATATGCATAAACTTGTTGAAGTCCCTTTCCCTGTT
GTGAATGCAATGATGAAATCATATGTTAAATCAAAACTCAAGCTTCTCAAAGGGTCAGGAACGAC
TGTTACGGAGAGAATCTTTAGAGAGTATTTTGAAATGGGGGTGGTGCCATCTCACATATCTAGTC
TCATTGACATGGGACAGGGGATCCTACACAATGCTTCTGATTTTTACGGTTTAATTAGTGAAAGG
TTTATCAATTATTGTATTGGTGTCATTTTTGGAGAGAGGCCAGAAGCCTATACATCAAGTGATGA
TCAGATCACTTTATTTGACAAGAGATTGAGTGACTTAGTTGATAGTGACCCAGAAGAAGTCCTTG
TCTTGCTGGAATTCCACTCTCACTTAAGTGGTTTGTTGAACAAGTTCATCAGTCCAAAAAGTGTG
GTTGGGCGGTTTGCAGCGGAATTCAAATCCAGATTTTATGTGTGGGGGGAGGAGGTCCCTCTCCT
CACGAAATTTGTGTCTGCGGCACTACACAATGTTAAGTGTAAAGAACCGCATCAACTTTGTGAGA
CAATAGATACGATTGCTGATCAAGCTATAGCAAATGGAGTTCCAGTTTTTTTAGTAAACTGTATC
CAGAGGAGGACACTGGATCTCTTGAAATATGCTAATTTCCCTTTAGATCCATTCTTGTTAAACAC
TCACACTGATGTAAAGGATTGGTTAGATGGTTCTAGAGGTTATAGAATCCAAAGACTCATTGAAG
AATTGTGTCCCAGTGAAACAAAGATCATGAGAAAACTTGTAAGAAGACTACATCACAAACTCAAG
AACGGTGAATGTAACGAGGAATTTTTTCTAGACCTCTTCAACAGGGAAAAGAAAGAGGCCATCCT
TCAATTGGGAGAGATTCTTGGTCTTGAGGATGATCTTAATGAGTTGGCAAGCATCAATTGGTTGA
ATCTGAATGAAATGTTCCCATTGAGGATGGTTCTGAGACAAAAAGTGGTTTACCCATCAGTAATG
ACCTTTCAAGAGGAAAAGATCCCCTCATTGATTAAAACACTCCAAAATAAGCTTTGTAGTAAGTT
CACAAGAGGTGCACAGAAGCTGTTGTCAGAGGCAATCAACAAATCAGCTTTTCAGAGTTGTGTCT
CATCCGGCTTTATAGGTCTCTGTAAGACTTTAGGAAGTAGGTGTGTGAGAAATAAAAACAGGGAA
AATATGTATATCAGAAAGGTGCTTGAAGATCTGACCATGGATGAACATGTCACAAGGGTTCACAA
ACAAGATGGTGTGATGTTGTACATTTGCGACAAGCAGAGACACCCAGAGGCTCACCGTGACCACA
TCAACCTTTTGAGGCCCCTTCTCTGGGACTACATTTGCATCTCATTGAGCAACTCTTTTGAGCTG
GGTGTTTGGGTTTTAGCAGAACCTGTGAAAGGAAAGAACGAGAGTAATTCGGCTGTTAGGCACTT
AAATCCATGTGATTATGTAGCAAGAAAACCTGAGAGTTCGAGACTACTAGAGGATAAAGTGAGTT
TGAATCATGTAATTCAATCTGTGAGGCGACTGTACCCCAAAATCTT

Figure 38 (cont'd)

TGAGGATCAGTTGCTCCCATTCATGTCTGATGTGAGCTCAAAAAATATGAGATGGAGTCCCAGGA
TTAAATTCCTTGACCTTTGTGTGCTGATTGACATCAACTCAGAGTCTTTGTCACTCATTTCTCAT
GTTGTCAAATGGAAGAGGGACGAACATTACACTGTGCTGTTTTCTGATCTCGTCAACTCTCACCA
ACGGTCAGACTCAAGTTTAGTTGATGAATTTGTTGTCAGCACAAGGGATGTCTGCAAGAACTTTT
TGAAGCAAGTGTATTTCGAATCATTTGTACGAGAGTTTGTTGCAACAGCTAGGACCTTAGGTAAC
TTTTCATGGTTCCCCCATAAGGACATGATGCCATCTGAAGATGGCGCTGAAGCACTGGGACCCTT
CCAATCATTTATTTTGAAAGTGGTGAACAAGAAAATAGAGAGGCCCATGTTTAGGAATGACTTGC
AGTTTGGTTTTGGTTGGTTCTCTTATCGTGTGGGGGATGTTGTGTGTAATGCCGCTATGTTAATT
AAGCAGGGTTTGACAGATCCAAAAGCATTTAAATCTTTAAGAGATTTGTGGGATTACATGCTCAG
CAGCACAGAGGGGATATTGGAGTTCTCAATCACAGTGGATTTCACACACAACCAGAACAACACTG
ACTGCTTGAGGAAATTTTCATTGATCTTTGTGGTTAAATGCCAATTACAGAGTCCAGGTGTAGCT
GATTACTTATCGTGCTCTCATTTCTTCAAAGGTGAGGTTGACAGGAGATTATTAGATGAGTGTCT
CAATCTGTTGAGGACAGACCCCATCTTTAAAGCGAATGATGGAGTCTTTGACATTAGGTCTGAAG
AGTTTGAAGATTACATGGAAGACCCTTTGACACTTGGTGATTCACTAGAACTTGAACTAATAGGT
TCTAGAAGGATTCTGAATGAGATCAAATCTACTGACTTTGAGAGGATAGGGCCTGAGTGGGAACC
TGTGCCTCTGACCATAAGGAAGGGTGCCCTCTTTGAGGGGAGGAACTTTGTTCAGAATATCTCTG
TGAAATTGGAGACAAAGGACATGAGGGTCTTTCTGGCAGAGCTCGAGGGCTGTGGAAAAAATTGGT
GATGTCCTCGGCAGCCTCCTCCTGCACCGATTCAGAACTGGTGAGCACTTGATGGAGTCAGAAAT
AAGTACAGTTCTTCAGGAGCTCTGCATGGACAGATCCGTCATGCTGACACCATTATCTTTTGTGC
CAGATTGGTTCACCTTCAGAGATTGTAGGCTCTGCTTCAGCAGGTCAAAGAACACTGTAATGTAT
GAGACAACTGGGGGCAGGTTCAGACTCAAGGGGAAATCCTGTGACGATTGGCTGGCGGAGCGGGT
GGCCGAGGAGATCGACTAG
(SEQ ID NO: 19)

Figure 38 (cont'd)

Translation =
LCMV P52-WE(L) LP
MDETIADLRELCLNYIEQDERLSRQKLNFLGQREPRMVLIEGLKLLSRCIEIDSADKSGCIHNHD
DKSVETILIDSGIVCPGLPLIIPDGYKLIDNSLILLECFVRSTPASFEKKFIEDTNKLACIKEDL
AVAGITLVPIVDGRCDYDNSFMPEWVNFKFRDLLFKLLEYSSQDEKVFEESEYFRLCESLKTTVD
KRSGMDSMKILKDARSFHNDEIMKMCHDGVNPNMSCDDVVFGINSFFGRFRRDLLNGKLKRNFQK
VSPGGLIKEFSELYETLTDNDDILMLSKEAVESCPLMRFITAETHGHERGSDANTEYERLLSMLN
KVKSLKLLNTRRRQLLNLDVLCLSSLIKQSISKGLENDKHWVGCCYSSVNDRLVSLQSTKEEFMR
LLKNRRKSRVHKKASLDELFRVSINEFIAKIQKCLSTVGLSFEHYGLSECLVQECHIPFAEFENF
MRAGTHPVMHYTKFEDYTFQPNIEQLRGLQSLRKLSSVCLALTNSMKTSSVARLRQNQLGSVRYQ
VVECKEVFCQIIKLDSEEYHLLYQKTGESSRCYSIQGPDGHLISFYADPKRFFLPIFSDEVLHNM
IDTMISWIRSCPDLKDSLIDIETALRTLILLMLTNPTKRNQKQVQNIRYLVMAIVSDFSSTSLMD
KLKEDLITPAEKVVYRLLRFLIRTIFGTGEKVLLSAKFKFMLNVSYLCHLITKETPDRLTDQIKC
FEKFFEPKSEFGFFVNPKETITPEEECVFYEQMKKFTGKDIDCQHSTPGVNLEIFSMMVSSFNNG
TLILKGEKRLNNLDPMTNSGCATALDLASNKSVVVNKHLNGERLLEYDFNKLLVSAVSQITEGFM
RKQKYKLRHSDYEYKVSKLVSRLVIGSRKTEVDKLEDDPVDVCFEGEEETSFFRSLEDKVSSTIT
RYNRGTRLNEGQGEGEFKNTKGLHHLQIILSGKRAYLRKVILSEISFHLVEDFDPSCLTNDDMRF
ICEAVEGSTELSPLYFTSAVKEQCGLDEMARNLCRKFFSEGDWFSCMKMILLQMNANAYSGKYRH
MQRQSLNFKFDWDKLEEDVRISERESNSESLSKALSLTKCMSAALKNLCFYSEESPTSYTSVGPD
SGRLKFALSYKEQVGGNRELYIGDLRTKMFTRLVEDYFESFSSFFSGSCLNNDKEFENAILSMTI
NVREGLLNYSMDHSKWGPMMCPFLFLMLLQNLKLGDDQYVRSGKDHVSTLLTWHMHKLVEVPFPV
VNAMMKSYVKSKLKLLKGSGTTVTERIFREYFEMGVVPSHISSLIDMGQGILHNASDFYGLISER
FINYCIGVIFGERPEAYTSSDDQITLFDKRLSDLVDSDPEEVLVLLEFHSHLSGLLNKFISPKSV
VGRFAAEFKSRFYVWGEEVPLLTKFVSAALHNVKCKEPHQLCETIDTIADQAIANGVPVFLVNCI
QRRTLDLLKYANFPLDPFLLNTHTDVKDWLDGSRGYRIQRLIEELCPSETKIMRKLVRRLHHKLK
NGECNEEFFLDLFNREKKEAILQLGEILGLEDDLNELASINWLNLNEMFPLRMVLRQKVVYPSVM
TFQEEKIPSLIKTLQNKLCSKFTRGAQKLLSEAINKSAFQSCVSSGFIGLCKTLGSRCVRNKNRE
NMYIRKVLEDLTMDEHVTRVHKQDGVMLYICDKQRHPEAHRDHINLLRPLLWDYICISLSNSFEL
GVWVLAEPVKGKNESNSAVRHLNPCDYVARKPESSRLLEDKVSLNHVIQSVRRLYPKIFEDQLLP
FMSDVSSKNMRWSPRIKFLDLCVLIDINSESLSLISHVVKWKRDEHYTVLFSDLVNSHQRSDSSL
VDEFVVSTRDVCKNFLKQVYFESFVREFVATARTLGNFSWFPHKDMMPSEDGAEALGPFQSFILK
VVNKKIERPMFRNDLQFGFGWFSYRVGDVVCNAAMLIKQGLTDPKAFKSLRDLWDYMLSSTEGIL
EFSITVDFTHNQNNTDCLRKFSLIFVVKCQLQSPGVADYLSCSHFFKGEVDRRLLDECLNLLRTD
PIFKANDGVFDIRSEEFEDYMEDPLTLGDSLELELIGSRRILNEIKSTDFERIGPEWEPVPLTIR
KGALFEGRNFVQNISVKLETKDMRVFLAELEGCGKIGDVLGSLLLHRFRTGEHLMESEISTVLQE
LCMDRSVMLTPLSFVPDWFTFRDCRLCFSRSKNTVMYETTGGRFRLKGKSCDDWLAERVAEEID
(SEQ ID NO: 20)

Figure 38 (cont'd)

C. Lymphocytic choriomeningitis virus (LCMV) strain Armstrong 53b

Lymphocytic choriomeningitis virus (LCMV) strain Armstrong 53b
Source: 1-3376 Segment = S
LCMV Armstrong S-Segment

CGCACCGGGGATCCTAGGCTTTTTGGATTGCGCTTTCCTCTAGATCAACTGGGTGTCAGGCCCTA
TCCTACAGAAGGATGGGTCAGATTGTGACAATGTTTGAGGCTCTGCCTCACATCATCGATGAGGT
GATCAACATTGTCATTATTGTGCTTATCGTGATCACGGGTATCAAGGCTGTCTACAATTTTGCCA
CCTGTGGGATATTCGCATTGATCAGTTTCCTACTTCTGGCTGGCAGGTCCTGTGGCATGTACGGT
CTTAAGGGACCCGACATTTACAAAGGAGTTTACCAATTTAAGTCAGTGGAGTTTGATATGTCACA
TCTGAACCTGACCATGCCCAACGCATGTTCAGCCAACAACTCCCACCATTACATCAGTATGGGGA
CTTCTGGACTAGAATTGACCTTCACCAATGATTCCATCATCAGTCACAACTTTTGCAATCTGACC
TCTGCCTTCAATAAAAAGACCTTTGACCACACACTCATGAGTATAGTTTCGAGCCTACACCTCAG
TATCAGAGGGAACTCCAACTATAAGGCAGTATCCTGCGACTTCAACAATGGCATAACCATCCAAT
ACAACTTGACATTCTCAAATGCACAAAGTGCTCAGAGCCAGTGTAGAACCTTCAGAGGTAGAGTC
CTAGATATGTTTAGAACTGCCTTCGGGGGGAAATACATGAGGAGTGGCTGGGGCTGGACAGGCTC
AGATGGCAAGACCACCTGGTGTAGCCAGACGAGTTACCAATACCTGATTATACAAAATAGAACCT
GGGAAAACCACTGCACATATGCAGGTCCTTTTGGGATGTCCAGGATTCTCCTTTCCCAAGAGAAG
ACTAAGTTCTTCACTAGGAGACTAGCGGGCACATTCACCTGGACTTTGTCAGACTCTTCAGGGGT
GGAGAATCCAGGTGGTTATTGCCTGACCAAATGGATGATTCTTGCTGCAGAGCTTAAGTGTTTCG
GGAACACAGCAGTTGCGAAATGCAATGTAAATCATGATGAAGAATTCTGTGACATGCTGCGACTA
ATTGACTACAACAAGGCTGCTTTGAGTAAGTTCAAAGAGGACGTAGAATCTGCCTTGCACTTATT
CAAAACAACAGTGAATTCTTTGATTTCAGATCAACTACTGATGAGGAACCACTTGAGAGATCTGA
TGGGGGTGCCATATTGCAATTACTCAAAGTTTTGGTACCTAGAACATGCAAAGACCGGCGAAACT
AGTGTCCCCAAGTGCTGGCTTGTCACCAATGGTTCTTACTTAAATGAGACCCACTTCAGTGATCA
AATCGAACAGGAAGCCGATAACATGATTACAGAGATGTTGAGGAAGGATTACATAAAGAGGCAGG
GGAGTACCCCCCTAGCATTGATGGACCTTCTGATGTTTTCCACATCTGCATATCTAGTCAGCATC
TTCCTGCACCTTGTCAAAATACCAACACACAGGCACATAAAAGGTGGCTCATGTCCAAAGCCACA
CCGATTAACCAACAAAGGAATTTGTAGTTGTGGTGCATTTAAGGTGCCTGGTGTAAAAACCGTCT
GGAAAAGACGCTGAAGAACAGCGCCTCCCTGACTCTCCACCTCGAAAGAGGTGGAGAGTCAGGGA
GGCCCAGAGGGTCTTAGAGTGTCACAACATTTGGGCCTCTAAAAATTAGGTCATGTGGCAGAATG
TTGTGAACAGTTTTCAGATCTGGGAGCCTTGCTTTGGAGGCGCTTTCAAAAATGATGCAGTCCAT
GAGTGCACAGTGCGGGGTGATCTCTTTCTTCTTTTTGTCCCTTACTATTCCAGTATGCATCTTAC
ACAACCAGCCATATTTGTCCCACACTTTGTCTTCATACTCCCTCGAAGCTTCCCTGGTCATTTCA
ACATCGATAAGCTTAATGTCCTTCCTATTCTGTGAGTCCAGAAGCTTTCTGATGTCATCGGAGCC
TTGACAGCTTAGAACCATCCCCTGCGGAAGAGCACCTATAACTGACGAGGTCAACCCGGGTTGCG
CATTGAAGAGGTCGGCAAGATCCATGCCGTGTGAGTACTTGGAATCTTGCTTGAATTGTTTTTGA
TCAACGGGTTCCCTGTAAAAGTGTATGAACTGCCCGTTCTGTGGTTGGAAAATTGCTATTTCCAC
TGGATCATTAAATCTACCCTCAATGTCAATCCATGTAGGAGCGTTGGGGTCAATTCCTCCCATGA
GGTCTTTTAAAAGCATTGTCTGGCTGTAGCTTAAGCCCACCTGAGGTGGACCTGCTGCTCCAGGC
GCTGGCCTGGGTGAGTTGACTGCAGGTTTCTCGCTTGTGAGATCAATTGTTGTGTTTTCCCATGC
TCTCCCCACAATCGATGTTCTACAAGCTATGTATGGCCATCCTTCACCTGAAAGGCAAACTTTAT
AGAGGATGTTTTCATAAGGGTTCCTGTCCCCAACTTGGTCTGAAACAAACATGTTGAGTTTTCTC
TTGGCCCCGAGAACTGCCTTCAAGAGGTCCTCGCTGTTGCTTGGCTTGATCAAAATTGACTCTAA
CATGTTACCCCCATCCAACAGGGCTGCCCCTGCCTTCACGGCAGCACCAAGACTAAAGTTATAGC
CAGAAATGTTGATGCTGGACTGCTGTTCAGTGATGACCCCCAGAACTGGGTGCTTGTCTTTCAGC
CTTTCAAGATCATTAAGATTTGGATACTTGACTGTGTAAAGCAAGCCAAGGTCTGTGAGCGCTTG
TACAACGTCATTGAGCGGAGTCTGTGACTGTTTGGCCATACAAGCCATAGTTAGACTTGGCATTG
TGCCAAATTGATTGTTCAAAAGTGATGAGTCTTTCACATCCCAAACTCTTACCACACCACTTGCA

Figure 38 (cont'd)

CCCTGCTGAGGCTTTCTCATCCCAACTATCTGTAGGATCTGAGATCTTTGGTCTAGTTGCTGTGT
TGTTAAGTTCCCCATATATACCCCTGAAGCCTGGGGCCTTTCAGACCTCATGATCTTGGCCTTCA
GCTTCTCAAGGTCAGCCGCAAGAGACATCAGTTCTTCTGCACTGAGCCTCCCCACTTTCAAAACA
TTCTTCTTTGATGTTGACTTTAAATCCACAAGAGAATGTACAGTCTGGTTGAGACTTCTGAGTCT
CTGTAGGTCTTTGTCATCTCTCTTTTCCTTCCTCATGATCCTCTGAACATTGCTGACCTCAGAGA
AGTCCAACCCATTCAGAAGGTTGGTTGCATCCTTAATGACAGCAGCCTTCACATCTGATGTGAAG
CTCTGCAATTCTCTTCTCAATGCTTGCGTCCATTGGAAGCTCTTAACTTCCTTAGACAAGGACAT
CTTGTTGCTCAATGGTTTCTCAAGACAAATGCGCAATCAAATGCCTAGGATCCACTGTGCG
(SEQ ID NO: 21)

Figure 38 (cont'd)

Lymphocytic choriomeningitis virus (LCMV) strain Armstrong 53b
Source: 1-7228 Segment = L
LCMV Armstrong L-Segment

CGCACCGGGGATCCTAGGCGTTTAGTTGCGCTGTTTGGTTGCACAACTTTCTTCGTGAGGCTGTC
AGAAGTGGACCTGGCTGATAGCGATGGGTCAAGGCAAGTCCAGAGAGGAGAAAGGCACCAATAGT
ACAAACAGGGCCGAAATCCTACCAGATACCACCTATCTTGGCCCTTTAAGCTGCAAATCTTGCTG
GCAGAAATTTGACAGCTTGGTAAGATGCCATGACCACTACCTTTGCAGGCACTGTTTAAACCTTC
TGCTGTCAGTATCCGACAGGTGTCCTCTTTGTAAATATCCATTACCAACCAGATTGAAGATATCA
ACAGCCCCAAGCTCTCCACCTCCCTACGAAGAGTAACACCGTCCGGCCCCGGCCCCGACAAACAG
CCCAGCACAAGGGAACCGCACGTCGCCCAACGCACACAGACACAGCACCCAACACAGAACACGCA
CACACACACACACACACACCCACACGCACGCGCCCCCACCACCGGGGGGCGCCCCCCCCCGGGGG
GCGGCCCCCCGGGAGCCCGGGCGGAGCCCCACGGAGATGCCCATCAGTCGATGTCCTCGGCCACC
GACCCGCCCAGCCAATCGTCGCAGGACCTCCCCTTGAGTCTAAACCTGCCCCCCACTGTTTCATA
CATCAAAGTGCTCCTAGATTTGCTAAAACAAAGTCTGCAATCCTTAAAGGCGAACCAGTCTGGCA
AAAGCGACAGTGGAATCAGCAGAATAGATCTGTCTATACATAGTTCCTGGAGGATTACACTTATC
TCTGAACCCAACAAATGTTCACCAGTTCTGAATCGATGCAGGAAGAGGTTCCCAAGGACATCACT
AATCTTTTCATAGCCCTCAAGTCCTGCTAGAAAGACTTTCATGTCCTTGGTCTCCAGCTTCACAA
TGATATTTTGGACAAGGTTTCTTCCTTCAAAAAGGGCACCCATCTTTACAGTCAGTGGCACAGGC
TCCCACTCAGGTCCAACTCTCTCAAAGTCAATAGATCTAATCCCATCCAGTATTCTTTTGGAGCC
CAACAACTCAAGCTCAAGAGAATCACCAAGTATCAAGGGATCTTCCATGTAATCCTCAAACTCTT
CAGATCTGATATCAAAGACACCATCGTTCACCTTGAAGACAGAGTCTGTCCTCAGTAAGTGGAGG
CATTCATCCAACATTCTTCTATCTATCTCACCCTTAAAGAGGTGAGAGCATGATAAAAGTTCAGC
CACACCTGGATTCTGTAATTGGCACCTAACCAAGAATATCAATGAAAATTTCCTTAAACAGTCAG
TATTATTCTGATTGTGCGTAAAGTCCACTGAAATTGAAAACTCCAATACCCCTTTTGTGTAGTTG
AGCATGTAGTCCCACAGATCCTTTAAGGATTTAAATGCCTTTGGGTTTGTCAGGCCCTGCCTAAT
CAACATGGCAGCATTACACACAACATCTCCCATTCGGTAAGAGAACCACCCAAAACCAAACTGCA
AATCATTCCTAAACATAGGCCTCTCCACATTTTTGTTCACCACCTTTGAGACAAATGATTGAAAG
GGGCCCAGTGCCTCAGCACCATCTTCAGATGGCATCATTTCTTTATGAGGGAACCATGAAAAATT
GCCTAATGTCCTGGTTGTTGCAACAAATTCTCGAACAAATGATTCAAAATACACCTGTTTTAAGA
AGTTCTTGCAGACATCCCTCGTGCTAACAACAAATTCATCAACCAGACTGGAGTCAGATCGCTGA
TGAGAATTGGCAAGGTCAGAAAACAGAACAGTGTAATGTTCATCCCTTTTCCACTTAACAACATG
AGAAATGAGTGACAAGGATTCTGAGTTAATATCAATTAAAACACAGAGGTCAAGGAATTTAATTC
TGGGACTCCACCTCATGTTTTTTGAGCTCATGTCAGACATAAATGGAAGAAGCTGATCCTCAAAG
ATCTTGGGATATAACCGCCTCACAGATTGAATCACTTGGTTCAAATTCACTTTGTCCTCCAGTAG
CCTTGAGCTCTCAGGCTTTCTTGCTACATAATCACATGGGTTTAAGTGCTTAAGAGTTAGGTTCT
CACTGTTATTCTTCCCTTTGGTCGGTTCTGCTAGGACCCAAACACCCAACTCAAAAGAGTTGCTC
AATGAAATACAAATGTAGTCCCAAAGAAGAGGCCTTAAAAGGCATATATGATCACGGTGGGCTTC
TGGATGAGACTGTTTGTCACAAATGTACAGCGTTATACCATCCCGATTGCAAACTCTTGTCACAT
GATCATCTGTGGTTAGATCCTCAAGCAGCTTTTTGATATACAGATTTTCCCTATTTTTGTTTCTC
ACACACCTGCTTCCTAGAGTTTTGCAAAGGCCTATAAAGCCAGATGAGATACAACTCTGGAAAGC
TGACTTGTTGATTGCTTCTGACAGCAGCTTCTGTGCACCCCTTGTGAATTTACTACAAAGTTTGT
TCTGGAGTGTCTTGATCAATGATGGGATTCTTTCCTCTTGGAAAGTCATCACTGATGGATAAACC
ACCTTTTGTCTTAAAACCATCCTTAATGGGAACATTTCATTCAAATTCAACCAGTTAACATCTGC
TAACTGATTCAGATCTTCTTCAAGACCGAGGAGGTCTCCCAATTGAAGAATGGCCTCCTTTTTAT
CTCTGTTAAATAGGTCTAAGAAAAATTCTTCATTAAATTCACCATTTTTGAGCTTATGATGCAGT
TTCCTTACAAGCTTTCTTACAACCTTTGTTTCATTAGGACACAGTTCCTCAATGAGTCTTTGTAT
TCTGTAACCTCTAGAACCATCCAGCCAATCTTTCACATCAGTGTTGGTATTCAGTAGAAATGGAT
CCAAAGGGAAATTGGCATACTTTAGGAGGTCCAGTGTTCTCCTTTGGATACTATTAACTAGGGAG
ACTGGGACGCCATTTGCGATGGCTTGATCTGCAATTGTATCTATTGTTTCACAAAGTTGATGTGG

Figure 38 (cont'd)

CTCTTTACACTTGACATTGTGTAGCGCTGCAGATACAAACTTTGTGAGAAGAGGGACTTCCTCCC
CCCATACATAGAATCTAGATTTAAATTCTGCAGCGAACCTCCCAGCCACACTTTTTGGGCTGATA
AATTTGTTTAACAAGCCGCTCAGATGAGATTGGAATTCCAACAGGACAAGGACTTCCTCCGGATC
ACTTACAACCAGGTCACTCAGCCTCCTATCAAATAAAGTGATCTGATCATCACTTGATGTGTAAG
CCTCTGGTCTTTCGCCAAAGATAACACCAATGCAGTAGTTGATGAACCTCTCGCTAAGCAAACCA
TAGAAGTCAGAAGCATTATGCAAGATTCCCTGCCCCATATCAATAAGGCTGGATATATGGGATGG
CACTATCCCCATTTCAAAATATTGTCTGAAAATTCTCTCAGTAACAGTTGTTTCTGAACCCCTGA
GAAGTTTTAGCTTCGACTTGACATATGATTTCATCATTGCATTCACAACAGGAAAGGGGACCTCG
ACAAGCTTATGCATGTGCCAAGTTAACAAAGTGCTAACATGATCTTTCCCGGAACGCACATACTG
GTCATCACCTAGTTTGAGATTTTGTAGAAACATTAAGAACAAAAATGGGCACATCATTGGTCCCC
ATTTGCTGTGATCCATACTATAGTTTAAGAACCCTTCCCGCACATTGATAGTCATTGACAAGATT
GCATTTTCAAATTCCTTATCATTGTTTAAACAGGAGCCTGAAAAGAAACTTGAAAAAGACTCAAA
ATAATCTTCTATTAACCTTGTGAACATTTTTGTCCTCAAATCTCCAATATAGAGTTCTCTATTTC
CCCCAACCTGCTCTTTATAAGATAGTGCAAATTTCAGCCTTCCAGAGTCAGGACCTACTGAGGTG
TATGATGTTGGTGATTCTTCTGAGTAGAAGCACAGATTTTTCAAAGCAGCACTCATACATTTTGT
CAACGACAGAGCTTTACTAAGGGACTCAGAATTACTTTCCCTCTCACTGATTCTCACGTCTTCTT
CCAGTTTGTCCCAGTCAAATTTGAAATTCAAGCCTTGCCTTTGCATATGCCTGTATTTCCCTGAG
TACGCATTTGCATTCATTTGCAACAGAATCATCTTCATGCAAGAAAACCAATCATTCTCAGAAAA
GAACTTTCTACAAAGGTTTTTTGCCATCTCATCGAGGCCACACTGATCTTTAATGACTGAGGTGA
AATACAAAGGTGACAGCTCTGTGGAACCCTCAACAGCCTCACAGATAAATTTCATGTCATCATTG
GTTAGACATGATGGGTCAAAGTCTTCTACTAAATGGAAAGATATTTCTGACAAGATAACTTTTCT
TAAGTGAGCCATCTTCCCTGTTAGAATAAGCTGTAAATGATGTAGTCCTTTTGTATTTGTAAGTT
TTTCTCCATCTCCTTTGTCATTGGCCCTCCTACCTCTTCTGTACCGTGCTATTGTGGTGTTGACC
TTTTCTTCGAGACTTTTGAAGAAGCTTGTCTCTTCTTCTCCATCAAAACATATTTCTGCCAGGTT
GTCTTCCGATCTCCCTGTCTCTTCTCCCTTGGAACCGATGACCAATCTAGAGACTAACTTGGAAA
CTTTATATTCATAGTCTGAGTGGCTCAACTTATACTTTTGTTTTCTTACGAAACTCTCCGTAATT
TGACTCACAGCACTAACAAGCAATTTGTTAAAGTCATATTCCAGAAGTCGTTCTCCATTTAGATG
CTTATTAACCACCACACTTTTGTTACTAGCAAGATCTAATGCTGTCGCACATCCAGAGTTAGTCA
TGGGATCTAGGCTGTTTAGCTTCTTCTCTCCTTTGAAAATTAAAGTGCCGTTGTTAAATGAAGAC
ACCATTAGGCTAAAGGCTTCCAGATTAACACCTGGAGTTGTATGCTGACAGTCAATTTCTTTACT
AGTGAATCTCTTCATTTGCTCATAGAACACACATTCTTCCTCAGGAGTGATTGCTTCCTTGGGGT
TGACAAAAAAACCAAATTGACTTTTGGGCTCAAAGAACTTTTCAAAACATTTTATCTGATCTGTT
AGCCTGTCAGGGGTCTCCTTTGTGATCAAATGACACAGGTATGACACATTCAACATAAATTTAAA
TTTTGCACTCAACAACACCTTCTCACCAGTACCAAAAATAGTTTTTATTAGGAATCTAAGCAGCT
TATACACCACCTTCTCAGCAGGTGTGATCAGATCCTCCCTCAACTTATCCATTAATGATGTAGAT
GAGAAATCTGACACTATTGCCATCACCAAATATCTGACACTCTGTACCTGCTTTTGATTTCTCTT
TG

Figure 38 (cont'd)

TTGGGTTGGTGAGCATTAGCAACAATAGGGTCCTCAGTGCAACCTCAATGTCGGTGAGACAGTCT
TTCAAATCAGGACATGATCTAATCCATGAAATCATGATGTCTATCATATTGTATAAGACCTCATC
TGAAAAAATTGGTAAAAAGAACCTTTTAGGATCTGCATAGAAGGAAATTAAATGACCATCCGGGC
CTTGTATGGAGTAGCACCTTGAAGATTCTCCAGTCTTCTGGTATAATAGGTGGTATTCTTCAGAG
TCCAGTTTTATTACTTGGCAAAACACTTCTTTGCATTCTACCACTTGATATCTCACAGACCCTAT
TTGATTTTGCCTTAGTCTAGCAACTGAGCTAGTTTTCATACTGTTTGTTAAGGCCAGACAAACAG
ATGATAATCTTCTCAGGCTCTGTATGTTCTTCAGCTGCTCTGTGCTGGGTTGGAAATTGTAATCT
TCAAACTTCGTATAATACATTATCGGGTGAGCTCCAATTTTCATAAAGTTCTCAAATTCAGTGAA
TGGTATGTGGCATTCTTGCTCAAGGTGTTCAGACAGTCCGTAATGCTCGAAACTCAGTCCCACCA
CTAACAGGCATTTTTGAATTTTTGCAATGAACTCACTAATAGACGCCCTAAACAATTCCTCAAAA
GACACCTTTCTAAACACCTTTGACTTTTTTCTATTCCTCAAAAGTCTAATGAACTCCTCTTTAGT
GCTGTGAAAGCTTACCAGCCTATCATTCACACTACTATAGCAACAACCCACCCAGTGTTTATCAT
TTTTTAACCCTTTGAATTTCGACTGTTTTATCAATGAGGAAAGACACAAAACATCCAGATTTAAC
AACTGTCTCCTTCTAGTATTCAACAGTTTCAAACTCTTGACTTTGTTTAACATAGAGAGGAGCCT
CTCATATTCAGTGCTAGTCTCACTTCCCCTTTCGTGCCCATGGGTCTCTGCAGTTATGAATCTCA
TCAAAGGACAGGATTCCACTGCCTCCCTGCTTAATGTTAAGATATCATCACTATCAGCAAGGTTT
TCATAGAGCTCAGAGAATTCCTTGATCAAGCCTTCAGGGTTTACTTTCTGAAAGTTTCTCTTTAA
TTTCCCACTTTCTAAATCTCTTCTAAACCTGCTGAAAAGAGAGTTTATTCCAAAAACCACATCAT
CACAGCTCATGTTGGGGTTGATGCCTTCGTGGCACATCCTCATAATTTCATCATTATGAGTTGAC
CTCGCATCTTTCAGAATTTTCATAGAGTCCATACCGGAGCGCTTGTCGATAGTAGTCTTCAGGGA
CTCACAGAGTCTAAAATATTCAGACTCTTCAAAGACTTTCTCATTTTGGTTAGAATACTCCAAAA
GTTTGAATAAAAGGTCTCTAAATTTGAAGTTTGCCCACTCTGGCATAAAACTATTATCATAATCA
CAACGACCATCTACTATTGGAACTAATGTGACACCCGCAACAGCAAGGTCTTCCCTGATGCATGC
CAATTTGTTAGTGTCCTCTATAAATTTCTTCTCAAAACTGGCTGGAGTGCTCCTAACAAAACACT
CAAGAAGAATGAGAGAATTGTCTATCAGCTTGTAACCATCAGGAATGATAAGTGGTAGTCCTGGG
CATACAATTCCAGACTCCACCAAAATTGTTTCCACAGACTTATCGTCGTGGTTGTGTGTGCAGCC
ACTCTTGTCTGCACTGTCTATTTCAATGCAGCGTGACAGCAACTTGAGTCCCTCAATCAGAACCA
TTCTGGGTTCCCTTTGTCCCAGAAAGTTGAGTTTCTGCCTTGACAACCTCTCATCCTGTTCTATA
TAGTTTAAACATAACTCTCTCAATTCTGAGATGATTTCATCCATTGCGCATCAAAAAGCCTAGGA
TCCTCGGTGCG
(SEQ ID NO: 22)

Figure 38 (cont'd)

Lymphocytic choriomeningitis virus (LCMV) strain Armstrong 53b
Source: 1-3376 Segment = S
Protein: Pre-glycoprotein polyprotein GP complex
Gene: GPC
LCMV Armstrong GPC

ATGGGTCAGATTGTGACAATGTTTGAGGCTCTGCCTCACATCATCGATGAGGTGATCAACATTGT
CATTATTGTGCTTATCGTGATCACGGGTATCAAGGCTGTCTACAATTTTGCCACCTGTGGGATAT
TCGCATTGATCAGTTTCCTACTTCTGGCTGGCAGGTCCTGTGGCATGTACGGTCTTAAGGGACCC
GACATTTACAAAGGAGTTTACCAATTTAAGTCAGTGGAGTTTGATATGTCACATCTGAACCTGAC
CATGCCCAACGCATGTTCAGCCAACAACTCCCACCATTACATCAGTATGGGGACTTCTGGACTAG
AATTGACCTTCACCAATGATTCCATCATCAGTCACAACTTTTGCAATCTGACCTCTGCCTTCAAT
AAAAAGACCTTTGACCACACACTCATGAGTATAGTTTCGAGCCTACACCTCAGTATCAGAGGGAA
CTCCAACTATAAGGCAGTATCCTGCGACTTCAACAATGGCATAACCATCCAATACAACTTGACAT
TCTCAAATGCACAAAGTGCTCAGAGCCAGTGTAGAACCTTCAGAGGTAGAGTCCTAGATATGTTT
AGAACTGCCTTCGGGGGGAAATACATGAGGAGTGGCTGGGGCTGGACAGGCTCAGATGGCAAGAC
CACCTGGTGTAGCCAGACGAGTTACCAATACCTGATTATACAAAATAGAACCTGGGAAAACCACT
GCACATATGCAGGTCCTTTTGGGATGTCCAGGATTCTCCTTTCCCAAGAGAAGACTAAGTTCTTC
ACTAGGAGACTAGCGGGCACATTCACCTGGACTTTGTCAGACTCTTCAGGGGTGGAGAATCCAGG
TGGTTATTGCCTGACCAAATGGATGATTCTTGCTGCAGAGCTTAAGTGTTTCGGGAACACAGCAG
TTGCGAAATGCAATGTAAATCATGATGAAGAATTCTGTGACATGCTGCGACTAATTGACTACAAC
AAGGCTGCTTTGAGTAAGTTCAAAGAGGACGTAGAATCTGCCTTGCACTTATTCAAAACAACAGT
GAATTCTTTGATTTCAGATCAACTACTGATGAGGAACCACTTGAGAGATCTGATGGGGGTGCCAT
ATTGCAATTACTCAAAGTTTTGGTACCTAGAACATGCAAAGACCGGCGAAACTAGTGTCCCCAAG
TGCTGGCTTGTCACCAATGGTTCTTACTTAAATGAGACCCACTTCAGTGATCAAATCGAACAGGA
AGCCGATAACATGATTACAGAGATGTTGAGGAAGGATTACATAAAGAGGCAGGGGAGTACCCCCC
TAGCATTGATGGACCTTCTGATGTTTTCCACATCTGCATATCTAGTCAGCATCTTCCTGCACCTT
GTCAAAATACCAACACACAGGCACATAAAAGGTGGCTCATGTCCAAAGCCACACCGATTAACCAA
CAAAGGAATTTGTAGTTGTGGTGCATTTAAGGTGCCTGGTGTAAAAACCGTCTGGAAAAGACGCT
GA
(SEQ ID NO: 23)

Translation =
LCMV Armstrong GPC

MGQIVTMFEALPHIIDEVINIVIIVLIVITGIKAVYNFATCGIFALISFLLLAGRSCGMYGLKGP
DIYKGVYQFKSVEFDMSHLNLTMPNACSANNSHHYISMGTSGLELTFTNDSIISHNFCNLTSAFN
KKTFDHTLMSIVSSLHLSIRGNSNYKAVSCDFNNGITIQYNLTFSNAQSAQSQCRTFRGRVLDMF
RTAFGGKYMRSGWGWTGSDGKTTWCSQTSYQYLIIQNRTWENHCTYAGPFGMSRILLSQEKTKFF
TRRLAGTFTWTLSDSSGVENPGGYCLTKWMILAAELKCFGNTAVAKCNVNHDEEFCDMLRLIDYN
KAALSKFKEDVESALHLFKTTVNSLISDQLLMRNHLRDLMGVPYCNYSKFWYLEHAKTGETSVPK
CWLVTNGSYLNETHFSDQIEQEADNMITEMLRKDYIKRQGSTPLALMDLLMFSTSAYLVSIFLHL
VKIPTHRHIKGGSCPKPHRLTNKGICSCGAFKVPGVKTVWKRR
(SEQ ID NO: 24)

Figure 38 (cont'd)

Lymphocytic choriomeningitis virus (LCMV) strain Armstrong 53b
Source: 1-3376 Segment = S
Protein: Nucleoprotein
Gene: NP
LCMV Armstrong NP

ATGTCCTTGTCTAAGGAAGTTAAGAGCTTCCAATGGACGCAAGCATTGAGAAGAGAATTGCAGAG
CTTCACATCAGATGTGAAGGCTGCTGTCATTAAGGATGCAACCAACCTTCTGAATGGGTTGGACT
TCTCTGAGGTCAGCAATGTTCAGAGGATCATGAGGAAGGAAAAGAGAGATGACAAAGACCTACAG
AGACTCAGAAGTCTCAACCAGACTGTACATTCTCTTGTGGATTTAAAGTCAACATCAAAGAAGAA
TGTTTTGAAAGTGGGGAGGCTCAGTGCAGAAGAACTGATGTCTCTTGCGGCTGACCTTGAGAAGC
TGAAGGCCAAGATCATGAGGTCTGAAAGGCCCCAGGCTTCAGGGGTATATATGGGGAACTTAACA
ACACAGCAACTAGACCAAAGATCTCAGATCCTACAGATAGTTGGGATGAGAAAGCCTCAGCAGGG
TGCAAGTGGTGTGGTAAGAGTTTGGGATGTGAAAGACTCATCACTTTTGAACAATCAATTTGGCA
CAATGCCAAGTCTAACTATGGCTTGTATGGCCAAACAGTCACAGACTCCGCTCAATGACGTTGTA
CAAGCGCTCACAGACCTTGGCTTGCTTTACACAGTCAAGTATCCAAATCTTAATGATCTTGAAAG
GCTGAAAGACAAGCACCCAGTTCTGGGGGTCATCACTGAACAGCAGTCCAGCATCAACATTTCTG
GCTATAACTTTAGTCTTGGTGCTGCCGTGAAGGCAGGGGCAGCCCTGTTGGATGGGGGTAACATG
TTAGAGTCAATTTTGATCAAGCCAAGCAACAGCGAGGACCTCTTGAAGGCAGTTCTCGGGGCCAA
GAGAAAACTCAACATGTTTGTTTCAGACCAAGTTGGGGACAGGAACCCTTATGAAAACATCCTCT
ATAAAGTTTGCCTTTCAGGTGAAGGATGGCCATACATAGCTTGTAGAACATCGATTGTGGGGAGA
GCATGGGAAAACACAACAATTGATCTCACAAGCGAGAAACCTGCAGTCAACTCACCCAGGCCAGC
GCCTGGAGCAGCAGGTCCACCTCAGGTGGGCTTAAGCTACAGCCAGACAATGCTTTTAAAAGACC
TCATGGGAGGAATTGACCCCAACGCTCCTACATGGATTGACATTGAGGGTAGATTTAATGATCCA
GTGGAAATAGCAATTTTCCAACCACAGAACGGGCAGTTCATACACTTTTACAGGGAACCCGTTGA
TCAAAAACAATTCAAGCAAGATTCCAAGTACTCACACGGCATGGATCTTGCCGACCTCTTCAATG
CGCAACCCGGGTTGACCTCGTCAGTTATAGGTGCTCTTCCGCAGGGGATGGTTCTAAGCTGTCAA
GGCTCCGATGACATCAGAAAGCTTCTGGACTCACAGAATAGGAAGGACATTAAGCTTATCGATGT
TGAAATGACCAGGGAAGCTTCGAGGGAGTATGAAGACAAAGTGTGGGACAAATATGGCTGGTTGT
GTAAGATGCATACTGGAATAGTAAGGGACAAAAAGAAGAAAGAGATCACCCCGCACTGTGCACTC
ATGGACTGCATCATTTTTGAAAGCGCCTCCAAAGCAAGGCTCCCAGATCTGAAAACTGTTCACAA
CATTCTGCCACATGACCTAATTTTTAGAGGCCCAAATGTTGTGACACTCTAA
(SEQ ID NO: 25)

Translation =
LCMV Armstrong NP

MSLSKEVKSFQWTQALRRELQSFTSDVKAAVIKDATNLLNGLDFSEVSNVQRIMRKEKRDDKDLQ
RLRSLNQTVHSLVDLKSTSKKNVLKVGRLSAEELMSLAADLEKLKAKIMRSERPQASGVYMGNLT
TQQLDQRSQILQIVGMRKPQQGASGVVRVWDVKDSSLLNNQFGTMPSLTMACMAKQSQTPLNDVV
QALTDLGLLYTVKYPNLNDLERLKDKHPVLGVITEQQSSINISGYNFSLGAAVKAGAALLDGGNM
LESILIKPSNSEDLLKAVLGAKRKLNMFVSDQVGDRNPYENILYKVCLSGEGWPYIACRTSIVGR
AWENTTIDLTSEKPAVNSPRPAPGAAGPPQVGLSYSQTMLLKDLMGGIDPNAPTWIDIEGRFNDP
VEIAIFQPQNGQFIHFYREPVDQKQFKQDSKYSHGMDLADLFNAQPGLTSSVIGALPQGMVLSCQ
GSDDIRKLLDSQNRKDIKLIDVEMTREASREYEDKVWDKYGWLCKMHTGIVRDKKKKEITPHCAL
MDCIIFESASKARLPDLKTVHNILPHDLIFRGPNVVTL
(SEQ ID NO: 26)

Figure 38 (cont'd)

Lymphocytic choriomeningitis virus (LCMV) strain Armstrong 53b
Source: 1-7228 Segment = L
Protein: RING finger protein Z
Gene: ZP
LCMV Armstrong ZP

ATGGGTCAAGGCAAGTCCAGAGAGGAGAAAGGCACCAATAGTACAAACAGGGCCGAAATCCTACC
AGATACCACCTATCTTGGCCCTTTAAGCTGCAAATCTTGCTGGCAGAAATTTGACAGCTTGGTAA
GATGCCATGACCACTACCTTTGCAGGCACTGTTTAAACCTTCTGCTGTCAGTATCCGACAGGTGT
CCTCTTTGTAAATATCCATTACCAACCAGATTGAAGATATCAACAGCCCCAAGCTCTCCACCTCC
CTACGAAGAGTAA
(SEQ ID NO: 27)

Translation =
LCMV Armstrong ZP

MGQGKSREEKGTNSTNRAEILPDTTYLGPLSCKSCWQKFDSLVRCHDHYLCRHCLNLLLSVSDRC
PLCKYPLPTRLKISTAPSSPPPYEE
(SEQ ID NO: 28)

Figure 38 (cont'd)

Lymphocytic choriomeningitis virus (LCMV) strain Armstrong 53b
Source: 1-7228 Segment = L
Protein: RNA-directed RNA polymerase L
Gene: LP
LCMV Armstrong LP

ATGGATGAAATCATCTCAGAATTGAGAGAGTTATGTTTAAACTATATAGAACAGGATGAGAGGTT
GTCAAGGCAGAAACTCAACTTTCTGGGACAAAGGGAACCCAGAATGGTTCTGATTGAGGGACTCA
AGTTGCTGTCACGCTGCATTGAAATAGACAGTGCAGACAAGAGTGGCTGCACACACAACCACGAC
GATAAGTCTGTGGAAACAATTTTGGTGGAGTCTGGAATTGTATGCCCAGGACTACCACTTATCAT
TCCTGATGGTTACAAGCTGATAGACAATTCTCTCATTCTTCTTGAGTGTTTTGTTAGGAGCACTC
CAGCCAGTTTTGAGAAGAAATTTATAGAGGACACTAACAAATTGGCATGCATCAGGGAAGACCTT
GCTGTTGCGGGTGTCACATTAGTTCCAATAGTAGATGGTCGTTGTGATTATGATAATAGTTTTAT
GCCAGAGTGGGCAAACTTCAAATTTAGAGACCTTTTATTCAAACTTTTGGAGTATTCTAACCAAA
ATGAGAAAGTCTTTGAAGAGTCTGAATATTTTAGACTCTGTGAGTCCCTGAAGACTACTATCGAC
AAGCGCTCCGGTATGGACTCTATGAAAATTCTGAAAGATGCGAGGTCAACTCATAATGATGAAAT
TATGAGGATGTGCCACGAAGGCATCAACCCCAACATGAGCTGTGATGATGTGGTTTTTGGAATAA
ACTCTCTTTTCAGCAGGTTTAGAAGAGATTTAGAAAGTGGGAAATTAAAGAGAAACTTTCAGAAA
GTAAACCCTGAAGGCTTGATCAAGGAATTCTCTGAGCTCTATGAAAACCTTGCTGATAGTGATGA
TATCTTAACATTAAGCAGGGAGGCAGTGGAATCCTGTCCTTTGATGAGATTCATAACTGCAGAGA
CCCATGGGCACGAAAGGGGAAGTGAGACTAGCACTGAATATGAGAGGCTCCTCTCTATGTTAAAC
AAAGTCAAGAGTTTGAAACTGTTGAATACTAGAAGGAGACAGTTGTTAAATCTGGATGTTTTGTG
TCTTTCCTCATTGATAAAACAGTCGAAATTCAAAGGGTTAAAAAATGATAAACACTGGGTGGGTT
GTTGCTATAGTAGTGTGAATGATAGGCTGGTAAGCTTTCACAGCACTAAAGAGGAGTTCATTAGA
CTTTTGAGGAATAGAAAAAAGTCAAAGGTGTTTAGAAAGGTGTCTTTTGAGGAATTGTTTAGGGC
GTCTATTAGTGAGTTCATTGCAAAAATTCAAAAATGCCTGTTAGTGGTGGGACTGAGTTTCGAGC
ATTACGGACTGTCTGAACACCTTGAGCAAGAATGCCACATACCATTCACTGAATTTGAGAACTTT
ATGAAAATTGGAGCTCACCCGATAATGTATTATACGAAGTTTGAAGATTACAATTTCCAACCCAG
CACAGAGCAGCTGAAGAACATACAGAGCCTGAGAAGATTATCATCTGTTTGTCTGGCCTTAACAA
ACAGTATGAAAACTAGCTCAGTTGCTAGACTAAGGCAAAATCAAATAGGGTCTGTGAGATATCAA
GTGGTAGAATGCAAAGAAGTGTTTTGCCAAGTAATAAAACTGGACTCTGAAGAATACCACCTATT
ATACCAGAAGACTGGAGAATCTTCAAGGTGCTACTCCATACAAGGCCCGGATGGTCATTTAATTT
CCTTCTATGCAGATCCTAAAAGGTTCTTTTTACCAATTTTTTCAGATGAGGTCTTATACAATATG
ATAGACATCATGATTTCATGGATTAGATCATGTCCTGATTTGAAAGACTGTCTCACCGACATTGA
GGTTGCACTGAGGACCCTATTGTTGCTAATGCTCACCAACCCAACAAAGAGAAATCAAAAGCAGG
TACAGAGTGTCAGATATTTGGTGATGGCAATAGTGTCAGATTTCTCATCTACATCATTAATGGAT
AAGTTGAGGGAGGATCTGATCACACCTGCTGAGAAGGTGGTGTATAAGCTGCTTAGATTCCTAAT
AAAAACTATTTTTGGTACTGGTGAGAAGGTGTTGTTGAGTGCAAAATTTAAATTTATGTTGAATG
TGTCATACCTGTGTCATTTGATCACAAAGGAGACCCCTGACAGGCTAACAGATCAGATAAAATGT
TTTGAAAAGTTCTTTGAGCCCAAAAGTCAATTTGGTTTTTTTGTCAACCCCAAGGAAGCAATCAC
TCCTGAGGAAGAATGTGTGTTCTATGAGCAAATGAAGAGATTCACTAGTAAAGAAATTGACTGTC
AGCATACAACTCCAGGTGTTAATCTGGAAGCCTTTAGCCTAATGGTGTCTTCATTTAACAACGGC
ACTTTAATTTTCAAAGGAGAGAAGAAGCTAAACAGCCTAGATCCCATGACTAACTCTGGATGTGC
GACAGCATTAGATCTTGCTAGTAACAAAAGTGTGGTGGTTAATAAGCATCTAAATGGAGAACGAC
TTCTGGAATATGACTTTAACAAATTGCTTGTTAGTGCTGTGAGTCAAATTACGGAGAGTTTCGTA
AGAAAACAAAAGTATAAGTTGAGCCACTCAGACTATGAATATAAAGTTTCCAAGTTAGTCTCTAG
ATTGGTCATCGGTTCCAAGGGAGAAGAGACAGGGAGATCGGAAGACAACCTGGCAGAAATATGTT
TTGATGGAGAAGAAGAGACAAGCTTCTTCAAAAGTCTCGAAGAAAAGGTCAACACCACAATAGCA
CGGTACAGAAGAGGTAGGAGGGCCAATGACAAAGGAGATGGAGAAAAACTTACAAATACAAAAGG
ACTACATCATTTACAGCTTATTCTAACAGGGAAGATGGCTCACTTAAGAAAAGTTATCTTGTCAG

Figure 38 (cont'd)

AAATATCTTTCCATTTAGTAGAAGACTTTGACCCATCATGTCTAACCAATGATGACATGAAATTT
ATCTGTGAGGCTGTTGAGGGTTCCACAGAGCTGTCACCTTTGTATTTCACCTCAGTCATTAAAGA
TCAGTGTGGCCTCGATGAGATGGCAAAAAACCTTTGTAGAAAGTTCTTTTCTGAGAATGATTGGT
TTTCTTGCATGAAGATGATTCTGTTGCAAATGAATGCAAATGCGTACTCAGGGAAATACAGGCAT
ATGCAAAGGCAAGGCTTGAATTTCAAATTTGACTGGGACAAACTGGAAGAAGACGTGAGAATCAG
TGAGAGGGAAAGTAATTCTGAGTCCCTTAGTAAAGCTCTGTCGTTGACAAAATGTATGAGTGCTG
CTTTGAAAAATCTGTGCTTCTACTCAGAAGAATCACCAACATCATACACCTCAGTAGGTCCTGAC
TCTGGAAGGCTGAAATTTGCACTATCTTATAAAGAGCAGGTTGGGGGAAATAGAGAACTCTATAT
TGGAGATTTGAGGACAAAAATGTTCACAAGGTTAATAGAAGATTATTTTGAGTCTTTTTCAAGTT
TCTTTTCAGGCTCCTGTTTAAACAATGATAAGGAATTTGAAAATGCAATCTTGTCAATGACTATC
AATGTGCGGGAAGGGTTCTTAAACTATAGTATGGATCACAGCAAATGGGGACCAATGATGTGCCC
ATTTTTGTTCTTAATGTTTCTACAAAATCTCAAACTAGGTGATGACCAGTATGTGCGTTCCGGGA
AAGATCATGTTAGCACTTTGTTAACTTGGCACATGCATAAGCTTGTCGAGGTCCCCTTTCCTGTT
GTGAATGCAATGATGAAATCATATGTCAAGTCGAAGCTAAAACTTCTCAGGGGTTCAGAAACAAC
TGTTACTGAGAGAATTTTCAGACAATATTTTGAAATGGGGATAGTGCCATCCCATATATCCAGCC
TTATTGATATGGGGCAGGGAATCTTGCATAATGCTTCTGACTTCTATGGTTTGCTTAGCGAGAGG
TTCATCAACTACTGCATTGGTGTTATCTTTGGCGAAAGACCAGAGGCTTACACATCAAGTGATGA
TCAGATCACTTTATTTGATAGGAGGCTGAGTGACCTGGTTGTAAGTGATCCGGAGGAAGTCCTTG
TCCTGTTGGAATTCCAATCTCATCTGAGCGGCTTGTTAAACAAATTTATCAGCCCAAAAAGTGTG
GCTGGGAGGTTCGCTGCAGAATTTAAATCTAGATTCTATGTATGGGGGGAGGAAGTCCCTCTTCT
CACAAAGTTTGTATCTGCAGCGCTACACAATGTCAAGTGTAAAGAGCCACATCAACTTTGTGAAA
CAATAGATACAATTGCAGATCAAGCCATCGCAAATGGCGTCCCAGTCTCCCTAGTTAATAGTATC
CAAAGGAGAACACTGGACCTCCTAAAGTATGCCAATTTCCCTTTGGATCCATTTCTACTGAATAC
CAACACTGATGTGAAAGATTGGCTGGATGGTTCTAGAGGTTACAGAATACAAAGACTCATTGAGG
AACTGTGTCCTAATGAAACAAAGGTTGTAAGAAAGCTTGTAAGGAAACTGCATCATAAGCTCAAA
AATGGTGAATTTAATGAAGAATTTTTCTTAGACCTATTTAACAGAGATAAAAAGGAGGCCATTCT
TCAATTGGGAGACCTCCTCGGTCTTGAAGAAGATCTGAATCAGTTAGCAGATGTTAACTGGTTGA
ATTTGAATGAAATGTTCCCATTAAGGATGGTTTTAAGACAAAAGGTGGTTTATCCATCAGTGATG
ACTTTCCAAGAGGAAAGAATCCCATCATTGATCAAGACACTCCAGAACAAACTTTGTAGTAAATT
CACAAGGGGTGCACAGAAGCTGCTGTCAGAAGCAATCAACAAGTCAGCTTTCCAGAGTTGTATCT
CATCTGGCTTTATAGGCCTTTGCAAAACTCTAGGAAGCAGGTGTGTGAGAAACAAAAATAGGGAA
AATCTGTATATCAAAAAGCTGCTTGAGGATCTAACCACAGATGATCATGTGACAAGAGTTTGCAA
TCGGGATGGTATAACGCTGTACATTTGTGACAAACAGTCTCATCCAGAAGCCCACCGTGATCATA
TATGCCTTTTAAGGCCTCTTCTTTGGGACTACATTTGTATTTCATTGAGCAACTCTTTTGAGTTG
GGTGTTTGGGTCCTAGCAGAACCGACCAAAGGGAAGAATAACAGTGAGAACCTAACTCTTAAGCA
CTTAAACCCATGTGATTATGTAGCA

Figure 38 (cont'd)

AGAAAGCCTGAGAGCTCAAGGCTACTGGAGGACAAAGTGAATTTGAACCAAGTGATTCAATCTGT
GAGGCGGTTATATCCCAAGATCTTTGAGGATCAGCTTCTTCCATTTATGTCTGACATGAGCTCAA
AAAACATGAGGTGGAGTCCCAGAATTAAATTCCTTGACCTCTGTGTTTTAATTGATATTAACTCA
GAATCCTTGTCACTCATTTCTCATGTTGTTAAGTGGAAAAGGGATGAACATTACACTGTTCTGTT
TTCTGACCTTGCCAATTCTCATCAGCGATCTGACTCCAGTCTGGTTGATGAATTTGTTGTTAGCA
CGAGGGATGTCTGCAAGAACTTCTTAAAACAGGTGTATTTTGAATCATTTGTTCGAGAATTTGTT
GCAACAACCAGGACATTAGGCAATTTTTCATGGTTCCCTCATAAAGAAATGATGCCATCTGAAGA
TGGTGCTGAGGCACTGGGCCCCTTTCAATCATTTGTCTCAAAGGTGGTGAACAAAAATGTGGAGA
GGCCTATGTTTAGGAATGATTTGCAGTTTGGTTTTGGGTGGTTCTCTTACCGAATGGGAGATGTT
GTGTGTAATGCTGCCATGTTGATTAGGCAGGGCCTGACAAACCCAAAGGCATTTAAATCCTTAAA
GGATCTGTGGGACTACATGCTCAACTACACAAAAGGGGTATTGGAGTTTTCAATTTCAGTGGACT
TTACGCACAATCAGAATAATACTGACTGTTTAAGGAAATTTTCATTGATATTCTTGGTTAGGTGC
CAATTACAGAATCCAGGTGTGGCTGAACTTTTATCATGCTCTCACCTCTTTAAGGGTGAGATAGA
TAGAAGAATGTTGGATGAATGCCTCCACTTACTGAGGACAGACTCTGTCTTCAAGGTGAACGATG
GTGTCTTTGATATCAGATCTGAAGAGTTTGAGGATTACATGGAAGATCCCTTGATACTTGGTGAT
TCTCTTGAGCTTGAGTTGTTGGGCTCCAAAAGAATACTGGATGGGATTAGATCTATTGACTTTGA
GAGAGTTGGACCTGAGTGGGAGCCTGTGCCACTGACTGTAAAGATGGGTGCCCTTTTTGAAGGAA
GAAACCTTGTCCAAAATATCATTGTGAAGCTGGAGACCAAGGACATGAAAGTCTTTCTAGCAGGA
CTTGAGGGCTATGAAAAGATTAGTGATGTCCTTGGGAACCTCTTCCTGCATCGATTCAGAACTGG
TGAACATTTGTTGGGTTCAGAGATAAGTGTAATCCTCCAGGAACTATGTATAGACAGATCTATTC
TGCTGATTCCACTGTCGCTTTTGCCAGACTGGTTCGCCTTTAAGGATTGCAGACTTTGTTTTAGC
AAATCTAGGAGCACTTTGATGTATGAAACAGTGGGGGGCAGGTTTAGACTCAAGGGGAGGTCCTG
CGACGATTGGCTGGGCGGGTCGGTGGCCGAGGACATCGACTGA
(SEQ ID NO: 29)

Figure 38 (cont'd)

Translation =
LCMV Armstrong LP
MDEIISELRELCLNYIEQDERLSRQKLNFLGQREPRMVLIEGLKLLSRCIEIDSADKSGCTHNHD
DKSVETILVESGIVCPGLPLIIPDGYKLIDNSLILLECFVRSTPASFEKKFIEDTNKLACIREDL
AVAGVTLVPIVDGRCDYDNSFMPEWANFKFRDLLFKLLEYSNQNEKVFEESEYFRLCESLKTTID
KRSGMDSMKILKDARSTHNDEIMRMCHEGINPNMSCDDVVFGINSLFSRFRRDLESGKLKRNFQK
VNPEGLIKEFSELYENLADSDDILTLSREAVESCPLMRFITAETHGHERGSETSTEYERLLSMLN
KVKSLKLLNTRRRQLLNLDVLCLSSLIKQSKFKGLKNDKHWVGCCYSSVNDRLVSFHSTKEEFIR
LLRNRKKSKVFRKVSFEELFRASISEFIAKIQKCLLVVGLSFEHYGLSEHLEQECHIPFTEFENF
MKIGAHPIMYYTKFEDYNFQPSTEQLKNIQSLRRLSSVCLALTNSMKTSSVARLRQNQIGSVRYQ
VVECKEVFCQVIKLDSEEYHLLYQKTGESSRCYSIQGPDGHLISFYADPKRFFLPIFSDEVLYNM
IDIMISWIRSCPDLKDCLTDIEVALRTLLLLMLTNPTKRNQKQVQSVRYLVMAIVSDFSSTSLMD
KLREDLITPAEKVVYKLLRFLIKTIFGTGEKVLLSAKFKFMLNVSYLCHLITKETPDRLTDQIKC
FEKFFEPKSQFGFFVNPKEAITPEEECVFYEQMKRFTSKEIDCQHTTPGVNLEAFSLMVSSFNNG
TLIFKGEKKLNSLDPMTNSGCATALDLASNKSVVVNKHLNGERLLEYDFNKLLVSAVSQITESFV
RKQKYKLSHSDYEYKVSKLVSRLVIGSKGEETGRSEDNLAEICFDGEEETSFFKSLEEKVNTTIA
RYRRGRRANDKGDGEKLTNTKGLHHLQLILTGKMAHLRKVILSEISFHLVEDFDPSCLTNDDMKF
ICEAVEGSTELSPLYFTSVIKDQCGLDEMAKNLCRKFFSENDWFSCMKMILLQMNANAYSGKYRH
MQRQGLNFKFDWDKLEEDVRISERESNSESLSKALSLTKCMSAALKNLCFYSEESPTSYTSVGPD
SGRLKFALSYKEQVGGNRELYIGDLRTKMFTRLIEDYFESFSSFFSGSCLNNDKEFENAILSMTI
NVREGFLNYSMDHSKWGPMMCPFLFLMFLQNLKLGDDQYVRSGKDHVSTLLTWHMHKLVEVPFPV
VNAMMKSYVKSKLKLLRGSETTVTERIFRQYFEMGIVPSHISSLIDMGQGILHNASDFYGLLSER
FINYCIGVIFGERPEAYTSSDDQITLFDRRLSDLVVSDPEEVLVLLEFQSHLSGLLNKFISPKSV
AGRFAAEFKSRFYVWGEEVPLLTKFVSAALHNVKCKEPHQLCETIDTIADQAIANGVPVSLVNSI
QRRTLDLLKYANFPLDPFLLNTNTDVKDWLDGSRGYRIQRLIEELCPNETKVVRKLVRKLHHKLK
NGEFNEEFFLDLFNRDKKEAILQLGDLLGLEEDLNQLADVNWLNLNEMFPLRMVLRQKVVYPSVM
TFQEERIPSLIKTLQNKLCSKFTRGAQKLLSEAINKSAFQSCISSGFIGLCKTLGSRCVRNKNRE
NLYIKKLLEDLTTDDHVTRVCNRDGITLYICDKQSHPEAHRDHICLLRPLLWDYICISLSNSFEL
GVWVLAEPTKGKNNSENLTLKHLNPCDYVARKPESSRLLEDKVNLNQVIQSVRRLYPKIFEDQLL
PFMSDMSSKNMRWSPRIKFLDLCVLIDINSESLSLISHVVKWKRDEHYTVLFSDLANSHQRSDSS
LVDEFVVSTRDVCKNFLKQVYFESFVREFVATTRTLGNFSWFPHKEMMPSEDGAEALGPFQSFVS
KVVNKNVERPMFRNDLQFGFGWFSYRMGDVVCNAAMLIRQGLTNPKAFKSLKDLWDYMLNYTKGV
LEFSISVDFTHNQNNTDCLRKFSLIFLVRCQLQNPGVAELLSCSHLFKGEIDRRMLDECLHLLRT
DSVFKVNDGVFDIRSEEFEDYMEDPLILGDSLELELLGSKRILDGIRSIDFERVGPEWEPVPLTV
KMGALFEGRNLVQNIIVKLETKDMKVFLAGLEGYEKISDVLGNLFLHRFRTGEHLLGSEISVILQ
ELCIDRSILLIPLSLLPDWFAFKDCRLCFSKSRSTLMYETVGGRFRLKGRSCDDWLGGSVAEDID
(SEQ ID NO: 30)

Figure 38 (cont'd)

D. Lymphocytic choriomeningitis virus (LCMV) strain Clone13

Lymphocytic choriomeningitis virus (LCMV) strain Clone13
Source: 1-3377 Segment = S
LCMV Clone13 S-Segment

GCGCACCGGGGATCCTAGGCTTTTTGGATTGCGCTTTCCTCTAGATCAACTGGGTGTCAGGCCCT
ATCCTACAGAAGGATGGGTCAGATTGTGACAATGTTTGAGGCTCTGCCTCACATCATCGATGAGG
TGATCAACATTGTCATTATTGTGCTTATCGTGATCACGGGTATCAAGGCTGTCTACAATTTTGCC
ACCTGTGGGATATTCGCATTGATCAGTTTCCTACTTCTGGCTGGCAGGTCCTGTGGCATGTACGG
TCTTAAGGGACCCGACATTTACAAAGGAGTTTACCAATTTAAGTCAGTGGAGTTTGATATGTCAC
ATCTGAACCTGACCATGCCCAACGCATGTTCAGCCAACAACTCCCACCATTACATCAGTATGGGG
ACTTCTGGACTAGAATTGACCTTCACCAATGATTCCATCATCAGTCACAACTTTTGCAATCTGAC
CTCTGCCTTCAACAAAAAGACCTTTGACCACACACTCATGAGTATAGTTTCGAGCCTACACCTCA
GTATCAGAGGGAACTCCAACTATAAGGCAGTATCCTGCGACTTCAACAATGGCATAACCATCCAA
TACAACTTGACATTCTCAGATGCACAAAGTGCTCAGAGCCAGTGTAGAACCTTCAGAGGTAGAGT
CCTAGATATGTTTAGAACTGCCTTCGGGGGGAAATACATGAGGAGTGGCTGGGGCTGGACAGGCT
CAGATGGCAAGACCACCTGGTGTAGCCAGACGAGTTACCAATACCTGATTATACAAAATAGAACC
TGGGAAAACCACTGCACATATGCAGGTCCTTTTGGGATGTCCAGGATTCTCCTTTCCCAAGAGAA
GACTAAGTTCCTCACTAGGAGACTAGCGGGCACATTCACCTGGACTTTGTCAGACTCTTCAGGGG
TGGAGAATCCAGGTGGTTATTGCCTGACCAAATGGATGATTCTTGCTGCAGAGCTTAAGTGTTTC
GGGAACACAGCAGTTGCGAAATGCAATGTAAATCATGATGAAGAATTCTGTGACATGCTGCGACT
AATTGACTACAACAAGGCTGCTTTGAGTAAGTTCAAAGAGGACGTAGAATCTGCCTTGCACTTAT
TCAAAACAACAGTGAATTCTTTGATTTCAGATCAACTACTGATGAGGAACCACTTGAGAGATCTG
ATGGGGGTGCCATATTGCAATTACTCAAAGTTTTGGTACCTAGAACATGCAAAGACCGGCGAAAC
TAGTGTCCCCAAGTGCTGGCTTGTCACCAATGGTTCTTACTTAAATGAGACCCACTTCAGTGACC
AAATCGAACAGGAAGCCGATAACATGATTACAGAGATGTTGAGGAAGGATTACATAAAGAGGCAG
GGGAGTACCCCCCTAGCATTGATGGACCTTCTGATGTTTTCCACATCTGCATATCTAGTCAGCAT
CTTCCTGCACCTTGTCAAAATACCAACACACAGGCACATAAAAGGTGGCTCATGTCCAAAGCCAC
ACCGATTAACCAACAAAGGAATTTGTAGTTGTGGTGCATTTAAGGTGCCTGGTGTAAAAACCGTC
TGGAAAAGACGCTGAAGAACAGCGCCTCCCTGACTCTCCACCTCGAAAGAGGTGGAGAGTCAGGG
AGGCCCAGAGGGTCTTAGAGTGTCACAACATTTGGGCCTCTAAAAATTAGGTCATGTGGCAGAAT
GTTGTGAACAGTTTTCAGATCTGGGAGCCTTGCTTTGGAGGCGCTTTCAAAAATGATGCAGTCCA
TGAGTGCACAGTGCGGGGTGATCTCTTTCTTCTTTTTGTCCCTTACTATTCCAGTATGCATCTTA
CACAACCAGCCATATTTGTCCCACACTTTGTCTTCATACTCCCTCGAAGCTTCCCTGGTCATTTC
AACATCGATAAGCTTAATGTCCTTCCTATTCTGTGAGTCCAGAAGCTTTCTGATGTCATCGGAGC
CTTGACAGCTTAGAACCATCCCCTGCGGAAGAGCACCTATAACTGACGAGGTCAACCCGGGTTGC
GCATTGAAGAGGTCGGCAAGATCCATGCCGTGTGAGTACTTGGAATCTTGCTTGAATTGTTTTTG
ATCAACGGGTTCCCTGTAAAAGTGTATGAACTGCCCGTTCTGTGGTTGGAAAATTGCTATTTCCA
CTGGATCATTAAATCTACCCTCAATGTCAATCCATGTAGGAGCGTTGGGGTCAATTCCTCCCATG
AGGTCTTTTAAAAGCATTGTCTGGCTGTAGCTTAAGCCCACCTGAGGTGGACCTGCTGCTCCAGG
CGCTGGCCTGGGTGAATTGACTGCAGGTTTCTCGCTTGTGAGATCAATTGTTGTGTTTTCCCATG
CTCTCCCCACAATCGATGTTCTACAAGCTATGTATGGCCATCCTTCACCTGAAAGGCAAACTTTA
TAGAGGATGTTTTCATAAGGGTTCCTGTCCCCAACTTGGTCTGAAACAAACATGTTGAGTTTTCT
CTTGGCCCCGAGAACTGCCTTCAAGAGGTCCTCGCTGTTGCTTGGCTTGATCAAAATTGACTCTA
ACATGTTACCCCCATCCAACAGGGCTGCCCCTGCCTTCACGGCAGCACCAAGACTAAAGTTATAG
CCAGAAATGTTGATGCTGGACTGCTGTTCAGTGATGACCCCCAGAACTGGGTGCTTGTCTTTCAG
CCTTTCAAGATCATTAAGATTTGGATACTTGACTGTGTAAAGCAAGCCAAGGTCTGTGAGCGCTT
GTACAACGTCATTGAGCGGAGTCTGTGACTGTTTGGCCATACAAGCCATAGTTAGACTTGGCATT
GTGCCAAATTGATTGTTCAAAAGTGATGAGTCTTTCACATCCCAAACTCTTACCACACCACTTGC

Figure 38 (cont'd)

ACCCTGCTGAGGCTTTCTCATCCCAACTATCTGTAGGATCTGAGATCTTTGGTCTAGTTGCTGTG
TTGTTAAGTTCCCCATATATACCCCTGAAGCCTGGGGCCTTTCAGACCTCATGATCTTGGCCTTC
AGCTTCTCAAGGTCAGCCGCAAGAGACATCAGTTCTTCTGCACTGAGCCTCCCCACTTTCAAAAC
ATTCTTCTTTGATGTTGACTTTAAATCCACAAGAGAATGTACAGTCTGGTTGAGACTTCTGAGTC
TCTGTAGGTCTTTGTCATCTCTCTTTTCCTTCCTCATGATCCTCTGAACATTGCTGACCTCAGAG
AAGTCCAACCCATTCAGAAGGTTGGTTGCATCCTTAATGACAGCAGCCTTCACATCTGATGTGAA
GCTCTGCAATTCTCTTCTCAATGCTTGCGTCCATTGGAAGCTCTTAACTTCCTTAGACAAGGACA
TCTTGTTGCTCAATGGTTTCTCAAGACAAATGCGCAATCAAATGCCTAGGATCCACTGTGCG
(SEQ ID NO: 31)

Figure 38 (cont'd)

Lymphocytic choriomeningitis virus (LCMV) strain Clone13
Source: 1-7229 Segment = L
LCMV Clone13 L-Segment

GCGCACCGGGGATCCTAGGCGTTTAGTTGCGCTGTTTGGTTGCACAACTTTCTTCGTGAGGCTGT
CAGAAGTGGACCTGGCTGATAGCGATGGGTCAAGGCAAGTCCAGAGAGGAGAAAGGCACCAATAG
TACAAACAGGGCCGAAATCCTACCAGATACCACCTATCTTGGCCCTTTAAGCTGCAAATCTTGCT
GGCAGAAATTTGACAGCTTGGTAAGATGCCATGACCACTACCTTTGCAGGCACTGTTTAAACCTT
CTGCTGTCAGTATCCGACAGGTGTCCTCTTTGTAAATATCCATTACCAACCAGATTGAAGATATC
AACAGCCCCAAGCTCTCCACCTCCCTACGAAGAGTAACACCGTCCGGCCCCGGCCCCGACAAACA
GCCCAGCACAAGGGAACCGCACGTCACCCAACGCACACAGACACAGCACCCAACACAGAACACGC
ACACACACACACACACACACACCCACACGCACGCGCCCCCACCACCGGGGGGCGCCCCCCCCCGGGG
GGCGGCCCCCCGGGAGCCCGGGCGGAGCCCCACGGAGATGCCCATCAGTCGATGTCCTCGGCCAC
CGACCCGCCCAGCCAATCGTCGCAGGACCTCCCCTTGAGTCTAAACCTGCCCCCCACTGTTTCAT
ACATCAAAGTGCTCCTAGATTTGCTAAAACAAAGTCTGCAATCCTTAAAGGCGAACCAGTCTGGC
AAAAGCGACAGTGGAATCAGCAGAATAGATCTGTCTATACATAGTTCCTGGAGGATTACACTTAT
CTCTGAACCCAACAAATGTTCACCAGTTCTGAATCGATGCAGGAAGAGGTTCCCAAGGACATCAC
TAATCTTTTCATAGCCCTCAAGTCCTGCTAGAAAGACTTTCATGTCCTTGGTCTCCAGCTTCACA
ATGATATTTTGGACAAGGTTTCTTCCTTCAAAAAGGGCACCCATCTTTACAGTCAGTGGCACAGG
CTCCCACTCAGGTCCAACTCTCTCAAAGTCAATAGATCTAATCCCATCCAGTATTCTTTTGGAGC
CCAACAACTCAAGCTCAAGAGAATCACCAAGTATCAAGGGATCTTCCATGTAATCCTCAAACTCT
TCAGATCTGATATCAAAGACACCATCGTTCACCTTGAAGACAGAGTCTGTCCTCAGTAAGTGGAG
GCATTCATCCAACATTCTTCTATCTATCTCACCCTTAAAGAGGTGAGAGCATGATAAAAGTTCAG
CCACACCTGGATTCTGTAATTGGCACCTAACCAAGAATATCAATGAAAATTTCCTTAAACAGTCA
GTATTATTCTGATTGTGCGTAAAGTCCACTGAAATTGAAAACTCCAATACCCCTTTTGTGTAGTT
GAGCATGTAGTCCCACAGATCCTTTAAGGATTTAAATGCCTTTGGGTTTGTCAGGCCCTGCCTAA
TCAACATGGCAGCATTACACACAACATCTCCCATTCGGTAAGAGAACCACCCAAAACCAAACTGC
AAATCATTCCTAAACATAGGCCTCTCCACATTTTTGTTCACCACCTTTGAGACAAATGATTGAAA
GGGGCCCAGTGCCTCAGCACCATCTTCAGATGGCATCATTTCTTTATGAGGGAACCATGAAAAAT
TGCCTAATGTCCTGGTTGTTGCAACAAATTCTCGAACAAATGATTCAAAATACACCTGTTTTAAG
AAGTTCTTGCAGACATCCCTCGTGCTAACAACAAATTCATCAACCAGACTGGAGTCAGATCGCTG
ATGAGAATTGGCAAGGTCAGAAAACAGAACAGTGTAATGTTCATCCCTTTTCCACTTAACAACAT
GAGAAATGAGTGACAAGGATTCTGAGTTAATATCAATTAAAACACAGAGGTCAAGGAATTTAATT
CTGGGACTCCACCTCATGTTTTTTGAGCTCATGTCAGACATAAATGGAAGAAGCTGATCCTCAAA
GATCTTGGGATATAGCCGCCTCACAGATTGAATCACTTGGTTCAAATTCACTTTGTCCTCCAGTA
GCCTTGAGCTCTCAGGCTTTCTTGCTACATAATCACATGGGTTTAAGTGCTTAAGAGTTAGGTTC
TCACTGTTATTCTTCCCTTTGGTCGGTTCTGCTAGGACCCAAACACCCAACTCAAAAGAGTTGCT
CAATGAAATACAAATGTAGTCCCAAAGAAGAGGCCTTAAAAGGCATATATGATCACGGTGGGCTT
CTGGATGAGACTGTTTGTCACAAATGTACAGCGTTATACCATCCCGATTGCAAACTCTTGTCACA
TGATCATCTGTGGTTAGATCCTCAAGCAGCTTTTTGATATACAGATTTTCCCTATTTTTGTTTCT
CACACACCTGCTTCCTAGAGTTTTGCAAAGGCCTATAAAGCCAGATGAGATACAACTCTGGAAAG
CTGACTTGTTGATTGCTTCTGACAGCAGCTTCTGTGCACCCCTTGTGAATTTACTACAAAGTTTG
TTCTGGAGTGTCTTGATCAATGATGGGATTCTTTCCTCTTGGAAAGTCATCACTGATGGATAAAC
CACCTTTTGTCTTAAAACCATCCTTAATGGGAACATTTCATTCAAATTCAACCAGTTAACATCTG
CTAACTGATTCAGATCTTCTTCAAGACCGAGGAGGTCTCCCAATTGAAGAATGGCCTCCTTTTTA
TCTCTGTTAAATAGGTCTAAGAAAAATTCTTCATTAAATTCACCATTTTTGAGCTTATGATGCAG
TTTCCTTACAAGCTTTCTTACAACCTTTGTTTCATTAGGACACAGTTCCTCAATGAGTCTTTGTA
TTCTGTAACCTCTAGAACCATCCAGCCAATCTTTCACATCAGTGTTGGTATTCAGTAGAAATGGA
TCCAAAGGGAAATTGGCATACTTTAGGAGGTCCAGTGTTCTCCTTTGGATACTATTAACTAGGGA
GACTGGGACGCCATTTGCGATGGCTTGATCTGCAATTGTATCTATTGTTTCACAAAGTTGATGTG

Figure 38 (cont'd)

GCTCTTTACACTTGACATTGTGTAGCGCTGCAGATACAAACTTTGTGAGAAGAGGGACTTCCTCC
CCCCATACATAGAATCTAGATTTAAATTCTGCAGCGAACCTCCCAGCCACACTTTTTGGGCTGAT
AAATTTGTTTAACAAGCCGCTCAGATGAGATTGGAATTCCAACAGGACAAGGACTTCCTCCGGAT
CACTTACAACCAGGTCACTCAGCCTCCTATCAAATAAAGTGATCTGATCATCACTTGATGTGTAA
GCCTCTGGTCTTTCGCCAAAGATAACACCAATGCAGTAGTTGATGAACCTCTCGCTAAGCAAACC
ATAGAAGTCAGAAGCATTATGCAAGATTCCCTGCCCCATATCAATAAGGCTGGATATATGGGATG
GCACTATCCCCATTTCAAAATATTGTCTGAAAATTCTCTCAGTAACAGTTGTTTCTGAACCCCTG
AGAAGTTTTAGCTTCGACTTGACATATGATTTCATCATTGCATTCACAACAGGAAAGGGGACCTC
GACAAGCTTATGCATGTGCCAAGTTAACAAAGTGCTAACATGATCTTTCCCGGAACGCACATACT
GGTCATCACCTAGTTTGAGATTTTGTAGAAACATTAAGAACAAAAATGGGCACATCATTGGTCCC
CATTTGCTGTGATCCATACTATAGTTTAAGAACCCTTCCCGCACATTGATAGTCATTGACAAGAT
TGCATTTTCAAATTCCTTATCATTGTTTAAACAGGAGCCTGAAAAGAAACTTGAAAAAGACTCAA
AATAATCTTCTATTAACCTTGTGAACATTTTTGTCCTCAAATCTCCAATATAGAGTTCTCTATTT
CCCCCAACCTGCTCTTTATAAGATAGTGCAAATTTCAGCCTTCCAGAGTCAGGACCTACTGAGGT
GTATGATGTTGGTGATTCTTCTGAGTAGAAGCACAGATTTTTCAAAGCAGCACTCATACATTGTG
TCAACGACAGAGCTTTACTAAGGGACTCAGAATTACTTTCCCTCTCACTGATTCTCACGTCTTCT
TCCAGTTTGTCCCAGTCAAATTTGAAATTCAAGCCTTGCCTTTGCATATGCCTGTATTTCCCTGA
GTACGCATTTGCATTCATTTGCAACAGAATCATCTTCATGCAAGAAAACCAATCATTCTCAGAAA
AGAACTTTCTACAAAGGTTTTTTGCCATCTCATCGAGGCCACACTGATCTTTAATGACTGAGGTG
AAATACAAAGGTGACAGCTCTGTGGAACCCTCAACAGCCTCACAGATAAATTTCATGTCATCATT
GGTTAGACATGATGGGTCAAAGTCTTCTACTAAATGGAAAGATATTTCTGACAAGATAACTTTTC
TTAAGTGAGCCATCTTCCCTGTTAGAATAAGCTGTAAATGATGTAGTCCTTTTGTATTTGTAAGT
TTTTCTCCATCTCCTTTGTCATTGGCCCTCCTACCTCTTCTGTACCGTGCTATTGTGGTGTTGAC
CTTTTCTTCGAGACTTTTGAAGAAGCTTGTCTCTTCTTCTCCATCAAAACATATTTCTGCCAGGT
TGTCTTCCGATCTCCCTGTCTCTTCTCCCTTGGAACCGATGACCAATCTAGAGACTAACTTGGAA
ACTTTATATTCATAGTCTGAGTGGCTCAACTTATACTTTTGTTTTCTTACGAAACTCTCCGTAAT
TTGACTCACAGCACTAACAAGCAATTTGTTAAAGTCATATTCCAGAAGTCGTTCTCCATTTAGAT
GCTTATTAACCACCACACTTTTGTTACTAGCAAGATCTAATGCTGTCGCACATCCAGAGTTAGTC
ATGGGATCTAGGCTGTTTAGCTTCTTCTCTCCTTTGAAAATTAAAGTGCCGTTGTTAAATGAAGA
CACCATTAGGCTAAAGGCTTCCAGATTAACACCTGGAGTTGTATGCTGACAGTCAATTTCTTTAC
TAGTGAATCTCTTCATTTGCTCATAGAACACACATTCTTCCTCAGGAGTGATTGCTTCCTTGGGG
TTGACAAAAAAACCAAATTGACTTTTGGGCTCAAAGAACTTTTCAAAACATTTTATCTGATCTGT
TAGCCTGTCAGGGGTCTCCTTTGTGATCAAATGACACAGGTATGACACATTCAACATAAATTTAA
ATTTTGCACTCAACAACACCTTCTCACCAGTACCAAAAATAGTTTTTATTAGGAATCTAAGCAGC
TTATACACCACCTTCTCAGCAGGTGTGATCAGATCCTCCCTCAACTTATCCATTAATGATGTAGA
TGAAAAATCTGACACTATTGCCATCACCAAATATCTGACACTCTGTACCTGCTTTTGATTTCTCT
TT

Figure 38 (cont'd)

GTTGGGTTGGTGAGCATTAGCAACAATAGGGTCCTCAGTGCAACCTCAATGTCGGTGAGACAGTC
TTTCAAATCAGGACATGATCTAATCCATGAAATCATGATGTCTATCATATTGTATAAGACCTCAT
CTGAAAAAATTGGTAAAAAGAACCTTTTAGGATCTGCATAGAAGGAAATTAAATGACCATCCGGG
CCTTGTATGGAGTAGCACCTTGAAGATTCTCCAGTCTTCTGGTATAATAGGTGGTATTCTTCAGA
GTCCAGTTTTATTACTTGGCAAAACACTTCTTTGCATTCTACCACTTGATATCTCACAGACCCTA
TTTGATTTTGCCTTAGTCTAGCAACTGAGCTAGTTTTCATACTGTTTGTTAAGGCCAGACAAACA
GATGATAATCTTCTCAGGCTCTGTATGTTCTTCAGCTGCTCTGTGCTGGGTTGGAAATTGTAATC
TTCAAACTTCGTATAATACATTATCGGGTGAGCTCCAATTTTCATAAAGTTCTCAAATTCAGTGA
ATGGTATGTGGCATTCTTGCTCAAGGTGTTCAGACAGTCCGTAATGCTCGAAACTCAGTCCCACC
ACTAACAGGCATTTTTGAATTTTTGCAATGAACTCACTAATAGATGCCCTAAACAATTCCTCAAA
AGACACCTTTCTAAACACCTTTGACTTTTTTCTATTCCTCAAAAGTCTAATGAACTCCTCTTTAG
TGCTGTGAAAGCTTACCAGCCTATCATTCACACTACTATAGCAACAACCCACCCAGTGTTTATCA
TTTTTTAACCCTTTGAATTTCGACTGTTTTATCAATGAGGAAAGACACAAAACATCCAGATTTAA
CAACTGTCTCCTTCTAGTATTCAACAGTTTCAAACTCTTGACTTTGTTTAACATAGAGAGGAGCC
TCTCATATTCAGTGCTAGTCTCACTTCCCCTTTCGTGCCCATGGGTCTCTGCAGTTATGAATCTC
ATCAAAGGACAGGATTCGACTGCCTCCCTGCTTAATGTTAAGATATCATCACTATCAGCAAGGTT
TTCATAGAGCTCAGAGAATTCCTTGATCAAGCCTTCAGGGTTTACTTTCTGAAAGTTTCTCTTTA
ATTTCCCACTTTCTAAATCTCTTCTAAACCTGCTGAAAAGAGAGTTTATTCCAAAAACCACATCA
TCACAGCTCATGTTGGGGTTGATGCCTTCGTGGCACATCCTCATAATTTCATCATTGTGAGTTGA
CCTCGCATCTTTCAGAATTTTCATAGAGTCCATACCGGAGCGCTTGTCGATAGTAGTCTTCAGGG
ACTCACAGAGTCTAAAATATTCAGACTCTTCAAAGACTTTCTCATTTTGGTTAGAATACTCCAAA
AGTTTGAATAAAAGGTCTCTAAATTTGAAGTTTGCCCACTCTGGCATAAAACTATTATCATAATC
ACAACGACCATCTACTATTGGAACTAATGTGACACCCGCAACAGCAAGGTCTTCCCTGATGCATG
CCAATTTGTTAGTGTCCTCTATAAATTTCTTCTCAAAACTGGCTGGAGTGCTCCTAACAAAACAC
TCAAGAAGAATGAGAGAATTGTCTATCAGCTTGTAACCATCAGGAATGATAAGTGGTAGTCCTGG
GCATACAATTCCAGACTCCACCAAAATTGTTTCCACAGACTTATCGTCGTGGTTGTGTGTGCAGC
CACTCTTGTCTGCACTGTCTATTTCAATGCAGCGTGACAGCAACTTGAGTCCCTCAATCAGAACC
ATTCTGGGTTCCCTTTGTCCCAGAAAGTTGAGTTTCTGCCTTGACAACCTCTCATCCTGTTCTAT
ATAGTTTAAACATAACTCTCTCAATTCTGAGATGATTTCATCCATTGCGCATCAAAAAGCCTAGG
ATCCTCGGTGCG
(SEQ ID NO: 32)

Figure 38 (cont'd)

Lymphocytic choriomeningitis virus (LCMV) strain Clone13
Source: 1-3377 Segment = S
Protein: Pre-glycoprotein polyprotein GP complex
Gene: GPC
LCMV Clone13 GPC

ATGGGTCAGATTGTGACAATGTTTGAGGCTCTGCCTCACATCATCGATGAGGTGATCAACATTGT
CATTATTGTGCTTATCGTGATCACGGGTATCAAGGCTGTCTACAATTTTGCCACCTGTGGGATAT
TCGCATTGATCAGTTTCCTACTTCTGGCTGGCAGGTCCTGTGGCATGTACGGTCTTAAGGGACCC
GACATTTACAAAGGAGTTTACCAATTTAAGTCAGTGGAGTTTGATATGTCACATCTGAACCTGAC
CATGCCCAACGCATGTTCAGCCAACAACTCCCACCATTACATCAGTATGGGGACTTCTGGACTAG
AATTGACCTTCACCAATGATTCCATCATCAGTCACAACTTTTGCAATCTGACCTCTGCCTTCAAC
AAAAAGACCTTTGACCACACACTCATGAGTATAGTTTCGAGCCTACACCTCAGTATCAGAGGGAA
CTCCAACTATAAGGCAGTATCCTGCGACTTCAACAATGGCATAACCATCCAATACAACTTGACAT
TCTCAGATGCACAAAGTGCTCAGAGCCAGTGTAGAACCTTCAGAGGTAGAGTCCTAGATATGTTT
AGAACTGCCTTCGGGGGGAAATACATGAGGAGTGGCTGGGGCTGGACAGGCTCAGATGGCAAGAC
CACCTGGTGTAGCCAGACGAGTTACCAATACCTGATTATACAAAATAGAACCTGGGAAAACCACT
GCACATATGCAGGTCCTTTTGGGATGTCCAGGATTCTCCTTTCCCAAGAGAAGACTAAGTTCCTC
ACTAGGAGACTAGCGGGCACATTCACCTGGACTTTGTCAGACTCTTCAGGGGTGGAGAATCCAGG
TGGTTATTGCCTGACCAAATGGATGATTCTTGCTGCAGAGCTTAAGTGTTTCGGGAACACAGCAG
TTGCGAAATGCAATGTAAATCATGATGAAGAATTCTGTGACATGCTGCGACTAATTGACTACAAC
AAGGCTGCTTTGAGTAAGTTCAAAGAGGACGTAGAATCTGCCTTGCACTTATTCAAAACAACAGT
GAATTCTTTGATTTCAGATCAACTACTGATGAGGAACCACTTGAGAGATCTGATGGGGGTGCCAT
ATTGCAATTACTCAAAGTTTTGGTACCTAGAACATGCAAAGACCGGCGAAACTAGTGTCCCCAAG
TGCTGGCTTGTCACCAATGGTTCTTACTTAAATGAGACCCACTTCAGTGACCAAATCGAACAGGA
AGCCGATAACATGATTACAGAGATGTTGAGGAAGGATTACATAAAGAGGCAGGGGAGTACCCCCC
TAGCATTGATGGACCTTCTGATGTTTTCCACATCTGCATATCTAGTCAGCATCTTCCTGCACCTT
GTCAAAATACCAACACACAGGCACATAAAAGGTGGCTCATGTCCAAAGCCACACCGATTAACCAA
CAAAGGAATTTGTAGTTGTGGTGCATTTAAGGTGCCTGGTGTAAAAACCGTCTGGAAAAGACGCT
GA
(SEQ ID NO: 33)

Translation =
LCMV Clone13 GPC

MGQIVTMFEALPHIIDEVINIVIIVLIVITGIKAVYNFATCGIFALISFLLLAGRSCGMYGLKGP
DIYKGVYQFKSVEFDMSHLNLTMPNACSANNSHHYISMGTSGLELTFTNDSIISHNFCNLTSAFN
KKTFDHTLMSIVSSLHLSIRGNSNYKAVSCDFNNGITIQYNLTFSDAQSAQSQCRTFRGRVLDMF
RTAFGGKYMRSGWGWTGSDGKTTWCSQTSYQYLIIQNRTWENHCTYAGPFGMSRILLSQEKTKFL
TRRLAGTFTWTLSDSSGVENPGGYCLTKWMILAAELKCFGNTAVAKCNVNHDEEFCDMLRLIDYN
KAALSKFKEDVESALHLFKTTVNSLISDQLLMRNHLRDLMGVPYCNYSKFWYLEHAKTGETSVPK
CWLVTNGSYLNETHFSDQIEQEADNMITEMLRKDYIKRQGSTPLALMDLLMFSTSAYLVSIFLHL
VKIPTHRHIKGGSCPKPHRLTNKGICSCGAFKVPGVKTVWKRR
(SEQ ID NO: 34)

Figure 38 (cont'd)

Lymphocytic choriomeningitis virus (LCMV) strain Clone13
Source: 1-3377 Segment = S
Protein: Nucleoprotein
Gene: NP
LCMV Clone13 NP

ATGTCCTTGTCTAAGGAAGTTAAGAGCTTCCAATGGACGCAAGCATTGAGAAGAGAATTGCAGAG
CTTCACATCAGATGTGAAGGCTGCTGTCATTAAGGATGCAACCAACCTTCTGAATGGGTTGGACT
TCTCTGAGGTCAGCAATGTTCAGAGGATCATGAGGAAGGAAAAGAGAGATGACAAAGACCTACAG
AGACTCAGAAGTCTCAACCAGACTGTACATTCTCTTGTGGATTTAAAGTCAACATCAAAGAAGAA
TGTTTTGAAAGTGGGGAGGCTCAGTGCAGAAGAACTGATGTCTCTTGCGGCTGACCTTGAGAAGC
TGAAGGCCAAGATCATGAGGTCTGAAAGGCCCCAGGCTTCAGGGGTATATATGGGGAACTTAACA
ACACAGCAACTAGACCAAAGATCTCAGATCCTACAGATAGTTGGGATGAGAAAGCCTCAGCAGGG
TGCAAGTGGTGTGGTAAGAGTTTGGGATGTGAAAGACTCATCACTTTTGAACAATCAATTTGGCA
CAATGCCAAGTCTAACTATGGCTTGTATGGCCAAACAGTCACAGACTCCGCTCAATGACGTTGTA
CAAGCGCTCACAGACCTTGGCTTGCTTTACACAGTCAAGTATCCAAATCTTAATGATCTTGAAAG
GCTGAAAGACAAGCACCCAGTTCTGGGGGTCATCACTGAACAGCAGTCCAGCATCAACATTTCTG
GCTATAACTTTAGTCTTGGTGCTGCCGTGAAGGCAGGGGCAGCCCTGTTGGATGGGGGTAACATG
TTAGAGTCAATTTTGATCAAGCCAAGCAACAGCGAGGACCTCTTGAAGGCAGTTCTCGGGGCCAA
GAGAAAACTCAACATGTTTGTTTCAGACCAAGTTGGGGACAGGAACCCTTATGAAAACATCCTCT
ATAAAGTTTGCCTTTCAGGTGAAGGATGGCCATACATAGCTTGTAGAACATCGATTGTGGGGAGA
GCATGGGAAAACACAACAATTGATCTCACAAGCGAGAAACCTGCAGTCAATTCACCCAGGCCAGC
GCCTGGAGCAGCAGGTCCACCTCAGGTGGGCTTAAGCTACAGCCAGACAATGCTTTTAAAAGACC
TCATGGGAGGAATTGACCCCAACGCTCCTACATGGATTGACATTGAGGGTAGATTTAATGATCCA
GTGGAAATAGCAATTTTCCAACCACAGAACGGGCAGTTCATACACTTTTACAGGGAACCCGTTGA
TCAAAAACAATTCAAGCAAGATTCCAAGTACTCACACGGCATGGATCTTGCCGACCTCTTCAATG
CGCAACCCGGGTTGACCTCGTCAGTTATAGGTGCTCTTCCGCAGGGGATGGTTCTAAGCTGTCAA
GGCTCCGATGACATCAGAAAGCTTCTGGACTCACAGAATAGGAAGGACATTAAGCTTATCGATGT
TGAAATGACCAGGGAAGCTTCGAGGGAGTATGAAGACAAAGTGTGGGACAAATATGGCTGGTTGT
GTAAGATGCATACTGGAATAGTAAGGGACAAAAAGAAGAAAGAGATCACCCCGCACTGTGCACTC
ATGGACTGCATCATTTTTGAAAGCGCCTCCAAAGCAAGGCTCCCAGATCTGAAAACTGTTCACAA
CATTCTGCCACATGACCTAATTTTTAGAGGCCCAAATGTTGTGACACTCTAA
(SEQ ID NO: 35)

Translation =
LCMV Armstrong NP

MSLSKEVKSFQWTQALRRELQSFTSDVKAAVIKDATNLLNGLDFSEVSNVQRIMRKEKRDDKDLQ
RLRSLNQTVHSLVDLKSTSKKNVLKVGRLSAEELMSLAADLEKLKAKIMRSERPQASGVYMGNLT
TQQLDQRSQILQIVGMRKPQQGASGVVRVWDVKDSSLLNNQFGTMPSLTMACMAKQSQTPLNDVV
QALTDLGLLYTVKYPNLNDLERLKDKHPVLGVITEQQSSINISGYNFSLGAAVKAGAALLDGGNM
LESILIKPSNSEDLLKAVLGAKRKLNMFVSDQVGDRNPYENILYKVCLSGEGWPYIACRTSIVGR
AWENTTIDLTSEKPAVNSPRPAPGAAGPPQVGLSYSQTMLLKDLMGGIDPNAPTWIDIEGRFNDP
VEIAIFQPQNGQFIHFYREPVDQKQFKQDSKYSHGMDLADLFNAQPGLTSSVIGALPQGMVLSCQ
GSDDIRKLLDSQNRKDIKLIDVEMTREASREYEDKVWDKYGWLCKMHTGIVRDKKKKEITPHCAL
MDCIIFESASKARLPDLKTVHNILPHDLIFRGPNVVTL
(SEQ ID NO: 36)

Figure 38 (cont'd)

Lymphocytic choriomeningitis virus (LCMV) strain Clone13
Source: 1-7229 Segment = L
Protein: RING finger protein Z
Gene: ZP
LCMV Clone13 ZP

ATGGGTCAAGGCAAGTCCAGAGAGGAGAAAGGCACCAATAGTACAAACAGGGCCGAAATCCTACC
AGATACCACCTATCTTGGCCCTTTAAGCTGCAAATCTTGCTGGCAGAAATTTGACAGCTTGGTAA
GATGCCATGACCACTACCTTTGCAGGCACTGTTTAAACCTTCTGCTGTCAGTATCCGACAGGTGT
CCTCTTTGTAAATATCCATTACCAACCAGATTGAAGATATCAACAGCCCCAAGCTCTCCACCTCC
CTACGAAGAGTAA
(SEQ ID NO: 37)

Translation =
LCMV Clone13 ZP

MGQGKSREEKGTNSTNRAEILPDTTYLGPLSCKSCWQKFDSLVRCHDHYLCRHCLNLLLSVSDRC
PLCKYPLPTRLKISTAPSSPPPYEE
(SEQ ID NO: 38)

Figure 38 (cont'd)

Lymphocytic choriomeningitis virus (LCMV) strain Clone13
Source: 1-7229 Segment = L
Protein: RNA-directed RNA polymerase L
Gene: LP
LCMV Clone13 LP

ATGGATGAAATCATCTCAGAATTGAGAGAGTTATGTTTAAACTATATAGAACAGGATGAGAGGTT
GTCAAGGCAGAAACTCAACTTTCTGGGACAAAGGGAACCCAGAATGGTTCTGATTGAGGGACTCA
AGTTGCTGTCACGCTGCATTGAAATAGACAGTGCAGACAAGAGTGGCTGCACACACAACCACGAC
GATAAGTCTGTGGAAACAATTTTGGTGGAGTCTGGAATTGTATGCCCAGGACTACCACTTATCAT
TCCTGATGGTTACAAGCTGATAGACAATTCTCTCATTCTTCTTGAGTGTTTTGTTAGGAGCACTC
CAGCCAGTTTTGAGAAGAAATTTATAGAGGACACTAACAAATTGGCATGCATCAGGGAAGACCTT
GCTGTTGCGGGTGTCACATTAGTTCCAATAGTAGATGGTCGTTGTGATTATGATAATAGTTTTAT
GCCAGAGTGGGCAAACTTCAAATTTAGAGACCTTTTATTCAAACTTTTGGAGTATTCTAACCAAA
ATGAGAAAGTCTTTGAAGAGTCTGAATATTTTAGACTCTGTGAGTCCCTGAAGACTACTATCGAC
AAGCGCTCCGGTATGGACTCTATGAAAATTCTGAAAGATGCGAGGTCAACTCACAATGATGAAAT
TATGAGGATGTGCCACGAAGGCATCAACCCCAACATGAGCTGTGATGATGTGGTTTTTGGAATAA
ACTCTCTTTTCAGCAGGTTTAGAAGAGATTTAGAAAGTGGGAAATTAAAGAGAAACTTTCAGAAA
GTAAACCCTGAAGGCTTGATCAAGGAATTCTCTGAGCTCTATGAAAACCTTGCTGATAGTGATGA
TATCTTAACATTAAGCAGGGAGGCAGTCGAATCCTGTCCTTTGATGAGATTCATAACTGCAGAGA
CCCATGGGCACGAAAGGGGAAGTGAGACTAGCACTGAATATGAGAGGCTCCTCTCTATGTTAAAC
AAAGTCAAGAGTTTGAAACTGTTGAATACTAGAAGGAGACAGTTGTTAAATCTGGATGTTTTGTG
TCTTTCCTCATTGATAAAACAGTCGAAATTCAAAGGGTTAAAAAATGATAAACACTGGGTGGGTT
GTTGCTATAGTAGTGTGAATGATAGGCTGGTAAGCTTTCACAGCACTAAAGAGGAGTTCATTAGA
CTTTTGAGGAATAGAAAAAAGTCAAAGGTGTTTAGAAAGGTGTCTTTTGAGGAATTGTTTAGGGC
ATCTATTAGTGAGTTCATTGCAAAAATTCAAAAATGCCTGTTAGTGGTGGGACTGAGTTTCGAGC
ATTACGGACTGTCTGAACACCTTGAGCAAGAATGCCACATACCATTCACTGAATTTGAGAACTTT
ATGAAAATTGGAGCTCACCCGATAATGTATTATACGAAGTTTGAAGATTACAATTTCCAACCCAG
CACAGAGCAGCTGAAGAACATACAGAGCCTGAGAAGATTATCATCTGTTTGTCTGGCCTTAACAA
ACAGTATGAAAACTAGCTCAGTTGCTAGACTAAGGCAAAATCAAATAGGGTCTGTGAGATATCAA
GTGGTAGAATGCAAAGAAGTGTTTTGCCAAGTAATAAAACTGGACTCTGAAGAATACCACCTATT
ATACCAGAAGACTGGAGAATCTTCAAGGTGCTACTCCATACAAGGCCCGGATGGTCATTTAATTT
CCTTCTATGCAGATCCTAAAAGGTTCTTTTTACCAATTTTTTCAGATGAGGTCTTATACAATATG
ATAGACATCATGATTTCATGGATTAGATCATGTCCTGATTTGAAAGACTGTCTCACCGACATTGA
GGTTGCACTGAGGACCCTATTGTTGCTAATGCTCACCAACCCAACAAAGAGAAATCAAAAGCAGG
TACAGAGTGTCAGATATTTGGTGATGGCAATAGTGTCAGATTTTTCATCTACATCATTAATGGAT
AAGTTGAGGGAGGATCTGATCACACCTGCTGAGAAGGTGGTGTATAAGCTGCTTAGATTCCTAAT
AAAAACTATTTTTGGTACTGGTGAGAAGGTGTTGTTGAGTGCAAAATTTAAATTTATGTTGAATG
TGTCATACCTGTGTCATTTGATCACAAAGGAGACCCCTGACAGGCTAACAGATCAGATAAAATGT
TTTGAAAAGTTCTTTGAGCCCAAAAGTCAATTTGGTTTTTTTGTCAACCCCAAGGAAGCAATCAC
TCCTGAGGAAGAATGTGTGTTCTATGAGCAAATGAAGAGATTCACTAGTAAAGAAATTGACTGTC
AGCATACAACTCCAGGTGTTAATCTGGAAGCCTTTAGCCTAATGGTGTCTTCATTTAACAACGGC
ACTTTAATTTTCAAAGGAGAGAAGAAGCTAAACAGCCTAGATCCCATGACTAACTCTGGATGTGC
GACAGCATTAGATCTTGCTAGTAACAAAAGTGTGGTGGTTAATAAGCATCTAAATGGAGAACGAC
TTCTGGAATATGACTTTAACAAATTGCTTGTTAGTGCTGTGAGTCAAATTACGGAGAGTTTCGTA
AGAAAACAAAAGTATAAGTTGAGCCACTCAGACTATGAATATAAAGTTTCCAAGTTAGTCTCTAG
ATTGGTCATCGGTTCCAAGGGAGAAGAGACAGGGAGATCGGAAGACAACCTGGCAGAAATATGTT
TTGATGGAGAAGAAGAGACAAGCTTCTTCAAAAGTCTCGAAGAAAAGGTCAACACCACAATAGCA
CGGTACAGAAGAGGTAGGAGGGCCAATGACAAAGGAGATGGAGAAAAACTTACAAATACAAAAGG
ACTACATCATTTACAGCTTATTCTAACAGGGAAGATGGCTCACTTAAGAAAAGTTATCTTGTCAG

Figure 38 (cont'd)

AAATATCTTTCCATTTAGTAGAAGACTTTGACCCATCATGTCTAACCAATGATGACATGAAATTT
ATCTGTGAGGCTGTTGAGGGTTCCACAGAGCTGTCACCTTTGTATTTCACCTCAGTCATTAAAGA
TCAGTGTGGCCTCGATGAGATGGCAAAAAACCTTTGTAGAAAGTTCTTTTCTGAGAATGATTGGT
TTTCTTGCATGAAGATGATTCTGTTGCAAATGAATGCAAATGCGTACTCAGGGAAATACAGGCAT
ATGCAAAGGCAAGGCTTGAATTTCAAATTTGACTGGGACAAACTGGAAGAAGACGTGAGAATCAG
TGAGAGGGAAAGTAATTCTGAGTCCCTTAGTAAAGCTCTGTCGTTGACACAATGTATGAGTGCTG
CTTTGAAAAATCTGTGCTTCTACTCAGAAGAATCACCAACATCATACACCTCAGTAGGTCCTGAC
TCTGGAAGGCTGAAATTTGCACTATCTTATAAAGAGCAGGTTGGGGGAAATAGAGAACTCTATAT
TGGAGATTTGAGGACAAAAATGTTCACAAGGTTAATAGAAGATTATTTTGAGTCTTTTTCAAGTT
TCTTTTCAGGCTCCTGTTTAAACAATGATAAGGAATTTGAAAATGCAATCTTGTCAATGACTATC
AATGTGCGGGAAGGGTTCTTAAACTATAGTATGGATCACAGCAAATGGGGACCAATGATGTGCCC
ATTTTTGTTCTTAATGTTTCTACAAAATCTCAAACTAGGTGATGACCAGTATGTGCGTTCCGGGA
AAGATCATGTTAGCACTTTGTTAACTTGGCACATGCATAAGCTTGTCGAGGTCCCCTTTCCTGTT
GTGAATGCAATGATGAAATCATATGTCAAGTCGAAGCTAAAACTTCTCAGGGGTTCAGAAACAAC
TGTTACTGAGAGAATTTTCAGACAATATTTTGAAATGGGGATAGTGCCATCCCATATATCCAGCC
TTATTGATATGGGGCAGGGAATCTTGCATAATGCTTCTGACTTCTATGGTTTGCTTAGCGAGAGG
TTCATCAACTACTGCATTGGTGTTATCTTTGGCGAAAGACCAGAGGCTTACACATCAAGTGATGA
TCAGATCACTTTATTTGATAGGAGGCTGAGTGACCTGGTTGTAAGTGATCCGGAGGAAGTCCTTG
TCCTGTTGGAATTCCAATCTCATCTGAGCGGCTTGTTAAACAAATTTATCAGCCCAAAAAGTGTG
GCTGGGAGGTTCGCTGCAGAATTTAAATCTAGATTCTATGTATGGGGGGAGGAAGTCCCTCTTCT
CACAAAGTTTGTATCTGCAGCGCTACACAATGTCAAGTGTAAAGAGCCACATCAACTTTGTGAAA
CAATAGATACAATTGCAGATCAAGCCATCGCAAATGGCGTCCCAGTCTCCCTAGTTAATAGTATC
CAAAGGAGAACACTGGACCTCCTAAAGTATGCCAATTTCCCTTTGGATCCATTTCTACTGAATAC
CAACACTGATGTGAAAGATTGGCTGGATGGTTCTAGAGGTTACAGAATACAAAGACTCATTGAGG
AACTGTGTCCTAATGAAACAAAGGTTGTAAGAAAGCTTGTAAGGAAACTGCATCATAAGCTCAAA
AATGGTGAATTTAATGAAGAATTTTTCTTAGACCTATTTAACAGAGATAAAAAGGAGGCCATTCT
TCAATTGGGAGACCTCCTCGGTCTTGAAGAAGATCTGAATCAGTTAGCAGATGTTAACTGGTTGA
ATTTGAATGAAATGTTCCCATTAAGGATGGTTTTAAGACAAAAGGTGGTTTATCCATCAGTGATG
ACTTTCCAAGAGGAAAGAATCCCATCATTGATCAAGACACTCCAGAACAAACTTTGTAGTAAATT
CACAAGGGGTGCACAGAAGCTGCTGTCAGAAGCAATCAACAAGTCAGCTTTCCAGAGTTGTATCT
CATCTGGCTTTATAGGCCTTTGCAAAACTCTAGGAAGCAGGTGTGTGAGAAACAAAAATAGGGAA
AATCTGTATATCAAAAAGCTGCTTGAGGATCTAACCACAGATGATCATGTGACAAGAGTTTGCAA
TCGGGATGGTATAACGCTGTACATTTGTGACAAACAGTCTCATCCAGAAGCCCACCGTGATCATA
TATGCCTTTTAAGGCCTCTTCTTTGGGACTACATTTGTATTTCATTGAGCAACTCTTTTGAGTTG
GGTGTTTGGGTCCTAGCAGAACCGACCAAAGGGAAGAATAACAGTGAGAACCTAACTCTTAAGCA
CTTAAACCCATGTGATTATGTAGCA

Figure 38 (cont'd)

AGAAAGCCTGAGAGCTCAAGGCTACTGGAGGACAAAGTGAATTTGAACCAAGTGATTCAATCTGT
GAGGCGGCTATATCCCAAGATCTTTGAGGATCAGCTTCTTCCATTTATGTCTGACATGAGCTCAA
AAAACATGAGGTGGAGTCCCAGAATTAAATTCCTTGACCTCTGTGTTTTAATTGATATTAACTCA
GAATCCTTGTCACTCATTTCTCATGTTGTTAAGTGGAAAAGGGATGAACATTACACTGTTCTGTT
TTCTGACCTTGCCAATTCTCATCAGCGATCTGACTCCAGTCTGGTTGATGAATTTGTTGTTAGCA
CGAGGGATGTCTGCAAGAACTTCTTAAAACAGGTGTATTTTGAATCATTTGTTCGAGAATTTGTT
GCAACAACCAGGACATTAGGCAATTTTTCATGGTTCCCTCATAAAGAAATGATGCCATCTGAAGA
TGGTGCTGAGGCACTGGGCCCCTTTCAATCATTTGTCTCAAAGGTGGTGAACAAAAATGTGGAGA
GGCCTATGTTTAGGAATGATTTGCAGTTTGGTTTTGGGTGGTTCTCTTACCGAATGGGAGATGTT
GTGTGTAATGCTGCCATGTTGATTAGGCAGGGCCTGACAAACCCAAAGGCATTTAAATCCTTAAA
GGATCTGTGGGACTACATGCTCAACTACACAAAAGGGGTATTGGAGTTTTCAATTTCAGTGGACT
TTACGCACAATCAGAATAATACTGACTGTTTAAGGAAATTTTCATTGATATTCTTGGTTAGGTGC
CAATTACAGAATCCAGGTGTGGCTGAACTTTTATCATGCTCTCACCTCTTTAAGGGTGAGATAGA
TAGAAGAATGTTGGATGAATGCCTCCACTTACTGAGGACAGACTCTGTCTTCAAGGTGAACGATG
GTGTCTTTGATATCAGATCTGAAGAGTTTGAGGATTACATGGAAGATCCCTTGATACTTGGTGAT
TCTCTTGAGCTTGAGTTGTTGGGCTCCAAAAGAATACTGGATGGGATTAGATCTATTGACTTTGA
GAGAGTTGGACCTGAGTGGGAGCCTGTGCCACTGACTGTAAAGATGGGTGCCCTTTTTGAAGGAA
GAAACCTTGTCCAAAATATCATTGTGAAGCTGGAGACCAAGGACATGAAAGTCTTTCTAGCAGGA
CTTGAGGGCTATGAAAAGATTAGTGATGTCCTTGGGAACCTCTTCCTGCATCGATTCAGAACTGG
TGAACATTTGTTGGGTTCAGAGATAAGTGTAATCCTCCAGGAACTATGTATAGACAGATCTATTC
TGCTGATTCCACTGTCGCTTTTGCCAGACTGGTTCGCCTTTAAGGATTGCAGACTTTGTTTTAGC
AAATCTAGGAGCACTTTGATGTATGAAACAGTGGGGGGCAGGTTTAGACTCAAGGGGAGGTCCTG
CGACGATTGGCTGGGCGGGTCGGTGGCCGAGGACATCGACTGA
(SEQ ID NO: 39)

Figure 38 (cont'd)

Translation =
LCMV Clone13 LP

MDEIISELRELCLNYIEQDERLSRQKLNFLGQREPRMVLIEGLKLLSRCIEIDSADKSGCTHNHD
DKSVETILVESGIVCPGLPLIIPDGYKLIDNSLILLECFVRSTPASFEKKFIEDTNKLACIREDL
AVAGVTLVPIVDGRCDYDNSFMPEWANFKFRDLLFKLLEYSNQNEKVFEESEYFRLCESLKTTID
KRSGMDSMKILKDARSTHNDEIMRMCHEGINPNMSCDDVVFGINSLFSRFRRDLESGKLKRNFQK
VNPEGLIKEFSELYENLADSDDILTLSREAVESCPLMRFITAETHGHERGSETSTEYERLLSMLN
KVKSLKLLNTRRRQLLNLDVLCLSSLIKQSKFKGLKNDKHWVGCCYSSVNDRLVSFHSTKEEFIR
LLRNRKKSKVFRKVSFEELFRASISEFIAKIQKCLLVVGLSFEHYGLSEHLEQECHIPFTEFENF
MKIGAHPIMYYTKFEDYNFQPSTEQLKNIQSLRRLSSVCLALTNSMKTSSVARLRQNQIGSVRYQ
VVECKEVFCQVIKLDSEEYHLLYQKTGESSRCYSIQGPDGHLISFYADPKRFFLPIFSDEVLYNM
IDIMISWIRSCPDLKDCLTDIEVALRTLLLLMLTNPTKRNQKQVQSVRYLVMAIVSDFSSTSLMD
KLREDLITPAEKVVYKLLRFLIKTIFGTGEKVLLSAKFKFMLNVSYLCHLITKETPDRLTDQIKC
FEKFFEPKSQFGFFVNPKEAITPEEECVFYEQMKRFTSKEIDCQHTTPGVNLEAFSLMVSSFNNG
TLIFKGEKKLNSLDPMTNSGCATALDLASNKSVVVNKHLNGERLLEYDFNKLLVSAVSQITESFV
RKQKYKLSHSDYEYKVSKLVSRLVIGSKGEETGRSEDNLAEICFDGEEETSFFKSLEEKVNTTIA
RYRRGRRANDKGDGEKLTNTKGLHHLQLILTGKMAHLRKVILSEISFHLVEDFDPSCLTNDDMKF
ICEAVEGSTELSPLYFTSVIKDQCGLDEMAKNLCRKFFSENDWFSCMKMILLQMNANAYSGKYRH
MQRQGLNFKFDWDKLEEDVRISERESNSESLSKALSLTQCMSAALKNLCFYSEESPTSYTSVGPD
SGRLKFALSYKEQVGGNRELYIGDLRTKMFTRLIEDYFESFSSFFSGSCLNNDKEFENAILSMTI
NVREGFLNYSMDHSKWGPMMCPFLFLMFLQNLKLGDDQYVRSGKDHVSTLLTWHMHKLVEVPFPV
VNAMMKSYVKSKLKLLRGSETTVTERIFRQYFEMGIVPSHISSLIDMGQGILHNASDFYGLLSER
FINYCIGVIFGERPEAYTSSDDQITLFDRRLSDLVVSDPEEVLVLLEFQSHLSGLLNKFISPKSV
AGRFAAEFKSRFYVWGEEVPLLTKFVSAALHNVKCKEPHQLCETIDTIADQAIANGVPVSLVNSI
QRRTLDLLKYANFPLDPFLLNTNTDVKDWLDGSRGYRIQRLIEELCPNETKVVRKLVRKLHHKLK
NGEFNEEFFLDLFNRDKKEAILQLGDLLGLEEDLNQLADVNWLNLNEMFPLRMVLRQKVVYPSVM
TFQEERIPSLIKTLQNKLCSKFTRGAQKLLSEAINKSAFQSCISSGFIGLCKTLGSRCVRNKNRE
NLYIKKLLEDLTTDDHVTRVCNRDGITLYICDKQSHPEAHRDHICLLRPLLWDYICISLSNSFEL
GVWVLAEPTKGKNNSENLTLKHLNPCDYVARKPESSRLLEDKVNLNQVIQSVRRLYPKIFEDQLL
PFMSDMSSKNMRWSPRIKFLDLCVLIDINSESLSLISHVVKWKRDEHYTVLFSDLANSHQRSDSS
LVDEFVVSTRDVCKNFLKQVYFESFVREFVATTRTLGNFSWFPHKEMMPSEDGAEALGPFQSFVS
KVVNKNVERPMFRNDLQFGFGWFSYRMGDVVCNAAMLIRQGLTNPKAFKSLKDLWDYMLNYTKGV
LEFSISVDFTHNQNNTDCLRKFSLIFLVRCQLQNPGVAELLSCSHLFKGEIDRRMLDECLHLLRT
DSVFKVNDGVFDIRSEEFEDYMEDPLILGDSLELELLGSKRILDGIRSIDFERVGPEWEPVPLTV
KMGALFEGRNLVQNIIVKLETKDMKVFLAGLEGYEKISDVLGNLFLHRFRTGEHLLGSEISVILQ
ELCIDRSILLIPLSLLPDWFAFKDCRLCFSKSRSTLMYETVGGRFRLKGRSCDDWLGGSVAEDID
(SEQ ID NO: 40)

VIRUS PARTICLES FOR THERAPEUTIC PURPOSES

CROSS REFERENCE TO RELATED APPLICATIONS

The present application claims the benefit of priority of European Patent Application No. 21159746.3 filed on Feb. 26, 2021, the contents of which are hereby incorporated by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Feb. 25, 2022, is named SCH-7600-US_SeqListing.txt and is 224 kilobytes in size.

FIELD OF THE INVENTION

The invention relates to a virus particle comprising a lymphocytic choriomeningitis virus (LCMV) S segment and an LCMV L segment, wherein the S segment comprises an open reading frame encoding a glycoprotein derived from LCMV strain WE, and wherein the L segment comprises an open reading frame encoding an L protein derived from LCMV strain Clone13. The invention also relates to related host cells, methods of producing such virus particles, pharmaceutical compositions comprising such virus particles, and medical uses of such virus particles.

BACKGROUND

LCMV belongs to the genus of Mammarenaviruses and can ubiquitously be isolated from mice and other rodents (Radoshitzky et al. (2020) in D. M. Knipe and P. M. Howley (eds.), Fields Virology). Intrauterine infection results in persistent infection of the offspring without clinical symptoms although the viral load may be very high (Radoshitzky et al. (2020) in D. M. Knipe and P. M. Howley (eds.), Fields Virology). Live virus is shed from infected animals lifelong via urine, saliva, nasal secretions and droppings resulting in symptomatic infection of exposed naïve rodents.

Humans become infected with LCMV through close contact with infected rodents or secretions from infected rodents, through solid organ transplantations or by vertical transplacental transmission. Human to human horizontal transmission other than through solid organ transplantation has not been reported. Postnatal infections in persons with an intact immune system are often asymptomatic or result in mild febrile illness. Mild and reversible neurological symptoms are rarely observed. Infection during pregnancy increases the risk for miscarriage, severe CNS or ocular malformations. Neurologic sequelae include spastic quadriparesis, mental retardation, seizures and visual impairment. In immune suppressed organ recipients LCMV infection can be fatal, however, less than 20 cases have been described to date.

LCMV strains have been divided into four different lineages grouping the most commonly used laboratory strains Armstrong and WE into lineage I (Radoshitzky et al. (2020) in D. M. Knipe and P. M. Howley (eds.), Fields Virology). These laboratory strains have a low pathogenic potential for healthy humans but can cause substantial disease and death in susceptible animals. In line with the clinical manifestations caused in susceptible animals by the two strains and derivatives derived thereof the Armstrong strain is categorized as neurotropic in contrast to the WE strain that is categorized as viscerotropic.

The LCMV genome consists of two negative stranded RNA segments named S(mall) and L(arge). The S segment encodes the surface Glycoprotein (GP) and the Nucleocapsid protein (NP) while the L segment encodes the viral polymerase (LP) and the Z protein (Radoshitzky et al. (2020) in D. M. Knipe and P. M. Howley (eds.), Fields Virology).

Certain LCMV WE strain derivatives have been described as effective agents for solid tumor treatment (WO 2016/166285 A1, WO 2020/053324 A1). However, LCMV stain WE has a by default biosafety level (BSL) 3 classification, which would preclude the use of such products, as production and application of such strains under BSL 3 conditions is virtually impossible.

Thus, there is an unmet need to provide viruses with a higher level of attenuation while having comparable or even improved anti-tumoral properties in comparison with LCMV stain WE. It is thus object of the invention to provide additional and/or improved viruses that are useful in therapy.

SUMMARY OF THE INVENTION

The invention relates to a virus particle comprising a lymphocytic choriomeningitis virus (LCMV) S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40, wherein the glycoprotein comprises at least one mutated amino acid residue in comparison with the glycoprotein sequence set forth in SEQ ID NO: 4.

The invention also relates to a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40, wherein the L protein comprises at position 1079 corresponding to the linear polypeptide sequence of SEQ ID NO: 40 an amino acid residue other than Lys.

The invention also relates to a virus particle comprising an LCMV S segment and an LCMV L segment, wherein the S segment comprises an open reading frame encoding a glycoprotein having at least 97% sequence identity to SEQ ID NO: 4 and an open reading frame encoding a nucleoprotein having at least 97% sequence identity to SEQ ID NO: 6, and wherein the L segment comprises an open reading frame encoding an L protein having at least 90% sequence identity to SEQ ID NO: 40 and an open reading frame encoding a Z protein having at least 90% sequence identity to SEQ ID NO: 38.

The invention also relates to a host cell comprising an LCMV S segment and an LCMV L segment as comprised in a virus particle of the invention.

The invention also relates to a host cell comprising cDNA of (a) an ORF encoding a glycoprotein, an ORF encoding an L protein, an ORF encoding a nucleoprotein, and an ORF encoding a Z protein as comprised in a virus particle of the invention; and/or (b) an LCMV S segment and an LCMV L segment as comprised in a virus particle of the invention.

The invention also relates to a method of producing a virus particle of the invention comprising cultivating the host cell of the invention under conditions suitable for virus particle formation.

The invention also relates to a pharmaceutical composition comprising a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40.

The invention also relates to a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40 for use in therapy, in particular in the treatment of cancer.

Figure 26:
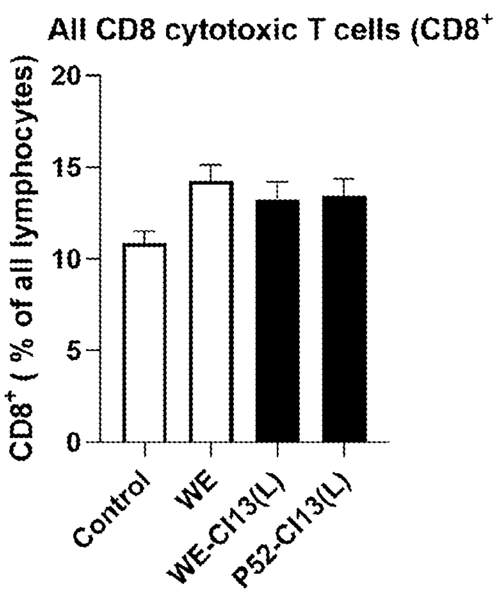

FIG. 26: Murine B16 tumor-bearing Bl/6 mice, LCMV wild type (WE) and recombinant strains with 2×10E4 PFU/animal i.v. at day 0, virus-specific (GP33) and CD8 T cells by flow cytometry from dLN and tumor at day 7 (n=5 animals/group).

Figure 27:
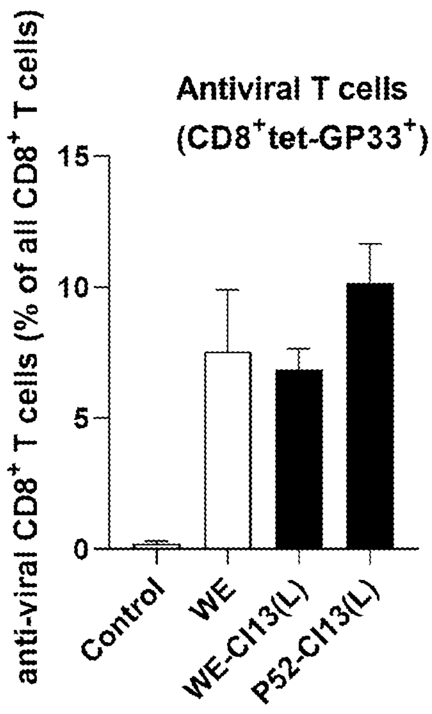

FIG. 27: Murine B16 tumor-bearing Bl/6 mice, LCMV wild type (WE) and recombinant strains with 2×10E4 PFU/animal i.v. at day 0, virus-specific (GP33) and CD8 T cells by flow cytometry from dLN and tumor at day 7 (n=5 animals/group).

Figure 28:
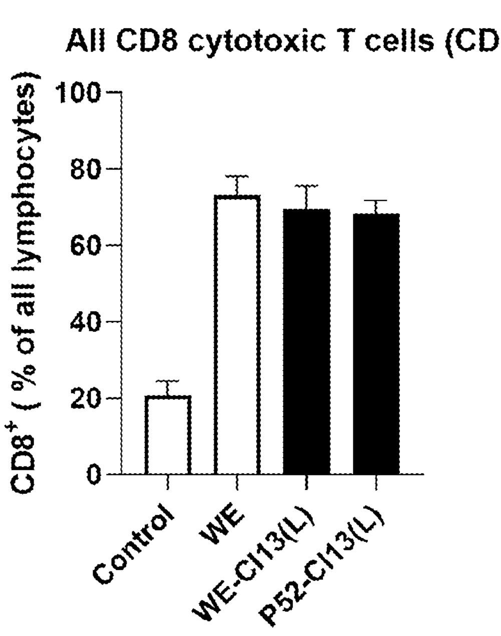

FIG. 28: Murine B16 tumor-bearing Bl/6 mice, LCMV wild type (WE) and recombinant strains with 2×10E4 PFU/animal i.v. at day 0, virus-specific (GP33) and CD8 T cells by flow cytometry from dLN and tumor at day 7 (n=5 animals/group).

Figure 29:
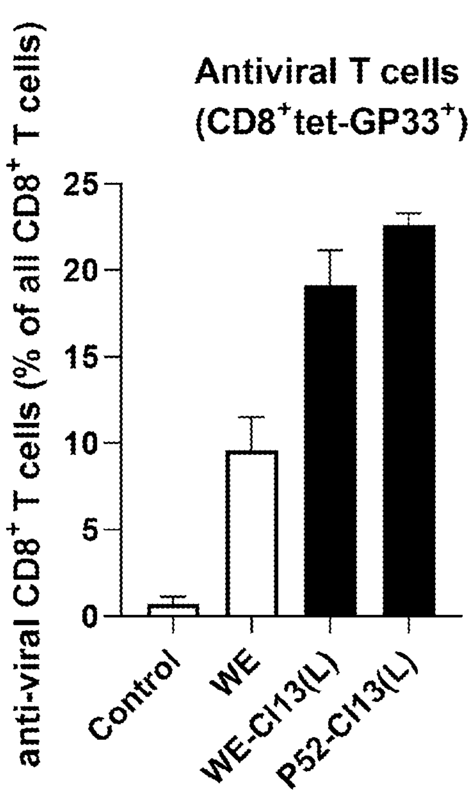

FIG. 29: Murine B16 tumor-bearing Bl/6 mice, LCMV wild type (WE) and recombinant strains with 2×10E4 PFU/animal i.v. at day 0, virus-specific (GP33) and CD8 T cells by flow cytometry from dLN and tumor at day 7 (n=5 animals/group).

Figure 30:
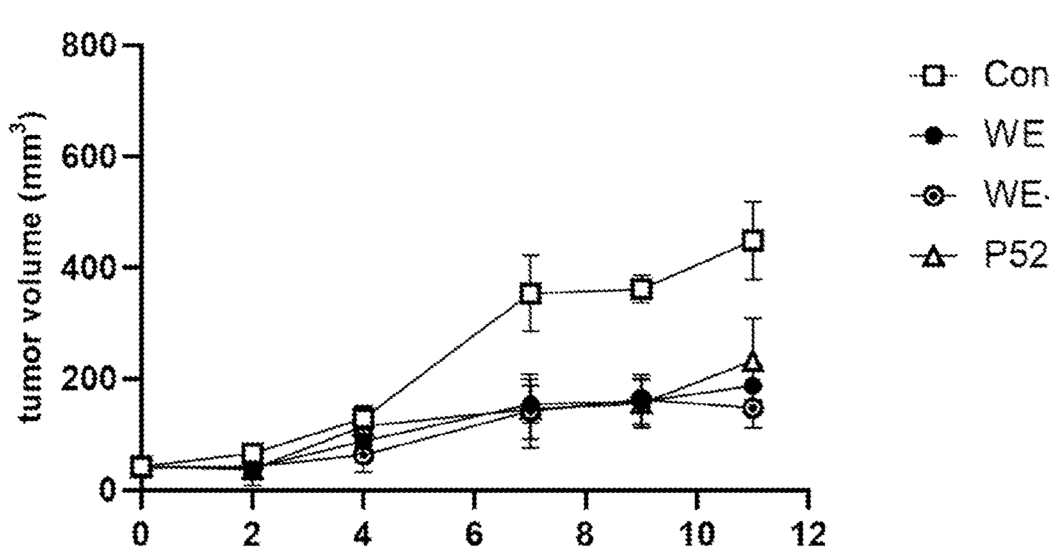

FIG. 30: Murine MC38 tumor-bearing Bl/6 mice, LCMV wild type (WE) and recombinant strains with 2×10E4 PFU/animal i.v. at day 0, tumor growth measurement for 11 days (n=4 animals/group), t-test for statistics.

Figure 31:
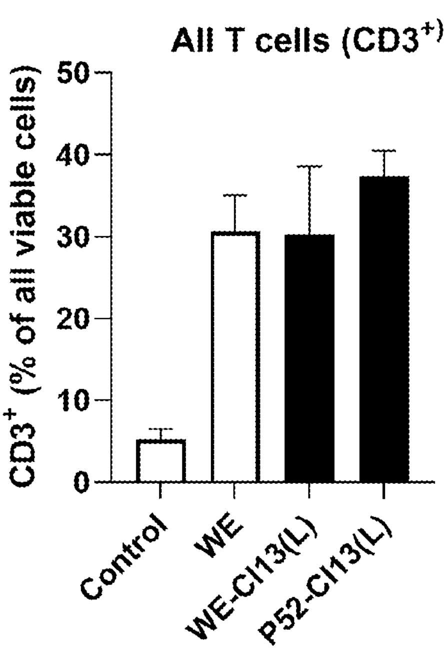

FIG. 31: Murine MC38 tumor-bearing Bl/6 mice, LCMV wild type (WE) and recombinant strains with 2×10E4 PFU/animal i.v. at day 0, tumor T cell measurement by flow cytometry at day 11, n=4 animals/arm, except for the P52-FP7-Cl13(L) group (n=3) due to experimental error (values near/below control).

Figure 32:
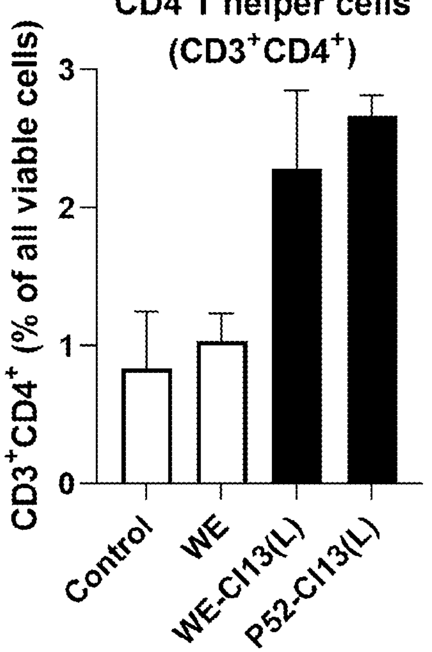

FIG. 32: Murine MC38 tumor-bearing Bl/6 mice, LCMV wild type (WE) and recombinant strains with 2×10E4 PFU/animal i.v. at day 0, tumor T helper cell measurement by flow cytometry at day 11, n=4 animals/arm, except for the P52-FP7-Cl13(L) group (n=3) due to experimental error (values near/below control).

Figure 33:
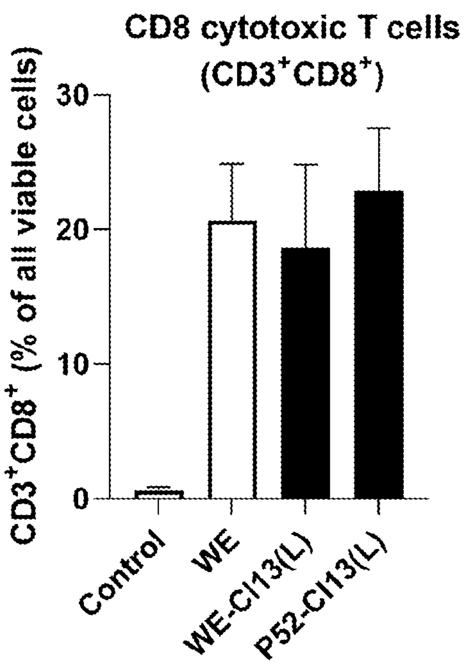

FIG. 33: Murine MC38 tumor-bearing Bl/6 mice, LCMV wild type (WE) and recombinant strains with 2×10E4 PFU/animal i.v. at day 0, tumor cytotoxic T cell measurement by flow cytometry at day 11, n=4 animals/arm, except for the P52-FP7-Cl13(L) group (n=3) due to experimental error (values near/below control).

Figure 34:
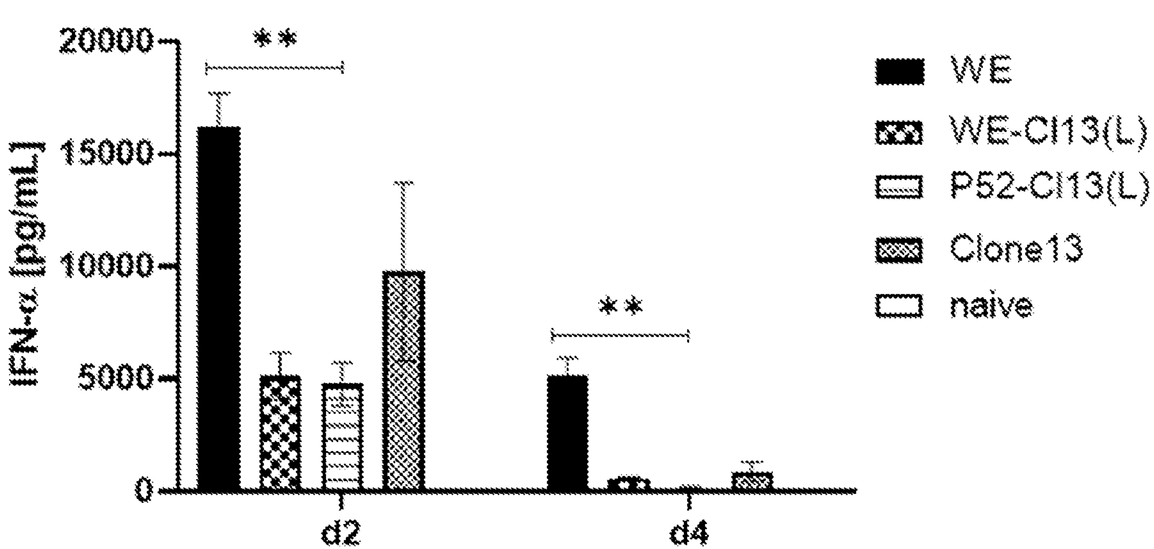
Figure 34:
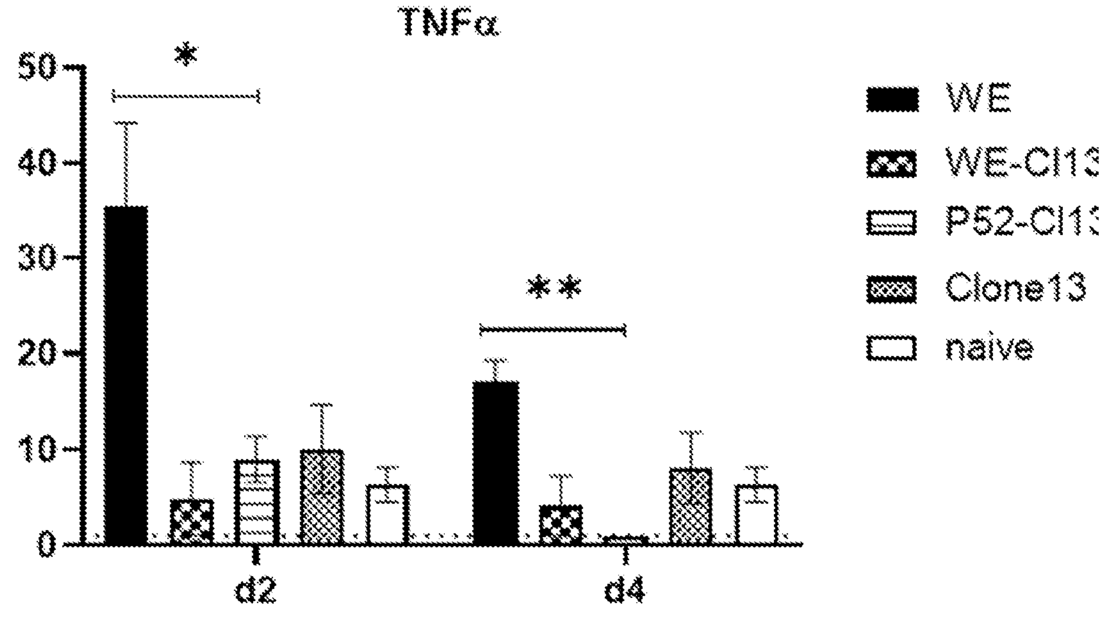
Figure 34:
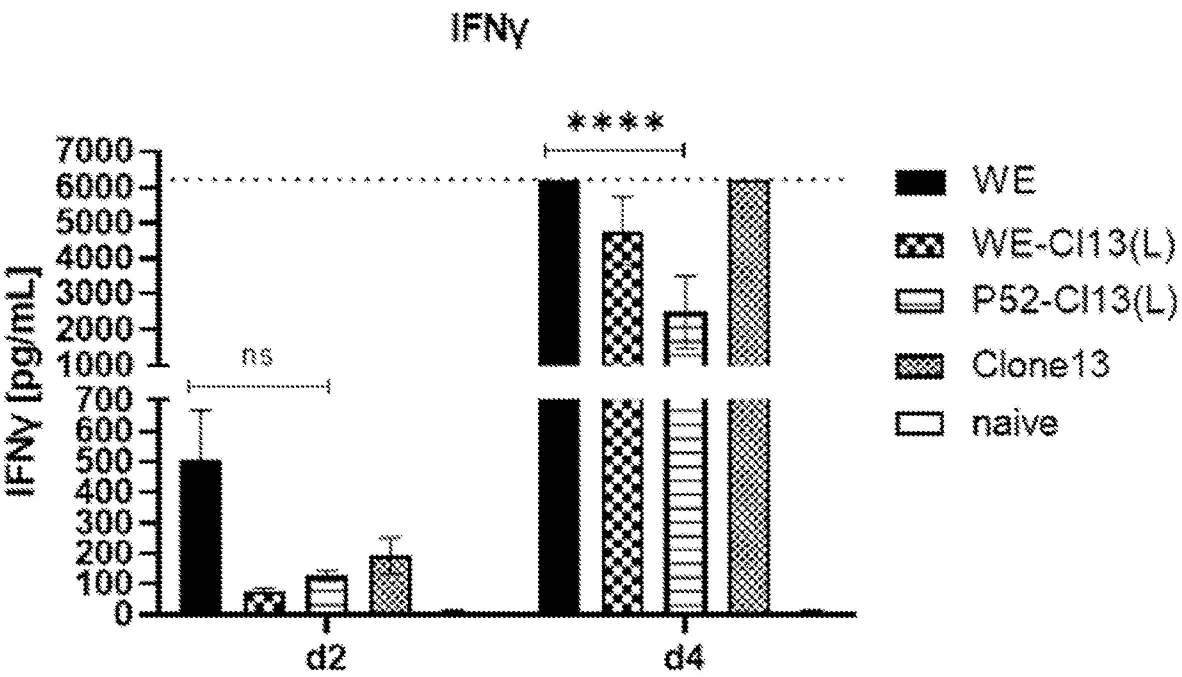

FIG. 34: Naïve Bl/6 mice, LCMV wild type (WE) and recombinant strains with 2×10E4 PFU/animal i.v. at day 0, cytokine LegendPlex days 2 and 4 (n=3 animals/group).

Figure 35:
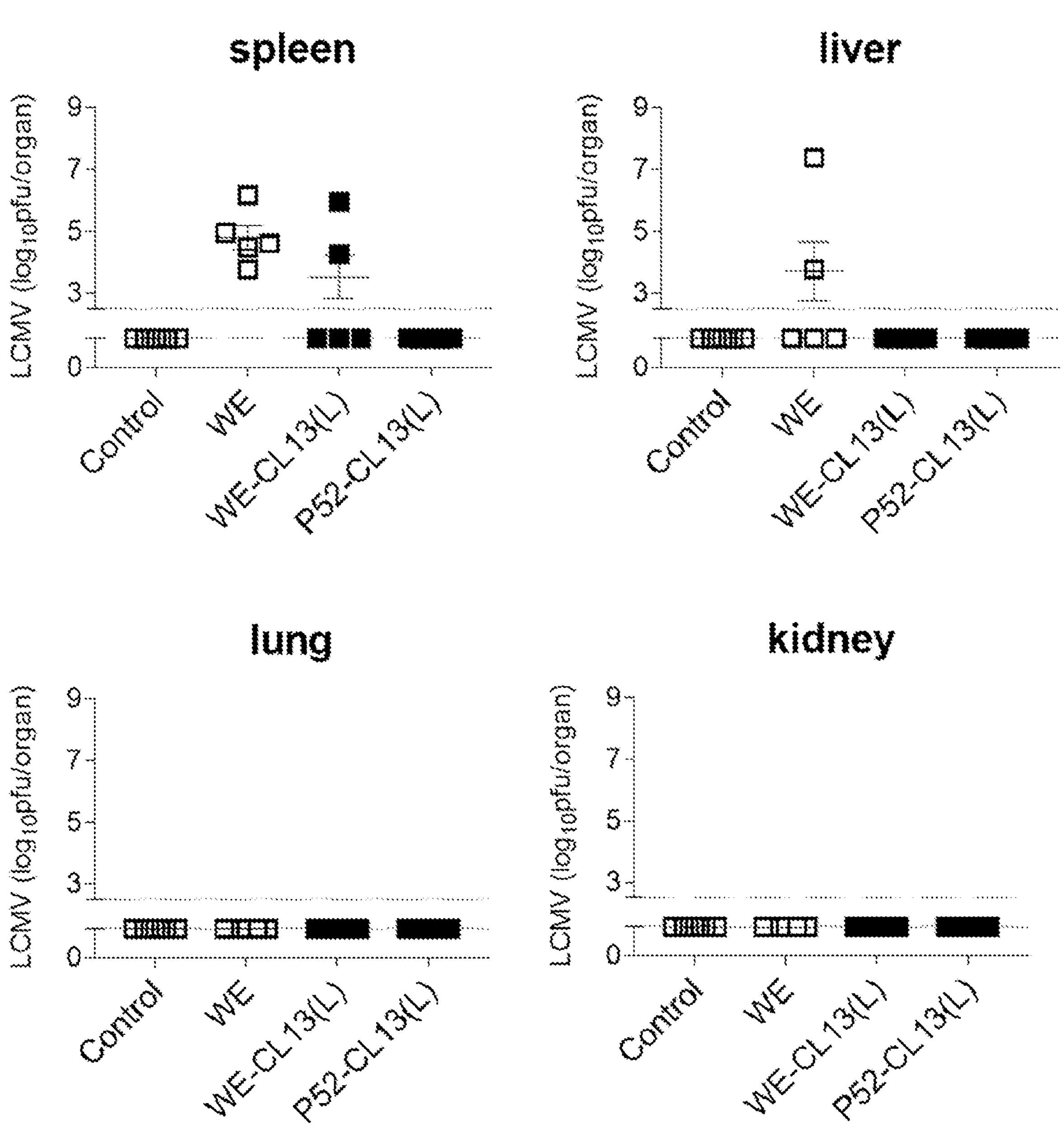
Figure 35:
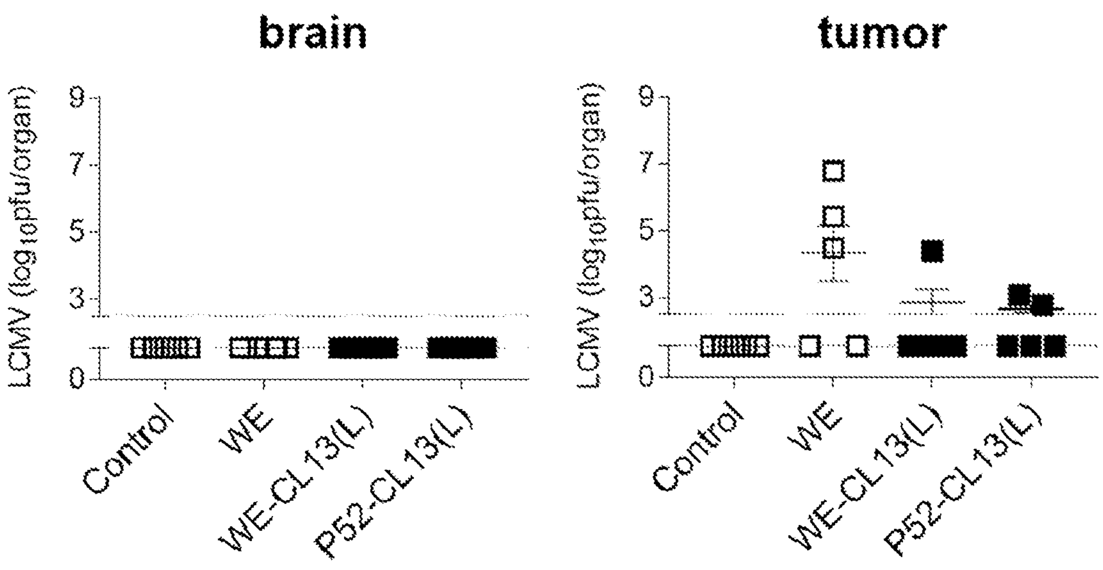

FIG. 35: Murine B16 tumor-bearing Bl/6 mice, LCMV wild type (WE) and recombinant strains with 2×10E4 PFU/animal i.v. at day 0, plaque-forming assay from the indicated organs at day 7 (n=5 animals/group).

Figure 36:
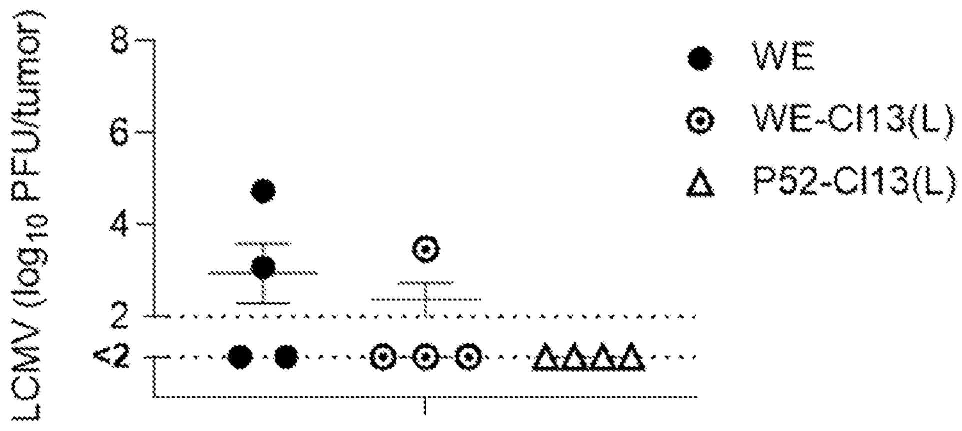

FIG. 36: Murine MC38 tumor-bearing Bl/6 mice, LCMV wild type (WE) and recombinant strains with 2×10E4 PFU/animal i.v. at day 0, plaque-forming assay from the indicated organs at day 11 (n=4 animals/group).

Figure 37:
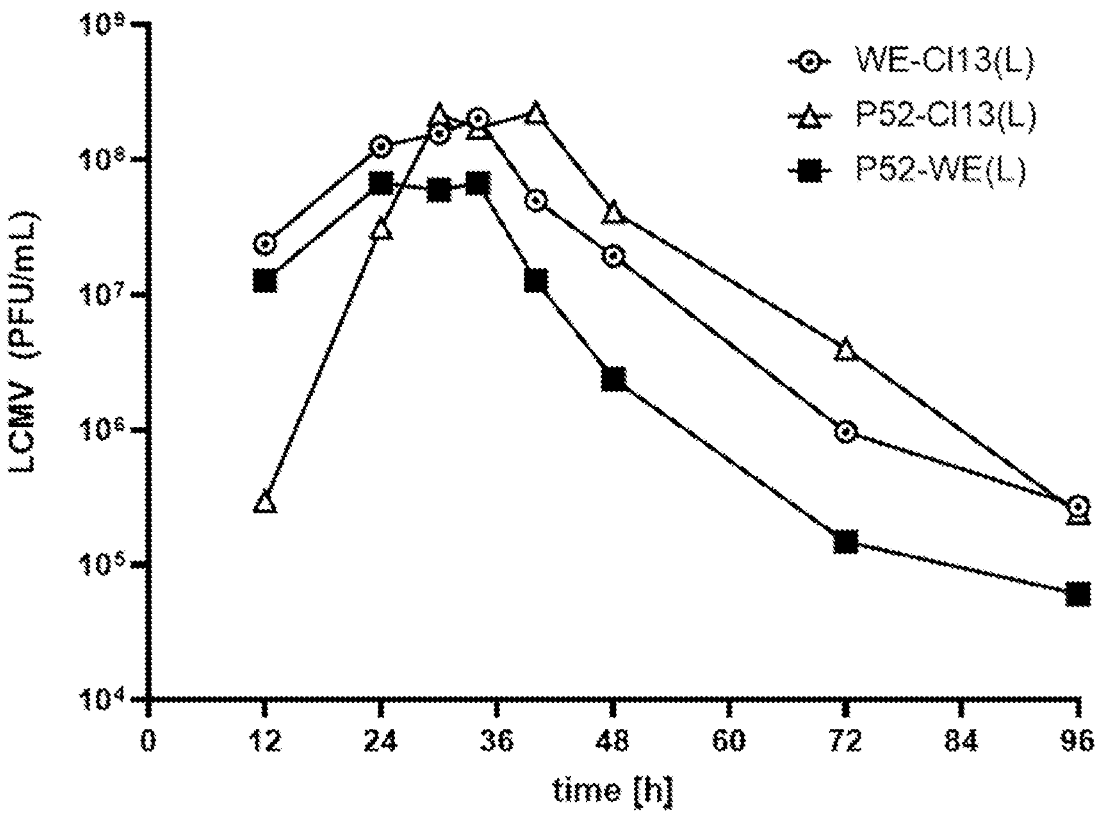

FIG. 37: FreeStyle 293-F suspension cells were infected with MOI=0.001 of LCMV strains WE-Cl13(L), P52-Cl13 (L) or P52-WE(L) at a density of $1.5\times10^6$ cells per mL. Supernatant was harvested on 12, 24, 30, 34, 40, 48, 72 and 96 hours post infection. LCMV titers in supernatant were analyzed via plaque-forming assay.

FIG. 38: Nucleic acid and amino acid sequences of the L segment, S segment, GPC, NP, ZP, and LP of LCMV strains A. WE, B. P52, C. Armstrong, and D. Clone13.

DETAILED DESCRIPTION

The inventors of the present application believe that pathogenicity of the WE strain may be consistently determined by elements located on the L segment, while the S segment of the WE and other LCMV strains is not contributing to pathogenicity. As such, replacement of the L segment of the WE strain by the corresponding segment of another LCMV strain, such as the Armstrong strain, Clone13 strain, and derivatives thereof, are believed to result in a reassorted laboratory strain that does no longer display the original pathogenic profile including liver pathogenicity in NHPs and other susceptible animals.

The inventors of the present application have then surprisingly found that a virus strain comprising elements of the S segment of the LCMV WE strain or derivatives thereof, which are believed not to contribute to pathogenicity, and elements of the L segment of the strain Clone13 or Armstrong or derivatives thereof, which are believed not to contribute to pathogenicity, have improved properties as compared to LCMV WE strain, in particular in tumor treatment. Such a virus strain is believed to no longer being able to induce LCMV specific disease including liver disease in NHPs, rodents or guinea pigs (Riviere et al. (1985) Journal of virology, 55: 704-09; Riviere et al. (1986) Med Microbiol Immunol, 175: 191-2; Baccala et al. (2014) Proc Natl Acad Sci USA, 111: 8925-30; Oldstone et al. (2018) Proceedings of the National Academy of Sciences, 115: E7814).

Studies conducted by the inventors of the present application with naïve and susceptible rodents do indeed demonstrate that a reassorted virus according to the invention may have decreased pathogenic properties as compared to LCMV WE strain including liver pathogenicity (Examples 16, 17, 18, 19, and 35). These results do confirm that a virus particle of the invention may result in virus-based products that can safely be handled during manufacturing and clinical investigation as pathogenic properties described for wild-type LCMV strains are reduced, including liver pathogenesis and neurotropism (Examples 10, 21, 24).

Beneath its severely reduced replication capacity (up to >100 times) in cells of different origin (Example 8 and 9), virus particles of the invention may demonstrate a strongly reduced potential to induce in vivo pathogenic cytokines in naïve animals, and at the same time any signs of induced organ pathogenicity may be absent (Examples 12-17). Notably, only virus particles comprising WE strain derived elements of the S segment and Clone13 strain derived elements of the L segment, but not virus particles comprising Clone13 strain derived elements of the S segment and WE strain derived elements of the L segment showed attenuated replication in Example 8, supporting the hypothesis that pathogenicity of the WE and Clone13 strain is determined by its L or S segment, respectively.

The FVB mouse strain, which exhibits a predisposition to viral induced pathologies (Schnell et al. (2012) PLoS Pathog, 8: e1003073), succumbs to a hemorrhagic fever-like illness including thrombocytopenia and hepatocellular necrosis when infected with LCMV. Importantly, the disease in FVB mice mimics LCMV disease in macaques and clinical signs of Argentine hemorrhagic fever (Schnell et al. (2012) PLoS Pathog, 8: e1003073). However, in contrast to LCMV strains WE, Clone13, and Armstrong, infection with a virus particle of the invention did not result in neither one reduced animal weight nor liver pathology or any other signs of hemorrhagic fever-like illness in Examples 14-17.

An important and surprising characteristic of the virus particles of the invention for clinical development is their retainment or even enhancement of strong anti-tumoral effects as described for the WE strain (Kalkavan et al. (2017) Nat Commun, 8: 14447)— despite their attenuation. A virus particle of the invention may be equipped with additional modifications to increase its tumor tropism (Examples 21-23). Such modifications may comprise mutations at positions 181 and/or 185 of the GP, in particular Arg 185→Trp and/or Ile 181→Met. Indeed, such virus particles may exhibit strong anti-tumoral effects in murine tumor models (Example 25) but may bear the attenuated phenotype of the WE-Clone13 strain from which it is derived (Examples 34 and 38). Pathogenicity of LCMV was reported as being mainly directed by the anti-viral functionality of the immune system and correlates with the strength of virus replication in infected organs (Lang et al. (2010) Cell Physiol Biochem, 26: 263-72). Such modified virus particles may result in a, compared to the WE strain, stronger early LCMV directed T cell response, the main anti-viral immune effector mechanism, and its organ distribution is controlled already early upon infection (Example 35).

In previous publications, LCMV was described as being able to induce organ damage (e.g., liver) due to an overshooting and deregulated innate (Th1 and pro-inflammatory cytokines) and adaptive (CD8 T cells) immune response (Lang et al. (2010) Cell Physiol Biochem, 26: 263-72; Schnell et al. (2012) PLoS Pathog, 8: e1003073; Oldstone et al. (2018) Proceedings of the National Academy of Sciences, 115: E7814). The inventors of the present application have surprisingly found that—although a similar pattern of the cytokine response to the wild type LCMV strains Armstrong, Clone13 and WE was observed—the strength of the immune response for a virus particle of the invention may be substantially lower. This observation is especially important for IFN-alpha, for which high cytokine levels early upon infection was linked to organ damage in respective animal models (Schnell et al. (2012) PLoS Pathog, 8: e1003073). The virus particles of the invention, in contrast, may induce especially early upon infection substantially lower IFN-alpha and IFN-gamma levels (Examples 12 and 13), which strongly points to a significantly lower potential for IFN-mediated detrimental effects (Baccala et al. (2014) Proc Natl Acad Sci USA, 111: 8925-30). In addition, the pro-inflammatory cytokines IL-6 and TNF-alpha, as well as IL-10 may also be substantially decreased at different time points (days 1 and 3) upon infection, indicating enhanced virus control (Lang et al. (2010) Cell Physiol Biochem, 26: 263-72; Schnell et al. (2012) PLoS Pathog, 8: e1003073).

Overall, the virus particles of the invention may exhibit a strongly attenuated phenotype and may show an even stronger in vivo attenuated immune phenotype, although retaining or even enhancing their anti-tumoral efficacy.

Accordingly, the present invention relates to a virus particle comprising an LCMV S segment and an LCMV L segment. The S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40.

The S segment may also comprise an open reading frame encoding a nucleoprotein. The nucleoprotein may have at least 97% sequence identity to SEQ ID NO: 6.

The L segment may also comprise an L segment. The L segment may comprise an open reading frame encoding a Z protein having at least 90% sequence identity to SEQ ID NO: 38.

The virus particle of the invention is preferably an arenavirus particle, more preferably a lymphocytic choriomeningitis virus (LCMV) particle.

The wild-type arenavirus genomic segments and ORFs are known in the art. In particular, the arenavirus genome consists of an S segment and an L segment. The S segment carries the ORFs encoding the GP and the NP. The L segment encodes the L protein and the Z protein. Both segments are flanked by the respective 5' and 3' UTRs.

The virus particles of the invention preferably comprise genomic segments that correspond to the genomic segments of a wild-type arenavirus. This means that the S segment carries the ORFs encoding the GP and the NP and that the L segment encodes the L protein and the Z protein. On the S segment, the ORF encoding the glycoprotein is under control of a 5' untranslated region (UTR) and the nucleoprotein is under control of a 3' UTR. On the L segment, the ORF encoding the L protein is under control of a 3' UTR and the ORF encoding the Z protein is under control of a 5' UTR. Accordingly, the genes of the virus particles of the disclosure are preferably located at their natural positions. The virus particle of the invention thus preferably has a bi-segmented genome. The genome of the virus particle of the invention preferably consists of one L segment and one S segment as described herein. Illustrative examples of LCMV S segments are shown in SEQ ID NOs: 1, 11, 21, and 31. Illustrative examples of LCMV L segments are shown in SEQ ID NOs: 2, 12, 22, and 32.

Several strains of LCMV are part of the present disclosure. As used herein, LCMV "WE", "strain WE", "WE strain", or the like refers to an LCMV having the genomic segments as shown in SEQ ID NOs: 1 and 2. As used herein, LCMV "P52", "P52-WE", "strain P52", "P52 strain", or the like refers to a variant/derivative of strain WE, which has the genomic segments as shown in SEQ ID NOs: 11 and 12. As used herein, LCMV "Armstrong", "strain Armstrong", "Armstrong strain", or the like refers to LCMV strain Armstrong 53b, which has the genomic segments as shown in SEQ ID NOs: 21 and 22. As used herein, LCMV "Clone13", "Cl13" "strain Clone13", "Clone13 strain", or the like refers to an LCMV which has the genomic segments as shown in SEQ ID NOs: 31 and 32.

The terms "glycoprotein", "GP", and "G protein", which are used interchangeably, refer to an LCMV-derived glycoprotein, which is considered to mediate receptor binding and membrane fusion. Illustrative examples of glycoproteins are shown in SEQ ID NOs: 4, 14, 24, and 34. Illustrative examples for genes that encode a glycoprotein are shown in SEQ ID NOs: 3, 13, 23, and 33.

The terms "L protein", and "LP", which are used interchangeably, refer to an LCMV-derived RNA polymerase L. Illustrative examples of L proteins are shown in SEQ ID NOs: 10, 20, 30, and 40. Illustrative examples for genes that encode an L protein are shown in SEQ ID NOs: 9, 19, 29, and 39.

The terms "nucleoprotein", "N protein", and "NP", which are used interchangeably, refer to an LCMV-derived nucleoprotein. Illustrative examples of nucleoproteins are shown in SEQ ID NOs: 6, 16, 26, and 36. Illustrative examples for genes that encode a nucleoprotein are shown in SEQ ID NOs: 5, 15, 25, and 35.

The terms "Z protein" or "ZP", which are used interchangeably, refer to an LCMV-derived small RING finger protein Z. Illustrative examples of Z proteins are shown in SEQ ID NOs: 8, 18, 28, and 38. Illustrative examples for genes that encode a Z protein are shown in SEQ ID NOs: 7, 17, 27, and 37.

A virus particle of the invention comprises a glycoprotein, wherein the glycoprotein may comprise at least one mutated amino acid residue in comparison with the glycoprotein sequence set forth in SEQ ID NO: 4. For example, the glycoprotein may comprise at least one mutated amino acid residue at position 181 and/or 185 in comparison with the glycoprotein sequence set forth in SEQ ID NO: 4. It is however preferred that the glycoprotein comprises a mutation at both positions in comparison with SEQ ID NO: 4. Preferred mutations at these positions are selected from Arg 185→Trp and Ile 181→Met. A virus particle thus can have any one or preferably both mutations.

Without wishing to be bound by theory, it is believed that the presence of the one or two above-mentioned mutations in the glycoprotein can improve the function of the LCMV (e.g., anti-tumoral activities), independent from the presence of other mutations, in particular of other mutations in other genes or proteins of LCMV.

A virus particle of the invention comprises an L protein, wherein the L protein may comprise at position 1079 corresponding to the linear polypeptide sequence of SEQ ID NO: 40 an amino acid residue other than Lys. The amino acid residue at this position is preferably a non-basic amino acid residue, more preferably a neutral hydrophilic amino acid residue, even more preferably an Asn or Gln, most preferably a Gln.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. Naturally occurring residues are divided into groups based on common side-chain properties: (1) hydrophobic: methionine, alanine, valine, leucine, iso-leucine; (2) neutral hydrophilic: cysteine, serine, threonine, asparagine, glutamine; (3) acidic: aspartic acid, glutamic acid; (4) basic: histidine, lysine, arginine; (5) residues that influence chain orientation: glycine, proline; and (6) aromatic: tryptophan, tyrosine, phenylalanine. In some embodiments. substitutions may entail exchanging a member of one of these classes for another class.

A virus particle of the invention comprises an S segment and an L segment, wherein the S segment is preferably derived from LCMV strain WE or a variant thereof and wherein the L segment is preferably derived from LCMV strain Clone13 or a variant thereof.

A variant of the L segment may have at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity to the sequence of the original L segment.

A virus particle disclosed herein may have an L segment that comprise or preferably consists of a sequence that has at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity, or is preferably identical, to a sequence set forth in SEQ ID NO: 21 or 31.

A variant of the S segment may have at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity to the sequence of the original S segment.

A virus particle disclosed herein may have an S segment that comprise or preferably consists of a sequence that has at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity, or is preferably identical, to a sequence set forth in SEQ ID NO: 1 or 11.

A virus particle of the invention comprising an LCMV preferably comprises S segment and an LCMV L segment, wherein the S segment comprises an open reading frame encoding a glycoprotein having at least 97% sequence identity to SEQ ID NO: 4 and an open reading frame encoding a nucleoprotein having at least 97% sequence identity to SEQ ID NO: 6, and wherein the L segment comprises an open reading frame encoding an L protein having at least 90% sequence identity to SEQ ID NO: 40 and an open reading frame encoding a Z protein having at least 90% sequence identity to SEQ ID NO: 38.

An open reading frame encoding a glycoprotein disclosed herein may encode a sequences that has at least about 98%, preferably at least about 98.5%, preferably at least about 99%, preferably at least about 99.1%, preferably at least about 99.2%, preferably at least about 99.3%, preferably at least about 99.4%, preferably at least about 99.5%, preferably at least about 99.5%, preferably at least about 99.7% sequence identity, or is preferably identical, to a sequence set forth in SEQ ID NO: 4 or 14.

An open reading frame encoding a glycoprotein disclosed herein may comprise a sequence that has at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, or is preferably identical, to a sequence set forth in SEQ ID NO: 3 or 13.

An open reading frame encoding an L protein disclosed herein may encode a sequences that has at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, or is preferably identical, to a sequence set forth in SEQ ID NO: 30 or 40.

An open reading frame encoding an L protein disclosed herein may have at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, preferably at least about 99.8%, preferably at least about 99.9% sequence identity, or is preferably identical, to a sequence set forth in SEQ ID NO: 29 or 39.

An open reading frame encoding a nucleoprotein disclosed herein may encode a sequence that has at least about 98%, preferably at least about 98.5%, preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in any one of in SEQ ID NO: 6 or 16.

An open reading frame encoding a nucleoprotein disclosed herein may have at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in SEQ ID NO: 5 or 15.

An open reading frame encoding a Z protein disclosed herein may encode a sequence that has at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in SEQ ID NO: 28 or 38.

An open reading frame encoding a Z protein disclosed herein may have at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is identical, to a sequence set forth in SEQ ID NO: 27 or 37.

A preferred virus particle comprises an LCMV S segment and an LCMV L segment, wherein the S segment comprises an open reading frame encoding a glycoprotein having at least 98.5% sequence identity to SEQ ID NO: 4 or 14, with SEQ ID NO: 14 being preferred, and an open reading frame encoding a nucleoprotein having at least 98.5% sequence identity to SEQ ID NO: 6 or 16, with SEQ ID NO: 16 being preferred, and wherein the L segment comprises an open reading frame encoding an L protein having at least 95% sequence identity to SEQ ID NO: 30 or 40, with SEQ ID NO: 40 being preferred, and an open reading frame encoding a Z protein having at least 95% sequence identity to SEQ ID NO: 28 or 38, with SEQ ID NO: 38 being preferred.

A preferred virus particle comprises an LCMV S segment and an LCMV L segment, wherein the S segment comprises an open reading frame encoding a glycoprotein having at least 98% sequence identity to SEQ ID NO: 4 or 14, with SEQ ID NO: 14 being preferred, and an open reading frame encoding a nucleoprotein having at least 98% sequence identity to SEQ ID NO: 6 or 16, with SEQ ID NO: 16 being preferred, and wherein the L segment comprises an open reading frame encoding an L protein having at least 98% sequence identity to SEQ ID NO: 30 or 40, with SEQ ID NO: 40 being preferred, and an open reading frame encoding a Z protein having at least 98% sequence identity to SEQ ID NO: 28 or 38, with SEQ ID NO: 38 being preferred.

A preferred virus particle comprises an LCMV S segment and an LCMV L segment, wherein the S segment comprises an open reading frame encoding a glycoprotein having at least 99% sequence identity to SEQ ID NO: 4 or 14, with SEQ ID NO: 14 being preferred, and an open reading frame encoding a nucleoprotein having at least 99% sequence identity to SEQ ID NO: 6 or 16, with SEQ ID NO: 16 being preferred, and wherein the L segment comprises an open reading frame encoding an L protein having at least 99% sequence identity to SEQ ID NO: 30 or 40, with SEQ ID NO: 40 being preferred, and an open reading frame encoding a Z protein having at least 99% sequence identity to SEQ ID NO: 28 or 38, with SEQ ID NO: 38 being preferred.

A preferred virus particle comprises an LCMV S segment and an LCMV L segment, wherein the S segment comprises an open reading frame encoding a glycoprotein having a sequence set forth in SEQ ID NO: 4 or 14, with SEQ ID NO: 14 being preferred, and an open reading frame encoding a nucleoprotein having a sequence set forth in SEQ ID NO: 6 or 16, with SEQ ID NO: 16 being preferred, and wherein the L segment comprises an open reading frame encoding an L protein having a sequence set forth in SEQ ID NO: 30 or 40, with SEQ ID NO: 40 being preferred, and an open reading frame encoding a Z protein having a sequence set forth in SEQ ID NO: 28 or 38, with SEQ ID NO: 38 being preferred.

A preferred virus particle comprises an LCMV S segment and an LCMV L segment, wherein the S segment comprises an open reading frame encoding a glycoprotein having a sequence set forth in SEQ ID NO: 4, and an open reading frame encoding a nucleoprotein having a sequence set forth in SEQ ID NO: 6, and wherein the L segment comprises an open reading frame encoding an L protein having a sequence set forth in SEQ ID NO: 40, and an open reading frame encoding a Z protein having a sequence set forth in SEQ ID NO: 38.

A preferred virus particle comprises an LCMV S segment and an LCMV L segment, wherein the S segment comprises an open reading frame encoding a glycoprotein having a sequence set forth in SEQ ID NO: 14, and an open reading frame encoding a nucleoprotein having a sequence set forth in SEQ ID NO: 16, and wherein the L segment comprises an open reading frame encoding an L protein having a sequence set forth in SEQ ID NO: 40, and an open reading frame encoding a Z protein having a sequence set forth in SEQ ID NO: 38.

A preferred virus particle comprises an LCMV S segment and an LCMV L segment, wherein the S segment comprises an open reading frame encoding a glycoprotein having a sequence set forth in SEQ ID NO: 4, and an open reading frame encoding a nucleoprotein having a sequence set forth in SEQ ID NO: 6, and wherein the L segment comprises an open reading frame encoding an L protein having a sequence set forth in SEQ ID NO: 30, and an open reading frame encoding a Z protein having a sequence set forth in SEQ ID NO: 28.

A preferred virus particle comprises an LCMV S segment and an LCMV L segment, wherein the S segment comprises an open reading frame encoding a glycoprotein having a sequence set forth in SEQ ID NO: 14, and an open reading frame encoding a nucleoprotein having a sequence set forth in SEQ ID NO: 16, and wherein the L segment comprises an open reading frame encoding an L protein having a sequence set forth in SEQ ID NO: 30, and an open reading frame encoding a Z protein having a sequence set forth in SEQ ID NO: 28.

A virus particle of the disclosure preferably does not comprise a heterologous ORF. A "heterologous ORF" in this context refers to an ORF from an organism other than an LCMV and/or a ORF encoding an artificial or synthetic protein.

The term "nucleic acid" as used herein may generally refer to DNA or RNA. DNA and RNA differ—among others—in their nucleobases. The complementary base to adenine in DNA is thymine, whereas in RNA, it is uracil. For the sake of simplification, the corresponding base to adenine is denoted as "t" throughout the application, which—depending on its context—may refer to thymine (in DNA) or uracil (in RNA).

The term "encoding" or "encode(s)" as used herein in the context of a nucleic acid, relates to a nucleic acid having a sequence that can be translated into a particular amino acid sequence that is encoded by the nucleic acid. The nucleic acid sequence may encompass the sequence of a coding strand and may also encompass the sequence of a strand that is complementary to the coding strand.

"Percent (%) sequence identity" with respect to sequences disclosed herein is defined as the percentage of amino acid residues or nucleotides in a candidate sequence that are pair-wise identical with the amino acid residues or nucleotides in a reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein. For determining sequence identity, uracil (e.g. in RNA) may be considered to be identical to thymine (e.g. in DNA).

The term "attenuation" as used herein, relates to a reduced capacity of a virus to replicate within a given host (cell), a reduced capacity of replicating in a healthy organ, and/or a reduced capacity of inducing cytokines. A virus particle of the invention is preferably attenuated.

The term "infectious" as used herein, relates to a virus' capacity to infect, i.e., enter, a given host cell. A virus particle of the invention is preferably infectious.

The term "replication competent" means that a virus has the ability to amplify and express its genetic material in infected cells and being able to produce further progeny in normal cells that are not genetically engineered. In particular, replication competent viruses do not require host cells that were engineered to express a viral gene for being capable of replication. A virus particle of the invention is preferably replication competent.

The term "pathogenic" as used herein, relates to a virus' capacity to cause disease, i.e., harm to an organism.

A virus particle of the invention may be capable of promoting a reduction of growth of a tumor that is at least as strong or even stronger as compared to LCMV strain WE and/or a virus particle comprising the same S segment as the virus particle and an L segment as shown in SEQ ID NO: 2. In particular, the virus particle may be capable of promoting a stronger reduction of growth of a cold tumor as compared to LCMV strain WE and/or a virus particle comprising the same S segment as the virus particle and an L segment as shown in SEQ ID NO: 2, preferably as measured in an assay as essentially described in Example 1.

A virus particle of the invention may be capable of inducing an adaptive immune activation that is at least as strong or even stronger as compared to LCMV strain WE and/or a virus particle comprising the same S segment as the virus particle and an L segment as shown in SEQ ID NO: 2, preferably as measured in an assay as essentially described in Example 3.

A virus particle of the invention may be capable of promoting a reduction of growth of a warm tumor that is at least as strong as compared to LCMV strain WE and/or a virus particle comprising the same S segment as the virus particle and an L segment as shown in SEQ ID NO: 2, preferably as measured in an assay as essentially described in Example 4.

As used herein a "hot" or "warm" tumor, which is used interchangeably, relates to a tumor having a T-cell-inflamed phenotype. Such tumors show signs of inflammation, meaning the tumor has already been infiltrated by T cells to fight the cancerous cells. Examples of cancers that are typically hot tumors include melanoma, bladder cancer, kidney cancer, head and neck cancer, and non-small cell lung cancer.

As used herein, a "cold tumor" relates to a tumor having a non-T-cell-inflamed phenotype, which has low T cell infiltration or which have not been infiltrated with T cells. Due to the lack of T cells, it difficult to provoke an immune response with immunotherapy drugs in such tumors. Examples of cancers that are typically cold tumors include breast cancer, ovarian cancer, prostate cancer, pancreatic cancer, and glioblastoma. The difference between hot tumors and cold tumors are described in detail in Gajewski et al. (2017) Adv Exp Med Biol. 1036:19-31 and Maleki Vareki (2018) Journal for ImmunoTherapy of Cancer 6:157.

A virus particle of the invention may be capable of inducing decreased levels of an interferon upon (preferably systemic) administration compared to LCMV strain WE, Armstrong, Clone13 and/or a virus particle comprising the same S segment as the virus particle and an L segment as shown in SEQ ID NO: 2, preferably as measured in an assay as essentially described in Example 12. The interferon is preferably selected from the group consisting of IFN-α nd IFN-β.

A virus particle of the invention may be capable of inducing a lower concentration of one or more Th1- and pro-inflammatory cytokines compared to LCMV strain WE, Armstrong, Clone13 and/or a virus particle comprising the same S segment as the virus particle and an L segment as shown in SEQ ID NO: 2, preferably as measured in an assay as essentially described in Example 13. The cytokine is preferably selected from the group consisting of IL-6, IL-10, TNFα, and IFNγ.

A virus particle of the invention may be capable of inducing a lower concentration of one or more Th1- and pro-inflammatory cytokines compared to LCMV strain WE, Armstrong, Clone13 and/or a virus particle comprising the same S segment as the virus particle and an L segment as shown in SEQ ID NO: 2, preferably as measured in an assay as essentially described in Example 13. The cytokine is preferably selected from the group consisting of IL-6, IL-10, TNFα, and IFNγ.

A virus particle of the invention may be less pathogenic in a mouse compared to LCMV strain WE, preferably as measured in an FVB/N mouse in an assay as essentially described in Example 14.

A virus particle of the invention may be capable of inducing a reduced degree of liver pathology in a mouse compared to LCMV strain WE and/or a virus particle comprising the same S segment as the virus particle and an L segment as shown in SEQ ID NO: 2, preferably as measured in an assay as essentially described in Example 18.

A virus particle of the invention may be capable of inducing a reduced degree of thrombocytopenia in a mouse compared to LCMV strain WE and/or a virus particle comprising the same S segment as the virus particle and an L segment as shown in SEQ ID NO: 2 or no detectable thrombocytopenia in a mouse, such as an FVB/N mouse, preferably as measured in an assay as essentially described in Example 15.

A virus particle of the invention may show reduced replication in healthy cells such as neuron cells compared to LCMV strain WE and/or a virus particle comprising the same S segment as the virus particle and an L segment as shown in SEQ ID NO: 2, preferably as measured in an assay as essentially described in Example 24.

A virus particle of the invention may show increased replication in tumor cells compared to LCMV strain WE, preferably as measured in an assay as essentially described in Example 24.

A virus particle of the invention may show reduced replication in a healthy organ compared to LCMV strain WE and/or a virus particle comprising the same S segment as the virus particle and an L segment as shown in SEQ ID NO: 2, preferably as measured in an assay as essentially described in Example 35.

The present invention also relates to a host cell comprising an LCMV S segment and an LCMV L segment as described for the virus particle of the invention.

The present invention also relates to a host cell comprising cDNA of an ORF encoding a glycoprotein as described for the virus particle of the invention, an ORF encoding an L protein as described for the virus particle of the invention, an ORF encoding a nucleoprotein as described for the virus particle of the invention, and an ORF encoding a Z protein as described for the virus particle of the invention.

The present invention also relates to a host cell comprising cDNA of an LCMV S segment and an LCMV L segment as described for the virus particle of the invention.

Techniques for the production of a cDNA are routine and conventional techniques of molecular biology and DNA manipulation and production. Any cloning technique known to the skilled artesian can be used. Such as techniques are well known and are available to the skilled artesian in laboratory manuals such as, Sambrook and Russell, Molecular Cloning: A laboratory Manual, 3rd edition, Cold Spring Harbor Laboratory N.Y. (2001).

A cDNA described herein can be incorporated into a plasmid. The cDNA described herein can be part of or can be incorporated into a DNA expression vector and optionally introduced into a host cell. A cDNA described herein or plasmid or vector comprising the cDNA preferably comprises a promoter. Specific examples of promoters include an RNA polymerase I promoter, an RNA polymerase II promoter, an RNA polymerase III promoter, a T7 promoter, an SP6 promoter or a T3 promoter.

A host cell can be any host cell suitable for cloning, expression, propagation, or production of the virus particle. A host cell can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HEK cells, BHK cells, HeLa cells or CHO cells) or primary mammalian cells. Preferred host cells include HEK cells, in particular HEK293 cells, such as HEK293T (CVCL 0063) or FreeStyle 293-F (CVCL_D603). FreeStyle 293-F cells are commercially available, e.g., from Thermo Fisher Scientific Inc. (Catalogue number 12338026). Preferred host cells also include BHK cells, such as BHK-21 cells (CVCL 1914). Preferred host cells also include WHO Vero RCB 10-87 cells (ATCC CCL 81).

The present invention also relates to a method of producing a virus particle of the invention. The method comprises cultivating a host cell of the invention under conditions suitable for virus particle formation.

The method of producing the virus particle can further comprise introducing into a host cell the cDNA described herein. The method of producing the virus particle can also comprise recovery and/or purification of the virus particle. Such recovery and/or purification methods are well-known to those skilled in the art.

The present invention also relates to a pharmaceutical composition comprising a virus particle disclosed herein. The virus particle preferably comprises an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40. The pharmaceutical composition may further comprise a pharmaceutically acceptable excipient or carrier. A carrier may be e.g., be selected from the group consisting of water, aqueous saline solution, aqueous buffer solution, cell culture medium and combinations of at least two of the foregoing carriers.

The present invention also relates to a virus particle disclosed herein for use in therapy. The virus particle preferably comprises an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40. The virus particle disclosed herein may be for use in the treatment of a cancer or tumor.

The present invention also relates to a use of a virus particle disclosed for the manufacture of a medicament. The virus particle preferably comprises an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40. The medicament is preferably for the treatment of a cancer or tumor.

The present invention also relates to a method of treating a disease comprising administering to a subject a virus particle disclosed herein. The subject is preferably in need thereof. The virus particle is preferably administered in an effective amount. The virus particle preferably comprises an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40. The disease is preferably a cancer or tumor.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as mice, sheep, dogs, horses, cats, cows, rats, pigs, apes such as cynomolgus monkeys and etc., to name only a few illustrative examples. Preferably, the mammal herein is human. The cancer or tumor may be a human or murine cancer or tumor, with a human cancer or tumor being preferred.

An "effective amount" is an amount sufficient to effect beneficial or desired results. An effective amount can be administered in one or more administrations.

The cancer or tumor may be any cancer or tumor disclosed herein. Generally, the cancer or tumor can be selected from the group consisting of carcinoma, melanoma, blastoma, lymphoma and sarcoma.

The term "carcinoma" in the context of the present disclosure should be understood to mean a malignant neoplasia of epithelial origin. A carcinoma is preferably selected from the group consisting of anal carcinoma, bronchial carcinoma, lung carcinoma, endometrial carcinoma, gallbladder carcinoma, bladder carcinoma, hepatocellular carcinoma, testicular carcinoma, colon carcinoma, colorectal carcinoma, rectal carcinoma, laryngeal carcinoma, esophageal carcinoma, gastric carcinoma, breast carcinoma, renal carcinoma, ovarian carcinoma, pancreatic carcinoma, pharyngeal carcinoma, oropharyngeal carcinoma, prostate carcinoma, thyroid carcinoma and cervical carcinoma.

The term "sarcoma" in the context of the present disclosure should be understood to mean a malignant neoplasia of mesodermal origin. A sarcoma can be selected from the group consisting of angiosarcoma, chondrosarcoma, Ewing sarcoma, fibrosarcoma, Kaposi sarcoma, liposarcoma, leiomyosarcoma, malignant fibrous histiocytoma, neurogenic sarcoma, osteosarcoma and rhabdomyosarcoma.

The term "melanoma" in the context of the present disclosure should be understood to mean a malignant neoplasia of melanocytic origin.

The term "lymphoma" in the context of the present disclosure should be understood to mean a malignant neoplasia of lymphocytic origin.

The term "blastoma" in the context of the present disclosure should be understood to mean a malignant neoplasia of embryonic origin.

The cancer or tumor to be treated may be a cold tumor. Preferred cold tumors include breast cancer, ovarian cancer, prostate cancer, pancreatic cancer, and glioblastoma.

The cancer or tumor to be treated may be a hot tumor. Preferred hot tumors include melanoma, bladder cancer, kidney cancer, head and neck cancer, and non-small cell lung cancer.

Preferred cancers or tumors to be treated include melanoma, colon carcinoma, fibrosarcoma, pancreas cancer, thyroid carcinoma, lung cancer, adenocarcinoma, and gastrointestinal cancer.

Generally, the virus particles disclosed herein can be administered via any suitable route that is known to the skilled person. Administration generally includes enteral and parenteral administration. Parenteral administration can include local administration, such as intramuscular, intraperitoneal, subcutaneous, or intratumoral administration. Alternatively, parenteral administration can include systemic administration, in particular intravenous administration, such as via injection or infusion.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

Throughout this specification and the claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms. E.g., the term "comprising" is meant to provide explicit support also for "consisting essentially of" and "consisting of", the term "consisting essentially of" is meant to provide explicit support also for "comprising" and "consisting of", the term "consisting of" is meant to provide explicit support also for "consisting essentially of" and "comprising".

The present invention is further characterized by the following items.

Item 1. A virus particle comprising a lymphocytic choriomeningitis virus (LCMV) S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40, wherein the glycoprotein comprises at least one mutated amino acid residue in comparison with the glycoprotein sequence set forth in SEQ ID NO: 4.

Item 2. The virus particle of item 1, wherein the glycoprotein comprises at least one mutated amino acid residue at position 181 and/or 185 in comparison with the glycoprotein sequence set forth in SEQ ID NO: 4, wherein the glycoprotein preferably comprises at least one mutation selected from Arg 185→Trp and Ile 181→Met in comparison with the glycoprotein sequence set forth in SEQ ID NO: 4.

Item 3. The virus particle of item 1 or 2, wherein the L protein comprises at position 1079 corresponding to the linear polypeptide sequence of SEQ ID NO: 40 an amino acid residue other than Lys, preferably a non-basic amino acid residue, preferably a neutral hydrophilic amino acid residue, preferably an Asn or Gln, preferably a Gln.

Item 4. A virus particle comprising a lymphocytic choriomeningitis virus (LCMV) S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40, wherein the L protein comprises at position 1079 corresponding to the linear polypeptide sequence of SEQ ID NO: 40 an amino acid residue other than Lys.

Item 5. The virus particle of item 4, wherein the L protein comprises at position 1079 corresponding to the linear polypeptide sequence of SEQ ID NO: 40 a non-basic amino acid residue, preferably a neutral hydrophilic amino acid residue, preferably an Asn or Gln, preferably a Gln.

Item 6. The virus particle of item 4 or 5, wherein the glycoprotein comprises at least one mutated amino acid residue in comparison with the glycoprotein sequence set forth in SEQ ID NO: 4, wherein the glycoprotein preferably comprises at least one mutated amino acid residue at position 181 and/or 185 in comparison with the glycoprotein sequence set forth in SEQ ID NO: 4, wherein the glycoprotein preferably comprises at least one mutation selected from Arg 185→Trp and Ile 181→Met in comparison with the glycoprotein sequence set forth in SEQ ID NO: 4.

Item 7. The virus particle of any one of the preceding items, wherein the S segment is derived from LCMV strain WE or a variant thereof and wherein the L segment is derived from LCMV strain Clone13 or a variant thereof.

Item 8. The virus particle of any one of the preceding items, wherein the S segment comprises an open reading frame encoding a nucleoprotein having at least 97% sequence identity to SEQ ID NO: 6.

Item 9. The virus particle of any one of the preceding items, wherein the L segment comprises an open reading frame encoding a Z protein having at least 90% sequence identity to SEQ ID NO: 38.

Item 10. A virus particle comprising a lymphocytic choriomeningitis virus (LCMV) S segment and an LCMV L segment, wherein the S segment comprises an open reading frame encoding a glycoprotein having at least 97% sequence identity to SEQ ID NO: 4 and an open reading frame encoding a nucleoprotein having at least 97% sequence identity to SEQ ID NO: 6, and wherein the L segment comprises an open reading frame encoding an L protein having at least 90% sequence identity to SEQ ID NO: 40 and an open reading frame encoding a Z protein having at least 90% sequence identity to SEQ ID NO: 38.

Item 11. The virus particle of item 10, wherein the glycoprotein comprises at least one mutated amino acid residue in comparison with the glycoprotein sequence set forth in SEQ ID NO: 4, wherein the glycoprotein preferably comprises at least one mutated amino acid residue at position 181 and/or 185 in comparison with the glycoprotein sequence set forth in SEQ ID NO: 4, wherein the glycoprotein preferably comprises at least one mutation selected from Arg 185→Trp and Ile 181→Met in comparison with the glycoprotein sequence set forth in SEQ ID NO: 4.

Item 12. The virus particle of item 10 or 11, wherein the L protein comprises at position 1079 corresponding the linear polypeptide sequence of SEQ ID NO: 40 an amino acid residue other than Lys, preferably a non-basic amino acid residue, preferably a neutral hydrophilic amino acid residue, preferably an Asn or Gln, preferably a Gln.

Item 13. The virus particle of any one of the preceding items, wherein the virus particle is capable of promoting a stronger reduction of growth of a tumor as compared to LCMV strain WE and/or a virus particle comprising the same S segment as the virus particle and an L segment as shown in SEQ ID NO: 2.

Item 14. The virus particle of any one of the preceding items, wherein the virus particle is capable of promoting a stronger reduction of growth of a cold tumor as compared to LCMV strain WE and/or a virus particle comprising the same S segment as the virus particle and an L segment as shown in SEQ ID NO: 2.

Item 15. The virus particle of any one of the preceding items, wherein the virus particle is capable of inducing a stronger adaptive immune activation as compared to LCMV strain WE and/or a virus particle comprising the same S segment as the virus particle and an L segment as shown in SEQ ID NO: 2.

Item 16. The virus particle of any one of the preceding items, wherein the virus particle is capable of promoting a reduction of growth of a warm tumor that is at least as strong as compared to LCMV strain WE and/or a virus particle comprising the same S segment as the virus particle and an L segment as shown in SEQ ID NO: 2.

Item 17. The virus particle of any one of the preceding items, wherein the virus particle is capable of inducing decreased levels of an interferon upon systemic administration compared to LCMV strain WE, Armstrong, Clone13 and/or a virus particle comprising the same S segment as the virus particle and an L segment as shown in SEQ ID NO: 2.

Item 18. The virus particle of any one of the preceding items, wherein the virus particle is capable of inducing a lower concentration of one or more Th1- and pro-inflammatory cytokines compared to LCMV strain WE, Armstrong, Clone13 and/or a virus particle comprising the same S segment as the virus particle and an L segment as shown in SEQ ID NO: 2.

Item 19. The virus particle of any one of the preceding items, wherein the virus particle is capable of inducing a lower concentration of one or more Th1- and pro-inflammatory cytokines compared to LCMV strain WE, Armstrong, Clone13 and/or a virus particle comprising the same S segment as the virus particle and an L segment as shown in SEQ ID NO: 2.

Item 20. The virus particle of any one of the preceding items, wherein the virus particle is less pathogenic in a mouse compared to LCMV strain WE.

Item 21. The virus particle of any one of the preceding items, wherein the virus particle is capable of inducing a reduced degree of liver pathology in a mouse compared to LCMV strain WE and/or a virus particle comprising the same S segment as the virus particle and an L segment as shown in SEQ ID NO: 2.

Item 22. The virus particle of any one of the preceding items, wherein the virus particle shows reduced replication in neuron cells compared to LCMV strain WE and/or a virus particle comprising the same S segment as the virus particle and an L segment as shown in SEQ ID NO: 2.

Item 23. The virus particle of any one of the preceding items, wherein the virus particle shows increased replication in tumor cells compared to LCMV strain WE.

Item 24. The virus particle of any one of the preceding items, wherein the virus particle shows reduced replication in a healthy organ compared to LCMV strain WE and/or a virus particle comprising the same S segment as the virus particle and an L segment as shown in SEQ ID NO: 2.

Item 25. The virus particle of any one of the preceding items, wherein the S segment comprises an open reading frame encoding a glycoprotein that has at least about 98%, preferably at least about 98.5%, preferably at least about 99%, preferably at least about 99.1%, preferably at least about 99.2%, preferably at least about 99.3%, preferably at least about 99.4%, preferably at least about 99.5%, preferably at least about 99.5%, preferably at least about 99.7% sequence identity, or is preferably identical, to a sequence set forth in SEQ ID NO: 4 or 14.

Item 26. The virus particle of any one of the preceding items, wherein the S segment comprises an open reading frame comprising a sequence that has at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, or is preferably identical, to a sequence set forth in SEQ ID NO: 3 or 13.

Item 27. The virus particle of any one of the preceding items, wherein the L segment comprises an open reading frame encoding an L protein having at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, or is preferably identical, to a sequence set forth in SEQ ID NO: 30 or 40.

Item 28. The virus particle of any one of the preceding items, wherein the L segment comprises an open reading frame comprising a sequence that has at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, preferably at least about 99.8%, preferably at least about 99.9% sequence identity, or is preferably identical, to a sequence set forth in SEQ ID NO: 29 or 39.

Item 29. The virus particle of any one of the preceding items, wherein the S segment comprises an open reading frame encoding a nucleoprotein, wherein said nucleoprotein has at least about 98%, preferably 98.5%, preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in any one of in SEQ ID NO: 6 or 16.

Item 30. The virus particle of any one of the preceding items, wherein the S segment comprises an open reading frame comprising a sequence that has at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in SEQ ID NO: 5 or 15.

Item 31. The virus particle of any one of the preceding items, wherein the L segment comprises an open reading frame encoding a Z protein having at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is preferably identical, to a sequence set forth in SEQ ID NO: 28 or 38.

Item 32. The virus particle of any one of the preceding items, wherein the L segment comprises an open reading frame comprising a sequence that has at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7%, sequence identity, or that is identical, to a sequence set forth in SEQ ID NO: 27 or 37.

Item 33. The virus particle of any one of the preceding items, wherein the S segment comprises a sequence that has at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity, or is preferably identical, to a sequence set forth in SEQ ID NO: 1 or 11.

Item 34. The virus particle of any one of the preceding items, wherein the L segment comprises a sequence that has at least about 83%, preferably at least about 84%, preferably at least about 85%, preferably at least about 86%, preferably at least about 87%, preferably at least about 88%, preferably at least about 89%, preferably at least about 90%, preferably at least about 91%, preferably at least about 92%, preferably at least about 93%, preferably at least about 94%, preferably at least about 95%, preferably at least about 96%, preferably at least about 97%, preferably at least about 98% preferably at least about 99%, preferably at least about 99.1%, preferably at least about 99.2%, preferably at least about 99.3%, preferably at least about 99.4%, preferably at least about 99.5%, preferably at least about 99.6%, preferably at least about 99.7% sequence identity, preferably at least about 99.7%, preferably at least about 99.8%, preferably at least about 99.9% sequence identity, or is preferably identical, to a sequence set forth in SEQ ID NO: 21 or 31.

Item 35. The virus particle of any one of the preceding items, wherein the virus particle is infectious.

Item 36. The virus particle of any one of the preceding items, wherein the virus particle is replication competent.

Item 37. The virus particle of any one of the preceding items, wherein the virus particle is attenuated.

Item 38. The virus particle of any one of the preceding items, wherein the ORF encoding the glycoprotein is under control of a 5' untranslated region (UTR).

Item 39. The virus particle of any one of the preceding items, wherein the ORF encoding the L protein is under control of a 3' untranslated region (UTR).

Item 40. The virus particle of any one of the preceding items, wherein the ORF encoding the nucleoprotein is under control of a 3' untranslated region (UTR).

Item 41. The virus particle of any one of the preceding items, wherein the ORF encoding the Z protein is under control of a 5' untranslated region (UTR).

Item 42. The virus particle of any one of the preceding items, wherein the virus particle has a bi-segmented genome.

Item 43. The virus particle of any one of the preceding items, wherein the virus particle is an arenavirus particle.

Item 44. The virus particle of any one of the preceding items, wherein the virus particle is an LCMV particle.

Item 45. The virus particle of any one of the preceding items, wherein the virus particle does not comprise an ORF from an organism other than an LCMV.

Item 46. A host cell comprising an LCMV S segment and an LCMV L segment as defined in any one of the preceding items.

Item 47. A host cell comprising cDNA of (a) an ORF encoding a glycoprotein as defined in any one of items 1-45, an ORF encoding an L protein as defined in any one of items 1-45, an ORF encoding a nucleoprotein as defined in any one of items 1-45, and an ORF encoding a Z protein as defined in any one of items 1-45; and/or (b) an LCMV S segment and an LCMV L segment as defined in any one of items 1-45.

Item 48. The host cell of item 46 or 47, wherein the host cell is a HEK293 cell.

Item 49. A method of producing a virus particle of any one of items 1-45 comprising cultivating the host cell of any one of items 46-48 under conditions suitable for virus particle formation.

Item 50. The method of item 49 further comprising recovery and/or purification of the virus particle.

Item 51. A pharmaceutical composition comprising a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40.

Item 52. The pharmaceutical composition of item 51, wherein the virus particle is a virus particle of any one of items 1-45.

Item 53. A virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40 for use in therapy.

Item 54. The virus particle for the use of item 53, wherein the virus particle is a virus particle of any one of items 1-45.

Item 55. The virus particle for the use of item 53 or 54, wherein the use is in the treatment of cancer.

Item 56. The virus particle for the use of any one of items 53-55, wherein the use is in the treatment of a human subject.

Item 57. The virus particle for the use of any one of items 53-56, wherein the use is in the treatment of a human cancer.

Item 58. The virus particle for the use of any one of items 53-57, wherein the use is in the treatment of a cold tumor.

Item 59. The virus particle for the use of any one of items 53-58, wherein the use is in the treatment of a hot tumor.

Item 60. The virus particle for the use of any one of items 53-59, wherein the use is in the treatment of a tumor selected from the group consisting of anal carcinoma, bronchial carcinoma, lung carcinoma, endometrial carcinoma, gallbladder carcinoma, bladder carcinoma, hepatocellular carcinoma, testicular carcinoma, colon carcinoma, colorectal carcinoma, colorectal carcinoma, hepatocellular carcinoma, testicular carcinoma, colon carcinoma, tumor of the bladder, bladder carcinoma, tumor of the bladder, hepatocellular carcinoma, lung carcinoma, lung carcinoma, endometrial carcinoma, colorectal carcinoma, rectal carcinoma, laryngeal carcinoma, esophageal carcinoma, gastric carcinoma, breast carcinoma, renal carcinoma, ovarian carcinoma, pancreatic carcinoma, pharyngeal carcinoma, oropharyngeal carcinoma, prostate carcinoma, thyroid carcinoma, Cervical cancer, angiosarcoma, chondrosarcoma, Ewing sarcoma, fibrosarcoma, Kaposi sarcoma, liposarcoma, leiomyosarcoma, malignant fibrosis histiocytoma, lymphoma, leukemia, neurogenic sarcoma, osteosarcoma and rhabdomyosarcoma.

Item 61. A use of a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40 for the manufacture of a medicament, wherein the medicament is preferably for the treatment of cancer.

Item 62. A method of treating a disease comprising administering to a subject in need thereof an effective amount of a virus particle comprising an LCMV S segment and an LCMV L segment, wherein the S segment comprises an open reading frame encoding a glycoprotein having at least 97% sequence identity to SEQ ID NO: 4, and wherein the L segment comprises an open reading frame encoding an L protein having at least 90% sequence identity to SEQ ID NO: 40, wherein the disease is preferably cancer.

EXAMPLES

Mice

Analysis of anti-tumoral effects was performed by using wild type animals on C57BL/6 background. For in vivo analysis of LCMV induced effects wildtype mouse strains C57BL/6, BALB/c or FVB/N were used. C57BL/6 and BALB/c strains are resistant to lethal infection caused by LCMV. FVB/N mice represent a highly susceptible mouse strain which develops a hemorrhagic fever like illness after infection with LCMV strain Clone13. Habitus was observed and weight was measured subsequent to LCMV treatment.

Cell Lines

MC57G (CVCL_4985) is a murine fibrosarcoma cell line, which show robust LCMV replication. Tramp-C2 is a murine prostate gland cell line (CVCL_3615). B16 (CVCL_F936) and B16-F10 (B16F10, CVCL_0159) are murine melanoma cell lines. B16-Ova represents the respective B16 cell line expressing ovalbumin as antigen. MC-38 (MC38, CVCL_B288) is a murine colon adenocarcinoma cell line. JAWSII is a murine, spontaneously immortalized cell line, which can be differentiated into dendritic like cells by treatment with GM-CSF (CVCL_3727). 511950 is a genetically engineered murine primary pancreas cancer cell line passaged less than 20 times (Mazur et al. (2015) Nature medicine 21(10): 1163-1171). Bone marrow derived dendritic cells (BMDCs) were differentiated from murine bone marrow in the presence of GM-CSF.

C643 (CVCL_5969) is a human anaplastic thyroid carcinoma cell line. NCI-H1975 (H1975, CVCL_1511) is a human lung adenocarcinoma cell line. A549 is human adenocarcinoma cell line (CVCL_0023). FTC133 is a human thyroid carcinoma cell line (CVCL_1219). GIST-T1 is a human gastrointestinal tumor cell line derived from pleural effusion (CVCL_4976). Hek293T (CVCL_0063) is a human embryonic kidney cell line, which shows robust LCMV replication. FreeStyle 293-F (CVCL_D603) is a derivative of Hek293 cells, propagated in Freestyle Medium. FreeStyle 293-F cells are the desired producer cell line for LCMV production.

UKE-Ma-Mel-51 (Mamel51, CVCL_A186) and UKE-Ma-Mel-86a (Ma-Mel-86a, CVCL_A221) are human primary melanoma cell lines derived from lymph node metastasis provided by Prof. Dr. Paschen, Klinik für Dermatologie, UK Essen. Primary human neurons were differentiated from human neuronal progenitor cells (NPC) kindly provided by Prof. Dr. Gopalakrishnan, HHU Düsseldorf. SkMM (Human Skeletal muscle myoblasts, Lonza CC-2580) are human primary skeletal myoblasts. Myotubes were differentiated from SkMM in the presence of SkGM-2, Horse Serum, Glutamine, Gentamicin and Dexamethasone. Differentiation was verified by staining with Anti-Myosin 4 AK (eBioscience, Clone MF-20).

BHK-21 cells represent a spontaneous immortalized fibroblast hamster cell line (CVCL_1914).

Viruses

The LCMV strain WE was obtained from the laboratory of Prof. Zinkernagel (Experimental Immunology, Zurich, Switzerland) and has been propagated in L929 cells or BHK-21 cells since 2008.

The LCMV strains Clone13 and Armstrong 53b were obtained from S. Basta, Queens University and R. M. Zinkernagel, University of Zurich, respectively. The LCMV reassortants WE-Cl13(L), P52-Cl13(L), P52-WE(L) and Cl13-WE(L) were rescued by transient transfection entirely from plasmids as described (Flatz et al. (2006) Proc Natl Acad Sci USA 103(12): 4663-4668). The viruses consist of the S-Segment of the LCMV strain WE or WE-derived P52 and the L-Segment of the LCMV strains Clone13 or WE. Viruses were propagated on BHK-21 or Freestyle 293F cells.

Generation of Recombinant Viruses

LCMV recombinant and reassortant viruses were generated entirely from plasmids. BHK-21 cells were transiently transfected with plasmids coding for the LCMV S segment, L segment as well as helper plasmids coding for the L polymerase and the nucleoprotein. The LCMV reassortant WE-Cl13(L) was generated using a WE S segment and the Clone13 L segment plasmid. The LCMV P52-Cl13(L) was rescued using a LCMV P52 S segment plasmid, which harbors two coding mutations in the glycoproteins, I181M and R185W, and a Clone13 L segment plasmid. The LCMV P52-WE(L) was generated using a LCMV P52 S segment plasmid and a LCMV WE L segment plasmid. The Cl13-WE(L) was generated using a LCMV Clone13 S segment plasmid and a WE L segment plasmid.

Determination of LCMV Infected Cells and Infiltration of Immune Cell in Tumor Tissue Ex Vivo by Immunofluorescence Immunohistofluorescence was used to detect LCMV and immune cell distribution in tumor tissues of LCMV treated or control treated tumor bearing mice. Tumor biopsies were cut into 7 μm thick sections and stained with a fluorochrome-labelled anti-LCMV-NP antibody (clone VL4), and antibody against CD8 (eBioscience) and visualized with a fluorescence microscope (Keyence) and photographed with an integrated CCD camera.

Determination of LCMV in Supernatant or Organs by Plaque-Forming Assay

To analyze LCMV replication capacity, tumor and primary cells were seeded out in 24-well plates (100.000 cells/well) and infected with LCMV at MOIs shown. Supernatant was harvested 24 h, 48 h or 72 h after infection. Analysis of LCMV production by FreeStyle 293-F cells was performed by seeding out $1.5\times10^6$ cells per mL and infection with LCMV at MOI=0.001. Supernatant was harvested after 12, 24, 30, 34, 40, 48, 72 and 96 hours post infection. Analysis of LCMV biodistribution was performed in infected tumor bearing and non-tumor bearing animals. Organs of infected mice were dissected and homogenized in cell culture medium. The supernatants were titrated and incubated on MC57G cells (100.000 cells/well). Methylcellulose overlay was added after three to four hours. LCMV infected plaques were stained with anti LCMV-NP antibody (clone VL4). Plaques were counted and infectious particles were determined as virus titer per mL of supernatant or per organ.

Determination of LCMV Infected Cells by Flow Cytometry

To analyze LCMV infectivity in tumor and primary cells, cells were seeded out in 96-well plates, infected with LCMV at MOI=0.1 or left untreated and incubated one hour on ice. After one hour, cells were transferred to 37° C. 20 h post infection, cells were harvested and intracellular LCMV staining was performed using fluorescent labelled LCMV NP antibody (clone VL4). Cells were analyzed via flow cytometry (LSR Fortessa, BD) and results were displayed as percent LCMV infected cells or mean fluorescent intensity (MFI).

Determination of Cytokine Production by Flow Cytometry

The intensity of immune activation by LCMV was analyzed by measuring cytokines in serum. Therefore, serum of naïve or infected mice, with or without tumors, was analyzed via LegendPlex analysis according to manufacturer's protocol (BioLegend).

Clinical Chemistry

The induction of liver pathology by LCMV was determined by measuring alanine aminotransferase (ALT) and aspartate aminotransferase (AST). Mice were bled on various days after LCMV infection and serum was extracted. Analysis of ALT and AST values was performed at Zentrallabor, Universitasklinkum Essen or Zentralinstitut für Klinische Chemie and Laboratoriumsdiagnostik, HHU Düsseldorf.

Analysis of Immune Cells by Flow Cytometry

To determine the effect of LCMV therapy immune cells were analyzed via flow cytometry (LSR Fortessa, BD). Thrombocytes were detected by their specific size and granularity. T cells were stained with specific fluorescent labelled antibodies for CD8, CD4, CD3 (eBioscience). LCMV specific T cells were stained using tetramer staining (NIH, Tetramer Facility).

Tumor Growth and Treatments

To measure the anti-tumoral effect of LCMV therapy, C57BL/6 mice (6-12 weeks old) were subcutaneously injected with $1\times10^6$ tumor cells (in 100 μL) into the right or left flank. After a visible tumor formation, animals were LCMV or control treated, and the mean tumor volume was determined. Endpoint analysis of tumor mass was performed by measuring the total weight (in g) of the tumor.

Statistical Analysis

For column diagrams the mean values were compared using unpaired two-sample Student's t-test. Tumor growth curves were compared using two-way ANOVA with Skidak's multiple comparison test. Data are presented as mean±SEM. The level of statistical significance was determined to be $p<0.05$.

Investigations

Example 1

Figure 1:
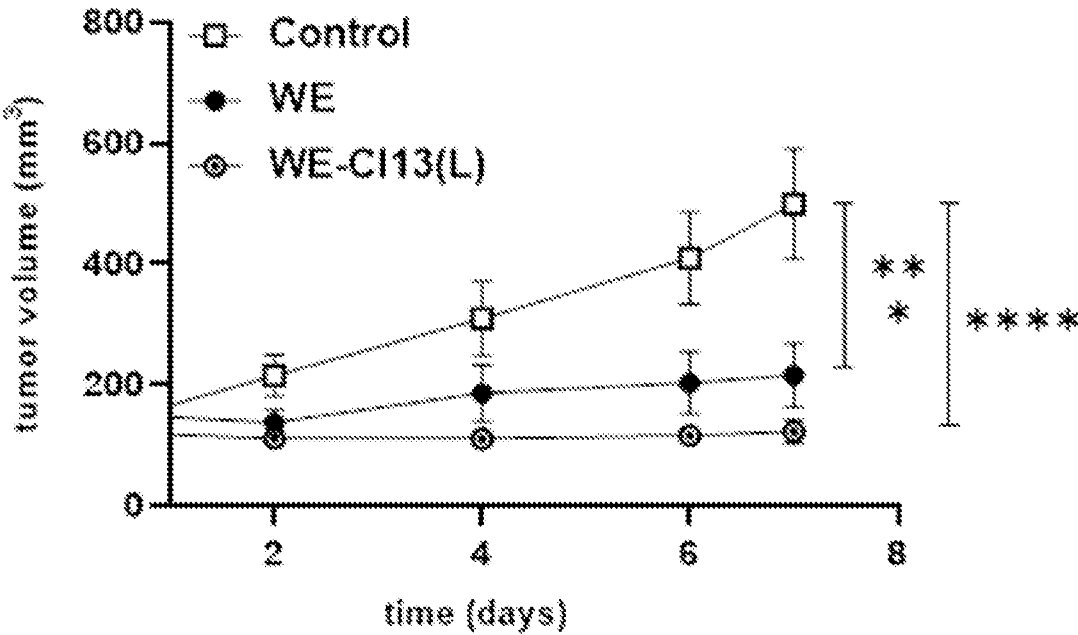
FIG. 1: Murine B16 tumor-bearing Bl/6 mice, LCMV wild type (WE) and recombinant strains with 2×10E4 PFU/animal i.v. at day 0, tumor growth measurement for 7 days and tumor mass at day 7 (n=5 animals/group), one way ANOVA and Dunnett's multiple comparisons tests for statistics.
Figure 1:
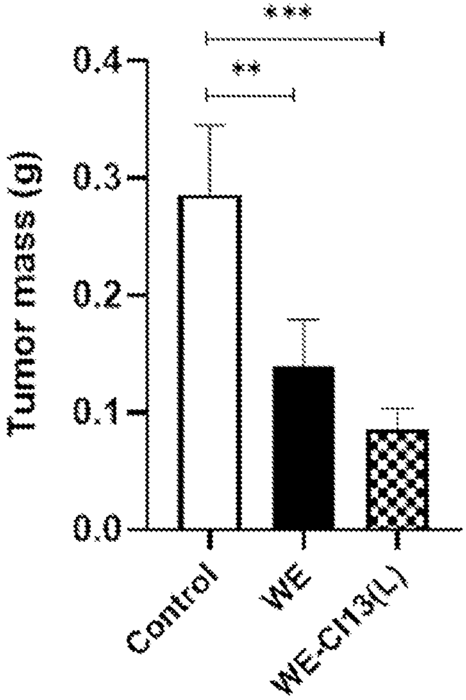

C57BL/6 mice were subcutaneously treated with B16 melanoma cells and intravenously infected with $2\times10^4$ PFU of the LCMV strains WE or WE-Cl13(L) or were control treated (n=5 animals per group). Tumor growth was measured over seven days. Tumor mass was taken at finalization (d7) (FIG. 1).

Thereby it was proven that LCMV WE-CL13(L) shows an increased antitumoral effect compared to wildtype LCMV strain WE in the non-immunogenic cold B16 melanoma tumor model. This model is an example for a cold tumor.

Example 2

Figure 2:
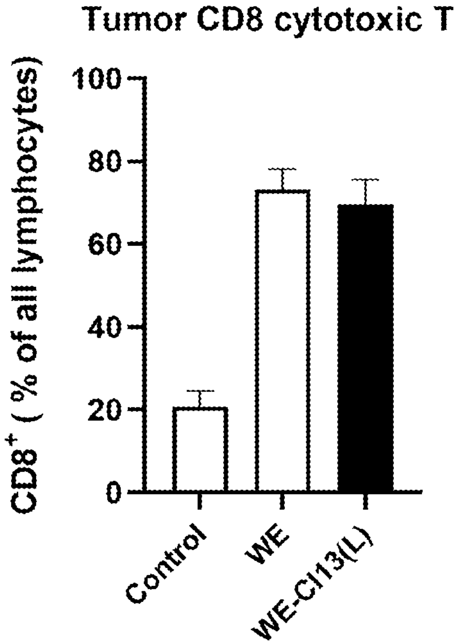
FIG. 2: Murine B16 tumor-bearing Bl/6 mice, LCMV wild type (WE) and recombinant strains with 2×10E4 PFU/animal i.v. at day 0, CD8 T cells by flow cytometry from tumor at day 7 (n=5 animals/group).

C57BL/6 mice were subcutaneously treated with B16 melanoma cells and intravenously infected with $2\times10^4$ PFU of LCMV strains WE or WE-Cl13(L) or were control treated (n=5 animals per group). Mice were sacrificed at day seven after infection. Tumor resident cytotoxic $CD8^+$ T cells were stained with fluorescently labelled antibody (CD8 eBioscience) and analyzed via flow cytometry (FIG. 2).

Thereby it was proven that LCMV strain WE-Cl13(L) enhances T cell infiltration into the tumor tissue.

Example 3

Figure 3:
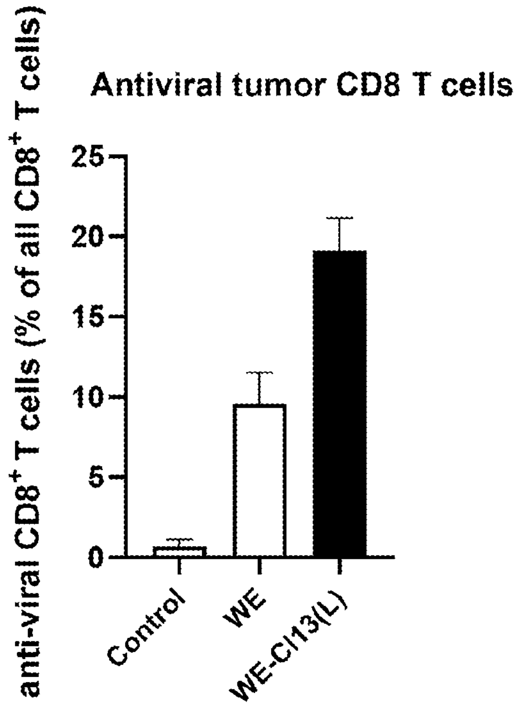
FIG. 3: Murine B16 tumor-bearing Bl/6 mice, LCMV wild type (WE) and recombinant strains with 2×10E4 PFU/animal i.v. at day 0, virus-specific (GP33) CD8 T cells by flow cytometry from tumor at day 7 (n=5 animals/group).

C57BL/6 mice were subcutaneously treated with B16 melanoma cells and intravenously infected with $2\times10^4$ PFU of LCMV strains WE or WE-Cl13(L) or were control treated (n=5 animals per group). Mice were sacrificed at day seven after infection. Tumor resident cytotoxic, antiviral $CD8^+$ GP33-tetramer positive T cells were analyzed via flow cytometry on day seven after infection (FIG. 3).

Thereby it was proven that LCMV strain WE-Cl13(L) induces a stronger adaptive immune activation than wildtype LCMV strain WE.

Example 4

Figure 4:
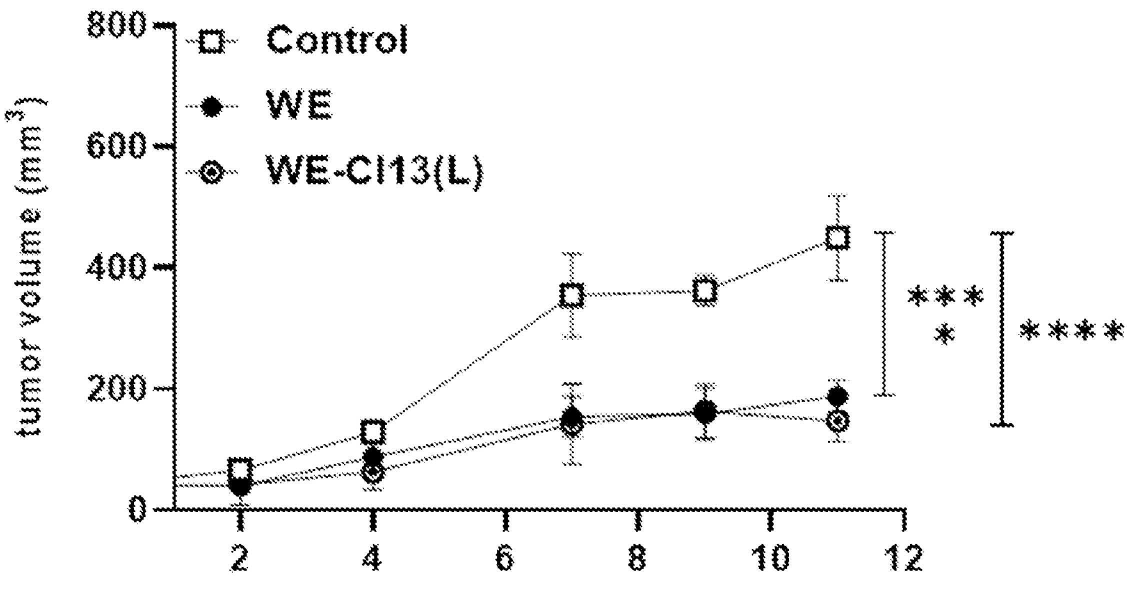
FIG. 4: Murine MC38 tumor-bearing Bl/6 mice, LCMV wild type (WE) and recombinant strains with 2×10E4 PFU/animal i.v. at day 0, tumor growth measurement for 11 days (n=4 animals/group), t-test for statistics.
Figure 5:
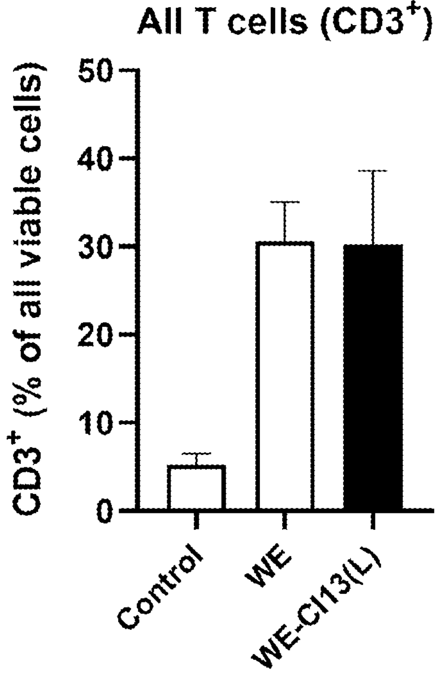
FIG. 5: Murine MC38 tumor-bearing Bl/6 mice, LCMV wild type (WE) and recombinant strains with 2×10E4 PFU/animal i.v. at day 0, tumor infiltrating T cells ($CD3^+$) measured via flow cytometry at day 11 (n=4 animals/group).

C57BL/6 mice were subcutaneously treated with MC38 colon carcinoma cells. Upon tumor formation mice were intravenously infected with $2\times10^4$ PFU of LCMV strains WE or WE-Cl13(L) or were control treated (n=4 animals per group). Tumor growth was observed for eleven days (FIG. 4).

Thereby it was proven that LCMV strain WE-Cl13(L) shows a strong tumor growth inhibiting effect in the immunogenic warm MC38 tumor model. This is a model for a warm tumor.

Example 5

C57BL/6 mice were subcutaneously treated with MC38 colon carcinoma cells. Upon tumor formation mice were intravenously infected with $2\times10^4$ PFU of LCMV strains WE or WE-Cl13(L) or were control treated (n=4 animals per group). Tumor tissue was dissected on day eleven after infection. Tumor infiltrating T cells ($CD3^+$) were stained via fluorescent labelled antibody (CD3, eBioscience) and measured via flow cytometry (Example 5).

Thereby it was proven that LCMV strain WE-Cl13(L) induces a strong T cell infiltration into the tumor.

Example 6

Figure 6:
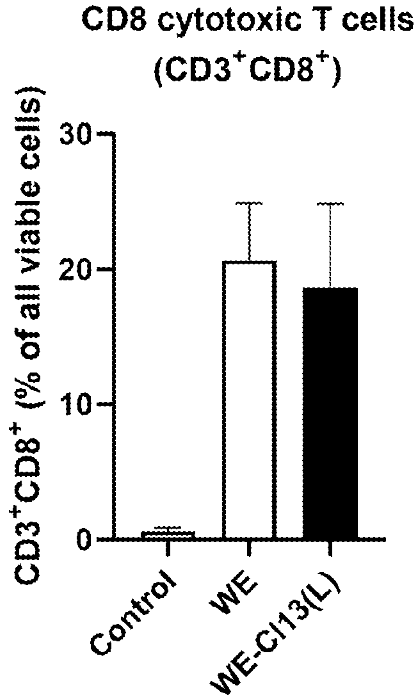
FIG. 6: Murine MC38 tumor-bearing Bl/6 mice, LCMV wild type (WE) and recombinant strains with 2×10E4 PFU/animal i.v. at day 0, tumor infiltrating cytotoxic T cells ($CD3^+CD8^+$) measured via flow cytometry at day 11 (n=4 animals/group).

C57BL/6 mice were subcutaneously treated with MC38 cells and intravenously infected with $2\times10^4$ PFU of LCMV strains WE or WE-Cl13(L) or were control treated (n=4 animals per group). Tumor tissue was dissected on day eleven after infection. Tumor infiltrating cytotoxic T cells ($CD3^+CD8^+$) were stained via fluorescent labelled antibodies (CD3, CD8, eBioscience) and analyzed via flow cytometry (FIG. 6).

Thereby it was proven that LCMV strain WE-Cl13(L) strongly enhances cytotoxic T cell infiltration into the tumor.

Example 7

Figure 7:
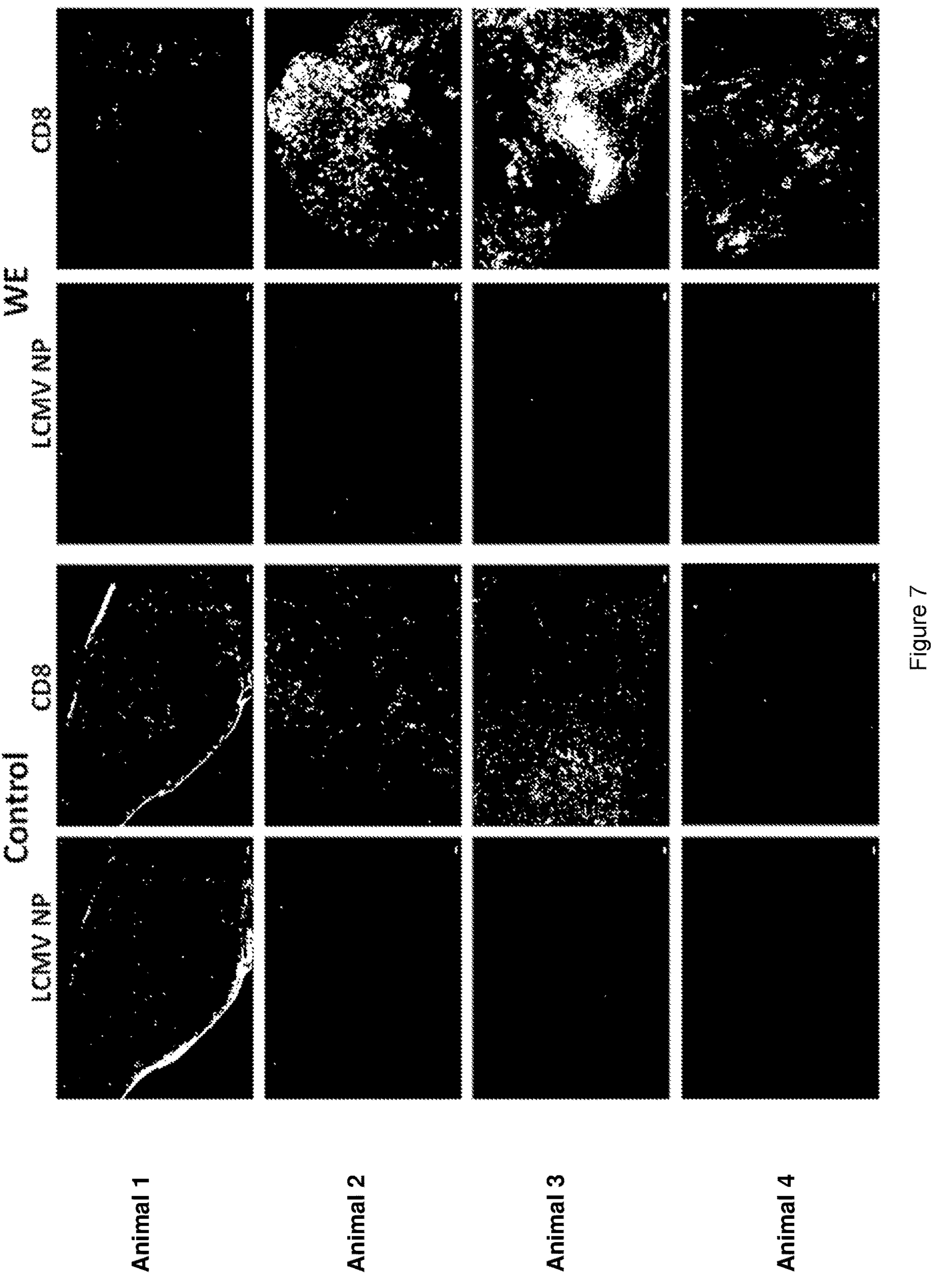
FIG. 7: Murine MC38 tumor-bearing Bl/6 mice, LCMV wild type (WE) and recombinant strains with 2×10E4 PFU/animal i.v. at day 0, tumor immunohistochemistry (IHC) for LCMV (NP protein$^+$) CD8 T cells ($CD8^+$) at day 11 (n=(3)4 animals/group).
Figure 7:
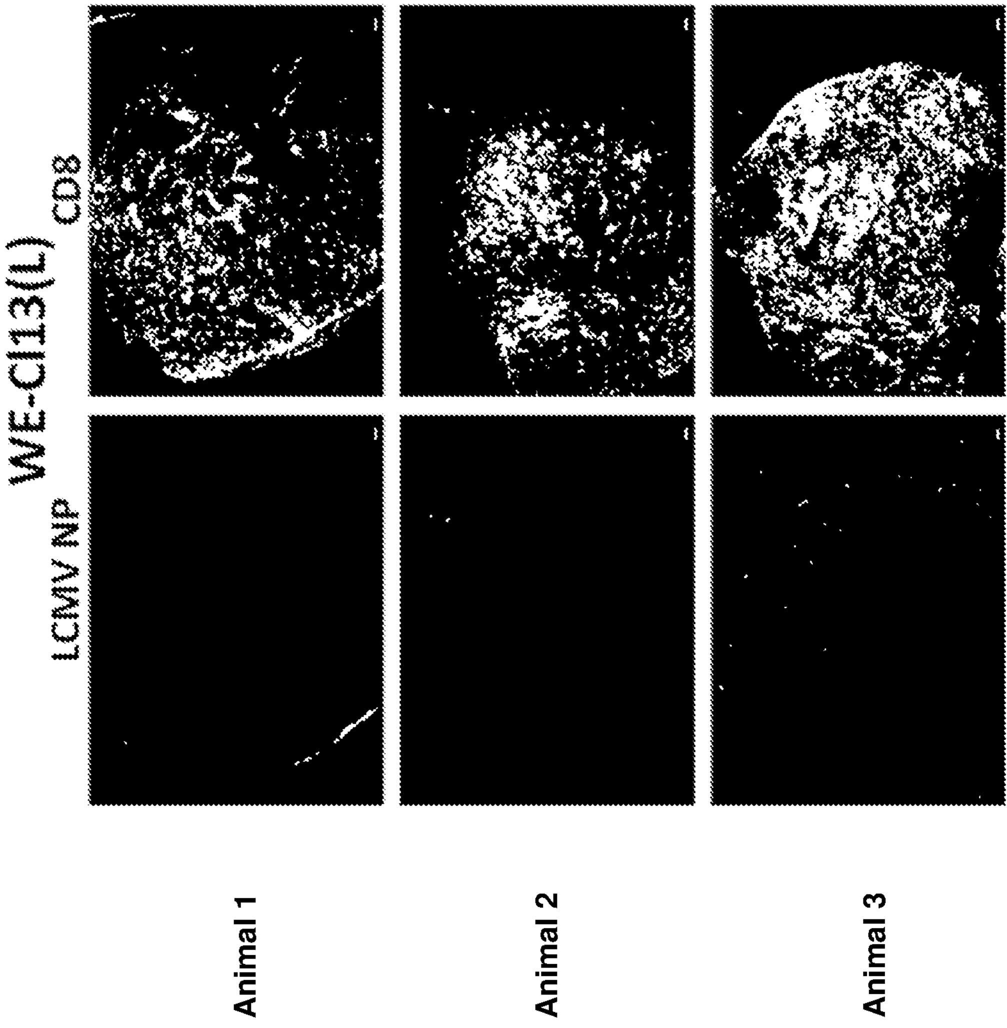

C57BL/6 mice were subcutaneously treated with MC38 cells and intravenously infected with $2\times10^4$ PFU of LCMV strains WE (n=4) or WE-Cl13(L) (n=3) or were control treated (n=4). Tumor tissue was histologically analyzed. Tumor sections (7 μm) were stained with fluorescent labelled antibodies for LCMV nucleoprotein (LCMV NP, clone VL4) and $CD8^+$ T cells (CD8) (FIG. 7).

Thereby it was proven that LCMV strain WE-Cl13(L) enhances cytotoxic T cell infiltration into the tumor independent of a specific local virus presence.

Example 8

Figure 8:
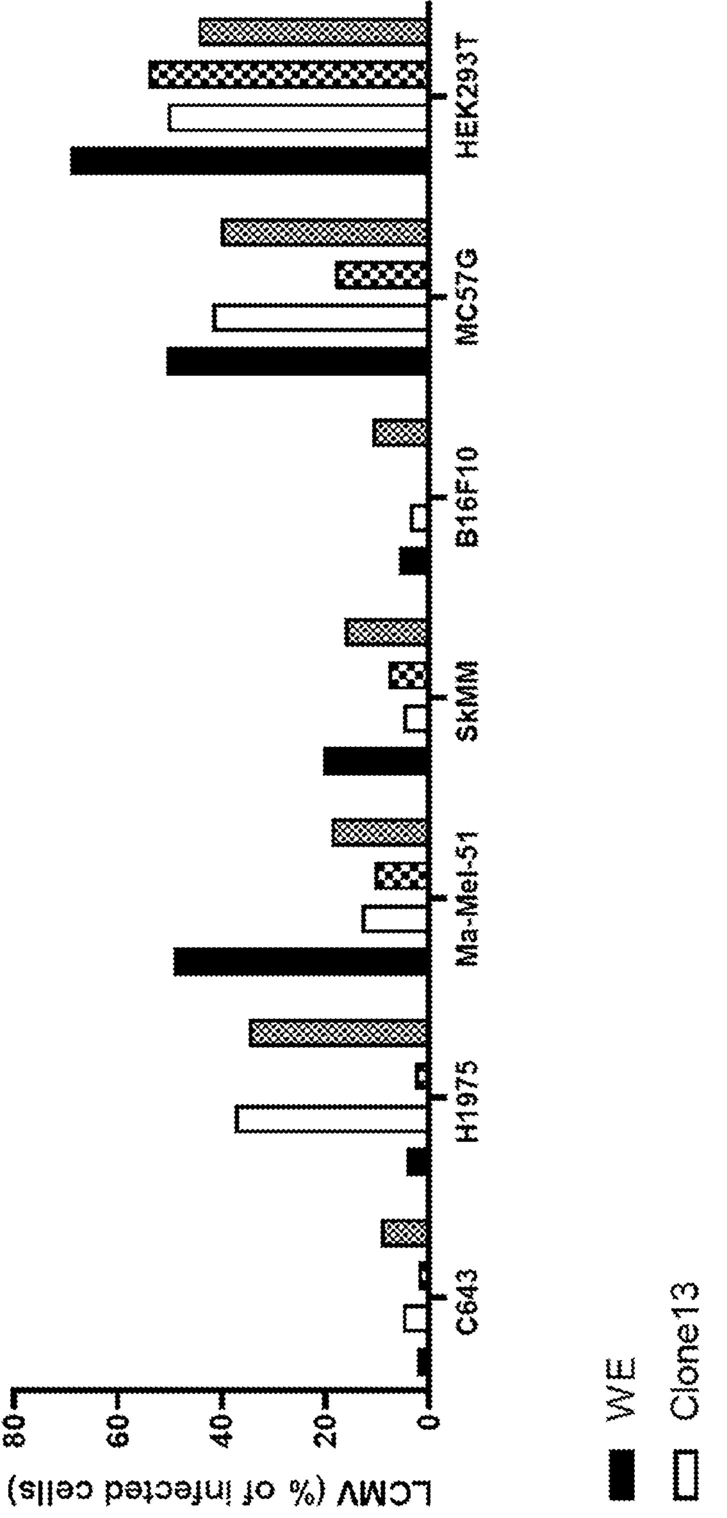
FIG. 8: In vitro replication for 20 h of wild type (WE, Clone13) and recombinant viruses at MOI=0.1 by flow cytometry (NP protein) in HEK293T and human tumor cell lines H1975 (lung), SkMM (myeloma), Ma-Mel-51 (melanoma), C643 (thyroid) and murine tumor cell lines MC-57 (fibrosarcoma) and B16F10 (melanoma).
Figure 9:
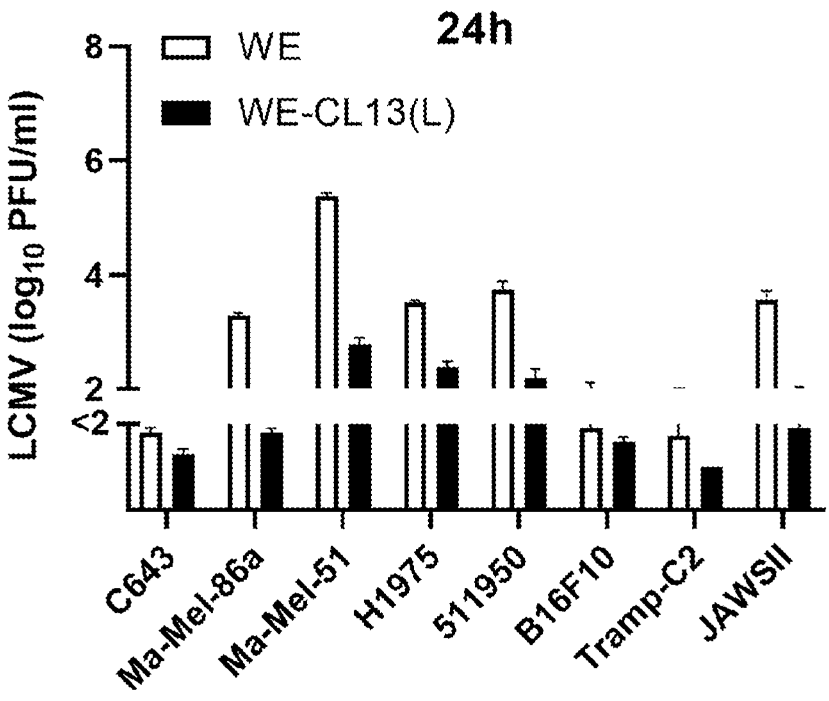
FIG. 9: In vitro replication for 24 h or 48 h of wild type (WE) and recombinant WE-Cl13 viruses at MOI=0.1 by colony formation assay on MC57 cells, in human tumor cell lines H1975 (lung), Mamel86a and 51 (melanoma), C643 (thyroid), murine tumor cell lines 511950 (pancreas), Tramp-C2 (prostate), B16.F10 (melanoma), and murine dendritic cell line JAWSII.
Figure 9:
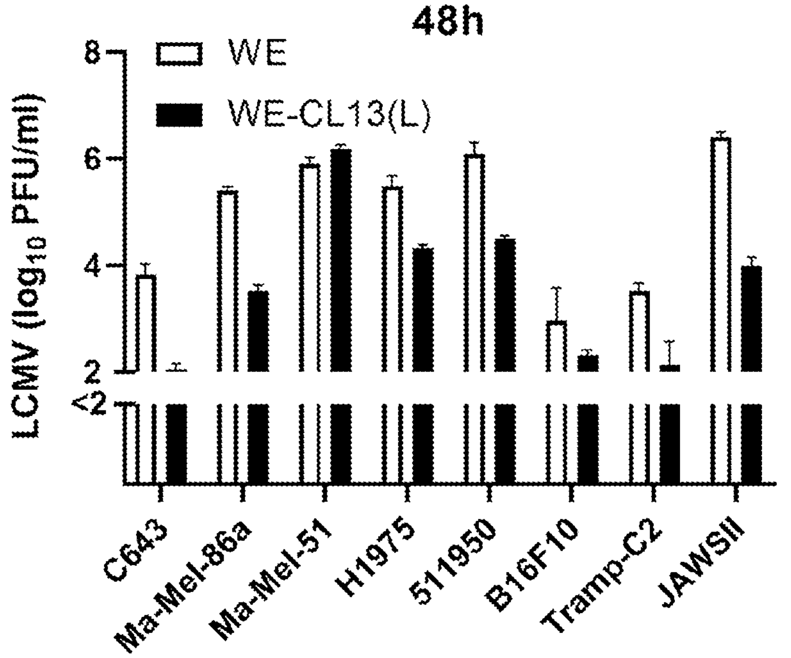

C643, H1975, Ma-Mel-51, SkMM, B16F10, MC57G and HEK293T cells were seeded out (100.000 cells/well) and infected with LCMV strains WE, Clone13, WE-Cl13(L) (WE S-Segment, Clone13 L-Segment) and Clone13-WE(L) (Clone13 S-Segment, WE L Segment) at MOI=0.1. Cells were cultured for 20 hours and intracellularly stained for presence of LCMV nucleoprotein via fluorescent labelled antibody (NP, Clone VL4). The percentage of infected cell from all cells was analyzed via flow cytometry (FIG. 8).

Thereby it was proven that the Clone13 L-Segment is responsible for the attenuation of the virus on all tumor cell lines but does not strongly decrease infection of producer cell line HEK293.

Example 9

C643, Ma-Mel-86a, Ma-Mel-51, 511950, B16F10, Tramp-C2 and JAWSII cells were seeded out (100.000 cells/well) and infected with LCMV strains WE and WE-Cl13(L) at MOI=0.1, 24 and 48 hours post infection supernatants were harvested and analyzed for LCMV replication via LCMV focus forming assay (Example 9).

Thereby it was proven that LCMV strain WE-Cl13(L) replication capacity is attenuated on tumor cells and antigen presenting cells (JAWSII).

Example 10

Figure 10:
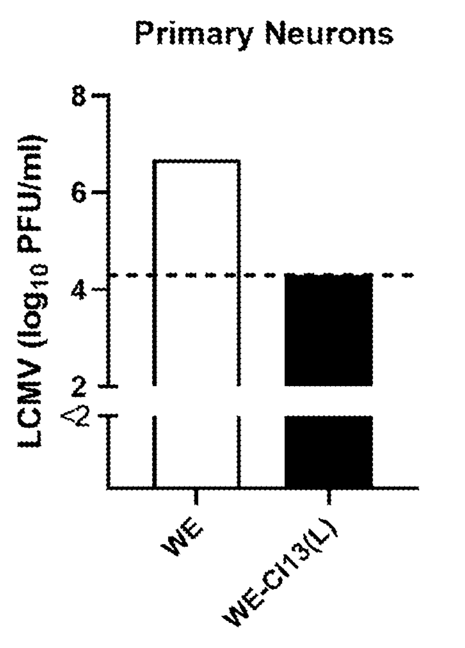
FIG. 10: In vitro replication for 48 h of wild type (WE) and recombinant viruses at MOI=0.1 by replication assay in human primary neurons, murine tumor cell line MC-57 (fibrosarcoma), murine MC57G cells, human lung adenocarcinoma cell line A549 and human thyroid carcinoma cell line FTC133, line: initial inoculum.
Figure 10:
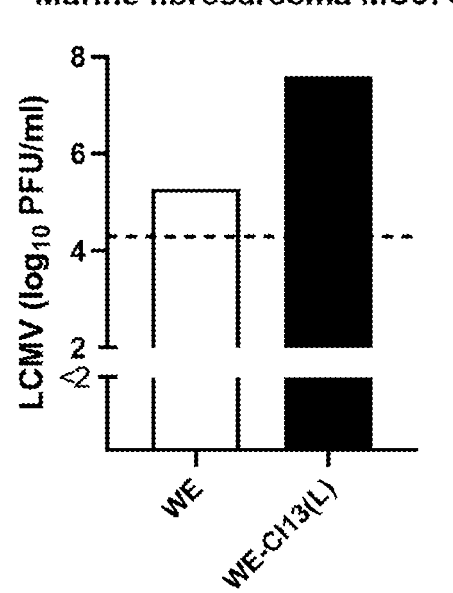
Figure 10:
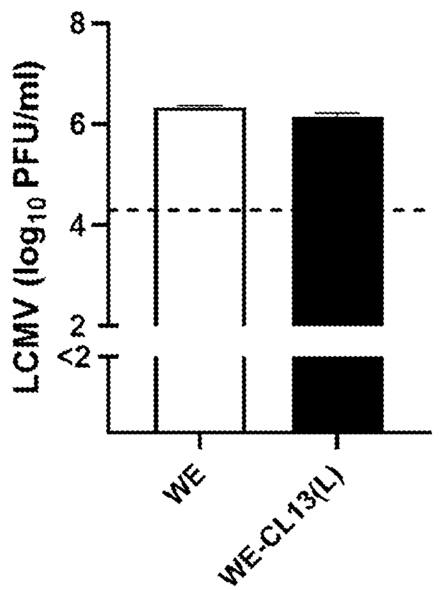
Figure 10:
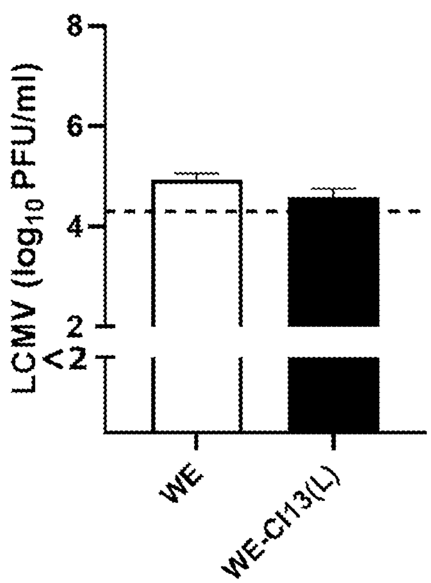

Primary human neurons, murine MC57G cells, human lung adenocarcinoma cell line A549 and human thyroid carcinoma cell line FTC133 were seeded out (100.000 cells/well) and infected at MOI=0.1 with LCMV WE and WE-Cl13(L). Supernatant was harvested after 48 hours and analyzed for LCMV replication via focus forming assay (FIG. 10).

Thereby it was proven that LCMV strain WE-Cl13(L) shows lack of neurotropism but simultaneously enhanced replication in susceptible tumor cells such as the murine fibrosarcoma cell line MC57G and robust replication on human cancer cell lines A549 and FTC133 compared to LCMV strain WE.

Example 11

Figure 11:
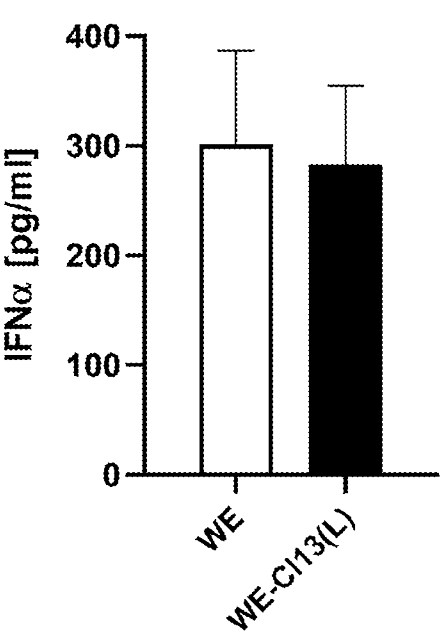
FIG. 11: Bone marrow-derived dendritic cells.

Bone marrow derived dendritic cells were infected with LCMV strains WE and WE-Cl13. Supernatants were harvested and analyzed for Interferon alpha protein via commercial Interferon alpha ELISA-Kit (FIG. 11).

Thereby it was proven that LCMV strain WE-Cl13(L) induces similar interferon response to LCMV WE upon in vitro infection of dendric cells.

Example 12

Figure 12:
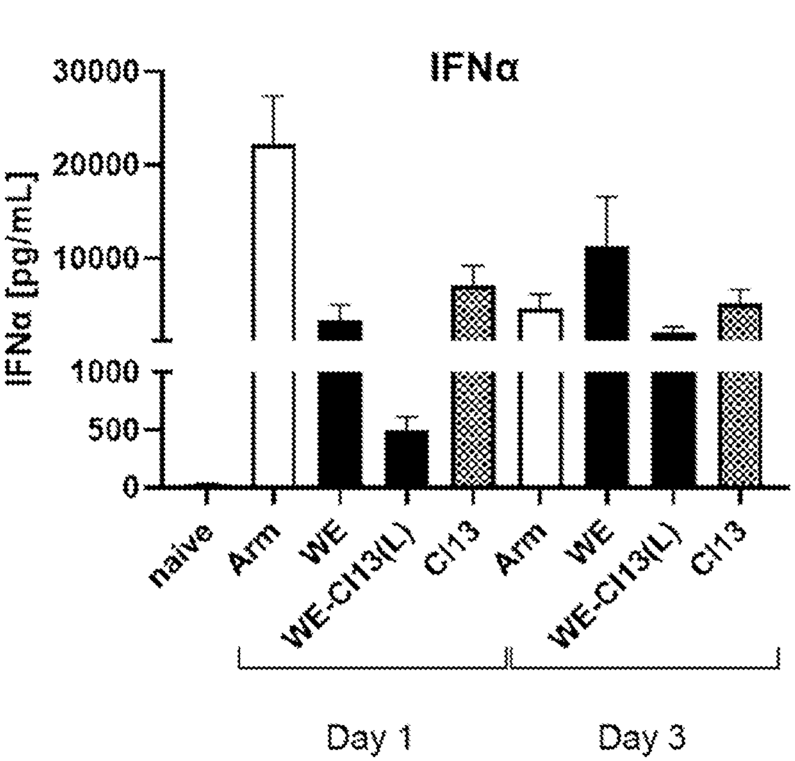
FIG. 12: Treatment of Bl/6 mice with 2×10E4 PFU/animal i.v., serum cytokines at days 1 and 3 p.i. Dotted line indicates lower detection limit.
Figure 12:
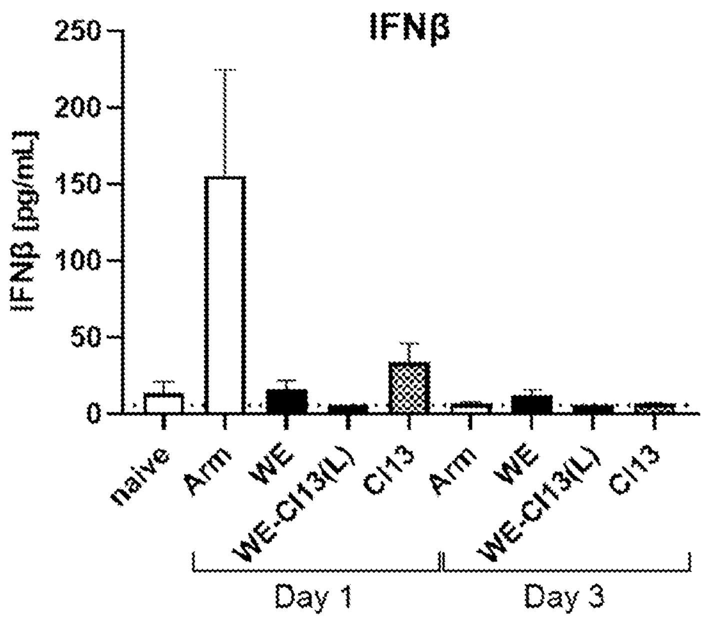

C57BL/6 mice were intravenously infected with $2\times10^4$ PFU of LCMV strains Armstrong (Arm, n=3), WE (n=3), WE-Cl13(L) (n=3) or Clone13 (Cl13, n=3) or left untreated (n=12). Blood was taken at day one and day three after infection. Serum cytokine concentrations of IFNα and IFNβ were analyzed via LegendPlex assay (BioLegend) (FIG. 12).

Thereby it was proven that LCMV WE-Cl13(L) reassortant induces decreased levels of Interferons in mice upon systemic administration.

Example 13

Figure 13:
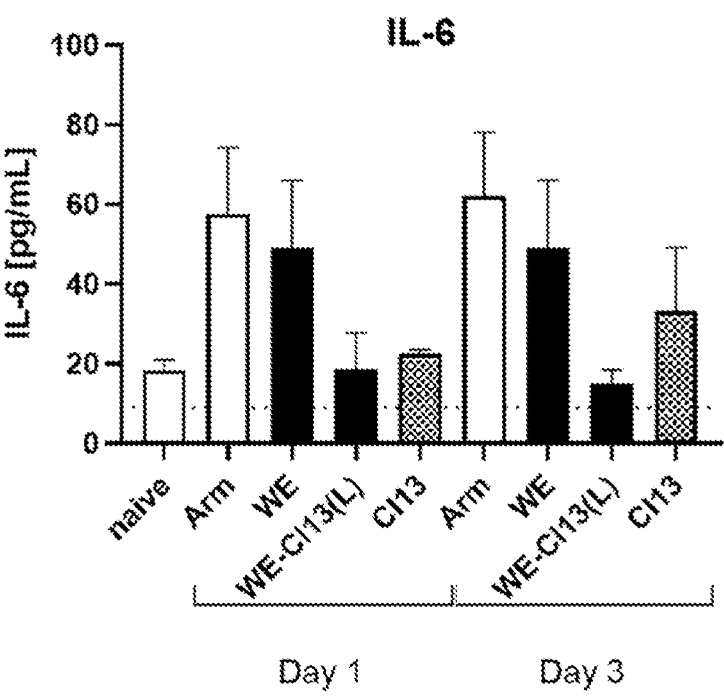
FIG. 13: Treatment of Bl/6 mice with 2×10E4PFU/animal i.v., serum cytokines at days 1 and 3 p.i. Dotted line indicates lower detection limit.
Figure 13:
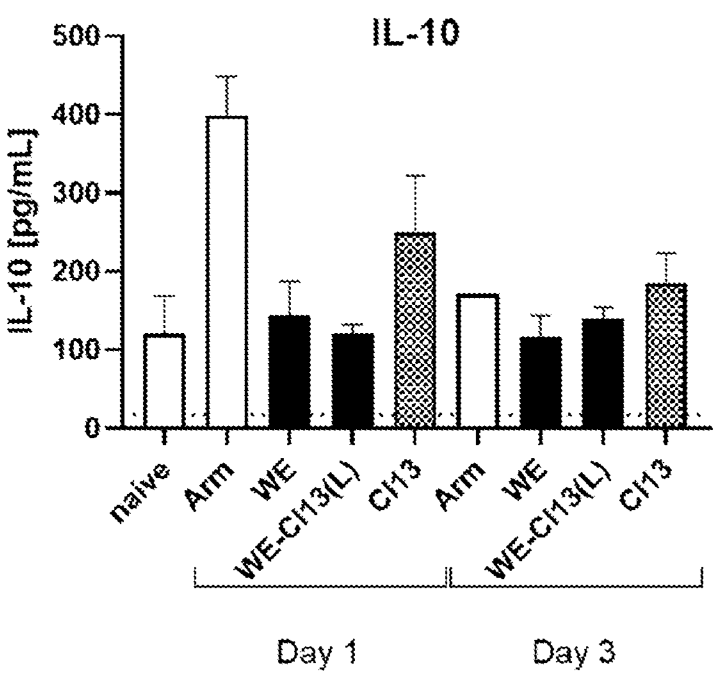
Figure 13:
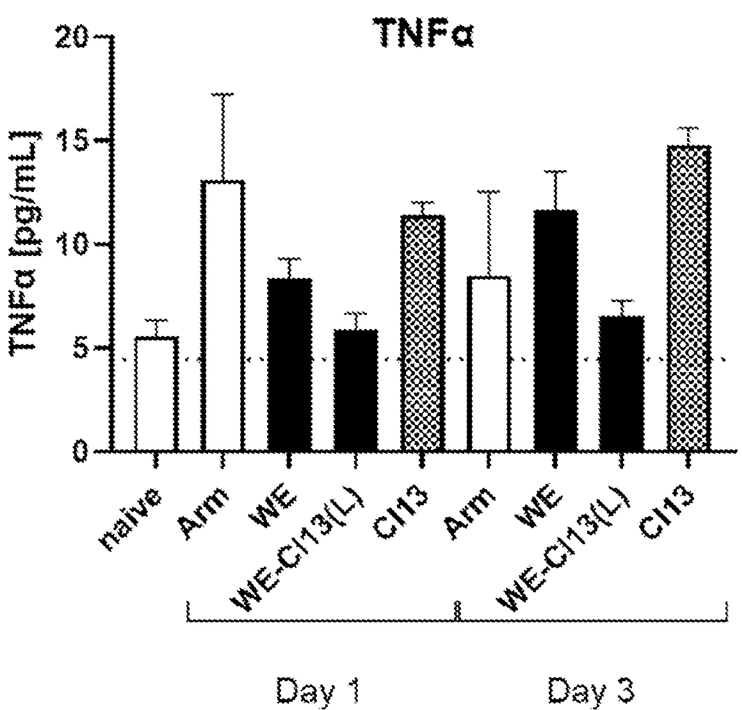
Figure 13:
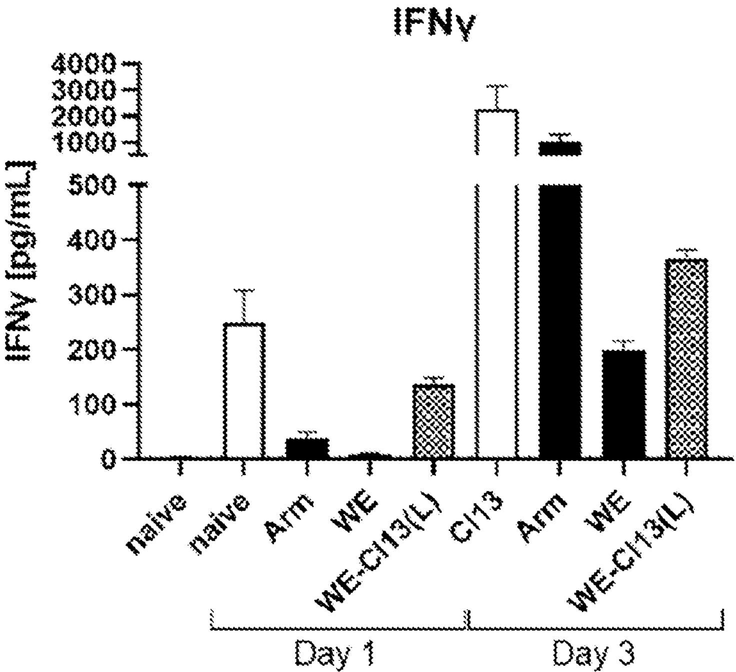

C57BL/6 mice were intravenously infected with $2\times10^4$ PFU of LCMV strains Armstrong (Arm, n=3), WE (n=3), WE-Cl13(L) (n=3) or Clone13 (Cl13, n=3) or left untreated (n=12). Blood was taken at day one and day three after infection. Serum cytokine concentrations of IL-6, Il-10, TNFα and IFNγ were analyzed via LegendPlex assay (BioLegend) (FIG. 13).

Thereby it was proven, that LCMV strain WE-CL13(L) induces lower concentrations of Th1- and pro-inflammatory cytokines in mice.

Example 14

Figures 14, 15:
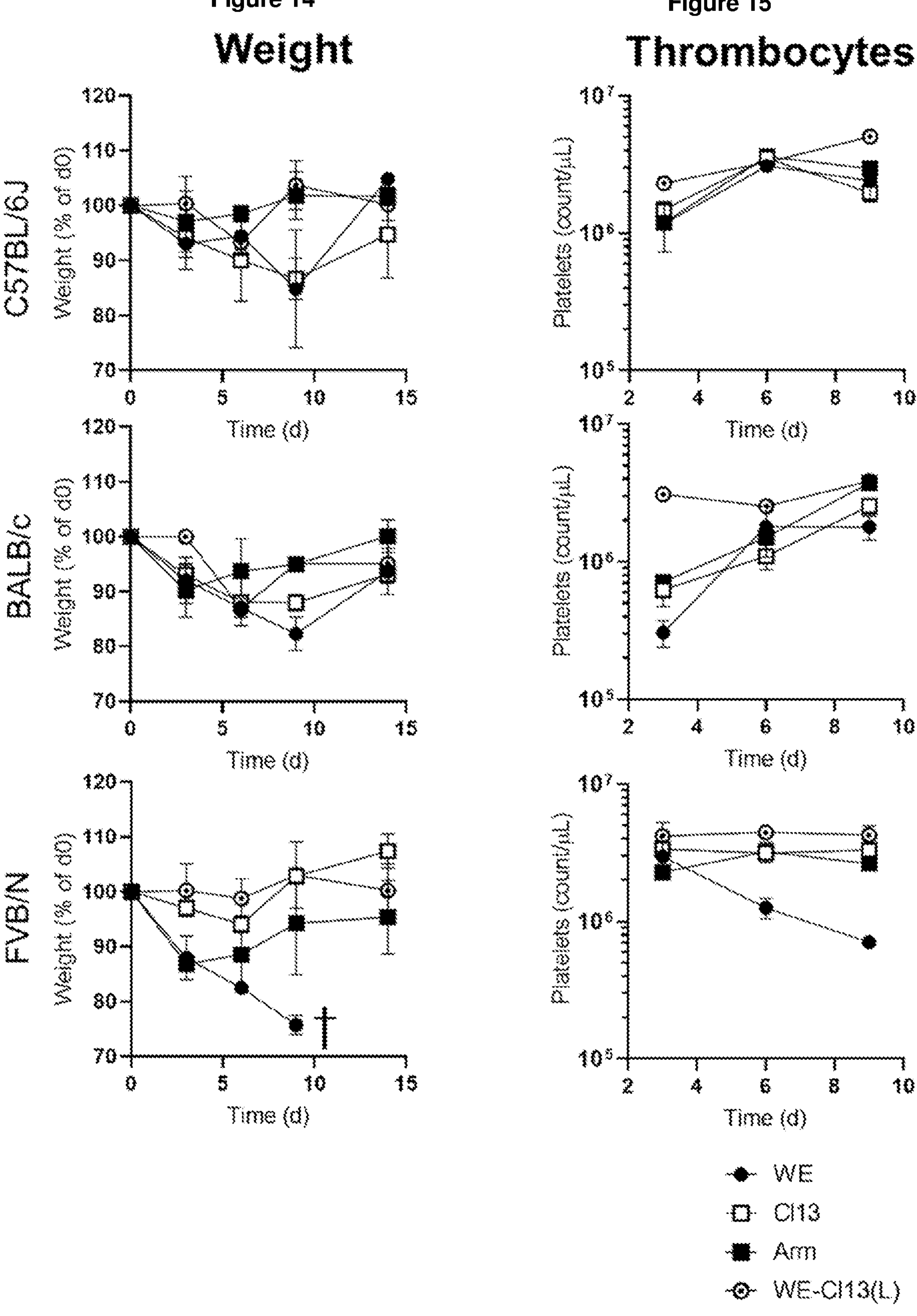
FIG. 14: Mouse strains with LCMV wild type (WE, Clone13, Arm) and recombinant (Clone13 L, WE S) strains with 2×10E6 PFU/animal i.v. at day 0 (n=3 animals/group).
FIG. 15: Mouse strains with LCMV wild type (WE, Clone13, Arm) and recombinant (Clone13 L, WE S) strains with 2×10E6 PFU/animal i.v. at day 0 (n=3 animals/group).

Wild type C57BL/6 or BALB/c mice or the highly susceptible mouse strain FVB/N were intravenously infected with $2\times10^6$ PFU of LCMV strains WE, Cl13 (Clone13), Arm (Armstrong) or WE-Cl13(L) (n=3). Weight was measured for a time span of 14 days. The weight was analyzed as percentage of weight on day of infection (FIG. 14).

Thereby it was proven that LCMV reassortant WE-Cl13 (L) does not induce lethal pathologies in the highly susceptible mouse strain FVB/N compared to wild type LCMV stain WE.

Example 15

Wild type C57BL/6 or BALB/c mice or the highly susceptible mouse strain FVB/N were intravenously infected with $2\times10^6$ PFU of LCMV strains WE, Cl13 (Clone13), Arm (Armstrong) or WE-Cl13(L) (N=3). Mice were bled at days three, six and nine. Platelets (Thrombocytes) were measured in full blood via flow cytometry. Total count of platelets per microliter of blood was analyzed (FIG. 15).

Thereby it was shown that LCMV strain WE-Cl13(L) does not induce thrombocytopenia in highly susceptible FVB/N and other mouse strains.

Example 16

Figures 16, 17:
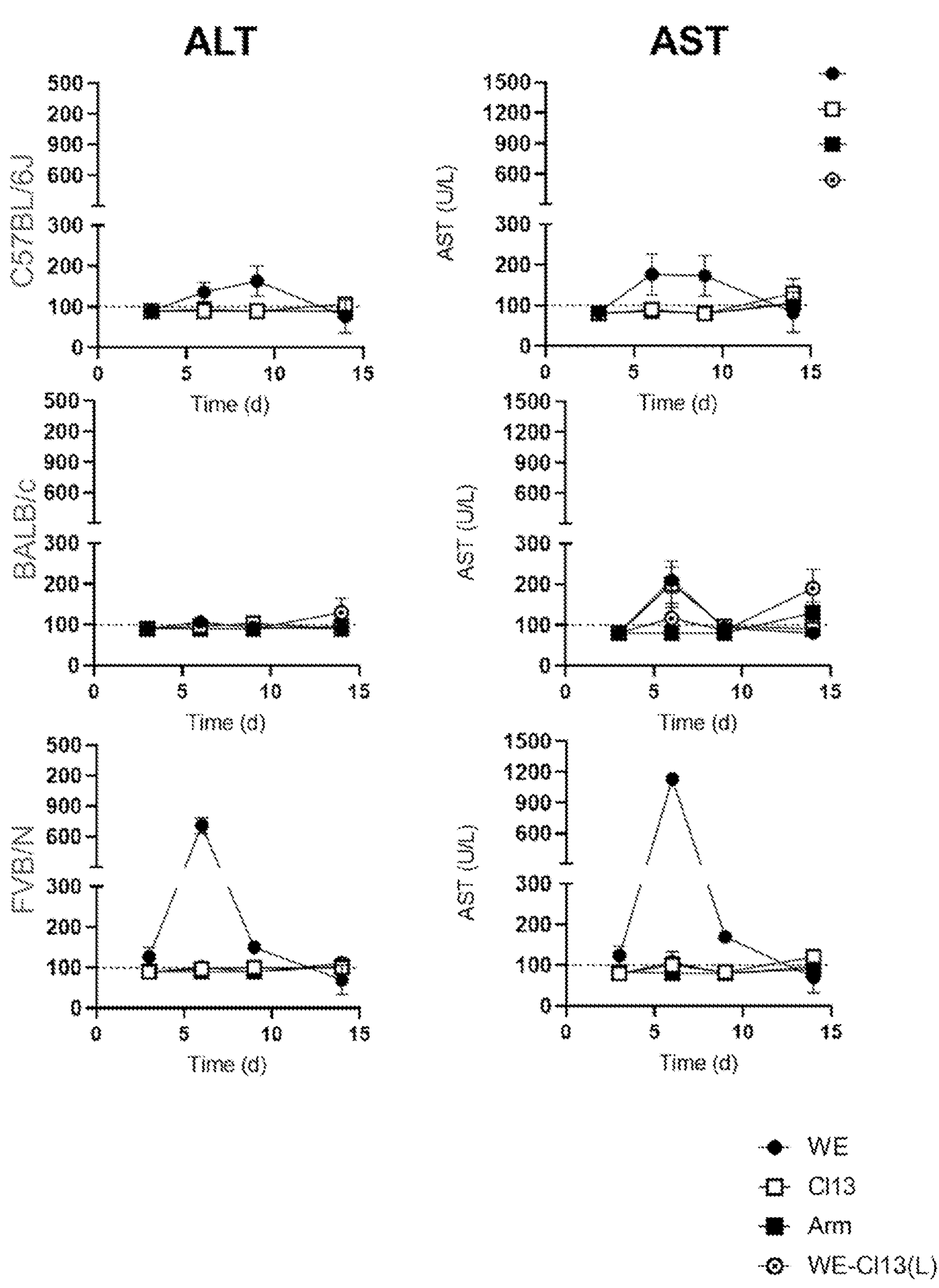
FIG. 16: Mouse strains with LCMV wild type (WE, Clone13, Arm) and recombinant (Clone13 L, WE S) strains with 2×10E6 PFU/animal i.v. at day 0 (n=3 animals/group).
FIG. 17: Mouse strains with LCMV wild type (WE, Clone13, Arm) and recombinant (Clone13 L, WE S) strains with 2×10E6 PFU/animal i.v. at day 0 (n=3 animals/group).

Wild type C57BL/6 or BALB/c mice or the highly susceptible mouse strain FVB/N were intravenously infected with $2\times10^6$ PFU of LCMV strains WE, Cl13 (Clone13), Arm (Armstrong) or WE-Cl13(L) (N=3). Mice were bled at days three, six, nine and fourteen. Serum levels of alanine aminotransferase (ALT) were analyzed (FIG. 16).

Thereby it was shown that LCMV WE-Cl13(L) does not induce liver pathology in highly susceptible FVB/N and other mouse strains.

Example 17

Wild type C57BL/6 or BALB/c mice or the highly susceptible mouse strain FVB/N were intravenously infected with $2\times10^6$ PFU of LCMV strains WE, Cl13 (Clone13), Arm (Armstrong) or WE-Cl13(L) (N=3). Mice were bled at days three, six, nine and fourteen. Serum levels of aspartate aminotransferase (AST) were analyzed (FIG. 17).

Thereby it was shown that LCMV WE-Cl13(L) does not induce liver pathology in highly susceptible FVB/N and other mouse strains.

Example 18

Figure 18:
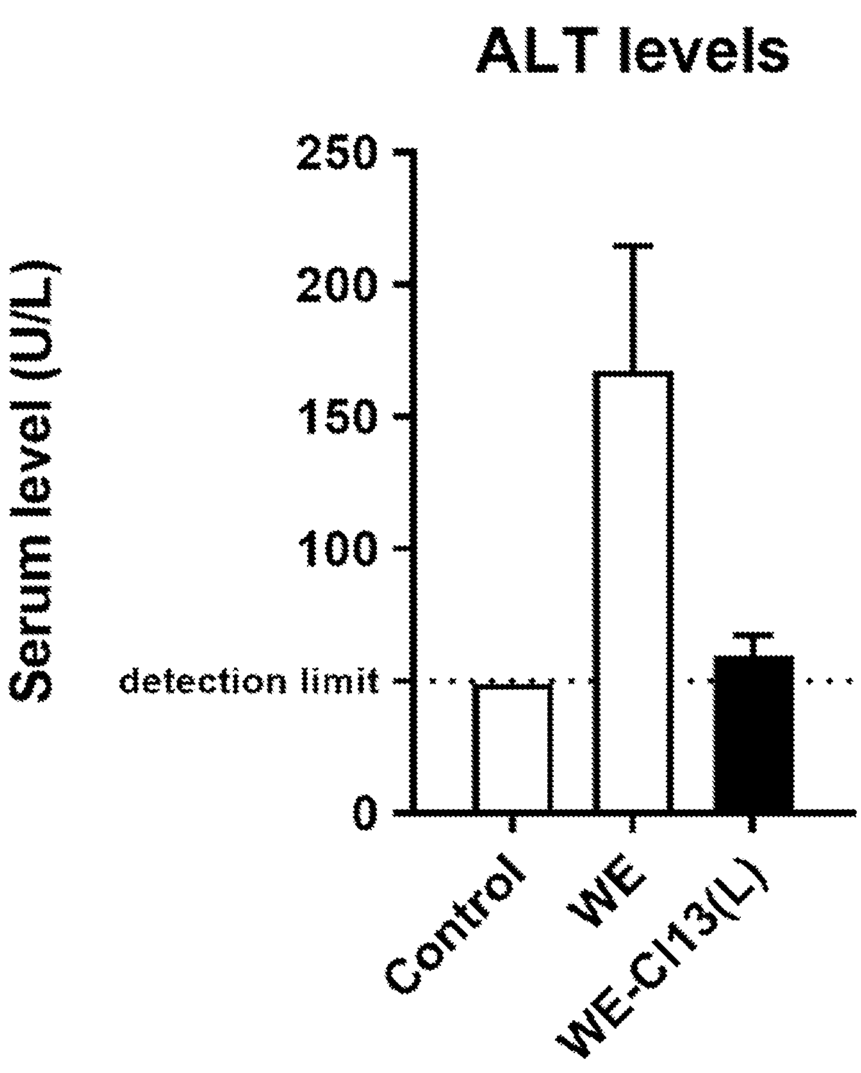
FIG. 18: ALT/AST serum levels upon i.v. treatment of B16 melanoma-bearing Bl/6 animals with 2×10E4 PFU/animal 7 days p.i.
Figure 18:
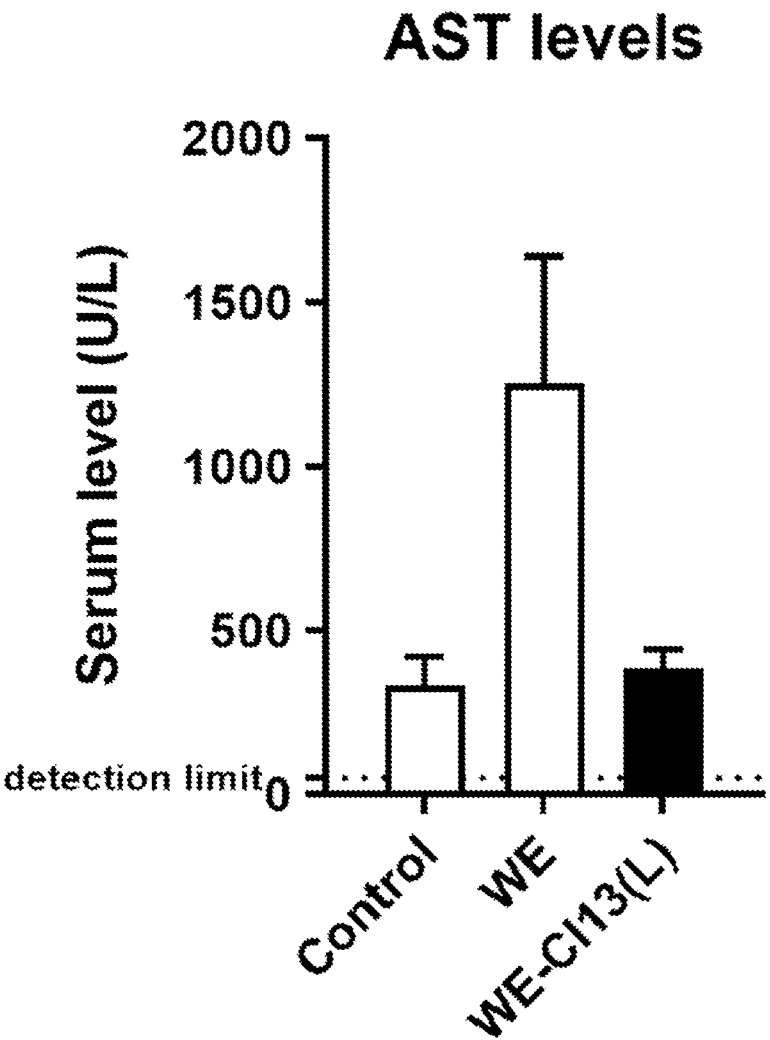

B16 melanoma tumor cells were injected subcutaneously into C57BL/6 mice. Mice were treated with $2\times10^4$ PFU of LCMV strains WE (n=4) or WE-Cl13(L) (n=5) or control treated (n=6). Blood was drawn at day seven after infection and serum levels of ALT and AST as indicators of liver pathology were analyzed (FIG. 18).

Thereby it was proven that LCMV strain WE-CL13(L) does not induce liver pathology after systemic administration in the presence of LCMV replication in the tumor.

Example 19

Figure 19:
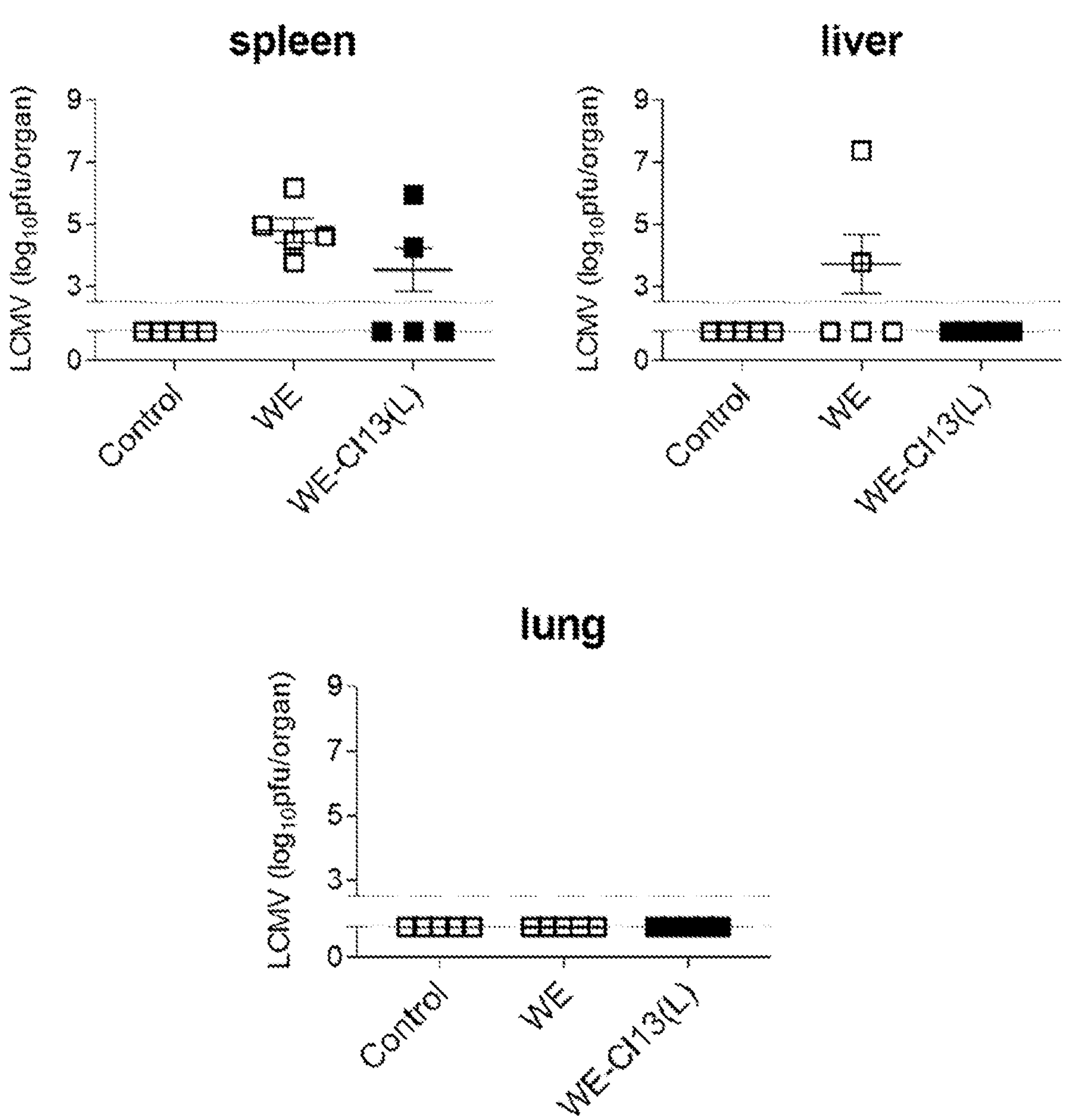
FIG. 19: Murine B16 tumor-bearing Bl/6 mice, LCMV wild type (WE) and recombinant strains with 2×10E4 PFU/animal i.v. at day 0, colony forming assay from the indicated organs at day 7 (n=5 animals/group).
Figure 19:
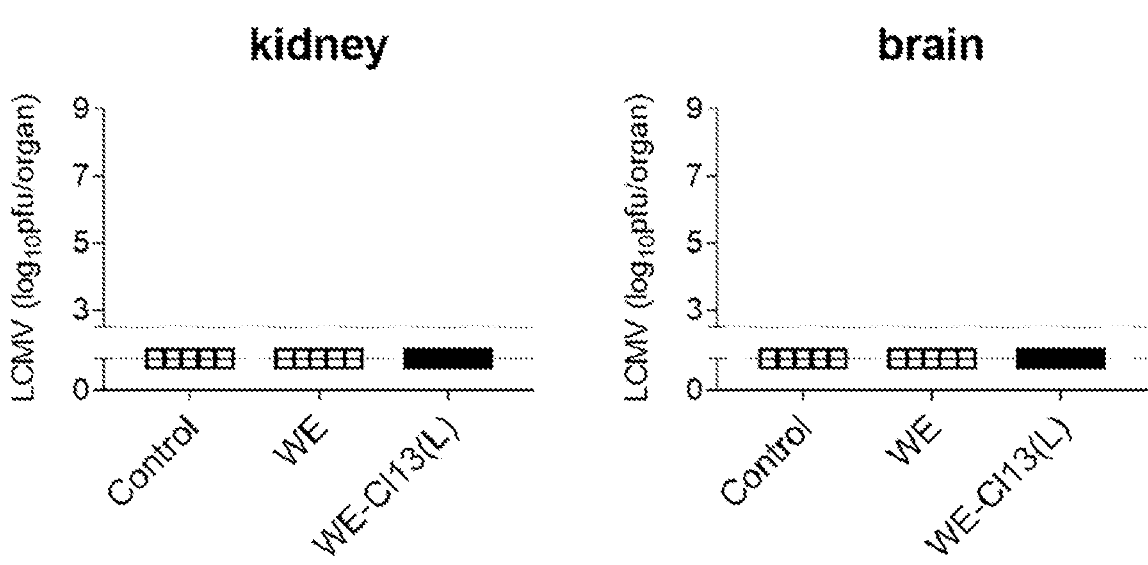

OVA expressing B16 tumor cells were injected in C57BL/6 mice subcutaneously. Mice were treated with $2\times10^4$ PFU of LCMV strains WE or WE-Cl13(L) intravenously or control treated (n=5). Mice were sacrificed on day seven after treatment and spleen, liver, lung, kidney and brain were analyzed for replicating LCMV particles via focus forming assay (FIG. 19).

Thereby it was shown that LCMV strain WE-Cl13(L) shows significantly decreased replication in healthy organs.

Example 20

Figure 20:
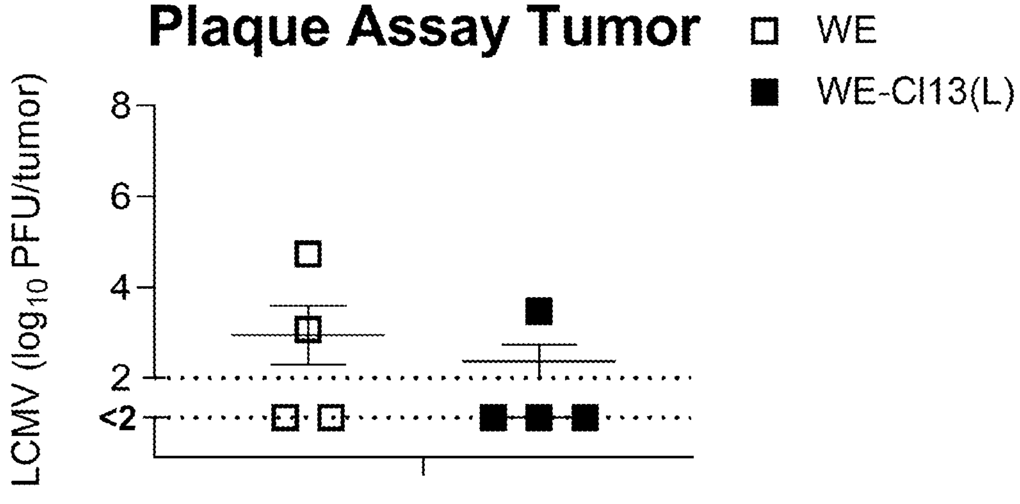
FIG. 20: Murine MC38 tumor-bearing Bl/6 mice, LCMV wild type (WE) and recombinant strains with 2×10E4 PFU/animal i.v. at day 0, plaque-forming assay from the indicated organs at day 11 (n=4 animals/group).

Murine MC38 tumor cells were subcutaneously transplanted in C57BL/6 mice. Mice were treated with $2\times10^4$ PFU of LCMV strains WE (n=4) or WE-Cl13(L) (n=4) via intravenous injection or control treated. Tumor tissue was analyzed for LCMV replication via focus forming assay on day eleven after infection (FIG. 20).

Thereby it was proven that LCMV strain WE-Cl13(L) replicates equally to LCMV strain WE in tumor tissue.

Example 21

Figure 21:
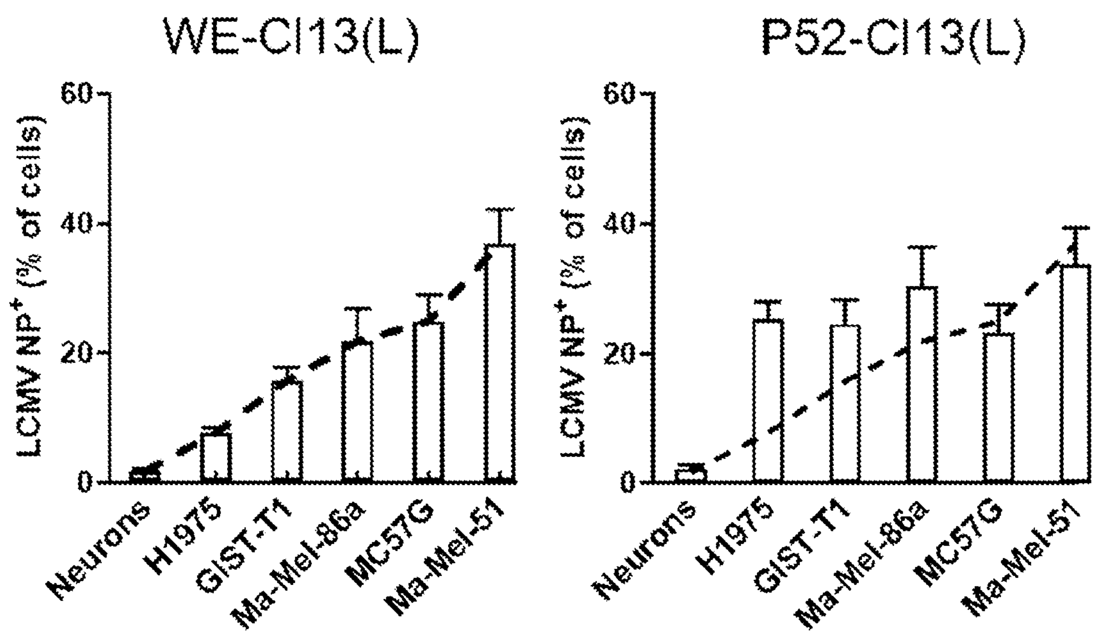
FIG. 21: In vitro replication for 20 h of wild type (WE) and recombinant viruses at MOI=0.1 by flow cytometry (NP protein) in human tumor cell lines H1975 (lung), GIST-T1 (gastrointestinal), Ma-Mel-86a and 51 (melanoma) and murine tumor cell line MC57G (fibrosarcoma). Line: replication of LCMV strain WE

Primary human neurons, lung adenocarcinoma cell line H1975, gastrointestinal cancer cell line GIST-T1, primary melanoma cell line Ma-Mel-86a, murine fibrosarcoma MC57G and primary melanoma cell line Ma-Mel-51 were seeded out (100.00 cells/well) and infected with MOI=0.1 of LCMV strains WE, WE-Cl13(L) or P52-Cl13(L). After 20 h, cells were intracellularly stained for LCMV nucleoprotein (NP, clone VL4). The percentage of LCMV infected cells (LCMV $NP^+$) was analyzed via flow cytometry (FIG. 21).

Thereby it was proven that LCMV reassortants LCMV WE-Cl13(L) and LCMV P52-Cl13(L) do not replicate in human neurons but that LCMV strain P52-Cl13(L) shows increased infectivity and replication in human and murine tumor cells.

Example 22

Figure 22:
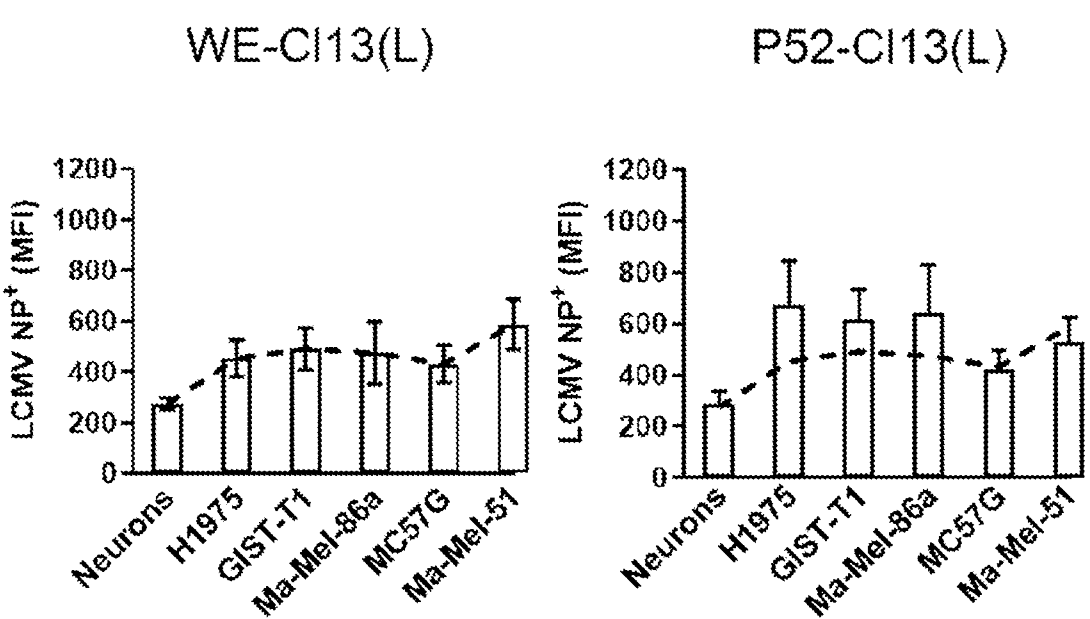
FIG. 22: In vitro replication for 20 h of wild type (WE) and recombinant viruses at MOI=0.1 by flow cytometry (NP protein) in human tumor cell lines H1975 (lung), Gist-T1 (gastrointestinal), Mamel86a and 51 (melanoma) and murine tumor cell line MC57G (fibrosarcoma). Line: replication of LCMV strain WE

Primary human neurons, lung adenocarcinoma cell line H1975, gastrointestinal cancer cell line GIST-T1, primary melanoma cell line Ma-Mel-86a, murine fibrosarcoma MC57G and primary melanoma cell line Ma-Mel-51 were seeded out (100.00 cells/well) and infected with MOI=0.1 of LCMV strains WE, WE-Cl13(L) or P52-Cl13(L). After 20 h, cells were intracellularly stained for LCMV nucleoprotein (NP, clone VL4). The fluorescent intensity of LCMV infected cells was analyzed via flow cytometry to investigate replication capacity in the cells (FIG. 22).

Thereby it was proven that LCMV strain P52-Cl13(L) shows enhanced replication in human and murine tumor cells.

Example 23

Figure 23:
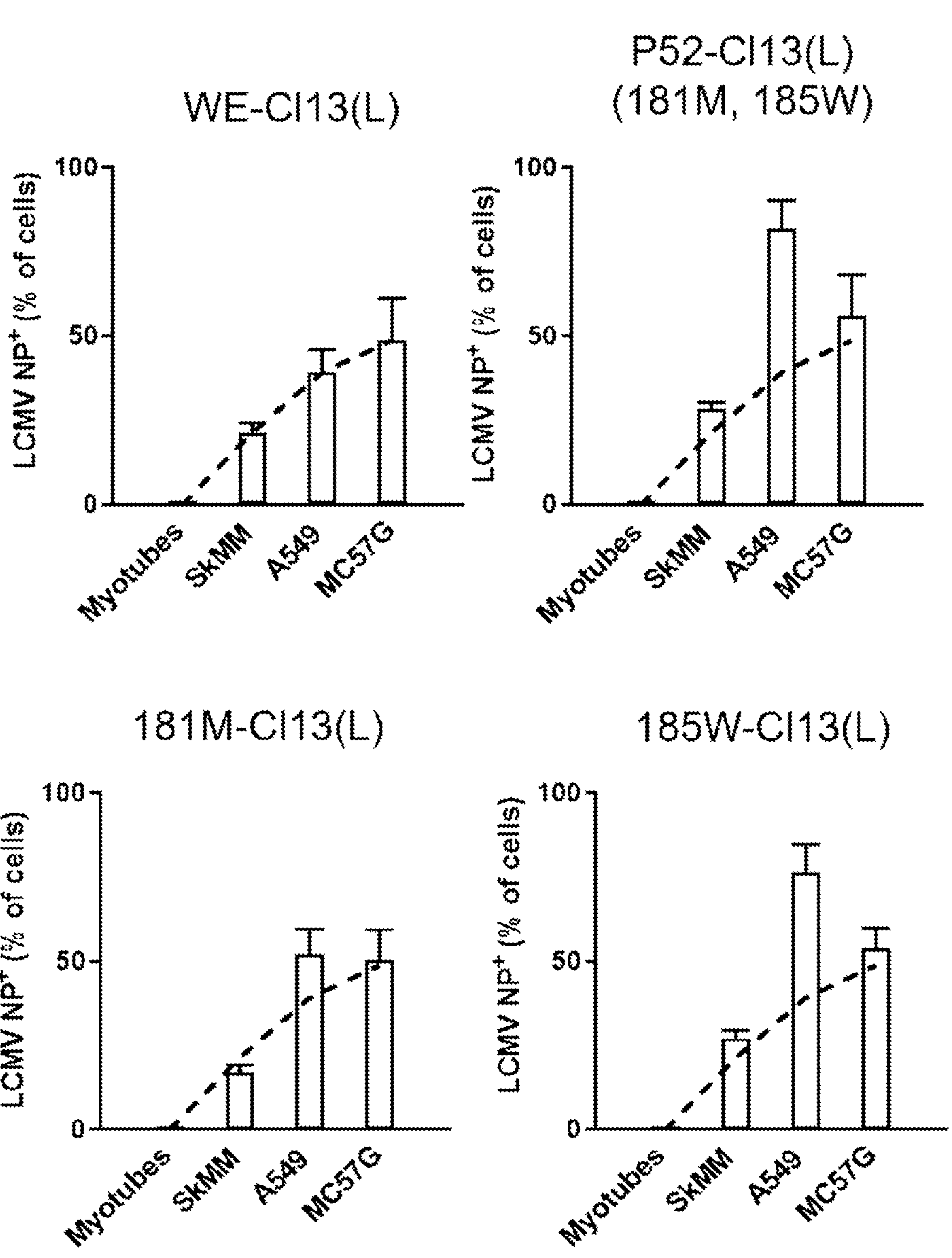
FIG. 23: Differentiated human muscle myoblasts, human skeletal muscle myoblasts (SkMM), lung adenocarcinoma cell line A549 and murine fibrosarcoma cell line MC57G were seeded out (100.000 cell/well) and infected with MOI=0.1 of LCMV strains WE, WE-Cl13(L), P52-Cl13(L), I181M-Cl13(L) or R185W-Cl13(L). After 20 h, cells were intracellularly stained for LCMV nucleoprotein (NP, clone VL4). The percentage of LCMV infected cells (LCMV NP$^+$) was analyzed via flow cytometry. Line: replication of LCMV strain WE

Differentiated human muscle myoblasts, human skeletal muscle myoblasts (SkMM), lung adenocarcinoma cell line A549 and murine fibrosarcoma cell line MC57G were seeded out (100.000 cell/well) and infected with MOI=0.1 of LCMV strains WE, WE-Cl13(L), P52-Cl13(L), I181M-Cl13 (L) or R185W-Cl13(L). After 20 h, cells were intracellularly stained for LCMV nucleoprotein (NP, clone VL4). The percentage of LCMV infected cells (LCMV $NP^+$) was analyzed via flow cytometry (FIG. 23).

Thereby it was shown that the mutations in the LCMV glycoprotein in positions 181 and 185 enhance the replication and infectivity in human and murine cancer cells but do not increase the tropism towards healthy human muscle cells.

Example 24

Figure 24:
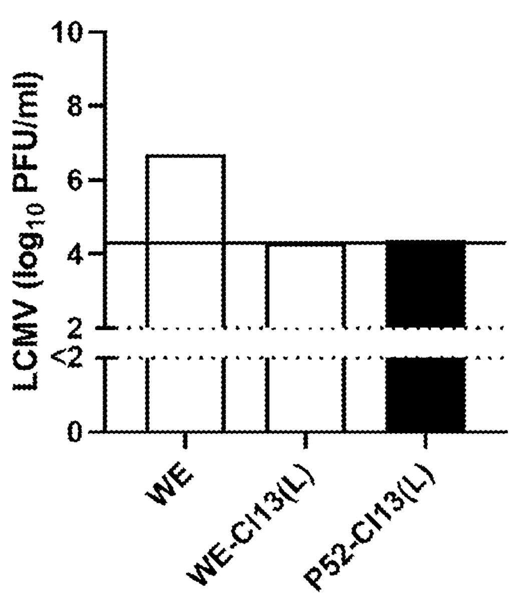
FIG. 24: In vitro replication for 48 h of wild type (WE) and recombinant viruses at MOI=0.1 by replication assay in human primary neurons and as a comparison murine tumor cell line MC57G (fibrosarcoma), line: initial inoculum.
Figure 24:
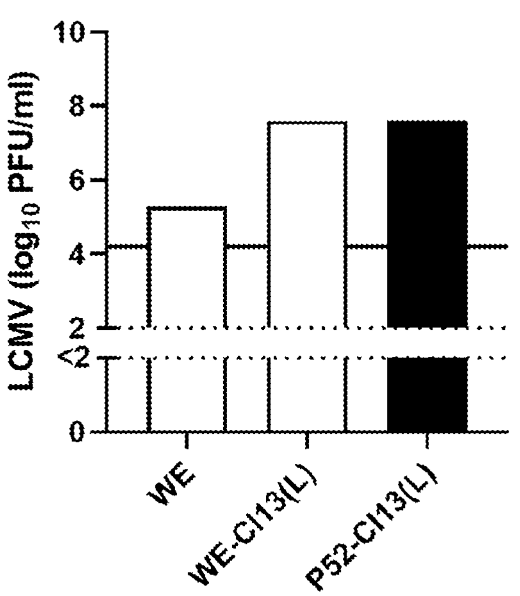

Primary human neurons and murine fibrosarcoma MC57G cells were tested for their LCMV replication potential. 100.000 cells per well were seeded out and infected with MOI=0.1 of LCMV strains WE, WE-Cl13(L) or P52-Cl13 (L). Supernatant was harvested 48 h after infection. Virus titers were analyzed by focus forming assay (FIG. 24).

Thereby it was proven that reassortant LCMV strains WE-Cl13(L) and P52-Cl13(L) do not show tropism towards healthy human neurons but show enhanced replication in murine cancer cells compared to wild type LCMV strain WE.

Example 25

Figure 25:
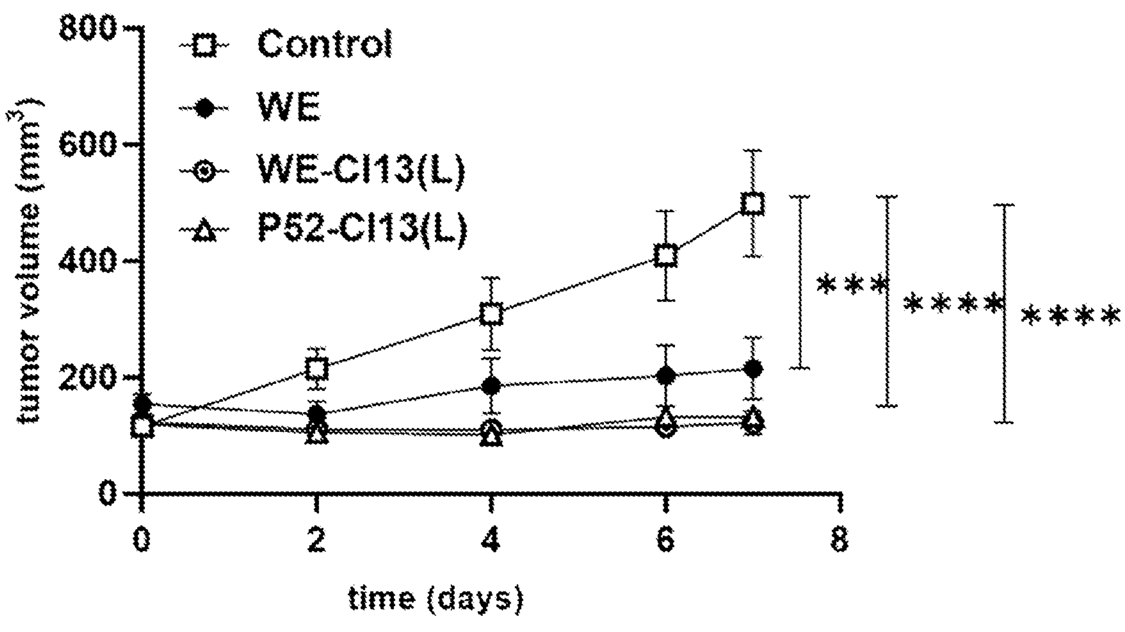
FIG. 25: Murine B16 tumor-bearing Bl/6 mice, LCMV wild type (WE) and recombinant strains with 2×10E4 PFU/ animal i.v. at day 0, tumor growth measurement for 7 days and tumor mass at day 7 (n=5 animals/group), one way ANOVA and Dunnett's multiple comparisons tests for statistics.
Figure 25:
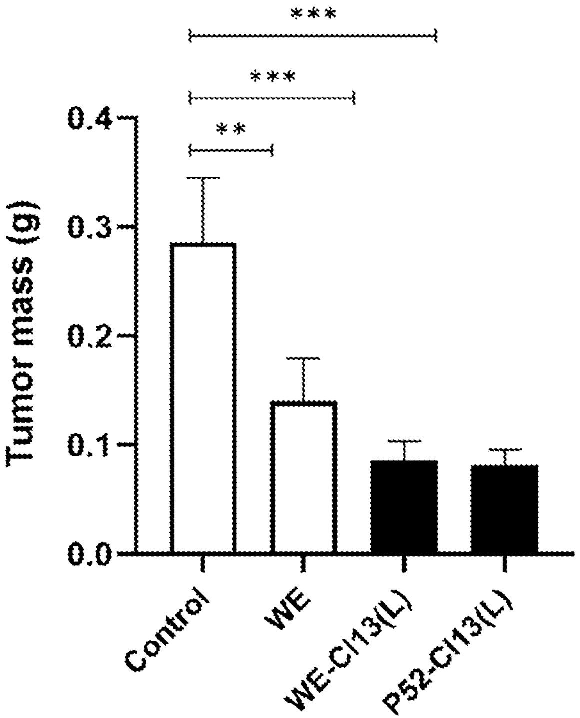

C57BL/6 mice were subcutaneously treated with murine melanoma B16 cells and intravenously infected with $2\times10^4$ PFU of LCMV strains WE, WE-Cl13(L) or P52-Cl13(L) or were control treated (n=5 animals per group). Tumor growth was measured over seven days. Tumor mass was measured at finalization (d7) (FIG. 25).

Thereby it was proven that LCMV strains WE-CL13(L) and P52-Cl13(L) show an increased antitumoral effect compared to wild type LCMV strain WE.

Example 26

C57BL/6 mice were subcutaneously treated with B16 melanoma cells and intravenously infected with $2\times10^4$ PFU of LCMV strains WE, WE-Cl13(L) or P52-Cl13(L) or were control treated (n=5 animals per group). Mice were sacrificed on day seven after infection. Tumor draining lymph node resident cytotoxic $CD8^+$ T cells were stained via fluorescent labelled anti-CD8 antibody (eBioscience) and analyzed via flow cytometry (FIG. 26).

Thereby it was proven that LCMV strains WE-CL13(L) and P52-Cl13(L) enhance cytotoxic T cell accumulation in tumor draining lymph nodes.

Example 27

C57BL/6 mice were subcutaneously treated with B16 melanoma cells and intravenously infected with $2\times10^4$ PFU of LCMV strains WE, WE-Cl13(L) or P52-Cl13(L) or were control treated (n=5 animals per group). Mice were sacrificed on day seven after infection. Tumor draining lymph node resident cytotoxic, antiviral $CD8^+$ GP33-tetramer positive T cells were stained via fluorescent labeled antibodies (eBioscience, NIH) and analyzed via flow cytometry on day seven after infection (FIG. 27).

Thereby it was proven that LCMV strain P52-Cl13(L) increases accumulation of virus specific T cells in tumor draining lymph nodes.

Example 28

C57BL/6 mice were subcutaneously treated with B16 melanoma cells and intravenously infected with $2\times10^4$ PFU of LCMV strains WE, WE-Cl13(L) or P52-Cl13(L) or were control treated (n=5 animals per group). Mice were sacrificed on day seven after infection. Tumor resident cytotoxic $CD8^+$ T cells were stained via fluorescent labelled anti-CD8 antibody (eBioscience) and analyzed via flow cytometry (FIG. 28).

Thereby it was proven that LCMV strains WE-CL13(L) and P52-Cl13(L) enhance cytotoxic T cell accumulation in tumor.

Example 29

C57BL/6 mice were subcutaneously treated with B16 melanoma cells and intravenously infected with $2\times10^4$ PFU of LCMV strains WE, WE-Cl13(L) or P52-Cl13(L) or were control treated (n=5 animals per group). Tumor draining lymph node resident cytotoxic, antiviral $CD8^+$ GP33-tetramer positive T cells were stained via fluorescent labeled antibodies (eBioscience, NIH) and analyzed via flow cytometry on day seven after infection (FIG. 29).

Thereby it was proven that treatment with LCMV strain P52-Cl13(L) strongly enhances antiviral T cell accumulation in tumor tissue.

Example 30

C57BL/6 mice were subcutaneously treated with murine MC38 colon carcinoma cells. After visible tumor formation mice were intravenously treated with $2\times10^4$ PFU of LCMV strains WE, WE-Cl13(L), P52-Cl13(L) or control treated (n=4). Tumor volume was measured until eleven days after infection (FIG. 30).

Thereby it was proven that LCMV strain P52-Cl13(L) induces strong tumor growth inhibition.

Example 31

C57BL/6 mice were subcutaneously treated with murine MC38 colon carcinoma cells. After visible tumor formation mice were intravenously treated with $2\times10^4$ PFU of LCMV strains WE, WE-Cl13(L), P52-Cl13(L) or control treated (n=4). Tumors were dissected on day eleven. T cells were stained with fluorescent anti-CD3 antibody (eBioscience) and analyzed via flow cytometry (FIG. 31).

Thereby it was proven that LCMV strain P52-Cl13(L) shows a clear tendency towards an enhanced T cell accumulation in tumor tissue compared to LCMV strains WE, WE-Cl13(L) and control treated tumors.

Example 32

C57BL/6 mice were subcutaneously treated with murine MC38 colon carcinoma cells. After visible tumor formation mice were intravenously treated with $2\times10^4$ PFU of LCMV strains WE, WE-Cl13(L), P52-Cl13(L) or control treated (n=4). Tumors were dissected on day eleven. T helper cells were stained with fluorescent anti-CD3 and anti-CD4 antibodies (eBioscience) and analyzed via flow cytometry (FIG. 32).

Thereby it was shown that LCMV strains WE-Cl13(L) and P52-Cl13(L) induce a stronger T helper cell infiltration into tumor tissue compared to tumors treated with wildtype LCMV strain WE or control treated.

Example 33

C57BL/6 mice were subcutaneously treated with murine MC38 colon carcinoma cells. After visible tumor formation mice were intravenously treated with $2\times10^4$ PFU of LCMV strains WE, WE-Cl13(L), P52-Cl13(L) or control treated (n=4). Tumors were dissected on day eleven. Cytotoxic T cells were stained with fluorescent anti-CD3 and anti-CD8 antibodies (eBioscience) and analyzed via flow cytometry (FIG. 33).

Thereby it was proven that LCMV strain P52-Cl13(L) enhances cytotoxic T cell accumulation in tumor compared to control treatment.

Example 34

C57BL/6 mice were intravenously infected with $2\times10^4$ PFU per mouse of LCMV strains WE, WE-Cl13(L), P52-Cl13(L) or left untreated (n=3). Blood was taken on day two and day four after infection. Serum cytokine levels of IFNα, TNFα and IFNγ were analyzed by LegendPlex assay (BioLegend) (FIG. 34).

Thereby it was proven that LCMV reassortant strains WE-Cl13(L) and P52-Cl13(L) induce reduced systemic cytokine levels compared to wildtype LCMV strains WE and Clone13.

Example 35

C57BL/6 mice were subcutaneously treated with B16-Ova melanoma cells and intravenously infected with $2\times10^4$ PFU of LCMV strains WE, WE-Cl13(L) or P52-Cl13(L) or were control treated (n=5 animals per group). Mice were sacrificed at day seven post infection. Spleen, liver, lung, kidney brain and tumor tissue were analyzed for LCMV replication via focus forming assay (FIG. 35).

Thereby it was shown that LCMV reassortant P52-Cl13 (L) displays a decreased replication in healthy organs by simultaneously showing measurable replication in tumor tissue.

Example 36

MC38 tumor cells were subcutaneously transplanted into C57BL/6 mice. After visible tumor formation mice were intravenously treated with $2\times10^4$ PFU of LCMV strains WE, WE-Cl13(L) or P52-Cl13(L). On day eleven after infection tumors were dissected an LCMV replication was analyzed via focus forming assay (FIG. 36).

Thereby it was proven that LCMV strain P52-CL13(L) persists shorter in mouse tumor tissue compared to strains WE and WE-Cl13(L).

Example 37

FreeStyle 293-F suspension cells were infected with MOI=0.001 of LCMV strains WE-Cl13(L), P52-Cl13(L) or P52-WE(L) at a density of $1.5\times10^6$ cells per mL. Supernatant was harvested on 12, 24, 30, 34, 40, 48, 72 and 96 hours post infection. LCMV titers in supernatant were analyzed via focus forming assay (FIG. 37).

Thereby it was proven that FreeStyle 293-F cells show enhanced replication of the LCMV reassortants WE-CL13 (L) and P52-Cl13(L) and display an ideal producer cell line for the production of LCMV reassortants.

Embodiments illustratively described herein may suitably be practiced in the absence of any element or elements, limitation or limitations, not specifically disclosed herein. Thus, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group.

Equivalents: Those skilled in the art will recognize or be able to ascertain using no more than routine experimentation, many equivalents to the specific embodiments of the invention described herein. Such equivalents are intended to be encompassed by the following claims.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent applications, scientific publications, manufacturer's specifications, instructions, etc.) are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

Further embodiments will become apparent from the following claims.

The invention claimed is:

1. A virus particle comprising:

a lymphocytic choriomeningitis virus (LCMV) S segment nucleic acid comprising an open reading frame encoding an LCMV glycoprotein having at least 99% sequence identity to SEQ ID NO: 14, and an open reading frame encoding an LCMV nucleoprotein having at least 99% sequence identity to SEQ ID NO: 6, wherein the open reading frame encoding the LCMV glycoprotein encodes a tryptophan at residue 185 and a methionine at residue 181 of the LCMV glycoprotein; and an LCMV L segment nucleic acid comprising an open reading frame encoding an LCMV L protein of SEQ ID NO: 40, and an open reading frame encoding an LCMV Z protein of SEQ ID NO: 38.

2. The virus particle of claim 1, wherein the virus particle is less pathogenic in a mouse compared to LCMV strain WE.

3. The virus particle of claim 1, wherein the virus particle shows increased replication in tumor cells compared to LCMV strain WE.

4. The virus particle of claim 1, wherein the virus particle shows reduced replication in a healthy organ compared to LCMV strain WE and/or a virus particle comprising the same S segment as the virus particle and an L segment as shown in SEQ ID NO: 2.

5. The virus particle of claim 1, wherein the virus particle has a bi-segmented genome.

6. The virus particle of claim 1, wherein the virus particle is an arenavirus particle.

7. A host cell line, wherein cells of the host cell line comprise an LCMV S segment and an LCMV L segment of claim 1.

8. A host cell line, wherein cells of the host cell line comprise cDNA of an LCMV S segment and an LCMV L segment of claim 1.

9. A pharmaceutical composition comprising a virus particle of claim 1.

10. The virus particle of claim 1, wherein the open reading frame encoding an LCMV glycoprotein has at least 99.7% % sequence identity to SEQ ID NO: 14, and the open reading frame encoding an LCMV nucleoprotein has at least 99.7% sequence identity to SEQ ID NO: 6.

* * * * *

SEQUENCE LISTING

```
<160> NUMBER OF SEQ ID NOS: 40

<210> SEQ ID NO 1
<211> LENGTH: 3376
<212> TYPE: DNA
<213> ORGANISM: Lymphocytic choriomeningitis virus (LCMV) strain WE

<400> SEQUENCE: 1

gcgcaccggg gatcctaggc tttttggatt gcgctttcct ttaggacaat tgggtgctgg      60

attctatcca ataaaaggat gggtcagatt gtgacaatgt ttgaggcttt gcctcacatc     120

attgatgagg tcatcaacat tgtcattatt gtgctcatta taatcacgag catcaaagct     180

gtgtacaatt tcgccacctg tgggatatta gcactggtca gcttcctttt tttggctggt     240

aggtcctgtg gcatgtacgg ccttaatggt cccgacatct ataaaggggt ttaccagttc     300

aaatcagtgg agtttgatat gtctcactta aatctgacga tgcccaatgc gtgctcagcc     360

aacaactctc atcactacat cagtatggga agctctggac tggagctaac tttcactaac     420

gactccatcc ttaatcacaa tttttgcaac ttaacctccg ctttcaacaa aaagactttt     480
```

```
gaccatacac tcatgagtat agtctcgagt ctgcacctca gtattagagg gaattccaac    540

cacaaagcag tgtcttgtga ttttaacaat ggcatcacca ttcaatacaa cttgtcattt    600

tcggacccac agagcgctat aagccagtgt aggactttca gaggtagagt cttggacatg    660

tttagaactg cctttggagg aaaatacatg agaagtggct ggggctgggc aggttcagat    720

ggcaagacca cttggtgcag ccaaacaagc tatcagtacc taatcataca aaacaggact    780

tgggaaaacc actgtagata tgcaggccct tttgggatgt ctagaatcct ctttgctcag    840

gaaaagacaa agtttctcac taggagactt gcaggcacat tcacctggac cctgtcagac    900

tcctcaggag tagaaaatcc aggtggttat tgcctgacca aatggatgat ccttgctgca    960

gagctcaaat gttttgggaa tacagctgtt gcaaaatgta atgtcaatca tgatgaagag   1020

ttctgtgaca tgctacgact aattgattac aacaaggccg ccctgagtaa gttcaagcaa   1080

gatgtagagt ctgccttgca tgtattcaaa acaacagtaa attctctgat ttccgatcag   1140

ctgttgatga ggaatcatct aagagatcta atgggggtac catactgtaa ttactcaaag   1200

ttctggtatc tggaacatgc taagactggt gagactagtg tacccaagtg ctggcttgtc   1260

actaatggct cctacttgaa tgagacccac tttagtgatc aaatcgaaca agaagcagat   1320

aacatgatca cagagatgtt gaggaaggac tacataaaaa gacaagggag tactccttta   1380

gccttaatgg atcttttgat gttttcaaca tcagcatatc taatcagcat ctttctgcat   1440

cttgtgaaga taccaacaca tagacacata aagggcggtt catgtccaaa gccacaccgc   1500

ttgaccaaca aggggatctg tagttgtggt gcattcaagg tgcctggtgt aaaaactatc   1560

tggaaaagac gctgatcagc agcgcctccc tgactctcca cctcgaaaga ggtggagagt   1620

cagggaggcc cagtgggtct tagagtgtca caacattggg tcctctgaag attaaatcat   1680

gtggcaggat gttgtgaacg gtttttagat cagggagtct tgccttggaa gcactctcaa   1740

aaatgatgca gtccatgagt gcacagtgtg gggtgatctc tttcttcttt ttgtctctca   1800

ctaccccagt gtgcattttg catagccagc catatttgtc ccacacttta tcttcatatt   1860

ctcttgaggc ctccttggtc atctcaacat caatgagttt tatgtccctt ctattttgtg   1920

agtccagaag ctttctgatg tcatcagaac cttgacagct caaaaccatc ccttgtggga   1980

gagcacctat aactgatgag gtcagcccag gctgtgcatt gaagagatca gcaagatcca   2040

tgccgtgtga atactttgag tcctgcttga attgcttctg gtccgtaggt tccctgtaaa   2100

aatgtatgaa ttgcccattt tgtggttgga atattgctat ctccactgga tcattgaacc   2160

tgccctcaat gtcaatccat gtgggagcat tgggatcaat ccctcccatc aagtctttca   2220

acagcattgt ctgactgtaa ctcaagccca cctgaggtgg gcctgctgct ccaggcactg   2280

gcctagatga gttggcaaca agtttttcat ttgtgagatc aattgttgtg ttctcccatg   2340

ctctccccac aactgacgtt ctacaggcta tgtatggcca tccttcacct gaaagacaga   2400

ctttataaag gatgttttca tagggatttc tatctccaac ttgatctgag acaaacatgt   2460

tgagtttctt cttggccccg aggactgctt ttaggagatc ctcactgttg ctcggtttga   2520

tcaagataga ttccagcatg ttccctccat ctagcagagc tgcccccgct ttcacagctg   2580

caccaagact gaaattataa ccagagatat tgatactaga ttgctgttca gtaatgaccc   2640

ccagaactgg gtgtttatcc tttagccttt caagatcact gagattcggg tatttgactg   2700

tgtaaagtaa gccaaggtct gtgagtgcct gcacaacatc attgagtggg gtctgtgact   2760

gttttgccat gcaagccatt gtcaggcttg gcattgtgcc gaactgattg ttcagaagtg   2820

atgagtcctt cacatcccaa acccttacta caccacttgc accctgctga ggtcttctca   2880
```

```
tcccaaccat ttgcagtatt tgggatcttt gatcaagttg ttgtgctgtc aaatttccca   2940

tgtagactcc agaagcttga ggcctctcag ttctcataat tttggccttc agcttctcaa   3000

gatcagctgc aagggtcatc aattcctctg cactaagtct tcccactttc agaacatttt   3060

tctttgatgt agacttcaga tcaacaagag aatgcacagt ctggttaaga ctcctgagtc   3120

tctgcaagtc tttatcatcc ctcctttcct ttctcatgat cctctgaacg ttgctgactt   3180

cagaaaagtc caacccattt agaagactgg ttgcgtcctt gatgacggca gcctttacat   3240

ctgatgtaaa actctgcaac tccctcctca acgcctgtgt ccactgaaag cttttgactt   3300

ctttggacaa agacattttg tcacacaatg aatttccaaa taaaagcgca attaaatgcc   3360

taggatccac tgtgcg                                                    3376
```

<210> SEQ ID NO 2
<211> LENGTH: 7236
<212> TYPE: DNA
<213> ORGANISM: Lymphocytic choriomeningitis virus (LCMV) strain WE

<400> SEQUENCE: 2

```
gcgcaccggg gatcctaggc gtttagttgc gctgctttat tgcacagctt cactctgcta     60

aaccatcagg aactgaccga tcatcagtca tgggccaagg caagtccaaa gaagaaaggg    120

acaccagcaa tacaggcaga gcagagcttt tgccagacac cacctatctt ggtcctctaa    180

attgtaaatc atgttggcag aaatttgaca gcttggttag atgccatgac cactatcttt    240

gcagacactg tctgaatctc ctgctgtcag tttccgacag atgtcctctc tgtaagtatc    300

cactgccaac caaactgaag gtgtcaacag tcccaagctc cccacctccc tatgaggagt    360

gacgccccag acctcgacac aacaggccac ccaacacaga aaaaccacac acaaaccggc    420

acacacagac acagcaacca gcacaaagcg cacgaaaaca cacacacaca cacacacaca    480

ccctcaccca cgcgcccccc cgcaccgccg ggggggcgcc cccccggggg gcagcccccc    540

gggggcccgg gcagggcccc gcggagatgc cggctagtcg atctcctcgg ccacccgctc    600

cgccagccaa tcgtcacagg atttcccctt gagtctgaac ctgcccccag ttgtctcata    660

cattacagtg ttctttgacc tgctgaagca gagcctacaa tctctgaagg tgaaccaatc    720

tggcacaaaa gataatggtg tcagcatgac ggatctgtcc atgcagagct cctgaagaac    780

tgtacttatt tctgactcca tcaagtgctc accagttctg aatcggtgca ggaggaggct    840

gccgaggaca tcaccaattt ttccacagcc ctcgagctct gccagaaaga ccctcatgtc    900

ctttgtctcc aatttcacag agatattctg aacaaagttc ctcccctcaa agagggcacc    960

cttccttatg gtcagaggca caggttccca ctcaggccct atcctctcaa agtcagtaga   1020

tttgatctca ttcagaatcc ttctagaacc tattagttca agttctagtg aatcaccaag   1080

tgtcaaaggg tcttccatgt aatcttcaaa ctcttcagac ctaatgtcaa agactccatc   1140

attcgcttta aagatggggt ctgtcctcaa cagattgaga cactcatcta ataatctcct   1200

gtcaacctca cctttgaaga aatgagagca cgataagtaa tcagctacac ctggactctg   1260

taattggcat ttaaccacaa agatcaatga aaatttcctc aagcagtcag tgttgttctg   1320

gttgtgtgtg aaatccactg tgattgagaa ctccaatatc ccctctgtgc tgctgagcat   1380

gtaatcccac aaatctctta aagatttaaa tgcttttgga tctgtcaaac cctgcttaat   1440

taacatagcg gcattacaca caacatcccc cacacgataa gagaaccaac caaaaccaaa   1500

ctgcaagtca ttcctaaaca tgggcctctc tattttcttg ttcaccactt tcaaaataaa   1560
```

-continued tgattggaag ggtcccagtg cttcagcgcc atcttcagat ggcatcatgt ccttatgggg 1620
gaaccatgaa aagttaccta aggtcctagc tgttgcaaca aactctcgta caaatgattc 1680
gaaatacact tgcttcaaaa agttcttgca gacatccctt gtgctgacaa caaattcatc 1740
aactaaactt gagtctgacc gttggtgaga gttgacgaga tcagaaaaca gcacagtgta 1800
atgttcgtcc ctcttccatt tgacaacatg agaaatgagt gacaaagact ctgagttgat 1860
gtcaatcagc acacaaaggt caaggaattt aatcctggga ctccatctca tattttttga 1920
gctcacatca gacatgaatg ggagcaactg atcctcaaag attttggggt acagtcgcct 1980
cacagattga attacatgat tcaaactcac tttatcctct agtagtctcg aactctcagg 2040
ttttcttgct acataatcac atggatttaa gtgcctaaca gccgaattac tctcgttctt 2100
tcctttcaca ggttctgcta aaacccaaac acccagctca aaagagttgc tcaatgagat 2160
gcaaatgtag tcccagagaa ggggcctcaa aaggttgatg tggtcacggt gagcctctgg 2220
gtgtctctgc ttgtcgcaaa tgtacaacat cacaccatct tgtttgtgaa cccttgtgac 2280
atgttcatcc atggtcagat cttcaagcac ctttctgata tacatatttt ccctgttttt 2340
atttctcaca cacctacttc ctaaagtctt acagagacct ataaagccgg atgagacaca 2400
actctgaaaa gctgatttgt tgattgcctc tgacaacagc ttctgtgcac ctcttgtgaa 2460
cttactacaa agcttatttt ggagtgtttt aatcaatgag gggatctttt cctcttgaaa 2520
ggtcattact gatgggtaaa ccactttttg tctcagaacc atcctcaatg ggaacatttc 2580
attcagattc aaccaattga tgcttgccaa ctcattaaga tcatcctcaa gaccaagaat 2640
ctctcccaat tgaaggatgg cctctttctt ttccctgttg aagaggtcta gaaaaaattc 2700
ctcgttacat tcaccgttct tgagtttgtg atgtagtctt cttacaagtt ttctcatgat 2760
ctttgtttca ctgggacaca attcttcaat gagtctttgg attctataac ctctagaacc 2820
atctaaccaa tcctttacat cagtgtgagt gtttaacaag aatggatcta aagggaaatt 2880
agcatatttc aagagatcca gtgtcctcct ctggatacag tttactaaaa aaactggaac 2940
tccatttgct atagcttgat cagcaatcgt atctattgtc tcacaaagtt gatgcggttc 3000
tttacactta acattgtgta gtgccgcaga cacaaatttc gtgaggagag ggacctcctc 3060
cccccacaca taaaatctgg atttgaattc cgctgcaaac cgcccaacca cactttttgg 3120
actgatgaac ttgttcaaca aaccacttaa gtgagagtgg aattccagca agacaaggac 3180
ttcttctggg tcactatcaa ctaagtcact caatctcttg tcaaataaag tgatctgatc 3240
atcacttgat gtataggctt ctggcctctc tccaaaaatg acaccaatac aataattgat 3300
aaacctttca ctaattaaac cgtaaaaatc agaagcattg tgtaggatcc cctgtcccat 3360
gtcaatgaga ctagatatgt gagatggcac cacccccatt tcaaaatact ctctaaagat 3420
tctctccgta acagtcgttc ctgacccttt gagaagcttg agttttgatt taacatatga 3480
tttcatcatt gcattcacaa cagggaaagg gacttcaaca agtttatgca tatgccaagt 3540
caacaaggtg ctaacatgat cttttccaga acgcacgtac tgatcatcac ccagtttgag 3600
attttggaga agcattaaga ataggaatgg gcacatcatt ggtccccatt tgctgtgatc 3660
catgctgtag tttaacaacc cttctctcac attgatagtc attgacaaga ttgcattttc 3720
aaactctttg tcattgttta aacaagatcc tgaaaagaaa ctagaaaagg attcaaaata 3780
atcttctacc aatcttgtga acatttttgt cctcaaatcc ccaatgtaaa gctctctatt 3840
tcccccaacc tgctctttgt atgacaatgc aaattttagt ctcccagagt cagggccaac 3900
tgaagtgtat gatgttggtg attcttctga gtaaaaacac agattcttta gagcagcact 3960

```
catgcatttt gtcaatgaaa gggccttact tagagattca gaattgcttt ccctttcact   4020
aattcttaca tcttcttcca atttgtccca gtcaaattta aaatttaagc tctgcctctg   4080
catgtgtctg tacttccctg aatacgcatt tgcattcatc tgtaacaaga tcatcttcat   4140
acatgagaac caatcaccct ctgagaagaa ctttctacag aggtttcttg ccatctcatc   4200
cagaccacat tgttctttga cagctgatgt aaaatacaat ggtgacagtt ctgttgaacc   4260
ttcaacagcc tcacaaataa acctcatgtc gtcattggtg agacaggatg gatcaaagtc   4320
ctctactaga tgaaatgaaa tttctgataa aatgactttc ctcagataag ctcttttacc   4380
tgacaaaata atctgaaggt ggtgtagtcc ttttgtgttc ttgaattctc cctccccttg   4440
cccttcatta agcctagtgc ctctattata ccgtgttatt gtggagctga ccttatcttc   4500
taaactcctg aaaaaacttg tctcctcctc cccctcgaaa cacacatcta ccggatcatc   4560
ttccaatttg tctacttctg ttttcctgga accgatgact aatctagaga caagctttga   4620
gaccttatat tcgtaatctg agtgtctcag cttatacttt tgtttcctca tgaagccctc   4680
tgtaatttgg ctcacagcac taacaagcaa tttgttaaaa tcatactcca aaagccgttc   4740
tccattcaga tgtttattga caaccacact tttgttgctt gcgagatcta atgctgtcgc   4800
acatccagag ttggtcatgg ggtccagatt gttgagcctt ttctcccctt ttagaattaa   4860
ggtgccattg ttgaatgaag ataccatcat gctaaagatc tctaaattaa caccaggggt   4920
tgaatgctga caatcaatat ctttaccggt gaacttcttc atttgttcat aaaaaacaca   4980
ttcctcttcg ggtgtgattg tttccttagg gttgacaaag aaaccaaact cactcttggg   5040
ctcaaagaac ttttcaaaac attttatctg atctgtcaat ctatcagggg tctcctttgt   5100
gatcaaatga cacaggtatg acacattcaa cataaacttg aattttgcac tcaataacac   5160
cttttcacca gtaccaaaaa ttgtcctaat caaaaaccga agcagcctgt acaccacttt   5220
ctcggcaggt gtgattagat cctccttcaa cttatccatt aatgaggtcg atgaaaagtc   5280
tgagacgatg gccatcacta aatacctaat attttgaacc tgcttttgat ttctctttgt   5340
tgggttggtg agcatcagta ggatcaatgt ccttagtgca gtctcaatgt caataagaga   5400
atcttttaag tcagggcatg acctaatcca tgaaatcatt gtgtctatca tgttgtgcaa   5460
cacctcatct gaaaaaattg gtaaaaagaa cctttttgga tctgcgtaaa aggaaatcaa   5520
gtgaccatcc ggaccttgta tggaataaca cctcgatgat tctccagttt tctgatatag   5580
tagatgatac tcttcggaat ccagttttat tatctggcaa aacacctctt tgcactccac   5640
cacttgatat ctcacagacc ccagttggtt ctgtctcaac cttgcaactg agcttgtttt   5700
catgctgttt gttagagcca aacaaacaga tgacagtttt ctcaaactct gtaaacccct   5760
caattgctct atgttaggct ggaaagtgta atcttcaaat tttgtgtaat gcattacagg   5820
atgagtcccg gctctcataa agttctcaaa ttcagcaaat ggtatatggc attcttgcac   5880
gaggcattct gatagtccgt aatgctcaaa actaagtccc actgttgata ggcatttctg   5940
gatttttgct atgaactcat ttatggatac cctaaaaagc tcatcaagag atgccttttt   6000
gtgcactctt gattttcttc tgttcttcaa aagtctcatg aattcttctt tggtactttg   6060
aaggctcaca agcctatcat tcacactact gtagcaacaa ccaacccaat gtttatcatt   6120
ttccaaccct ttggaaattg actgcttaat aagtgaagaa agacataaga catctaagtt   6180
cagcagctgt ctccttctag tgtttaataa ttttaaactt ttcaccttgt tcaacataga   6240
gagtagcctt tcatactcag tgttagcatc gcttcctctc tcatgcccat gggtctctgc   6300
```

```
tgtaatgaac ctcattaagg ggcaggattc aactgcctct ttgctcaaca ttaatatgtc   6360

atcattatca gtaagggttt cataaagttc agagaattcc ttgattaagc ccccagggct   6420

gaccttttgg aaattccttt tgagtttccc atttaacagg tccctcctaa acctgccaaa   6480

aaaggaattt atgccaaaga ccacatcatc gcaactcatg ttggggttga caccatcgtg   6540

gcacattttc ataatctcat cgttatgaaa tgatcttgcg tctttcaaaa ttttcattga   6600

gtccatgccg gaacgtttgt caacagtggt cttaagagac tcacagagcc tgaagtattc   6660

agactcctca aaaactttct catcttgact agaatactcc aggagtttaa ataggaggtc   6720

tctgaactta aaattcaccc attctggcat gaaactgtta tcataatcac aacgaccatc   6780

cactattgga accagtgtga tgcctgcaac agcaagatct tctttgatgc atgctagttt   6840

gttggtgtcc tcaatgaact tcttttcaaa actagctggt gtgcttctaa caaaacattc   6900

aagaagaata agggaattgt caatcaactt ataaccatca gggatgatga gtggcagtcc   6960

tggacacaca atcccagagt ctattaggat tgtttcaaca gatttgtcat cgtggttgtg   7020

tatgcaacca cttttgtctg cactgtctat ctctatacag cgtgataaca atttgagtcc   7080

ctcaattagc accattctgg gttctctttg tcccaggaag ttgagttttt gccttgacag   7140

cctctcgtcc tgttctatgt aatttagaca caactctctc aaatctgcaa tagtttcatc   7200

cattgcgcat caaaaagcct aggatcctcg gtgcgc                             7236
```

<210> SEQ ID NO 3
<211> LENGTH: 1497
<212> TYPE: DNA
<213> ORGANISM: Lymphocytic choriomeningitis virus (LCMV) strain WE

<400> SEQUENCE: 3

```
atgggtcaga ttgtgacaat gtttgaggct ttgcctcaca tcattgatga ggtcatcaac     60

attgtcatta ttgtgctcat tataatcacg agcatcaaag ctgtgtacaa tttcgccacc    120

tgtgggatat tagcactggt cagcttcctt tttttggctg gtaggtcctg tggcatgtac    180

ggccttaatg gtcccgacat ctataaaggg gtttaccagt tcaaatcagt ggagtttgat    240

atgtctcact taaatctgac gatgcccaat gcgtgctcag ccaacaactc tcatcactac    300

atcagtatgg gaagctctgg actggagcta actttcacta acgactccat ccttaatcac    360

aatttttgca acttaacctc cgctttcaac aaaaagactt ttgaccatac actcatgagt    420

atagtctcga gtctgcacct cagtattaga gggaattcca accacaaagc agtgtcttgt    480

gattttaaca atggcatcac cattcaatac aacttgtcat tttcggaccc acagagcgct    540

ataagccagt gtaggacttt cagaggtaga gtcttggaca tgtttagaac tgcctttgga    600

ggaaaataca tgagaagtgg ctggggctgg gcaggttcag atggcaagac cacttggtgc    660

agccaaacaa gctatcagta cctaatcata caaaacagga cttgggaaaa ccactgtaga    720

tatgcaggcc cttttgggat gtctagaatc ctctttgctc aggaaaagac aaagtttctc    780

actaggagac ttgcaggcac attcacctgg accctgtcag actcctcagg agtagaaaat    840

ccaggtggtt attgcctgac caaatggatg atccttgctg cagagctcaa atgttttggg    900

aatacagctg ttgcaaaatg taatgtcaat catgatgaag agttctgtga catgctacga    960

ctaattgatt acaacaaggc cgccctgagt aagttcaagc aagatgtaga gtctgccttg   1020

catgtattca aaacaacagt aaattctctg atttccgatc agctgttgat gaggaatcat   1080

ctaagagatc taatgggggt accatactgt aattactcaa agttctggta tctggaacat   1140

gctaagactg gtgagactag tgtacccaag tgctggcttg tcactaatgg ctcctacttg   1200
```

```
aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497


<210> SEQ ID NO 4
<211> LENGTH: 498
<212> TYPE: PRT
<213> ORGANISM: Lymphocytic choriomeningitis virus (LCMV) strain WE

<400> SEQUENCE: 4

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Ile Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320
```

```
Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg


<210> SEQ ID NO 5
<211> LENGTH: 1677
<212> TYPE: DNA
<213> ORGANISM: Lymphocytic choriomeningitis virus (LCMV) strain WE

<400> SEQUENCE: 5

atgtctttgt ccaaagaagt caaaagcttt cagtggacac aggcgttgag gagggagttg      60

cagagtttta catcagatgt aaaggctgcc gtcatcaagg acgcaaccag tcttctaaat     120

gggttggact tttctgaagt cagcaacgtt cagaggatca tgagaaagga aaggagggat     180

gataaagact tgcagagact caggagtctt aaccagactg tgcattctct tgttgatctg     240

aagtctacat caaagaaaaa tgttctgaaa gtgggaagac ttagtgcaga ggaattgatg     300

acccttgcag ctgatcttga gaagctgaag gccaaaatta tgagaactga gaggcctcaa     360

gcttctggag tctacatggg aaatttgaca gcacaacaac ttgatcaaag atcccaaata     420

ctgcaaatgg ttgggatgag aagacctcag cagggtgcaa gtggtgtagt aagggtttgg     480

gatgtgaagg actcatcact tctgaacaat cagttcggca caatgccaag cctgacaatg     540

gcttgcatgg caaaacagtc acagacccca ctcaatgatg ttgtgcaggc actcacagac     600

cttggcttac tttacacagt caaataccgg aatctcagtg atcttgaaag gctaaaggat     660

aaacacccag ttctgggggt cattactgaa cagcaatcta gtatcaatat ctctggttat     720

aatttcagtc ttggtgcagc tgtgaaagcg ggggcagctc tgctagatgg agggaacatg     780

ctggaatcta tcttgatcaa accgagcaac agtgaggatc tcctaaaagc agtcctcggg     840

gccaagaaga aactcaacat gtttgtctca gatcaagttg gagatagaaa tccctatgaa     900

aacatccttt ataaagtctg tctttcaggt gaaggatggc catacatagc ctgtagaacg     960

tcagttgtgg ggagagcatg ggagaacaca acaattgatc tcacaaatga aaaacttgtt    1020

gccaactcat ctaggccagt gcctggagca gcaggcccac ctcaggtggg cttgagttac    1080
```

```
agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677
```

```
<210> SEQ ID NO 6
<211> LENGTH: 558
<212> TYPE: PRT
<213> ORGANISM: Lymphocytic choriomeningitis virus (LCMV) strain WE

<400> SEQUENCE: 6

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270
```

```
Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

```
<210> SEQ ID NO 7
<211> LENGTH: 273
<212> TYPE: DNA
<213> ORGANISM: Lymphocytic choriomeningitis virus (LCMV) strain WE

<400> SEQUENCE: 7

atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273


<210> SEQ ID NO 8
<211> LENGTH: 90
<212> TYPE: PRT
<213> ORGANISM: Lymphocytic choriomeningitis virus (LCMV) strain WE

<400> SEQUENCE: 8
```

```
Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90


<210> SEQ ID NO 9
<211> LENGTH: 6630
<212> TYPE: DNA
<213> ORGANISM: Lymphocytic choriomeningitis virus (LCMV) strain WE

<400> SEQUENCE: 9

atggatgaaa ctattgcaga tttgagagag ttgtgtctaa attacataga acaggacgag      60

aggctgtcaa ggcaaaaact caacttcctg ggacaaagag aacccagaat ggtgctaatt     120

gagggactca aattgttatc acgctgtata gagatagaca gtgcagacaa aagtggttgc     180

atacacaacc acgatgacaa atctgttgaa acaatcctaa tagactctgg gattgtgtgt     240

ccaggactgc cactcatcat ccctgatggt tataagttga ttgacaattc ccttattctt     300

cttgaatgtt ttgttagaag cacaccagct agttttgaaa agaagttcat tgaggacacc     360

aacaaactag catgcatcaa agaagatctt gctgttgcag gcatcacact ggttccaata     420

gtggatggtc gttgtgatta tgataacagt ttcatgccag aatgggtgaa ttttaagttc     480

agagacctcc tatttaaact cctggagtat tctagtcaag atgagaaagt ttttgaggag     540

tctgaatact tcaggctctg tgagtctctt aagaccactg ttgacaaacg ttccggcatg     600

gactcaatga aaattttgaa agacgcaaga tcatttcata acgatgagat tatgaaaatg     660

tgccacgatg gtgtcaaccc caacatgagt tgcgatgatg tggtctttgg cataaattcc     720

ttttttggca ggtttaggag ggacctgtta aatgggaaac tcaaaaggaa tttccaaaag     780

gtcagccctg gggcttaat caaggaattc tctgaacttt atgaaaccct tactgataat      840

gatgacatat taatgttgag caaagaggca gttgaatcct gccccttaat gaggttcatt     900

acagcagaga cccatgggca tgagagagga agcgatgcta acactgagta tgaaaggcta     960

ctctctatgt tgaacaaggt gaaaagttta aaattattaa acactagaag gagacagctg    1020

ctgaacttag atgtcttatg tctttcttca cttattaagc agtcaatttc caaagggttg    1080

gaaaatgata aacattgggt tggttgttgc tacagtagtg tgaatgatag gcttgtgagc    1140

cttcaaagta ccaaagaaga attcatgaga cttttgaaga acagaagaaa atcaagagtg    1200

cacaaaaagg catctcttga tgagcttttt agggtatcca taaatgagtt catagcaaaa    1260

atccagaaat gcctatcaac agtgggactt agttttgagc attacggact atcagaatgc    1320

ctcgtgcaag aatgccatat accatttgct gaatttgaga actttatgag agccgggact    1380

catcctgtaa tgcattacac aaaatttgaa gattacactt tccagcctaa catagagcaa    1440

ttgaggggtt tacagagttt gagaaaactg tcatctgttt gtttggctct aacaaacagc    1500

atgaaaacaa gctcagttgc aaggttgaga cagaaccaac tggggtctgt gagatatcaa    1560
```

```
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaaccccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
tttatcaatt attgtattgg tgtcattttt ggagagaggc cagaagccta tacatcaagt   3960
```

```
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag tttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttccccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtgggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc atttcttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaata tctctgtgaa attggagaca   6300
```

```
aaggacatga gggtctttct ggcagagctc gagggctgtg gaaaaattgg tgatgtcctc   6360

ggcagcctcc tcctgcaccg attcagaact ggtgagcact tgatggagtc agaaataagt   6420

acagttcttc aggagctctg catggacaga tccgtcatgc tgacaccatt atcttttgtg   6480

ccagattggt tcaccttcag agattgtagg ctctgcttca gcaggtcaaa gaacactgta   6540

atgtatgaga caactggggg caggttcaga ctcaagggga aatcctgtga cgattggctg   6600

gcggagcggg tggccgagga gatcgactag                                    6630


<210> SEQ ID NO 10
<211> LENGTH: 2209
<212> TYPE: PRT
<213> ORGANISM: Lymphocytic choriomeningitis virus (LCMV) strain WE

<400> SEQUENCE: 10

Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
305                 310                 315                 320
```

```
Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735
```

-continued

```
Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Ser  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Val Glu  Asp Tyr Phe
    1130                1135                1140

Glu Ser  Phe Ser Ser Phe Phe  Ser Gly Ser Cys Leu  Asn Asn Asp
```

```
    1145                1150                1155

Lys Glu  Phe Glu Asn Ala Ile  Leu Ser Met Thr Ile  Asn Val Arg
    1160                1165                1170

Glu Gly  Leu Leu Asn Tyr Ser  Met Asp His Ser Lys  Trp Gly Pro
    1175                1180                1185

Met Met  Cys Pro Phe Leu Phe  Leu Met Leu Leu Gln  Asn Leu Lys
    1190                1195                1200

Leu Gly  Asp Asp Gln Tyr Val  Arg Ser Gly Lys Asp  His Val Ser
    1205                1210                1215

Thr Leu  Leu Thr Trp His Met  His Lys Leu Val Glu  Val Pro Phe
    1220                1225                1230

Pro Val  Val Asn Ala Met Met  Lys Ser Tyr Val Lys  Ser Lys Leu
    1235                1240                1245

Lys Leu  Leu Lys Gly Ser Gly  Thr Thr Val Thr Glu  Arg Ile Phe
    1250                1255                1260

Arg Glu  Tyr Phe Glu Met Gly  Val Val Pro Ser His  Ile Ser Ser
    1265                1270                1275

Leu Ile  Asp Met Gly Gln Gly  Ile Leu His Asn Ala  Ser Asp Phe
    1280                1285                1290

Tyr Gly  Leu Ile Ser Glu Arg  Phe Ile Asn Tyr Cys  Ile Gly Val
    1295                1300                1305

Ile Phe  Gly Glu Arg Pro Glu  Ala Tyr Thr Ser Ser  Asp Asp Gln
    1310                1315                1320

Ile Thr  Leu Phe Asp Lys Arg  Leu Ser Asp Leu Val  Asp Ser Asp
    1325                1330                1335

Pro Glu  Glu Val Leu Val Leu  Leu Glu Phe His Ser  His Leu Ser
    1340                1345                1350

Gly Leu  Leu Asn Lys Phe Ile  Ser Pro Lys Ser Val  Val Gly Arg
    1355                1360                1365

Phe Ala  Ala Glu Phe Lys Ser  Arg Phe Tyr Val Trp  Gly Glu Glu
    1370                1375                1380

Val Pro  Leu Leu Thr Lys Phe  Val Ser Ala Ala Leu  His Asn Val
    1385                1390                1395

Lys Cys  Lys Glu Pro His Gln  Leu Cys Glu Thr Ile  Asp Thr Ile
    1400                1405                1410

Ala Asp  Gln Ala Ile Ala Asn  Gly Val Pro Val Phe  Leu Val Asn
    1415                1420                1425

Cys Ile  Gln Arg Arg Thr Leu  Asp Leu Leu Lys Tyr  Ala Asn Phe
    1430                1435                1440

Pro Leu  Asp Pro Phe Leu Leu  Asn Thr His Thr Asp  Val Lys Asp
    1445                1450                1455

Trp Leu  Asp Gly Ser Arg Gly  Tyr Arg Ile Gln Arg  Leu Ile Glu
    1460                1465                1470

Glu Leu  Cys Pro Ser Glu Thr  Lys Ile Met Arg Lys  Leu Val Arg
    1475                1480                1485

Arg Leu  His His Lys Leu Lys  Asn Gly Glu Cys Asn  Glu Glu Phe
    1490                1495                1500

Phe Leu  Asp Leu Phe Asn Arg  Glu Lys Lys Glu Ala  Ile Leu Gln
    1505                1510                1515

Leu Gly  Glu Ile Leu Gly Leu  Glu Asp Asp Leu Asn  Glu Leu Ala
    1520                1525                1530

Ser Ile  Asn Trp Leu Asn Leu  Asn Glu Met Phe Pro  Leu Arg Met
    1535                1540                1545
```

```
Val Leu  Arg Gln Lys Val Val  Tyr Pro Ser Val Met  Thr Phe Gln
    1550                 1555                 1560

Glu Glu  Lys Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Val Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Met Tyr Ile Arg  Lys Val Leu Glu Asp  Leu Thr Met
    1625                 1630                 1635

Asp Glu  His Val Thr Arg Val  His Lys Gln Asp Gly  Val Met Leu
    1640                 1645                 1650

Tyr Ile  Cys Asp Lys Gln Arg  His Pro Glu Ala His  Arg Asp His
    1655                 1660                 1665

Ile Asn  Leu Leu Arg Pro Leu  Leu Trp Asp Tyr Ile  Cys Ile Ser
    1670                 1675                 1680

Leu Ser  Asn Ser Phe Glu Leu  Gly Val Trp Val Leu  Ala Glu Pro
    1685                 1690                 1695

Val Lys  Gly Lys Asn Glu Ser  Asn Ser Ala Val Arg  His Leu Asn
    1700                 1705                 1710

Pro Cys  Asp Tyr Val Ala Arg  Lys Pro Glu Ser Ser  Arg Leu Leu
    1715                 1720                 1725

Glu Asp  Lys Val Ser Leu Asn  His Val Ile Gln Ser  Val Arg Arg
    1730                 1735                 1740

Leu Tyr  Pro Lys Ile Phe Glu  Asp Gln Leu Leu Pro  Phe Met Ser
    1745                 1750                 1755

Asp Val  Ser Ser Lys Asn Met  Arg Trp Ser Pro Arg  Ile Lys Phe
    1760                 1765                 1770

Leu Asp  Leu Cys Val Leu Ile  Asp Ile Asn Ser Glu  Ser Leu Ser
    1775                 1780                 1785

Leu Ile  Ser His Val Val Lys  Trp Lys Arg Asp Glu  His Tyr Thr
    1790                 1795                 1800

Val Leu  Phe Ser Asp Leu Val  Asn Ser His Gln Arg  Ser Asp Ser
    1805                 1810                 1815

Ser Leu  Val Asp Glu Phe Val  Val Ser Thr Arg Asp  Val Cys Lys
    1820                 1825                 1830

Asn Phe  Leu Lys Gln Val Tyr  Phe Glu Ser Phe Val  Arg Glu Phe
    1835                 1840                 1845

Val Ala  Thr Ala Arg Thr Leu  Gly Asn Phe Ser Trp  Phe Pro His
    1850                 1855                 1860

Lys Asp  Met Met Pro Ser Glu  Asp Gly Ala Glu Ala  Leu Gly Pro
    1865                 1870                 1875

Phe Gln  Ser Phe Ile Leu Lys  Val Val Asn Lys Lys  Ile Glu Arg
    1880                 1885                 1890

Pro Met  Phe Arg Asn Asp Leu  Gln Phe Gly Phe Gly  Trp Phe Ser
    1895                 1900                 1905

Tyr Arg  Val Gly Asp Val Val  Cys Asn Ala Ala Met  Leu Ile Lys
    1910                 1915                 1920

Gln Gly  Leu Thr Asp Pro Lys  Ala Phe Lys Ser Leu  Arg Asp Leu
    1925                 1930                 1935
```

Trp Asp Tyr Met Leu Ser Ser Thr Glu Gly Ile Leu Glu Phe Ser
    1940                1945                1950

Ile Thr Val Asp Phe Thr His Asn Gln Asn Asn Thr Asp Cys Leu
    1955                1960                1965

Arg Lys Phe Ser Leu Ile Phe Val Val Lys Cys Gln Leu Gln Ser
    1970                1975                1980

Pro Gly Val Ala Asp Tyr Leu Ser Cys Ser His Phe Phe Lys Gly
    1985                1990                1995

Glu Val Asp Arg Arg Leu Leu Asp Glu Cys Leu Asn Leu Leu Arg
    2000                2005                2010

Thr Asp Pro Ile Phe Lys Ala Asn Asp Gly Val Phe Asp Ile Arg
    2015                2020                2025

Ser Glu Glu Phe Glu Asp Tyr Met Glu Asp Pro Leu Thr Leu Gly
    2030                2035                2040

Asp Ser Leu Glu Leu Glu Leu Ile Gly Ser Arg Arg Ile Leu Asn
    2045                2050                2055

Glu Ile Lys Ser Thr Asp Phe Glu Arg Ile Gly Pro Glu Trp Glu
    2060                2065                2070

Pro Val Pro Leu Thr Ile Arg Lys Gly Ala Leu Phe Glu Gly Arg
    2075                2080                2085

Asn Phe Val Gln Asn Ile Ser Val Lys Leu Glu Thr Lys Asp Met
    2090                2095                2100

Arg Val Phe Leu Ala Glu Leu Glu Gly Cys Gly Lys Ile Gly Asp
    2105                2110                2115

Val Leu Gly Ser Leu Leu Leu His Arg Phe Arg Thr Gly Glu His
    2120                2125                2130

Leu Met Glu Ser Glu Ile Ser Thr Val Leu Gln Glu Leu Cys Met
    2135                2140                2145

Asp Arg Ser Val Met Leu Thr Pro Leu Ser Phe Val Pro Asp Trp
    2150                2155                2160

Phe Thr Phe Arg Asp Cys Arg Leu Cys Phe Ser Arg Ser Lys Asn
    2165                2170                2175

Thr Val Met Tyr Glu Thr Thr Gly Gly Arg Phe Arg Leu Lys Gly
    2180                2185                2190

Lys Ser Cys Asp Asp Trp Leu Ala Glu Arg Val Ala Glu Glu Ile
    2195                2200                2205

Asp

<210> SEQ ID NO 11
<211> LENGTH: 3376
<212> TYPE: DNA
<213> ORGANISM: Lymphocytic choriomeningitis virus (LCMV) strain P52-WE

<400> SEQUENCE: 11
gcgcaccggg gatcctaggc tttttggatt gcgctttcct ttaggacaat tgggtgctgg 60
attctatcca ataaaaggat gggtcagatt gtgacaatgt ttgaggcttt gcctcacatc 120
attgatgagg tcatcaacat tgtcattatt gtgctcatta taatcacgag catcaaagct 180
gtgtacaatt tcgccacctg tgggatatta gcactggtca gcttcctttt tttggctggt 240
aggtcctgtg gcatgtacgg ccttaatggt cccgacatct ataaaggggt ttaccagttc 300
aaatcagtgg agtttgatat gtctcactta aatctgacga tgcccaatgc gtgctcagcc 360
aacaactctc atcactacat cagtatggga agctctggac tggagctaac tttcactaac 420
gactccatcc ttaatcacaa tttttgcaac ttaacctccg ctttcaacaa aaagactttt 480

```
gaccatacac tcatgagtat agtctcgagt ctgcacctca gtattagagg gaattccaac    540
cacaaagcag tgtcttgtga ttttaacaat ggcatcacca ttcaatacaa cttgtcattt    600
tcggacccac agagcgctat gagccagtgt tggactttca gaggtagagt cttggacatg    660
tttagaactg cctttggagg aaaatacatg agaagtggct ggggctgggc aggttcagat    720
ggcaagacca cttggtgcag ccaaacaagc tatcagtacc taatcataca aaacaggact    780
tgggaaaacc actgtagata tgcaggccct tttgggatgt ctagaatcct ctttgctcag    840
gaaaagacaa agtttctcac taggagactt gcaggcacat tcacctggac cctgtcagac    900
tcctcaggag tagaaaatcc aggtggttat tgcctgacca aatggatgat ccttgctgca    960
gagctcaaat gttttgggaa tacagctgtt gcaaaatgta atgtcaatca tgatgaagag   1020
ttctgtgaca tgctacgact aattgattac aacaaggccg ccctgagtaa gttcaagcaa   1080
gatgtagagt ctgccttgca tgtattcaaa acaacagtaa attctctgat ttccgatcag   1140
ctgttgatga ggaatcatct aagagatcta atgggggtac catactgtaa ttactcaaag   1200
ttctggtatc tggaacatgc taagactggt gagactagtg tacccaagtg ctggcttgtc   1260
actaatggct cctacttgaa tgagacccac tttagtgatc aaatcgaaca agaagcagat   1320
aacatgatca cagagatgtt gaggaaggac tacataaaaa gacaagggag tactccttta   1380
gccttaatgg atcttttgat gttttcaaca tcagcatatc taatcagcat ctttctgcat   1440
cttgtgaaga taccaacaca tagacacata aagggcggtt catgtccaaa gccacaccgc   1500
ttgaccaaca aggggatctg tagttgtggt gcattcaagg tgcctggtgt aaaaactatc   1560
tggaaaagac gctgatcagc agcgcctccc tgactctcca cctcgaaaga ggtggagagt   1620
cagggaggcc cagtgggtct tagagtgtca caacattggg tcctctgaag attaaatcat   1680
gtggcaggat gttgtgaacg gtttttagat cagggagtct tgccttggaa gcactctcaa   1740
aaatgatgca gtccatgagt gcacagtgtg gggtgatctc tttcttcttt ttgtctctca   1800
ctaccccagt gtgcattttg catagccagc catatttgtc ccacacttta tcttcatatt   1860
ctcttgaggc ctccttggtc atctcaacat caatgagttt tatgtccctt ctattttgtg   1920
agtccagaag ctttctgatg tcatcagaac cttgacagct caaaaccatc ccttgtggga   1980
gagcacctat aactgatgag gtcagcccag gctgtgcatt gaagagatca gcaagatcca   2040
tgccgtgtga atactttgag tcctgcttga attgcttctg gtccgtaggt tccctgtaaa   2100
aatgtatgaa ttgcccattt tgtggttgga atattgctat ctccactgga tcattgaacc   2160
tgccctcaat gtcaatccat gtgggagcat tgggatcaat ccctcccatc aagtctttca   2220
acagcattgt ctgactgtaa ctcaagccca cctgaggtgg gcctgctgct ccaggcactg   2280
gcctagatga gttggcaaca agtttttcat ttgtgagatc aattgttgtg ttctcccatg   2340
ctctccccac aactgacgtt ctacaggcta tgtatggcca tccttcacct gaaagacaga   2400
ctttataaag gatgttttca tagggatttc tatctccaac ttgatctgag acaaacatgt   2460
tgagtttctt cttggccccg aggactgctt ttaggagatc ctcactgttg ctcggtttga   2520
tcaagataga ttccagcatg ttccctccat ctagcagagc tgccccccgct ttcacagctg   2580
caccaagact gaaattataa ccagagatat tgatactaga ttgctgttca gtaatgaccc   2640
ccagaactgg gtgtttatcc tttagccttt caagatcact gagattcggg tatttgactg   2700
tgtaaagtaa gccaaggtct gtgagtgcct gcacaacatc attgagtggg gtctgtgact   2760
gttttgccat gcaagccatt gtcaggcttg gcattgtgcc gaactgattg ttcagaagtg   2820
```

```
atgagtcctt cacatcccaa acccttacta caccacttgc accctgctga ggtcttctca   2880

tcccaaccat ttgcagtatt tgggatcttt gatcaagttg ttgtgctgtc aaatttccca   2940

tgtagactcc agaagcttga ggcctctcag ttctcataat tttggccttc agcttctcaa   3000

gatcagctgc aagggtcatc aattcctctg cactaagtct tcccactttc agaacatttt   3060

tctttgatgt agacttcaga tcaacaagag aatgcacagt ctggttaaga ctcctgagtc   3120

tctgcaagtc tttatcatcc ctcctttcct ttctcatgat cctctgaacg ttgctgactt   3180

cagaaaagtc caacccattt agaagactgg ttgcgtcctt gatgacggca gcctttacat   3240

ctgatgtaaa actctgcaac tccctcctca acgcctgtgt ccactgaaag cttttgactt   3300

ctttggacaa agacattttg tcacacaatg aatttccaaa taaaagcgca attaaatgcc   3360

taggatccac tgtgcg                                                    3376


<210> SEQ ID NO 12
<211> LENGTH: 7236
<212> TYPE: DNA
<213> ORGANISM: Lymphocytic choriomeningitis virus (LCMV) strain P52-WE

<400> SEQUENCE: 12

gcgcaccggg gatcctaggc gtttagttgc gctgctttat tgcacagctt cactctgcta     60

aaccatcagg aactgaccga tcatcagtca tgggccaagg caagtccaaa gaagaaaggg    120

acaccagcaa tacaggcaga gcagagcttt tgccagacac cacctatctt ggtcctctaa    180

attgtaaatc atgttggcag aaatttgaca gcttggttag atgccatgac cactatcttt    240

gcagacactg tctgaatctc ctgctgtcag tttccgacag atgtcctctc tgtaagtatc    300

cactgccaac caaactgaag gtgtcaacag tcccaagctc cccacctccc tatgaggagt    360

gacgccccag acctcgacac aacaggccac ccaacacaga aaaaccacac acaaaccggc    420

acacacagac acagcaacca gcacaaagcg cacgaaaaca cacacacaca cacacacaca    480

ccctcaccca cgcgcccccc cgcaccgccg ggggggcgcc cccccggggg gcagcccccc    540

gggggcccgg gcagggcccc gcggagatgc cggctagtcg atctcctcgg ccacccgctc    600

cgccagccaa tcgtcacagg atttcccctt gagtctgaac ctgcccccag ttgtctcata    660

cattacagtg ttctttgacc tgctgaagca gagcctacaa tctctgaagg tgaaccaatc    720

tggcacaaaa gataatggtg tcagcatgac ggatctgtcc atgcagagct cctgaagaac    780

tgtacttatt tctgactcca tcaagtgctc accagttctg aatcggtgca ggaggaggct    840

gccgaggaca tcaccaattt ttccacagcc ctcgagctct gccagaaaga ccctcatgtc    900

ctttgtctcc aatttcacag agatattctg aacaaagttc ctcccctcaa agagggcacc    960

cttccttatg gtcagaggca caggttccca ctcaggccct atcctctcaa agtcagtaga   1020

tttgatctca ttcagaatcc ttctagaacc tattagttca agttctagtg aatcaccaag   1080

tgtcaaaggg tcttccatgt aatcttcaaa ctcttcagac ctaatgtcaa agactccatc   1140

attcgcttta aagatggggt ctgtcctcaa cagattgaga cactcatcta ataatctcct   1200

gtcaacctca cctttgaaga aatgagagca cgataagtaa tcagctacac ctggactctg   1260

taattggcat ttaaccacaa agatcaatga aaatttcctc aagcagtcag tgttgttctg   1320

gttgtgtgtg aaatccactg tgattgagaa ctccaatatc ccctctgtgc tgctgagcat   1380

gtaatcccac aaatctctta aagatttaaa tgcttttgga tctgtcaaac cctgcttaat   1440

taacatagcg gcattacaca caacatcccc cacacgataa gagaaccaac caaaaccaaa   1500

ctgcaagtca ttcctaaaca tgggcctctc tattttcttg ttcaccactt tcaaaataaa   1560
```

```
tgattggaag ggtcccagtg cttcagcgcc atcttcagat ggcatcatgt ccttatgggg   1620

gaaccatgaa aagttaccta aggtcctagc tgttgcaaca aactctcgta caaatgattc   1680

gaaatacact tgcttcaaaa agttcttgca gacatccctt gtgctgacaa caaattcatc   1740

aactaaactt gagtctgacc gttggtgaga gttgacgaga tcagaaaaca gcacagtgta   1800

atgttcgtcc ctcttccatt tgacaacatg agaaatgagt gacaaagact ctgagttgat   1860

gtcaatcagc acacaaaggt caaggaattt aatcctggga ctccatctca tattttttga   1920

gctcacatca gacatgaatg ggagcaactg atcctcaaag attttggggt acagtcgcct   1980

cacagattga attacatgat tcaaactcac tttatcctct agtagtctcg aactctcagg   2040

ttttcttgct acataatcac atggatttaa gtgcctaaca gccgaattac tctcgttctt   2100

tcctttcaca ggttctgcta aaacccaaac acccagctca aaagagttgc tcaatgagat   2160

gcaaatgtag tcccagagaa ggggcctcaa aaggttgatg tggtcacggt gagcctctgg   2220

gtgtctctgc ttgtcgcaaa tgtacaacat cacaccatct tgtttgtgaa cccttgtgac   2280

atgttcatcc atggtcagat cttcaagcac ctttctgata tacatatttt ccctgttttt   2340

atttctcaca cacctacttc ctaaagtctt acagagacct ataaagccgg atgagacaca   2400

actctgaaaa gctgatttgt tgattgcctc tgacaacagc ttctgtgcac ctcttgtgaa   2460

cttactacaa agcttatttt ggagtgtttt aatcaatgag ggatcttttt cctcttgaaa   2520

ggtcattact gatgggtaaa ccactttttg tctcagaacc atcctcaatg ggaacatttc   2580

attcagattc aaccaattga tgcttgccaa ctcattaaga tcatcctcaa gaccaagaat   2640

ctctcccaat tgaaggatgg cctctttctt ttccctgttg aagaggtcta gaaaaaattc   2700

ctcgttacat tcaccgttct tgagtttgtg atgtagtctt cttacaagtt ttctcatgat   2760

ctttgtttca ctgggacaca attcttcaat gagtctttgg attctataac ctctagaacc   2820

atctaaccaa tcctttacat cagtgtgagt gtttaacaag aatggatcta aagggaaatt   2880

agcatatttc aagagatcca gtgtcctcct ctggatacag tttactaaaa aaactggaac   2940

tccatttgct atagcttgat cagcaatcgt atctattgtc tcacaaagtt gatgcggttc   3000

tttacactta acattgtgta gtgccgcaga cacaaatttc gtgaggagag ggacctcctc   3060

cccccacaca taaaatctgg atttgaattc cgctgcaaac cgcccaacca cactttttgg   3120

actgatgaac ttgttcaaca aaccacttaa gtgagagtgg aattccagca agacaaggac   3180

ttcttctggg tcactatcaa ctaagtcact caatctcttg tcaaataaag tgatctgatc   3240

atcacttgat gtataggctt ctggcctctc tccaaaaatg acaccaatac aataattgat   3300

aaacctttca ctaattaaac cgtaaaaatc agaagcattg tgtaggatcc cctgtcccat   3360

gtcaatgaga ctagatatgt gagatggcac cacccccatt tcaaaatact ctctaaagat   3420

tctctccgta acagtcgttc ctgacccttt gagaagcttg agttttgatt taacatatga   3480

tttcatcatt gcattcacaa cagggaaagg gacttcaaca agtttatgca tatgccaagt   3540

caacaaggtg ctaacatgat cttttccaga acgcacgtac tgatcatcac ccagtttgag   3600

attttggaga agcattaaga ataggaatgg gcacatcatt ggtccccatt tgctgtgatc   3660

catgctgtag tttaacaacc cttctctcac attgatagtc attgacaaga ttgcattttc   3720

aaactctttg tcattgttta aacaagatcc tgaaaagaaa ctagaaaagg attcaaaata   3780

atcttctacc aatcttgtga acatttttgt cctcaaatcc ccaatgtaaa gctctctatt   3840

tcccccaacc tgctctttgt atgacaatgc aaattttagt ctcccagagt cagggccaac   3900
```

-continued

```
tgaagtgtat gatgttggtg attcttctga gtaaaaacac agattcttta gagcagcact   3960
catgcatttt gtcaatgaaa gggccttact tagagattca gaattgcttt ccctttcact   4020
aattcttaca tcttcttcca atttgtccca gtcaaattta aaatttaagc tctgcctctg   4080
catgtgtctg tacttccctg aatacgcatt tgcattcatc tgtaacaaga tcatcttcat   4140
acatgagaac caatcaccct ctgagaagaa ctttctacag aggtttcttg ccatctcatc   4200
cagaccacat tgttctttga cagctgatgt aaaatacaat ggtgacagtt ctgttgaacc   4260
ttcaacagcc tcacaaataa acctcatgtc gtcattggtg agacaggatg gatcaaagtc   4320
ctctactaga tgaaatgaaa tttctgataa aatgactttc ctcagataag ctcttttacc   4380
tgacaaaata atctgaaggt ggtgtagtcc ttttgtgttc ttgaattctc cctccccttg   4440
cccttcatta agcctagtgc ctctattata ccgtgttatt gtggagctga ccttatcttc   4500
taaactcctg aaaaaacttg tctcctcctc cccctcgaaa cacacatcta ccggatcatc   4560
ttccaatttg tctacttctg ttttcctgga accgatgact aatctagaga caagctttga   4620
gaccttatat tcgtaatctg agtgtctcag cttatacttt tgtttcctca tgaagccctc   4680
tgtaatttgg ctcacagcac taacaagcaa tttgttaaaa tcatactcca aaagccgttc   4740
tccattcaga tgtttattga caaccacact tttgttgctt gcgagatcta atgctgtcgc   4800
acatccagag ttggtcatgg ggtccagatt gttgagcctt ttctcccctt ttagaattaa   4860
ggtgccattg ttgaatgaag ataccatcat gctaaagatc tctaaattaa caccaggggt   4920
tgaatgctga caatcaatat ctttaccggt gaacttcttc atttgttcat aaaaaacaca   4980
ttcctcttcg ggtgtgattg tttccttagg gttgacaaag aaaccaaact cactcttggg   5040
ctcaaagaac ttttcaaaac attttatctg atctgtcaat ctatcagggg tctcctttgt   5100
gatcaaatga cacaggtatg acacattcaa cataaacttg aattttgcac tcaataacac   5160
cttttcacca gtaccaaaaa ttgtcctaat caaaaaccga agcagcctgt acaccacttt   5220
ctcggcaggt gtgattagat cctccttcaa cttatccatt aatgaggtcg atgaaaagtc   5280
tgagacgatg gccatcacta aatacctaat attttgaacc tgcttttgat ttctctttgt   5340
tgggttggtg agcatcagta ggatcaatgt ccttagtgca gtctcaatgt caataagaga   5400
atcttttaag tcagggcatg acctaatcca tgaaatcatt gtgtctatca tgttgtgcaa   5460
cacctcatct gaaaaaattg gtaaaaagaa cctttttgga tctgcgtaaa aggaaatcaa   5520
gtgaccatcc ggaccttgta tggaataaca cctcgatgat tctccagttt tctgatatag   5580
tagatgatac tcttcggaat ccagttttat tatctggcaa aacacctctt tgcactccac   5640
cacttgatat ctcacagacc ccagttggtt ctgtctcaac cttgcaactg agcttgtttt   5700
catgctgttt gttagagcca aacaaacaga tgacagtttt ctcaaactct gtaaacccct   5760
caattgctct atgttaggct ggaaagtgta atcttcaaat tttgtgtaat gcattacagg   5820
atgagtcccg gctctcataa agttctcaaa ttcagcaaat ggtatatggc attcttgcac   5880
gaggcattct gatagtccgt aatgctcaaa actaagtccc actgttgata ggcatttctg   5940
gatttttgct atgaactcat ttatggatac cctaaaaagc tcatcaagag atgccttttt   6000
gtgcactctt gattttcttc tgttcttcaa aagtctcatg aattcttctt tggtactttg   6060
aaggctcaca agcctatcat tcacactact gtagcaacaa ccaacccaat gtttatcatt   6120
ttccaaccct ttggaaattg actgcttaat aagtgaagaa agacataaga catctaagtt   6180
cagcagctgt ctccttctag tgtttaataa ttttaaactt ttcaccttgt tcaacataga   6240
gagtagcctt tcatactcag tgttagcatc gcttcctctc tcatgcccat gggtctctgc   6300
```

```
tgtaatgaac ctcattaagg ggcaggattc aactgcctct ttgctcaaca ttaatatgtc   6360
atcattatca gtaagggttt cataaagttc agagaattcc ttgattaagc ccccagggct   6420
gacctttggg aaattccttt tgagtttccc atttaacagg tccctcctaa acctgccaaa   6480
aaaggaattt atgccaaaga ccacatcatc gcaactcatg ttggggttga caccatcgtg   6540
gcacattttc ataatctcat cgttatgaaa tgatcttgcg tctttcaaaa ttttcattga   6600
gtccatgccg gaacgtttgt caacagtggt cttaagagac tcacagagcc tgaagtattc   6660
agactcctca aaaactttct catcttgact agaatactcc aggagtttaa ataggaggtc   6720
tctgaactta aaattcaccc attctggcat gaaactgtta tcataatcac aacgaccatc   6780
cactattgga accagtgtga tgcctgcaac agcaagatct tctttgatgc atgctagttt   6840
gttggtgtcc tcaatgaact tcttttcaaa actagctggt gtgcttctaa caaaacattc   6900
aagaagaata agggaattgt caatcaactt ataaccatca gggatgatga gtggcagtcc   6960
tggacacaca atcccagagt ctattaggat tgtttcaaca gatttgtcat cgtggttgtg   7020
tatgcaacca cttttgtctg cactgtctat ctctatacag cgtgataaca atttgagtcc   7080
ctcaattagc accattctgg gttctctttg tcccaggaag ttgagttttt gccttgacag   7140
cctctcgtcc tgttctatgt aatttagaca caactctctc aaatctgcaa tagtttcatc   7200
cattgcgcat caaaaagcct aggatcctcg gtgcgc                             7236
```

<210> SEQ ID NO 13
<211> LENGTH: 1497
<212> TYPE: DNA
<213> ORGANISM: Lymphocytic choriomeningitis virus (LCMV) strain P52-WE

<400> SEQUENCE: 13

```
atgggtcaga ttgtgacaat gtttgaggct ttgcctcaca tcattgatga ggtcatcaac     60
attgtcatta ttgtgctcat tataatcacg agcatcaaag ctgtgtacaa tttcgccacc    120
tgtgggatat tagcactggt cagcttcctt tttttggctg gtaggtcctg tggcatgtac    180
ggccttaatg gtcccgacat ctataaaggg gtttaccagt tcaaatcagt ggagtttgat    240
atgtctcact taaatctgac gatgcccaat gcgtgctcag ccaacaactc tcatcactac    300
atcagtatgg gaagctctgg actggagcta actttcacta acgactccat ccttaatcac    360
aatttttgca acttaacctc cgctttcaac aaaaagactt ttgaccatac actcatgagt    420
atagtctcga gtctgcacct cagtattaga gggaattcca accacaaagc agtgtcttgt    480
gattttaaca atggcatcac cattcaatac aacttgtcat tttcggaccc acagagcgct    540
atgagccagt gttggacttt cagaggtaga gtcttggaca tgtttagaac tgcctttgga    600
ggaaaataca tgagaagtgg ctggggctgg gcaggttcag atggcaagac cacttggtgc    660
agccaaacaa gctatcagta cctaatcata caaaacagga cttgggaaaa ccactgtaga    720
tatgcaggcc cttttgggat gtctagaatc ctctttgctc aggaaaagac aaagtttctc    780
actaggagac ttgcaggcac attcacctgg accctgtcag actcctcagg agtagaaaat    840
ccaggtggtt attgcctgac caaatggatg atccttgctg cagagctcaa atgttttggg    900
aatacagctg ttgcaaaatg taatgtcaat catgatgaag agttctgtga catgctacga    960
ctaattgatt acaacaaggc cgccctgagt aagttcaagc aagatgtaga gtctgccttg   1020
catgtattca aaacaacagt aaattctctg atttccgatc agctgttgat gaggaatcat   1080
ctaagagatc taatgggggt accatactgt aattactcaa agttctggta tctggaacat   1140
```

```
gctaagactg gtgagactag tgtacccaag tgctggcttg tcactaatgg ctcctacttg   1200

aatgagaccc actttagtga tcaaatcgaa caagaagcag ataacatgat cacagagatg   1260

ttgaggaagg actacataaa aagacaaggg agtactcctt tagccttaat ggatcttttg   1320

atgttttcaa catcagcata tctaatcagc atctttctgc atcttgtgaa gataccaaca   1380

catagacaca taaagggcgg ttcatgtcca aagccacacc gcttgaccaa caaggggatc   1440

tgtagttgtg gtgcattcaa ggtgcctggt gtaaaaacta tctggaaaag acgctga      1497


<210> SEQ ID NO 14
<211> LENGTH: 498
<212> TYPE: PRT
<213> ORGANISM: Lymphocytic choriomeningitis virus (LCMV) strain P52-WE

<400> SEQUENCE: 14

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Met Ser Gln Cys Trp Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320
```

```
Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg
```

<210> SEQ ID NO 15
<211> LENGTH: 1677
<212> TYPE: DNA
<213> ORGANISM: Lymphocytic choriomeningitis virus (LCMV) strain P52-WE

<400> SEQUENCE: 15

```
atgtctttgt ccaaagaagt caaaagcttt cagtggacac aggcgttgag gagggagttg      60

cagagtttta catcagatgt aaaggctgcc gtcatcaagg acgcaaccag tcttctaaat     120

gggttggact tttctgaagt cagcaacgtt cagaggatca tgagaaagga aaggagggat     180

gataaagact tgcagagact caggagtctt aaccagactg tgcattctct tgttgatctg     240

aagtctacat caaagaaaaa tgttctgaaa gtgggaagac ttagtgcaga ggaattgatg     300

acccttgcag ctgatcttga gaagctgaag gccaaaatta tgagaactga gaggcctcaa     360

gcttctggag tctacatggg aaatttgaca gcacaacaac ttgatcaaag atcccaaata     420

ctgcaaatgg ttgggatgag aagacctcag cagggtgcaa gtggtgtagt aagggtttgg     480

gatgtgaagg actcatcact tctgaacaat cagttcggca caatgccaag cctgacaatg     540

gcttgcatgg caaaacagtc acagacccca ctcaatgatg ttgtgcaggc actcacagac     600

cttggcttac tttacacagt caaatacccg aatctcagtg atcttgaaag gctaaaggat     660

aaacacccag ttctgggggt cattactgaa cagcaatcta gtatcaatat ctctggttat     720

aatttcagtc ttggtgcagc tgtgaaagcg ggggcagctc tgctagatgg agggaacatg     780

ctggaatcta tcttgatcaa accgagcaac agtgaggatc tcctaaaagc agtcctcggg     840

gccaagaaga aactcaacat gtttgtctca gatcaagttg gagatagaaa tccctatgaa     900

aacatccttt ataaagtctg tctttcaggt gaaggatggc catacatagc ctgtagaacg     960

tcagttgtgg ggagagcatg ggagaacaca acaattgatc tcacaaatga aaaacttgtt    1020

gccaactcat ctaggccagt gcctggagca gcaggcccac ctcaggtggg cttgagttac    1080
```

```
agtcagacaa tgctgttgaa agacttgatg ggagggattg atcccaatgc tcccacatgg   1140

attgacattg agggcaggtt caatgatcca gtggagatag caatattcca accacaaaat   1200

gggcaattca tacattttta cagggaacct acggaccaga agcaattcaa gcaggactca   1260

aagtattcac acggcatgga tcttgctgat ctcttcaatg cacagcctgg gctgacctca   1320

tcagttatag gtgctctccc acaagggatg gttttgagct gtcaaggttc tgatgacatc   1380

agaaagcttc tggactcaca aaatagaagg gacataaaac tcattgatgt tgagatgacc   1440

aaggaggcct caagagaata tgaagataaa gtgtgggaca aatatggctg gctatgcaaa   1500

atgcacactg ggtagtgag agacaaaaag aagaaagaga tcaccccaca ctgtgcactc   1560

atggactgca tcatttttga gagtgcttcc aaggcaagac tccctgatct aaaaaccgtt   1620

cacaacatcc tgccacatga tttaatcttc agaggaccca atgttgtgac actctaa      1677
```

```
<210> SEQ ID NO 16
<211> LENGTH: 558
<212> TYPE: PRT
<213> ORGANISM: Lymphocytic choriomeningitis virus (LCMV) strain P52-WE

<400> SEQUENCE: 16

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Arg Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Thr Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270
```

```
Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Lys Leu Val Ala Asn Ser Ser Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Val Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 17
<211> LENGTH: 273
<212> TYPE: DNA
<213> ORGANISM: Lymphocytic choriomeningitis virus (LCMV) strain P52-WE

<400> SEQUENCE: 17

```
atgggccaag gcaagtccaa agaagaaagg gacaccagca atacaggcag agcagagctt      60

ttgccagaca ccacctatct tggtcctcta aattgtaaat catgttggca gaaatttgac     120

agcttggtta gatgccatga ccactatctt tgcagacact gtctgaatct cctgctgtca     180

gtttccgaca gatgtcctct ctgtaagtat ccactgccaa ccaaactgaa ggtgtcaaca     240

gtcccaagct ccccacctcc ctatgaggag tga                                  273
```

<210> SEQ ID NO 18
<211> LENGTH: 90
<212> TYPE: PRT
<213> ORGANISM: Lymphocytic choriomeningitis virus (LCMV) strain P52-WE

<400> SEQUENCE: 18

```
Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Pro Pro Pro Tyr Glu Glu
                85                  90
```

<210> SEQ ID NO 19
<211> LENGTH: 6630
<212> TYPE: DNA
<213> ORGANISM: Lymphocytic choriomeningitis virus (LCMV) strain P52-WE

<400> SEQUENCE: 19

```
atggatgaaa ctattgcaga tttgagagag ttgtgtctaa attacataga acaggacgag     60

aggctgtcaa ggcaaaaact caacttcctg ggacaaagag aacccagaat ggtgctaatt    120

gagggactca aattgttatc acgctgtata gagatagaca gtgcagacaa aagtggttgc    180

atacacaacc acgatgacaa atctgttgaa acaatcctaa tagactctgg gattgtgtgt    240

ccaggactgc cactcatcat ccctgatggt tataagttga ttgacaattc ccttattctt    300

cttgaatgtt ttgttagaag cacaccagct agttttgaaa agaagttcat tgaggacacc    360

aacaaactag catgcatcaa agaagatctt gctgttgcag gcatcacact ggttccaata    420

gtggatggtc gttgtgatta tgataacagt ttcatgccag aatgggtgaa ttttaagttc    480

agagacctcc tatttaaact cctggagtat tctagtcaag atgagaaagt ttttgaggag    540

tctgaatact tcaggctctg tgagtctctt aagaccactg ttgacaaacg ttccggcatg    600

gactcaatga aaattttgaa agacgcaaga tcatttcata acgatgagat tatgaaaatg    660

tgccacgatg gtgtcaaccc caacatgagt tgcgatgatg tggtctttgg cataaattcc    720

ttttttggca ggtttaggag ggacctgtta aatgggaaac tcaaaaggaa tttccaaaag    780

gtcagccctg gggcttaat caaggaattc tctgaacttt atgaaaccct tactgataat    840

gatgacatat taatgttgag caaagaggca gttgaatcct gccccttaat gaggttcatt    900

acagcagaga cccatgggca tgagagagga agcgatgcta acactgagta tgaaaggcta    960

ctctctatgt tgaacaaggt gaaaagttta aaattattaa acactagaag gagacagctg   1020

ctgaacttag atgtcttatg tctttcttca cttattaagc agtcaatttc caaagggttg   1080

gaaaatgata aacattgggt tggttgttgc tacagtagtg tgaatgatag gcttgtgagc   1140

cttcaaagta ccaaagaaga attcatgaga cttttgaaga acagaagaaa atcaagagtg   1200

cacaaaaagg catctcttga tgagcttttt agggtatcca taaatgagtt catagcaaaa   1260

atccagaaat gcctatcaac agtgggactt agttttgagc attacggact atcagaatgc   1320

ctcgtgcaag aatgccatat accatttgct gaatttgaga actttatgag agccgggact   1380

catcctgtaa tgcattacac aaaatttgaa gattacactt tccagcctaa catagagcaa   1440

ttgaggggtt tacagagttt gagaaaactg tcatctgttt gtttggctct aacaaacagc   1500

atgaaaacaa gctcagttgc aaggttgaga cagaaccaac tggggtctgt gagatatcaa   1560
```

```
gtggtggagt gcaaagaggt gttttgccag ataataaaac tggattccga agagtatcat   1620
ctactatatc agaaaactgg agaatcatcg aggtgttatt ccatacaagg tccggatggt   1680
cacttgattt ccttttacgc agatccaaaa aggttctttt taccaatttt ttcagatgag   1740
gtgttgcaca acatgataga cacaatgatt tcatggatta ggtcatgccc tgacttaaaa   1800
gattctctta ttgacattga gactgcacta aggacattga tcctactgat gctcaccaac   1860
ccaacaaaga gaaatcaaaa gcaggttcaa aatattaggt atttagtgat ggccatcgtc   1920
tcagactttt catcgacctc attaatggat aagttgaagg aggatctaat cacacctgcc   1980
gagaaagtgg tgtacaggct gcttcggttt ttgattagga caatttttgg tactggtgaa   2040
aaggtgttat tgagtgcaaa attcaagttt atgttgaatg tgtcatacct gtgtcatttg   2100
atcacaaagg agacccctga tagattgaca gatcagataa aatgttttga aaagttcttt   2160
gagcccaaga gtgagtttgg tttctttgtc aaccctaagg aaacaatcac acccgaagag   2220
gaatgtgttt tttatgaaca aatgaagaag ttcaccggta aagatattga ttgtcagcat   2280
tcaacccctg gtgttaattt agagatcttt agcatgatgg tatcttcatt caacaatggc   2340
accttaattc taaaagggga gaaaaggctc aacaatctgg accccatgac caactctgga   2400
tgtgcgacag cattagatct cgcaagcaac aaaagtgtgg ttgtcaataa acatctgaat   2460
ggagaacggc ttttggagta tgattttaac aaattgcttg ttagtgctgt gagccaaatt   2520
acagagggct tcatgaggaa acaaaagtat aagctgagac actcagatta cgaatataag   2580
gtctcaaagc ttgtctctag attagtcatc ggttccagga aaacagaagt agacaaattg   2640
gaagatgatc cggtagatgt gtgtttcgag ggggaggagg agacaagttt tttcaggagt   2700
ttagaagata aggtcagctc cacaataaca cggtataata gaggcactag gcttaatgaa   2760
gggcaagggg agggagaatt caagaacaca aaaggactac accaccttca gattattttg   2820
tcaggtaaaa gagcttatct gaggaaagtc attttatcag aaatttcatt tcatctagta   2880
gaggactttg atccatcctg tctcaccaat gacgacatga ggtttatttg tgaggctgtt   2940
gaaggttcaa cagaactgtc accattgtat tttacatcag ctgtcaaaga acaatgtggt   3000
ctggatgaga tggcaagaaa cctctgtaga aagttcttct cagagggtga ttggttctca   3060
tgtatgaaga tgatcttgtt acagatgaat gcaaatgcgt attcagggaa gtacagacac   3120
atgcagaggc agagcttaaa ttttaaattt gactgggaca aattggaaga agatgtaaga   3180
attagtgaaa gggaaagcaa ttctgaatct ctaagtaagg ccctttcatt gacaaaatgc   3240
atgagtgctg ctctaaagaa tctgtgtttt tactcagaag aatcaccaac atcatacact   3300
tcagttggcc ctgactctgg gagactaaaa tttgcattgt catacaaaga gcaggttggg   3360
ggaaatagag agctttacat tggggatttg aggacaaaaa tgttcacaag attggtagaa   3420
gattattttg aatccttttc tagtttcttt tcaggatctt gtttaaacaa tgacaaagag   3480
tttgaaaatg caatcttgtc aatgactatc aatgtgagag aagggttgtt aaactacagc   3540
atggatcaca gcaaatgggg accaatgatg tgcccattcc tattcttaat gcttctccaa   3600
aatctcaaac tgggtgatga tcagtacgtg cgttctggaa aagatcatgt tagcaccttg   3660
ttgacttggc atatgcataa acttgttgaa gtccctttcc ctgttgtgaa tgcaatgatg   3720
aaatcatatg ttaaatcaaa actcaagctt ctcaaagggt caggaacgac tgttacggag   3780
agaatcttta gagagtattt tgaaatgggg gtggtgccat ctcacatatc tagtctcatt   3840
gacatgggac aggggatcct acacaatgct tctgattttt acggtttaat tagtgaaagg   3900
```

```
tttatcaatt attgtattgg tgtcattttt ggagagaggc cagaagccta tacatcaagt   3960
gatgatcaga tcactttatt tgacaagaga ttgagtgact tagttgatag tgacccagaa   4020
gaagtccttg tcttgctgga attccactct cacttaagtg gtttgttgaa caagttcatc   4080
agtccaaaaa gtgtggttgg gcggtttgca gcggaattca aatccagatt ttatgtgtgg   4140
ggggaggagg tccctctcct cacgaaattt gtgtctgcgg cactacacaa tgttaagtgt   4200
aaagaaccgc atcaactttg tgagacaata gatacgattg ctgatcaagc tatagcaaat   4260
ggagttccag tttttttagt aaactgtatc cagaggagga cactggatct cttgaaatat   4320
gctaatttcc ctttagatcc attcttgtta aacactcaca ctgatgtaaa ggattggtta   4380
gatggttcta gaggttatag aatccaaaga ctcattgaag aattgtgtcc cagtgaaaca   4440
aagatcatga gaaaacttgt aagaagacta catcacaaac tcaagaacgg tgaatgtaac   4500
gaggaatttt ttctagacct cttcaacagg gaaaagaaag aggccatcct tcaattggga   4560
gagattcttg gtcttgagga tgatcttaat gagttggcaa gcatcaattg gttgaatctg   4620
aatgaaatgt tcccattgag gatggttctg agacaaaaag tggtttaccc atcagtaatg   4680
acctttcaag aggaaaagat cccctcattg attaaaacac tccaaaataa gctttgtagt   4740
aagttcacaa gaggtgcaca gaagctgttg tcagaggcaa tcaacaaatc agcttttcag   4800
agttgtgtct catccggctt tataggtctc tgtaagactt taggaagtag gtgtgtgaga   4860
aataaaaaca gggaaaatat gtatatcaga aaggtgcttg aagatctgac catggatgaa   4920
catgtcacaa gggttcacaa acaagatggt gtgatgttgt acatttgcga caagcagaga   4980
cacccagagg ctcaccgtga ccacatcaac cttttgaggc cccttctctg ggactacatt   5040
tgcatctcat tgagcaactc ttttgagctg ggtgtttggg ttttagcaga acctgtgaaa   5100
ggaaagaacg agagtaattc ggctgttagg cacttaaatc catgtgatta tgtagcaaga   5160
aaacctgaga gttcgagact actagaggat aaagtgagtt tgaatcatgt aattcaatct   5220
gtgaggcgac tgtaccccaa aatctttgag gatcagttgc tcccattcat gtctgatgtg   5280
agctcaaaaa atatgagatg gagtcccagg attaaattcc ttgacctttg tgtgctgatt   5340
gacatcaact cagagtcttt gtcactcatt tctcatgttg tcaaatggaa gagggacgaa   5400
cattacactg tgctgttttc tgatctcgtc aactctcacc aacggtcaga ctcaagttta   5460
gttgatgaat ttgttgtcag cacaagggat gtctgcaaga actttttgaa gcaagtgtat   5520
ttcgaatcat ttgtacgaga gtttgttgca acagctagga ccttaggtaa cttttcatgg   5580
ttccccccata aggacatgat gccatctgaa gatggcgctg aagcactggg acccttccaa   5640
tcatttattt tgaaagtggt gaacaagaaa atagagaggc ccatgtttag gaatgacttg   5700
cagtttggtt ttggttggtt ctcttatcgt gtgggggatg ttgtgtgtaa tgccgctatg   5760
ttaattaagc agggtttgac agatccaaaa gcatttaaat ctttaagaga tttgtgggat   5820
tacatgctca gcagcacaga ggggatattg gagttctcaa tcacagtgga tttcacacac   5880
aaccagaaca acactgactg cttgaggaaa ttttcattga tctttgtggt taaatgccaa   5940
ttacagagtc caggtgtagc tgattactta tcgtgctctc atttcttcaa aggtgaggtt   6000
gacaggagat tattagatga gtgtctcaat ctgttgagga cagaccccat ctttaaagcg   6060
aatgatggag tctttgacat taggtctgaa gagtttgaag attacatgga agaccctttg   6120
acacttggtg attcactaga acttgaacta ataggttcta gaaggattct gaatgagatc   6180
aaatctactg actttgagag gatagggcct gagtgggaac ctgtgcctct gaccataagg   6240
aagggtgccc tctttgaggg gaggaacttt gttcagaata tctctgtgaa attggagaca   6300
```

```
aaggacatga gggtctttct ggcagagctc gagggctgtg gaaaaattgg tgatgtcctc   6360

ggcagcctcc tcctgcaccg attcagaact ggtgagcact tgatggagtc agaaataagt   6420

acagttcttc aggagctctg catggacaga tccgtcatgc tgacaccatt atcttttgtg   6480

ccagattggt tcaccttcag agattgtagg ctctgcttca gcaggtcaaa gaacactgta   6540

atgtatgaga caactggggg caggttcaga ctcaagggga aatcctgtga cgattggctg   6600

gcggagcggg tggccgagga gatcgactag                                    6630


<210> SEQ ID NO 20
<211> LENGTH: 2209
<212> TYPE: PRT
<213> ORGANISM: Lymphocytic choriomeningitis virus (LCMV) strain P52-WE

<400> SEQUENCE: 20

Met Asp Glu Thr Ile Ala Asp Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Thr Ile Leu Ile Asp Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Val Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Met Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Ser Cys Asp Asp Val Val Phe Gly Ile Asn Ser
225                 230                 235                 240

Phe Phe Gly Arg Phe Arg Arg Asp Leu Leu Asn Gly Lys Leu Lys Arg
                245                 250                 255

Asn Phe Gln Lys Val Ser Pro Gly Gly Leu Ile Lys Glu Phe Ser Glu
            260                 265                 270

Leu Tyr Glu Thr Leu Thr Asp Asn Asp Asp Ile Leu Met Leu Ser Lys
        275                 280                 285

Glu Ala Val Glu Ser Cys Pro Leu Met Arg Phe Ile Thr Ala Glu Thr
    290                 295                 300

His Gly His Glu Arg Gly Ser Asp Ala Asn Thr Glu Tyr Glu Arg Leu
```

```
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Ile Ser Lys Gly Leu Glu Asn Asp Lys His Trp Val Gly
        355                 360                 365

Cys Cys Tyr Ser Ser Val Asn Asp Arg Leu Val Ser Leu Gln Ser Thr
    370                 375                 380

Lys Glu Glu Phe Met Arg Leu Leu Lys Asn Arg Arg Lys Ser Arg Val
385                 390                 395                 400

His Lys Lys Ala Ser Leu Asp Glu Leu Phe Arg Val Ser Ile Asn Glu
                405                 410                 415

Phe Ile Ala Lys Ile Gln Lys Cys Leu Ser Thr Val Gly Leu Ser Phe
            420                 425                 430

Glu His Tyr Gly Leu Ser Glu Cys Leu Val Gln Glu Cys His Ile Pro
        435                 440                 445

Phe Ala Glu Phe Glu Asn Phe Met Arg Ala Gly Thr His Pro Val Met
    450                 455                 460

His Tyr Thr Lys Phe Glu Asp Tyr Thr Phe Gln Pro Asn Ile Glu Gln
465                 470                 475                 480

Leu Arg Gly Leu Gln Ser Leu Arg Lys Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Ile Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Leu Ile Asp Ile Glu Thr
        595                 600                 605

Ala Leu Arg Thr Leu Ile Leu Leu Met Leu Thr Asn Pro Thr Lys Arg
    610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Arg Leu Leu Arg Phe Leu Ile
            660                 665                 670

Arg Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Thr Ile
                725                 730                 735
```

```
Thr Pro Glu Glu Glu Cys Val Phe Tyr Glu Gln Met Lys Lys Phe Thr
            740                 745                 750

Gly Lys Asp Ile Asp Cys Gln His Ser Thr Pro Gly Val Asn Leu Glu
        755                 760                 765

Ile Phe Ser Met Met Val Ser Ser Phe Asn Asn Gly Thr Leu Ile Leu
    770                 775                 780

Lys Gly Glu Lys Arg Leu Asn Asn Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Gly Phe Met Arg Lys Gln
        835                 840                 845

Lys Tyr Lys Leu Arg His Ser Asp Tyr Glu Tyr Lys Val Ser Lys Leu
    850                 855                 860

Val Ser Arg Leu Val Ile Gly Ser Arg Lys Thr Glu Val Asp Lys Leu
865                 870                 875                 880

Glu Asp Asp Pro Val Asp Val Cys Phe Glu Gly Glu Glu Glu Thr Ser
                885                 890                 895

Phe Phe Arg Ser Leu Glu Asp Lys Val Ser Ser Thr Ile Thr Arg Tyr
            900                 905                 910

Asn Arg Gly Thr Arg Leu Asn Glu Gly Gln Gly Glu Gly Glu Phe Lys
        915                 920                 925

Asn Thr Lys Gly Leu His His Leu Gln Ile Ile Leu Ser Gly Lys Arg
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Asp Met Arg Phe Ile
                965                 970                 975

Cys Glu Ala Val Glu Gly Ser Thr Glu Leu Ser Pro Leu Tyr Phe Thr
            980                 985                 990

Ser Ala Val Lys Glu Gln Cys Gly  Leu Asp Glu Met Ala  Arg Asn Leu
        995                 1000                1005

Cys Arg  Lys Phe Phe Ser Glu  Gly Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Ser  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Val Glu  Asp Tyr Phe
    1130                 1135                 1140
```

```
Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Leu Leu Asn Tyr Ser  Met Asp His Ser Lys  Trp Gly Pro
    1175                 1180                 1185

Met Met  Cys Pro Phe Leu Phe  Leu Met Leu Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Lys Gly Ser Gly  Thr Thr Val Thr Glu  Arg Ile Phe
    1250                 1255                 1260

Arg Glu  Tyr Phe Glu Met Gly  Val Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Ile Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Lys Arg  Leu Ser Asp Leu Val  Asp Ser Asp
    1325                 1330                 1335

Pro Glu  Glu Val Leu Val Leu  Leu Glu Phe His Ser  His Leu Ser
    1340                 1345                 1350

Gly Leu  Leu Asn Lys Phe Ile  Ser Pro Lys Ser Val  Val Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Phe  Leu Val Asn
    1415                 1420                 1425

Cys Ile  Gln Arg Arg Thr Leu  Asp Leu Leu Lys Tyr  Ala Asn Phe
    1430                 1435                 1440

Pro Leu  Asp Pro Phe Leu Leu  Asn Thr His Thr Asp  Val Lys Asp
    1445                 1450                 1455

Trp Leu  Asp Gly Ser Arg Gly  Tyr Arg Ile Gln Arg  Leu Ile Glu
    1460                 1465                 1470

Glu Leu  Cys Pro Ser Glu Thr  Lys Ile Met Arg Lys  Leu Val Arg
    1475                 1480                 1485

Arg Leu  His His Lys Leu Lys  Asn Gly Glu Cys Asn  Glu Glu Phe
    1490                 1495                 1500

Phe Leu  Asp Leu Phe Asn Arg  Glu Lys Lys Glu Ala  Ile Leu Gln
    1505                 1510                 1515

Leu Gly  Glu Ile Leu Gly Leu  Glu Asp Asp Leu Asn  Glu Leu Ala
    1520                 1525                 1530

Ser Ile  Asn Trp Leu Asn Leu  Asn Glu Met Phe Pro  Leu Arg Met
```

```
    1535                1540                1545

Val Leu  Arg Gln Lys Val Val  Tyr Pro Ser Val Met  Thr Phe Gln
    1550                1555                1560

Glu Glu  Lys Ile Pro Ser Leu  Ile Lys Thr Leu Gln  Asn Lys Leu
    1565                1570                1575

Cys Ser  Lys Phe Thr Arg Gly  Ala Gln Lys Leu Leu  Ser Glu Ala
    1580                1585                1590

Ile Asn  Lys Ser Ala Phe Gln  Ser Cys Val Ser Ser  Gly Phe Ile
    1595                1600                1605

Gly Leu  Cys Lys Thr Leu Gly  Ser Arg Cys Val Arg  Asn Lys Asn
    1610                1615                1620

Arg Glu  Asn Met Tyr Ile Arg  Lys Val Leu Glu Asp  Leu Thr Met
    1625                1630                1635

Asp Glu  His Val Thr Arg Val  His Lys Gln Asp Gly  Val Met Leu
    1640                1645                1650

Tyr Ile  Cys Asp Lys Gln Arg  His Pro Glu Ala His  Arg Asp His
    1655                1660                1665

Ile Asn  Leu Leu Arg Pro Leu  Leu Trp Asp Tyr Ile  Cys Ile Ser
    1670                1675                1680

Leu Ser  Asn Ser Phe Glu Leu  Gly Val Trp Val Leu  Ala Glu Pro
    1685                1690                1695

Val Lys  Gly Lys Asn Glu Ser  Asn Ser Ala Val Arg  His Leu Asn
    1700                1705                1710

Pro Cys  Asp Tyr Val Ala Arg  Lys Pro Glu Ser Ser  Arg Leu Leu
    1715                1720                1725

Glu Asp  Lys Val Ser Leu Asn  His Val Ile Gln Ser  Val Arg Arg
    1730                1735                1740

Leu Tyr  Pro Lys Ile Phe Glu  Asp Gln Leu Leu Pro  Phe Met Ser
    1745                1750                1755

Asp Val  Ser Ser Lys Asn Met  Arg Trp Ser Pro Arg  Ile Lys Phe
    1760                1765                1770

Leu Asp  Leu Cys Val Leu Ile  Asp Ile Asn Ser Glu  Ser Leu Ser
    1775                1780                1785

Leu Ile  Ser His Val Val Lys  Trp Lys Arg Asp Glu  His Tyr Thr
    1790                1795                1800

Val Leu  Phe Ser Asp Leu Val  Asn Ser His Gln Arg  Ser Asp Ser
    1805                1810                1815

Ser Leu  Val Asp Glu Phe Val  Val Ser Thr Arg Asp  Val Cys Lys
    1820                1825                1830

Asn Phe  Leu Lys Gln Val Tyr  Phe Glu Ser Phe Val  Arg Glu Phe
    1835                1840                1845

Val Ala  Thr Ala Arg Thr Leu  Gly Asn Phe Ser Trp  Phe Pro His
    1850                1855                1860

Lys Asp  Met Met Pro Ser Glu  Asp Gly Ala Glu Ala  Leu Gly Pro
    1865                1870                1875

Phe Gln  Ser Phe Ile Leu Lys  Val Val Asn Lys Lys  Ile Glu Arg
    1880                1885                1890

Pro Met  Phe Arg Asn Asp Leu  Gln Phe Gly Phe Gly  Trp Phe Ser
    1895                1900                1905

Tyr Arg  Val Gly Asp Val Val  Cys Asn Ala Ala Met  Leu Ile Lys
    1910                1915                1920

Gln Gly  Leu Thr Asp Pro Lys  Ala Phe Lys Ser Leu  Arg Asp Leu
    1925                1930                1935
```

```
Trp Asp  Tyr Met Leu Ser Ser  Thr Glu Gly Ile Leu  Glu Phe Ser
    1940                 1945                 1950

Ile Thr  Val Asp Phe Thr His  Asn Gln Asn Asn Thr  Asp Cys Leu
    1955                 1960                 1965

Arg Lys  Phe Ser Leu Ile Phe  Val Val Lys Cys Gln  Leu Gln Ser
    1970                 1975                 1980

Pro Gly  Val Ala Asp Tyr Leu  Ser Cys Ser His Phe  Phe Lys Gly
    1985                 1990                 1995

Glu Val  Asp Arg Arg Leu Leu  Asp Glu Cys Leu Asn  Leu Leu Arg
    2000                 2005                 2010

Thr Asp  Pro Ile Phe Lys Ala  Asn Asp Gly Val Phe  Asp Ile Arg
    2015                 2020                 2025

Ser Glu  Glu Phe Glu Asp Tyr  Met Glu Asp Pro Leu  Thr Leu Gly
    2030                 2035                 2040

Asp Ser  Leu Glu Leu Glu Leu  Ile Gly Ser Arg Arg  Ile Leu Asn
    2045                 2050                 2055

Glu Ile  Lys Ser Thr Asp Phe  Glu Arg Ile Gly Pro  Glu Trp Glu
    2060                 2065                 2070

Pro Val  Pro Leu Thr Ile Arg  Lys Gly Ala Leu Phe  Glu Gly Arg
    2075                 2080                 2085

Asn Phe  Val Gln Asn Ile Ser  Val Lys Leu Glu Thr  Lys Asp Met
    2090                 2095                 2100

Arg Val  Phe Leu Ala Glu Leu  Glu Gly Cys Gly Lys  Ile Gly Asp
    2105                 2110                 2115

Val Leu  Gly Ser Leu Leu Leu  His Arg Phe Arg Thr  Gly Glu His
    2120                 2125                 2130

Leu Met  Glu Ser Glu Ile Ser  Thr Val Leu Gln Glu  Leu Cys Met
    2135                 2140                 2145

Asp Arg  Ser Val Met Leu Thr  Pro Leu Ser Phe Val  Pro Asp Trp
    2150                 2155                 2160

Phe Thr  Phe Arg Asp Cys Arg  Leu Cys Phe Ser Arg  Ser Lys Asn
    2165                 2170                 2175

Thr Val  Met Tyr Glu Thr Thr  Gly Gly Arg Phe Arg  Leu Lys Gly
    2180                 2185                 2190

Lys Ser  Cys Asp Asp Trp Leu  Ala Glu Arg Val Ala  Glu Glu Ile
    2195                 2200                 2205

Asp
```

<210> SEQ ID NO 21
<211> LENGTH: 3376
<212> TYPE: DNA
<213> ORGANISM: Lymphocytic choriomeningitis virus (LCMV) strain Armstrong 53b

<400> SEQUENCE: 21

```
cgcaccgggg atcctaggct ttttggattg cgctttcctc tagatcaact gggtgtcagg     60

ccctatccta cagaaggatg ggtcagattg tgacaatgtt tgaggctctg cctcacatca    120

tcgatgaggt gatcaacatt gtcattattg tgcttatcgt gatcacgggt atcaaggctg    180

tctacaattt tgccacctgt gggatattcg cattgatcag tttcctactt ctggctggca    240

ggtcctgtgg catgtacggt cttaagggac ccgacattta caaaggagtt taccaattta    300

agtcagtgga gtttgatatg tcacatctga acctgaccat gcccaacgca tgttcagcca    360

acaactccca ccattacatc agtatgggga cttctggact agaattgacc ttcaccaatg    420
```

```
attccatcat cagtcacaac ttttgcaatc tgacctctgc cttcaataaa aagacctttg    480
accacacact catgagtata gtttcgagcc tacacctcag tatcagaggg aactccaact    540
ataaggcagt atcctgcgac ttcaacaatg gcataaccat ccaatacaac ttgacattct    600
caaatgcaca aagtgctcag agccagtgta gaaccttcag aggtagagtc ctagatatgt    660
ttagaactgc cttcgggggg aaatacatga ggagtggctg gggctggaca ggctcagatg    720
gcaagaccac ctggtgtagc cagacgagtt accaatacct gattatacaa aatagaacct    780
gggaaaacca ctgcacatat gcaggtcctt ttgggatgtc caggattctc ctttcccaag    840
agaagactaa gttcttcact aggagactag cgggcacatt cacctggact ttgtcagact    900
cttcaggggt ggagaatcca ggtggttatt gcctgaccaa atggatgatt cttgctgcag    960
agcttaagtg tttcgggaac acagcagttg cgaaatgcaa tgtaaatcat gatgaagaat   1020
tctgtgacat gctgcgacta attgactaca acaaggctgc tttgagtaag ttcaaagagg   1080
acgtagaatc tgccttgcac ttattcaaaa caacagtgaa ttctttgatt tcagatcaac   1140
tactgatgag gaaccacttg agagatctga tgggggtgcc atattgcaat tactcaaagt   1200
tttggtacct agaacatgca aagaccggcg aaactagtgt ccccaagtgc tggcttgtca   1260
ccaatggttc ttacttaaat gagacccact tcagtgatca aatcgaacag gaagccgata   1320
acatgattac agagatgttg aggaaggatt acataaagag gcaggggagt acccccctag   1380
cattgatgga ccttctgatg ttttccacat ctgcatatct agtcagcatc ttcctgcacc   1440
ttgtcaaaat accaacacac aggcacataa aaggtggctc atgtccaaag ccacaccgat   1500
taaccaacaa aggaatttgt agttgtggtg catttaaggt gcctggtgta aaaaccgtct   1560
ggaaaagacg ctgaagaaca gcgcctccct gactctccac ctcgaaagag gtggagagtc   1620
agggaggccc agagggtctt agagtgtcac aacatttggg cctctaaaaa ttaggtcatg   1680
tggcagaatg ttgtgaacag ttttcagatc tgggagcctt gctttggagg cgctttcaaa   1740
aatgatgcag tccatgagtg cacagtgcgg ggtgatctct ttcttctttt tgtcccttac   1800
tattccagta tgcatcttac acaaccagcc atatttgtcc cacactttgt cttcatactc   1860
cctcgaagct tccctggtca tttcaacatc gataagctta atgtccttcc tattctgtga   1920
gtccagaagc tttctgatgt catcggagcc ttgacagctt agaaccatcc cctgcggaag   1980
agcacctata actgacgagg tcaacccggg ttgcgcattg aagaggtcgg caagatccat   2040
gccgtgtgag tacttggaat cttgcttgaa ttgtttttga tcaacgggtt ccctgtaaaa   2100
gtgtatgaac tgcccgttct gtggttggaa aattgctatt tccactggat cattaaatct   2160
accctcaatg tcaatccatg taggagcgtt ggggtcaatt cctcccatga ggtcttttaa   2220
aagcattgtc tggctgtagc ttaagcccac ctgaggtgga cctgctgctc caggcgctgg   2280
cctgggtgag ttgactgcag gtttctcgct tgtgagatca attgttgtgt tttcccatgc   2340
tctccccaca atcgatgttc tacaagctat gtatggccat ccttcacctg aaaggcaaac   2400
tttatagagg atgttttcat aagggttcct gtccccaact tggtctgaaa caaacatgtt   2460
gagttttctc ttggccccga gaactgcctt caagaggtcc tcgctgttgc ttggcttgat   2520
caaaattgac tctaacatgt tacccccatc caacagggct gcccctgcct tcacggcagc   2580
accaagacta aagttatagc cagaaatgtt gatgctggac tgctgttcag tgatgacccc   2640
cagaactggg tgcttgtctt tcagcctttc aagatcatta agatttggat acttgactgt   2700
gtaaagcaag ccaaggtctg tgagcgcttg tacaacgtca ttgagcggag tctgtgactg   2760
```

```
tttggccata caagccatag ttagacttgg cattgtgcca aattgattgt tcaaaagtga   2820

tgagtctttc acatcccaaa ctcttaccac accacttgca ccctgctgag gctttctcat   2880

cccaactatc tgtaggatct gagatctttg gtctagttgc tgtgttgtta agttccccat   2940

atatacccct gaagcctggg gcctttcaga cctcatgatc ttggccttca gcttctcaag   3000

gtcagccgca agagacatca gttcttctgc actgagcctc cccactttca aaacattctt   3060

ctttgatgtt gactttaaat ccacaagaga atgtacagtc tggttgagac ttctgagtct   3120

ctgtaggtct ttgtcatctc tcttttcctt cctcatgatc ctctgaacat tgctgacctc   3180

agagaagtcc aacccattca gaaggttggt tgcatcctta atgacagcag ccttcacatc   3240

tgatgtgaag ctctgcaatt ctcttctcaa tgcttgcgtc cattggaagc tcttaacttc   3300

cttagacaag gacatcttgt tgctcaatgg tttctcaaga caaatgcgca atcaaatgcc   3360

taggatccac tgtgcg                                                  3376
```

<210> SEQ ID NO 22
<211> LENGTH: 7228
<212> TYPE: DNA
<213> ORGANISM: Lymphocytic choriomeningitis virus (LCMV) strain
Armstrong 53b

<400> SEQUENCE: 22

```
cgcaccgggg atcctaggcg tttagttgcg ctgtttggtt gcacaacttt cttcgtgagg     60

ctgtcagaag tggacctggc tgatagcgat gggtcaaggc aagtccagag aggagaaagg    120

caccaatagt acaaacaggg ccgaaatcct accagatacc acctatcttg gccctttaag    180

ctgcaaatct tgctggcaga aatttgacag cttggtaaga tgccatgacc actacctttg    240

caggcactgt ttaaaccttc tgctgtcagt atccgacagg tgtcctcttt gtaaatatcc    300

attaccaacc agattgaaga tatcaacagc cccaagctct ccacctccct acgaagagta    360

acaccgtccg gccccggccc cgacaaacag cccagcacaa gggaaccgca cgtcgcccaa    420

cgcacacaga cacagcaccc aacacagaac acgcacacac acacacacac acacccacac    480

gcacgcgccc ccaccaccgg ggggcgcccc cccccggggg gcggcccccc gggagcccgg    540

gcggagcccc acggagatgc ccatcagtcg atgtcctcgg ccaccgaccc gcccagccaa    600

tcgtcgcagg acctcccctt gagtctaaac ctgcccccca ctgtttcata catcaaagtg    660

ctcctagatt tgctaaaaca aagtctgcaa tccttaaagg cgaaccagtc tggcaaaagc    720

gacagtggaa tcagcagaat agatctgtct atacatagtt cctggaggat tacacttatc    780

tctgaaccca acaaatgttc accagttctg aatcgatgca ggaagaggtt cccaaggaca    840

tcactaatct tttcatagcc ctcaagtcct gctagaaaga ctttcatgtc cttggtctcc    900

agcttcacaa tgatattttg gacaaggttt cttccttcaa aaagggcacc catctttaca    960

gtcagtggca caggctccca ctcaggtcca actctctcaa agtcaataga tctaatccca   1020

tccagtattc ttttggagcc caacaactca agctcaagag aatcaccaag tatcaaggga   1080

tcttccatgt aatcctcaaa ctcttcagat ctgatatcaa agacaccatc gttcaccttg   1140

aagacagagt ctgtcctcag taagtggagg cattcatcca acattcttct atctatctca   1200

cccttaaaga ggtgagagca tgataaaagt tcagccacac ctggattctg taattggcac   1260

ctaaccaaga atatcaatga aaatttcctt aaacagtcag tattattctg attgtgcgta   1320

aagtccactg aaattgaaaa ctccaatacc ccttttgtgt agttgagcat gtagtcccac   1380

agatccttta aggatttaaa tgcctttggg tttgtcaggc cctgcctaat caacatggca   1440
```

-continued

```
gcattacaca caacatctcc cattcggtaa gagaaccacc caaaaccaaa ctgcaaatca   1500
ttcctaaaca taggcctctc cacatttttg ttcaccacct ttgagacaaa tgattgaaag   1560
gggcccagtg cctcagcacc atcttcagat ggcatcattt ctttatgagg gaaccatgaa   1620
aaattgccta atgtcctggt tgttgcaaca aattctcgaa caaatgattc aaaatacacc   1680
tgttttaaga agttcttgca gacatccctc gtgctaacaa caaattcatc aaccagactg   1740
gagtcagatc gctgatgaga attggcaagg tcagaaaaca gaacagtgta atgttcatcc   1800
cttttccact taacaacatg agaaatgagt gacaaggatt ctgagttaat atcaattaaa   1860
acacagaggt caaggaattt aattctggga ctccacctca tgttttttga gctcatgtca   1920
gacataaatg gaagaagctg atcctcaaag atcttgggat ataaccgcct cacagattga   1980
atcacttggt tcaaattcac tttgtcctcc agtagccttg agctctcagg ctttcttgct   2040
acataatcac atgggtttaa gtgcttaaga gttaggttct cactgttatt cttccctttg   2100
gtcggttctg ctaggaccca aacacccaac tcaaaagagt tgctcaatga aatacaaatg   2160
tagtcccaaa gaagaggcct taaaaggcat atatgatcac ggtgggcttc tggatgagac   2220
tgtttgtcac aaatgtacag cgttatacca tcccgattgc aaactcttgt cacatgatca   2280
tctgtggtta gatcctcaag cagctttttg atatacagat tttccctatt tttgtttctc   2340
acacacctgc ttcctagagt tttgcaaagg cctataaagc cagatgagat acaactctgg   2400
aaagctgact tgttgattgc ttctgacagc agcttctgtg caccccttgt gaatttacta   2460
caaagtttgt tctggagtgt cttgatcaat gatgggattc tttcctcttg gaaagtcatc   2520
actgatggat aaaccacctt ttgtcttaaa accatcctta atgggaacat ttcattcaaa   2580
ttcaaccagt taacatctgc taactgattc agatcttctt caagaccgag gaggtctccc   2640
aattgaagaa tggcctcctt tttatctctg ttaaataggt ctaagaaaaa ttcttcatta   2700
aattcaccat ttttgagctt atgatgcagt ttccttacaa gctttcttac aacctttgtt   2760
tcattaggac acagttcctc aatgagtctt tgtattctgt aacctctaga accatccagc   2820
caatctttca catcagtgtt ggtattcagt agaaatggat ccaaagggaa attggcatac   2880
tttaggaggt ccagtgttct cctttggata ctattaacta gggagactgg gacgccattt   2940
gcgatggctt gatctgcaat tgtatctatt gtttcacaaa gttgatgtgg ctctttacac   3000
ttgacattgt gtagcgctgc agatacaaac tttgtgagaa gagggacttc ctcccccccat   3060
acatagaatc tagatttaaa ttctgcagcg aacctcccag ccacactttt tgggctgata   3120
aatttgttta acaagccgct cagatgagat tggaattcca acaggacaag gacttcctcc   3180
ggatcactta caaccaggtc actcagcctc ctatcaaata aagtgatctg atcatcactt   3240
gatgtgtaag cctctggtct ttcgccaaag ataacaccaa tgcagtagtt gatgaacctc   3300
tcgctaagca aaccatagaa gtcagaagca ttatgcaaga ttccctgccc catatcaata   3360
aggctggata tatgggatgg cactatcccc atttcaaaat attgtctgaa aattctctca   3420
gtaacagttg tttctgaacc cctgagaagt tttagcttcg acttgacata tgatttcatc   3480
attgcattca caacaggaaa ggggacctcg acaagcttat gcatgtgcca agttaacaaa   3540
gtgctaacat gatctttccc ggaacgcaca tactggtcat cacctagttt gagattttgt   3600
agaaacatta agaacaaaaa tgggcacatc attggtcccc atttgctgtg atccatacta   3660
tagtttaaga acccttcccg cacattgata gtcattgaca agattgcatt ttcaaattcc   3720
ttatcattgt ttaaacagga gcctgaaaag aaacttgaaa aagactcaaa ataatcttct   3780
attaaccttg tgaacatttt tgtcctcaaa tctccaatat agagttctct atttccccca   3840
```

```
acctgctctt tataagatag tgcaaatttc agccttccag agtcaggacc tactgaggtg   3900
tatgatgttg gtgattcttc tgagtagaag cacagatttt tcaaagcagc actcatacat   3960
tttgtcaacg acagagcttt actaagggac tcagaattac tttccctctc actgattctc   4020
acgtcttctt ccagtttgtc ccagtcaaat ttgaaattca agccttgcct ttgcatatgc   4080
ctgtatttcc ctgagtacgc atttgcattc atttgcaaca gaatcatctt catgcaagaa   4140
aaccaatcat tctcagaaaa gaactttcta caaaggtttt ttgccatctc atcgaggcca   4200
cactgatctt taatgactga ggtgaaatac aaaggtgaca gctctgtgga accctcaaca   4260
gcctcacaga taaatttcat gtcatcattg gttagacatg atgggtcaaa gtcttctact   4320
aaatggaaag atatttctga caagataact tttcttaagt gagccatctt ccctgttaga   4380
ataagctgta aatgatgtag tccttttgta tttgtaagtt tttctccatc tcctttgtca   4440
ttggccctcc tacctcttct gtaccgtgct attgtggtgt tgaccttttc ttcgagactt   4500
ttgaagaagc ttgtctcttc ttctccatca aaacatattt ctgccaggtt gtcttccgat   4560
ctccctgtct cttctccctt ggaaccgatg accaatctag agactaactt ggaaacttta   4620
tattcatagt ctgagtggct caacttatac ttttgttttc ttacgaaact ctccgtaatt   4680
tgactcacag cactaacaag caatttgtta aagtcatatt ccagaagtcg ttctccattt   4740
agatgcttat taaccaccac acttttgtta ctagcaagat ctaatgctgt cgcacatcca   4800
gagttagtca tgggatctag gctgtttagc ttcttctctc ctttgaaaat taaagtgccg   4860
ttgttaaatg aagacaccat taggctaaag gcttccagat taacacctgg agttgtatgc   4920
tgacagtcaa tttctttact agtgaatctc ttcatttgct catagaacac acattcttcc   4980
tcaggagtga ttgcttcctt ggggttgaca aaaaaaccaa attgactttt gggctcaaag   5040
aacttttcaa aacattttat ctgatctgtt agcctgtcag ggtctccctt tgtgatcaaa   5100
tgacacaggt atgacacatt caacataaat ttaaattttg cactcaacaa caccttctca   5160
ccagtaccaa aaatagtttt tattaggaat ctaagcagct tatacaccac cttctcagca   5220
ggtgtgatca gatcctccct caacttatcc attaatgatg tagatgagaa atctgacact   5280
attgccatca ccaaatatct gacactctgt acctgctttt gatttctctt tgttgggttg   5340
gtgagcatta gcaacaatag ggtcctcagt gcaacctcaa tgtcggtgag acagtctttc   5400
aaatcaggac atgatctaat ccatgaaatc atgatgtcta tcatattgta taagacctca   5460
tctgaaaaaa ttggtaaaaa gaacctttta ggatctgcat agaaggaaat taaatgacca   5520
tccgggcctt gtatggagta gcaccttgaa gattctccag tcttctggta taataggtgg   5580
tattcttcag agtccagttt tattacttgg caaaacactt ctttgcattc taccacttga   5640
tatctcacag accctatttg attttgcctt agtctagcaa ctgagctagt tttcatactg   5700
tttgttaagg ccagacaaac agatgataat cttctcaggc tctgtatgtt cttcagctgc   5760
tctgtgctgg gttggaaatt gtaatcttca aacttcgtat aatacattat cgggtgagct   5820
ccaattttca taaagttctc aaattcagtg aatggtatgt ggcattcttg ctcaaggtgt   5880
tcagacagtc cgtaatgctc gaaactcagt cccaccacta acaggcattt ttgaattttt   5940
gcaatgaact cactaataga cgccctaaac aattcctcaa aagacacctt tctaaacacc   6000
tttgactttt ttctattcct caaaagtcta atgaactcct ctttagtgct gtgaaagctt   6060
accagcctat cattcacact actatagcaa caacccaccc agtgtttatc attttttaac   6120
cctttgaatt tcgactgttt tatcaatgag gaaagacaca aaacatccag atttaacaac   6180
```

```
tgtctccttc tagtattcaa cagtttcaaa ctcttgactt tgtttaacat agagaggagc   6240

ctctcatatt cagtgctagt ctcacttccc ctttcgtgcc catgggtctc tgcagttatg   6300

aatctcatca aaggacagga ttccactgcc tccctgctta atgttaagat atcatcacta   6360

tcagcaaggt tttcatagag ctcagagaat tccttgatca agccttcagg gtttactttc   6420

tgaaagtttc tctttaattt cccactttct aaatctcttc taaacctgct gaaaagagag   6480

tttattccaa aaaccacatc atcacagctc atgttggggt tgatgccttc gtggcacatc   6540

ctcataattt catcattatg agttgacctc gcatctttca gaattttcat agagtccata   6600

ccggagcgct tgtcgatagt agtcttcagg gactcacaga gtctaaaata ttcagactct   6660

tcaaagactt tctcattttg gttagaatac tccaaaagtt tgaataaaag gtctctaaat   6720

ttgaagtttg cccactctgg cataaaacta ttatcataat cacaacgacc atctactatt   6780

ggaactaatg tgacacccgc aacagcaagg tcttccctga tgcatgccaa tttgttagtg   6840

tcctctataa atttcttctc aaaactggct ggagtgctcc taacaaaaca ctcaagaaga   6900

atgagagaat tgtctatcag cttgtaacca tcaggaatga taagtggtag tcctgggcat   6960

acaattccag actccaccaa aattgtttcc acagacttat cgtcgtggtt gtgtgtgcag   7020

ccactcttgt ctgcactgtc tatttcaatg cagcgtgaca gcaacttgag tccctcaatc   7080

agaaccattc tgggttccct ttgtcccaga aagttgagtt tctgccttga caacctctca   7140

tcctgttcta tatagtttaa acataactct ctcaattctg agatgatttc atccattgcg   7200

catcaaaaag cctaggatcc tcggtgcg                                      7228
```

<210> SEQ ID NO 23
<211> LENGTH: 1497
<212> TYPE: DNA
<213> ORGANISM: Lymphocytic choriomeningitis virus (LCMV) strain Armstrong 53b

<400> SEQUENCE: 23

```
atgggtcaga ttgtgacaat gtttgaggct ctgcctcaca tcatcgatga ggtgatcaac     60

attgtcatta ttgtgcttat cgtgatcacg ggtatcaagg ctgtctacaa ttttgccacc    120

tgtgggatat tcgcattgat cagtttccta cttctggctg gcaggtcctg tggcatgtac    180

ggtcttaagg gacccgacat ttacaaagga gtttaccaat ttaagtcagt ggagtttgat    240

atgtcacatc tgaacctgac catgcccaac gcatgttcag ccaacaactc ccaccattac    300

atcagtatgg ggacttctgg actagaattg accttcacca atgattccat catcagtcac    360

aacttttgca atctgacctc tgccttcaat aaaaagacct ttgaccacac actcatgagt    420

atagtttcga gcctacacct cagtatcaga gggaactcca actataaggc agtatcctgc    480

gacttcaaca atggcataac catccaatac aacttgacat tctcaaatgc acaaagtgct    540

cagagccagt gtagaacctt cagaggtaga gtcctagata tgtttagaac tgccttcggg    600

gggaaataca tgaggagtgg ctggggctgg acaggctcag atggcaagac cacctggtgt    660

agccagacga gttaccaata cctgattata caaaatagaa cctgggaaaa ccactgcaca    720

tatgcaggtc cttttgggat gtccaggatt ctcctttccc aagagaagac taagttcttc    780

actaggagac tagcgggcac attcacctgg actttgtcag actcttcagg ggtggagaat    840

ccaggtggtt attgcctgac caaatggatg attcttgctg cagagcttaa gtgtttcggg    900

aacacagcag ttgcgaaatg caatgtaaat catgatgaag aattctgtga catgctgcga    960

ctaattgact acaacaaggc tgctttgagt aagttcaaag aggacgtaga atctgccttg   1020
```

```
cacttattca aaacaacagt gaattctttg atttcagatc aactactgat gaggaaccac   1080

ttgagagatc tgatgggggt gccatattgc aattactcaa agttttggta cctagaacat   1140

gcaaagaccg gcgaaactag tgtccccaag tgctggcttg tcaccaatgg ttcttactta   1200

aatgagaccc acttcagtga tcaaatcgaa caggaagccg ataacatgat tacagagatg   1260

ttgaggaagg attacataaa gaggcagggg agtacccccc tagcattgat ggaccttctg   1320

atgttttcca catctgcata tctagtcagc atcttcctgc accttgtcaa aataccaaca   1380

cacaggcaca taaaaggtgg ctcatgtcca aagccacacc gattaaccaa caaaggaatt   1440

tgtagttgtg gtgcatttaa ggtgcctggt gtaaaaaccg tctggaaaag acgctga      1497


<210> SEQ ID NO 24
<211> LENGTH: 498
<212> TYPE: PRT
<213> ORGANISM: Lymphocytic choriomeningitis virus (LCMV) strain
      Armstrong 53b

<400> SEQUENCE: 24

Met Gly Gln Ile Val Thr Met Phe Glu Ala Leu Pro His Ile Ile Asp
1               5                   10                  15

Glu Val Ile Asn Ile Val Ile Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asn
                165                 170                 175

Ala Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Phe Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285
```

```
Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Val Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg


<210> SEQ ID NO 25
<211> LENGTH: 1677
<212> TYPE: DNA
<213> ORGANISM: Lymphocytic choriomeningitis virus (LCMV) strain
      Armstrong 53b

<400> SEQUENCE: 25

atgtccttgt ctaaggaagt taagagcttc caatggacgc aagcattgag aagagaattg      60

cagagcttca catcagatgt gaaggctgct gtcattaagg atgcaaccaa ccttctgaat     120

gggttggact tctctgaggt cagcaatgtt cagaggatca tgaggaagga aaagagagat     180

gacaaagacc tacagagact cagaagtctc aaccagactg tacattctct tgtggattta     240

aagtcaacat caaagaagaa tgttttgaaa gtggggaggc tcagtgcaga agaactgatg     300

tctcttgcgg ctgaccttga gaagctgaag gccaagatca tgaggtctga aaggccccag     360

gcttcagggg tatatatggg gaacttaaca acacagcaac tagaccaaag atctcagatc     420

ctacagatag ttgggatgag aaagcctcag cagggtgcaa gtggtgtggt aagagtttgg     480

gatgtgaaag actcatcact tttgaacaat caatttggca caatgccaag tctaactatg     540

gcttgtatgg ccaaacagtc acagactccg ctcaatgacg ttgtacaagc gctcacagac     600

cttggcttgc tttacacagt caagtatcca aatcttaatg atcttgaaag gctgaaagac     660

aagcacccag ttctgggggt catcactgaa cagcagtcca gcatcaacat ttctggctat     720

aactttagtc ttggtgctgc cgtgaaggca ggggcagccc tgttggatgg gggtaacatg     780

ttagagtcaa ttttgatcaa gccaagcaac agcgaggacc tcttgaaggc agttctcggg     840

gccaagagaa aactcaacat gtttgtttca gaccaagttg ggacaggaa cccttatgaa     900
```

```
aacatcctct ataaagtttg cctttcaggt gaaggatggc catacatagc ttgtagaaca    960

tcgattgtgg ggagagcatg ggaaaacaca acaattgatc tcacaagcga gaaacctgca   1020

gtcaactcac ccaggccagc gcctggagca gcaggtccac ctcaggtggg cttaagctac   1080

agccagacaa tgcttttaaa agacctcatg ggaggaattg accccaacgc tcctacatgg   1140

attgacattg agggtagatt taatgatcca gtggaaatag caattttcca accacagaac   1200

gggcagttca tacactttta cagggaaccc gttgatcaaa aacaattcaa gcaagattcc   1260

aagtactcac acggcatgga tcttgccgac ctcttcaatg cgcaacccgg gttgacctcg   1320

tcagttatag gtgctcttcc gcaggggatg gttctaagct gtcaaggctc cgatgacatc   1380

agaaagcttc tggactcaca gaataggaag gacattaagc ttatcgatgt tgaaatgacc   1440

agggaagctt cgagggagta tgaagacaaa gtgtgggaca aatatggctg gttgtgtaag   1500

atgcatactg gaatagtaag ggacaaaaag aagaaagaga tcaccccgca ctgtgcactc   1560

atggactgca tcatttttga aagcgcctcc aaagcaaggc tcccagatct gaaaactgtt   1620

cacaacattc tgccacatga cctaattttt agaggcccaa atgttgtgac actctaa      1677
```

```
<210> SEQ ID NO 26
<211> LENGTH: 558
<212> TYPE: PRT
<213> ORGANISM: Lymphocytic choriomeningitis virus (LCMV) strain
      Armstrong 53b

<400> SEQUENCE: 26

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125

Leu Thr Thr Gln Gln Leu Asp Gln Arg Ser Gln Ile Leu Gln Ile Val
    130                 135                 140

Gly Met Arg Lys Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Asn Asp Leu Glu Arg Leu Lys Asp Lys His Pro Val
    210                 215                 220

Leu Gly Val Ile Thr Glu Gln Gln Ser Ser Ile Asn Ile Ser Gly Tyr
```

```
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Pro Ala Val Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 27
<211> LENGTH: 273
<212> TYPE: DNA
<213> ORGANISM: Lymphocytic choriomeningitis virus (LCMV) strain Armstrong 53b

<400> SEQUENCE: 27

```
atgggtcaag gcaagtccag agaggagaaa ggcaccaata gtacaaacag ggccgaaatc      60

ctaccagata ccacctatct tggcccttta agctgcaaat cttgctggca gaaatttgac     120

agcttggtaa gatgccatga ccactacctt tgcaggcact gtttaaacct tctgctgtca     180

gtatccgaca ggtgtcctct ttgtaaatat ccattaccaa ccagattgaa gatatcaaca     240
```

gccccaagct ctccacctcc ctacgaagag taa 273

<210> SEQ ID NO 28
<211> LENGTH: 90
<212> TYPE: PRT
<213> ORGANISM: Lymphocytic choriomeningitis virus (LCMV) strain
Armstrong 53b

<400> SEQUENCE: 28

Met Gly Gln Gly Lys Ser Arg Glu Glu Lys Gly Thr Asn Ser Thr Asn
1 5 10 15

Arg Ala Glu Ile Leu Pro Asp Thr Thr Tyr Leu Gly Pro Leu Ser Cys
20 25 30

Lys Ser Cys Trp Gln Lys Phe Asp Ser Leu Val Arg Cys His Asp His
35 40 45

Tyr Leu Cys Arg His Cys Leu Asn Leu Leu Leu Ser Val Ser Asp Arg
50 55 60

Cys Pro Leu Cys Lys Tyr Pro Leu Pro Thr Arg Leu Lys Ile Ser Thr
65 70 75 80

Ala Pro Ser Ser Pro Pro Pro Tyr Glu Glu
85 90

<210> SEQ ID NO 29
<211> LENGTH: 6633
<212> TYPE: DNA
<213> ORGANISM: Lymphocytic choriomeningitis virus (LCMV) strain
Armstrong 53b

<400> SEQUENCE: 29
atggatgaaa tcatctcaga attgagagag ttatgtttaa actatataga acaggatgag 60
aggttgtcaa ggcagaaact caactttctg ggacaaaggg aacccagaat ggttctgatt 120
gagggactca agttgctgtc acgctgcatt gaaatagaca gtgcagacaa gagtggctgc 180
acacacaacc acgacgataa gtctgtggaa acaattttgg tggagtctgg aattgtatgc 240
ccaggactac cacttatcat tcctgatggt tacaagctga tagacaattc tctcattctt 300
cttgagtgtt ttgttaggag cactccagcc agttttgaga agaaatttat agaggacact 360
aacaaattgg catgcatcag ggaagacctt gctgttgcgg gtgtcacatt agttccaata 420
gtagatggtc gttgtgatta tgataatagt tttatgccag agtgggcaaa cttcaaattt 480
agagaccttt tattcaaact tttggagtat tctaaccaaa atgagaaagt ctttgaagag 540
tctgaatatt ttagactctg tgagtccctg aagactacta tcgacaagcg ctccggtatg 600
gactctatga aaattctgaa agatgcgagg tcaactcata atgatgaaat tatgaggatg 660
tgccacgaag gcatcaaccc caacatgagc tgtgatgatg tggtttttgg aataaactct 720
cttttcagca ggtttagaag agatttagaa agtgggaaat taaagagaaa ctttcagaaa 780
gtaaaccctg aaggcttgat caaggaattc tctgagctct atgaaaacct tgctgatagt 840
gatgatatct taacattaag cagggaggca gtggaatcct gtcctttgat gagattcata 900
actgcagaga cccatgggca cgaaagggga agtgagacta gcactgaata tgagaggctc 960
ctctctatgt taaacaaagt caagagtttg aaactgttga atactagaag gagacagttg 1020
ttaaatctgg atgttttgtg tctttcctca ttgataaaac agtcgaaatt caaagggtta 1080
aaaaatgata aacactgggt gggttgttgc tatagtagtg tgaatgatag gctggtaagc 1140
tttcacagca ctaaagagga gttcattaga cttttgagga atagaaaaaa gtcaaaggtg 1200
tttagaaagg tgtcttttga ggaattgttt agggcgtcta ttagtgagtt cattgcaaaa 1260
attcaaaaat gcctgttagt ggtgggactg agtttcgagc attacggact gtctgaacac 1320
cttgagcaag aatgccacat accattcact gaatttgaga actttatgaa aattggagct 1380
cacccgataa tgtattatac gaagtttgaa gattacaatt tccaacccag cacagagcag 1440
ctgaagaaca tacagagcct gagaagatta tcatctgttt gtctggcctt aacaaacagt 1500
atgaaaacta gctcagttgc tagactaagg caaaatcaaa tagggtctgt gagatatcaa 1560
gtggtagaat gcaaagaagt gttttgccaa gtaataaaac tggactctga agaataccac 1620
ctattatacc agaagactgg agaatcttca aggtgctact ccatacaagg cccggatggt 1680
catttaattt ccttctatgc agatcctaaa aggttctttt taccaatttt ttcagatgag 1740
gtcttataca atatgataga catcatgatt tcatggatta gatcatgtcc tgatttgaaa 1800
gactgtctca ccgacattga ggttgcactg aggaccctat tgttgctaat gctcaccaac 1860
ccaacaaaga gaaatcaaaa gcaggtacag agtgtcagat atttggtgat ggcaatagtg 1920
tcagatttct catctacatc attaatggat aagttgaggg aggatctgat cacacctgct 1980
gagaaggtgg tgtataagct gcttagattc ctaataaaaa ctatttttgg tactggtgag 2040
aaggtgttgt tgagtgcaaa atttaaattt atgttgaatg tgtcatacct gtgtcatttg 2100
atcacaaagg agacccctga caggctaaca gatcagataa aatgttttga aaagttcttt 2160
gagcccaaaa gtcaatttgg ttttttttgtc aaccccaagg aagcaatcac tcctgaggaa 2220
gaatgtgtgt tctatgagca aatgaagaga ttcactagta aagaaattga ctgtcagcat 2280
acaactccag gtgttaatct ggaagccttt agcctaatgg tgtcttcatt taacaacggc 2340
actttaattt tcaaaggaga gaagaagcta aacagcctag atcccatgac taactctgga 2400
tgtgcgacag cattagatct tgctagtaac aaaagtgtgg tggttaataa gcatctaaat 2460
ggagaacgac ttctggaata tgactttaac aaattgcttg ttagtgctgt gagtcaaatt 2520
acggagagtt tcgtaagaaa acaaaagtat aagttgagcc actcagacta tgaatataaa 2580
gtttccaagt tagtctctag attggtcatc ggttccaagg gagaagagac agggagatcg 2640
gaagacaacc tggcagaaat atgttttgat ggagaagaag agacaagctt cttcaaaagt 2700
ctcgaagaaa aggtcaacac cacaatagca cggtacagaa gaggtaggag ggccaatgac 2760
aaaggagatg gagaaaaact tacaaataca aaaggactac atcatttaca gcttattcta 2820
acagggaaga tggctcactt aagaaaagtt atcttgtcag aaatatcttt ccatttagta 2880
gaagactttg acccatcatg tctaaccaat gatgacatga aatttatctg tgaggctgtt 2940
gagggttcca cagagctgtc acctttgtat ttcacctcag tcattaaaga tcagtgtggc 3000
ctcgatgaga tggcaaaaaa cctttgtaga aagttctttt ctgagaatga ttggttttct 3060
tgcatgaaga tgattctgtt gcaaatgaat gcaaatgcgt actcagggaa atacaggcat 3120
atgcaaaggc aaggcttgaa tttcaaattt gactgggaca aactggaaga agacgtgaga 3180
atcagtgaga gggaaagtaa ttctgagtcc cttagtaaag ctctgtcgtt gacaaaatgt 3240
atgagtgctg ctttgaaaaa tctgtgcttc tactcagaag aatcaccaac atcatacacc 3300
tcagtaggtc ctgactctgg aaggctgaaa tttgcactat cttataaaga gcaggttggg 3360
ggaaatagag aactctatat tggagatttg aggacaaaaa tgttcacaag gttaatagaa 3420
gattattttg agtctttttc aagtttcttt tcaggctcct gtttaaacaa tgataaggaa 3480
tttgaaaatg caatcttgtc aatgactatc aatgtgcggg aagggttctt aaactatagt 3540
atggatcaca gcaaatgggg accaatgatg tgcccatttt tgttcttaat gtttctacaa 3600

```
aatctcaaac taggtgatga ccagtatgtg cgttccggga aagatcatgt tagcactttg   3660
ttaacttggc acatgcataa gcttgtcgag gtcccctttc ctgttgtgaa tgcaatgatg   3720
aaatcatatg tcaagtcgaa gctaaaactt ctcaggggtt cagaaacaac tgttactgag   3780
agaattttca gacaatattt tgaaatgggg atagtgccat cccatatatc cagccttatt   3840
gatatggggc agggaatctt gcataatgct tctgacttct atggtttgct tagcgagagg   3900
ttcatcaact actgcattgg tgttatcttt ggcgaaagac cagaggctta cacatcaagt   3960
gatgatcaga tcactttatt tgataggagg ctgagtgacc tggttgtaag tgatccggag   4020
gaagtccttg tcctgttgga attccaatct catctgagcg gcttgttaaa caaatttatc   4080
agcccaaaaa gtgtggctgg gaggttcgct gcagaattta aatctagatt ctatgtatgg   4140
ggggaggaag tccctcttct cacaaagttt gtatctgcag cgctacacaa tgtcaagtgt   4200
aaagagccac atcaactttg tgaaacaata gatacaattg cagatcaagc catcgcaaat   4260
ggcgtcccag tctccctagt taatagtatc caaaggagaa cactggacct cctaaagtat   4320
gccaatttcc ctttggatcc atttctactg aataccaaca ctgatgtgaa agattggctg   4380
gatggttcta gaggttacag aatacaaaga ctcattgagg aactgtgtcc taatgaaaca   4440
aaggttgtaa gaaagcttgt aaggaaactg catcataagc tcaaaaaatgg tgaatttaat   4500
gaagaatttt tcttagacct atttaacaga gataaaaagg aggccattct tcaattggga   4560
gacctcctcg gtcttgaaga agatctgaat cagttagcag atgttaactg gttgaatttg   4620
aatgaaatgt tcccattaag gatggtttta agacaaaagg tggtttatcc atcagtgatg   4680
actttccaag aggaaagaat cccatcattg atcaagacac tccagaacaa actttgtagt   4740
aaattcacaa ggggtgcaca gaagctgctg tcagaagcaa tcaacaagtc agctttccag   4800
agttgtatct catctggctt tataggcctt tgcaaaactc taggaagcag gtgtgtgaga   4860
aacaaaaata gggaaaatct gtatatcaaa aagctgcttg aggatctaac cacagatgat   4920
catgtgacaa gagtttgcaa tcgggatggt ataacgctgt acatttgtga caaacagtct   4980
catccagaag cccaccgtga tcatatatgc cttttaaggc ctcttctttg ggactacatt   5040
tgtatttcat tgagcaactc ttttgagttg ggtgtttggg tcctagcaga accgaccaaa   5100
gggaagaata acagtgagaa cctaactctt aagcacttaa acccatgtga ttatgtagca   5160
agaaagcctg agagctcaag gctactggag gacaaagtga atttgaacca agtgattcaa   5220
tctgtgaggc ggttatatcc caagatcttt gaggatcagc ttcttccatt tatgtctgac   5280
atgagctcaa aaaacatgag gtggagtccc agaattaaat tccttgacct ctgtgtttta   5340
attgatatta actcagaatc cttgtcactc atttctcatg ttgttaagtg gaaaagggat   5400
gaacattaca ctgttctgtt ttctgacctt gccaattctc atcagcgatc tgactccagt   5460
ctggttgatg aatttgttgt tagcacgagg gatgtctgca agaacttctt aaaacaggtg   5520
tattttgaat catttgttcg agaatttgtt gcaacaacca ggacattagg caatttttca   5580
tggttccctc ataaagaaat gatgccatct gaagatggtg ctgaggcact gggccccttt   5640
caatcatttg tctcaaaggt ggtgaacaaa aatgtggaga ggcctatgtt taggaatgat   5700
ttgcagtttg gttttgggtg gttctcttac cgaatgggag atgttgtgtg taatgctgcc   5760
atgttgatta ggcagggcct gacaaaccca aaggcattta aatccttaaa ggatctgtgg   5820
gactacatgc tcaactacac aaaagggggta ttggagtttt caatttcagt ggactttacg   5880
cacaatcaga ataatactga ctgtttaagg aaattttcat tgatattctt ggttaggtgc   5940
caattacaga atccaggtgt ggctgaactt ttatcatgct ctcacctctt taagggtgag   6000
```

```
atagatagaa gaatgttgga tgaatgcctc cacttactga ggacagactc tgtcttcaag   6060

gtgaacgatg gtgtctttga tatcagatct gaagagtttg aggattacat ggaagatccc   6120

ttgatacttg gtgattctct tgagcttgag ttgttgggct ccaaaagaat actggatggg   6180

attagatcta ttgactttga gagagttgga cctgagtggg agcctgtgcc actgactgta   6240

aagatgggtg ccctttttga aggaagaaac cttgtccaaa atatcattgt gaagctggag   6300

accaaggaca tgaaagtctt tctagcagga cttgagggct atgaaaagat tagtgatgtc   6360

cttgggaacc tcttcctgca tcgattcaga actggtgaac atttgttggg ttcagagata   6420

agtgtaatcc tccaggaact atgtatagac agatctattc tgctgattcc actgtcgctt   6480

ttgccagact ggttcgcctt taaggattgc agactttgtt ttagcaaatc taggagcact   6540

ttgatgtatg aaacagtggg gggcaggttt agactcaagg ggaggtcctg cgacgattgg   6600

ctgggcgggt cggtggccga ggacatcgac tga                                6633
```

<210> SEQ ID NO 30
<211> LENGTH: 2210
<212> TYPE: PRT
<213> ORGANISM: Lymphocytic choriomeningitis virus (LCMV) strain Armstrong 53b

<400> SEQUENCE: 30

```
Met Asp Glu Ile Ile Ser Glu Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Thr His Asn His
    50                  55                  60

Asp Asp Lys Ser Val Glu Thr Ile Leu Val Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Arg Glu
        115                 120                 125

Asp Leu Ala Val Ala Gly Val Thr Leu Val Pro Ile Val Asp Gly Arg
    130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205

Ala Arg Ser Thr His Asn Asp Glu Ile Met Arg Met Cys His Glu Gly
    210                 215                 220

Ile Asn Pro Asn Met Ser Cys Asp Asp Val Val Phe Gly Ile Asn Ser
225                 230                 235                 240

Leu Phe Ser Arg Phe Arg Arg Asp Leu Glu Ser Gly Lys Leu Lys Arg
                245                 250                 255
```

```
Asn Phe Gln Lys Val Asn Pro Glu Gly Leu Ile Lys Glu Phe Ser Glu
            260                 265                 270

Leu Tyr Glu Asn Leu Ala Asp Ser Asp Asp Ile Leu Thr Leu Ser Arg
        275                 280                 285

Glu Ala Val Glu Ser Cys Pro Leu Met Arg Phe Ile Thr Ala Glu Thr
    290                 295                 300

His Gly His Glu Arg Gly Ser Glu Thr Ser Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Phe Lys Gly Leu Lys Asn Asp Lys His Trp Val Gly
        355                 360                 365

Cys Cys Tyr Ser Ser Val Asn Asp Arg Leu Val Ser Phe His Ser Thr
    370                 375                 380

Lys Glu Glu Phe Ile Arg Leu Leu Arg Asn Arg Lys Lys Ser Lys Val
385                 390                 395                 400

Phe Arg Lys Val Ser Phe Glu Glu Leu Phe Arg Ala Ser Ile Ser Glu
                405                 410                 415

Phe Ile Ala Lys Ile Gln Lys Cys Leu Leu Val Val Gly Leu Ser Phe
            420                 425                 430

Glu His Tyr Gly Leu Ser Glu His Leu Glu Gln Glu Cys His Ile Pro
        435                 440                 445

Phe Thr Glu Phe Glu Asn Phe Met Lys Ile Gly Ala His Pro Ile Met
    450                 455                 460

Tyr Tyr Thr Lys Phe Glu Asp Tyr Asn Phe Gln Pro Ser Thr Glu Gln
465                 470                 475                 480

Leu Lys Asn Ile Gln Ser Leu Arg Arg Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Ile Gly Ser Val Arg Tyr Gln Val Val Glu Cys Lys Glu Val Phe
        515                 520                 525

Cys Gln Val Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu Tyr Asn Met Ile Asp Ile Met Ile Ser Trp
            580                 585                 590

Ile Arg Ser Cys Pro Asp Leu Lys Asp Cys Leu Thr Asp Ile Glu Val
        595                 600                 605

Ala Leu Arg Thr Leu Leu Leu Leu Met Leu Thr Asn Pro Thr Lys Arg
    610                 615                 620

Asn Gln Lys Gln Val Gln Ser Val Arg Tyr Leu Val Met Ala Ile Val
625                 630                 635                 640

Ser Asp Phe Ser Ser Thr Ser Leu Met Asp Lys Leu Arg Glu Asp Leu
                645                 650                 655

Ile Thr Pro Ala Glu Lys Val Val Tyr Lys Leu Leu Arg Phe Leu Ile
            660                 665                 670
```

```
Lys Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Gln Phe Gly Phe Phe Val Asn Pro Lys Glu Ala Ile
                725                 730                 735

Thr Pro Glu Glu Glu Cys Val Phe Tyr Glu Gln Met Lys Arg Phe Thr
            740                 745                 750

Ser Lys Glu Ile Asp Cys Gln His Thr Thr Pro Gly Val Asn Leu Glu
        755                 760                 765

Ala Phe Ser Leu Met Val Ser Ser Phe Asn Asn Gly Thr Leu Ile Phe
    770                 775                 780

Lys Gly Glu Lys Lys Leu Asn Ser Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Ser Phe Val Arg Lys Gln
        835                 840                 845

Lys Tyr Lys Leu Ser His Ser Asp Tyr Glu Tyr Lys Val Ser Lys Leu
    850                 855                 860

Val Ser Arg Leu Val Ile Gly Ser Lys Gly Glu Glu Thr Gly Arg Ser
865                 870                 875                 880

Glu Asp Asn Leu Ala Glu Ile Cys Phe Asp Gly Glu Glu Glu Thr Ser
                885                 890                 895

Phe Phe Lys Ser Leu Glu Glu Lys Val Asn Thr Thr Ile Ala Arg Tyr
            900                 905                 910

Arg Arg Gly Arg Arg Ala Asn Asp Lys Gly Asp Gly Glu Lys Leu Thr
        915                 920                 925

Asn Thr Lys Gly Leu His His Leu Gln Leu Ile Leu Thr Gly Lys Met
    930                 935                 940

Ala His Leu Arg Lys Val Ile Leu Ser Glu Ile Ser Phe His Leu Val
945                 950                 955                 960

Glu Asp Phe Asp Pro Ser Cys Leu Thr Asn Asp Asp Met Lys Phe Ile
                965                 970                 975

Cys Glu Ala Val Glu Gly Ser Thr Glu Leu Ser Pro Leu Tyr Phe Thr
            980                 985                 990

Ser Val Ile Lys Asp Gln Cys Gly  Leu Asp Glu Met Ala  Lys Asn Leu
        995                 1000                 1005

Cys Arg  Lys Phe Phe Ser Glu  Asn Asp Trp Phe Ser  Cys Met Lys
    1010                 1015                 1020

Met Ile  Leu Leu Gln Met Asn  Ala Asn Ala Tyr Ser  Gly Lys Tyr
    1025                 1030                 1035

Arg His  Met Gln Arg Gln Gly  Leu Asn Phe Lys Phe  Asp Trp Asp
    1040                 1045                 1050

Lys Leu  Glu Glu Asp Val Arg  Ile Ser Glu Arg Glu  Ser Asn Ser
    1055                 1060                 1065

Glu Ser  Leu Ser Lys Ala Leu  Ser Leu Thr Lys Cys  Met Ser Ala
    1070                 1075                 1080

Ala Leu  Lys Asn Leu Cys Phe  Tyr Ser Glu Glu Ser  Pro Thr Ser
```

```
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Ile Glu  Asp Tyr Phe
    1130                1135                1140

Glu Ser  Phe Ser Ser Phe Phe  Ser Gly Ser Cys Leu  Asn Asn Asp
    1145                1150                1155

Lys Glu  Phe Glu Asn Ala Ile  Leu Ser Met Thr Ile  Asn Val Arg
    1160                1165                1170

Glu Gly  Phe Leu Asn Tyr Ser  Met Asp His Ser Lys  Trp Gly Pro
    1175                1180                1185

Met Met  Cys Pro Phe Leu Phe  Leu Met Phe Leu Gln  Asn Leu Lys
    1190                1195                1200

Leu Gly  Asp Asp Gln Tyr Val  Arg Ser Gly Lys Asp  His Val Ser
    1205                1210                1215

Thr Leu  Leu Thr Trp His Met  His Lys Leu Val Glu  Val Pro Phe
    1220                1225                1230

Pro Val  Val Asn Ala Met Met  Lys Ser Tyr Val Lys  Ser Lys Leu
    1235                1240                1245

Lys Leu  Leu Arg Gly Ser Glu  Thr Thr Val Thr Glu  Arg Ile Phe
    1250                1255                1260

Arg Gln  Tyr Phe Glu Met Gly  Ile Val Pro Ser His  Ile Ser Ser
    1265                1270                1275

Leu Ile  Asp Met Gly Gln Gly  Ile Leu His Asn Ala  Ser Asp Phe
    1280                1285                1290

Tyr Gly  Leu Leu Ser Glu Arg  Phe Ile Asn Tyr Cys  Ile Gly Val
    1295                1300                1305

Ile Phe  Gly Glu Arg Pro Glu  Ala Tyr Thr Ser Ser  Asp Asp Gln
    1310                1315                1320

Ile Thr  Leu Phe Asp Arg Arg  Leu Ser Asp Leu Val  Val Ser Asp
    1325                1330                1335

Pro Glu  Glu Val Leu Val Leu  Leu Glu Phe Gln Ser  His Leu Ser
    1340                1345                1350

Gly Leu  Leu Asn Lys Phe Ile  Ser Pro Lys Ser Val  Ala Gly Arg
    1355                1360                1365

Phe Ala  Ala Glu Phe Lys Ser  Arg Phe Tyr Val Trp  Gly Glu Glu
    1370                1375                1380

Val Pro  Leu Leu Thr Lys Phe  Val Ser Ala Ala Leu  His Asn Val
    1385                1390                1395

Lys Cys  Lys Glu Pro His Gln  Leu Cys Glu Thr Ile  Asp Thr Ile
    1400                1405                1410

Ala Asp  Gln Ala Ile Ala Asn  Gly Val Pro Val Ser  Leu Val Asn
    1415                1420                1425

Ser Ile  Gln Arg Arg Thr Leu  Asp Leu Leu Lys Tyr  Ala Asn Phe
    1430                1435                1440

Pro Leu  Asp Pro Phe Leu Leu  Asn Thr Asn Thr Asp  Val Lys Asp
    1445                1450                1455

Trp Leu  Asp Gly Ser Arg Gly  Tyr Arg Ile Gln Arg  Leu Ile Glu
    1460                1465                1470

Glu Leu  Cys Pro Asn Glu Thr  Lys Val Val Arg Lys  Leu Val Arg
    1475                1480                1485
```

```
Lys Leu  His His Lys Leu Lys  Asn Gly Glu Phe Asn  Glu Glu Phe
    1490                 1495                 1500

Phe Leu  Asp Leu Phe Asn Arg  Asp Lys Lys Glu Ala  Ile Leu Gln
    1505                 1510                 1515

Leu Gly  Asp Leu Leu Gly Leu  Glu Glu Asp Leu Asn  Gln Leu Ala
    1520                 1525                 1530

Asp Val  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Arg Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Ile Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Leu Tyr Ile Lys  Lys Leu Leu Glu Asp  Leu Thr Thr
    1625                 1630                 1635

Asp Asp  His Val Thr Arg Val  Cys Asn Arg Asp Gly  Ile Thr Leu
    1640                 1645                 1650

Tyr Ile  Cys Asp Lys Gln Ser  His Pro Glu Ala His  Arg Asp His
    1655                 1660                 1665

Ile Cys  Leu Leu Arg Pro Leu  Leu Trp Asp Tyr Ile  Cys Ile Ser
    1670                 1675                 1680

Leu Ser  Asn Ser Phe Glu Leu  Gly Val Trp Val Leu  Ala Glu Pro
    1685                 1690                 1695

Thr Lys  Gly Lys Asn Asn Ser  Glu Asn Leu Thr Leu  Lys His Leu
    1700                 1705                 1710

Asn Pro  Cys Asp Tyr Val Ala  Arg Lys Pro Glu Ser  Ser Arg Leu
    1715                 1720                 1725

Leu Glu  Asp Lys Val Asn Leu  Asn Gln Val Ile Gln  Ser Val Arg
    1730                 1735                 1740

Arg Leu  Tyr Pro Lys Ile Phe  Glu Asp Gln Leu Leu  Pro Phe Met
    1745                 1750                 1755

Ser Asp  Met Ser Ser Lys Asn  Met Arg Trp Ser Pro  Arg Ile Lys
    1760                 1765                 1770

Phe Leu  Asp Leu Cys Val Leu  Ile Asp Ile Asn Ser  Glu Ser Leu
    1775                 1780                 1785

Ser Leu  Ile Ser His Val Val  Lys Trp Lys Arg Asp  Glu His Tyr
    1790                 1795                 1800

Thr Val  Leu Phe Ser Asp Leu  Ala Asn Ser His Gln  Arg Ser Asp
    1805                 1810                 1815

Ser Ser  Leu Val Asp Glu Phe  Val Val Ser Thr Arg  Asp Val Cys
    1820                 1825                 1830

Lys Asn  Phe Leu Lys Gln Val  Tyr Phe Glu Ser Phe  Val Arg Glu
    1835                 1840                 1845

Phe Val  Ala Thr Thr Arg Thr  Leu Gly Asn Phe Ser  Trp Phe Pro
    1850                 1855                 1860

His Lys  Glu Met Met Pro Ser  Glu Asp Gly Ala Glu  Ala Leu Gly
    1865                 1870                 1875
```

```
Pro Phe  Gln Ser Phe Val Ser  Lys Val Val Asn Lys  Asn Val Glu
    1880                 1885                 1890

Arg Pro  Met Phe Arg Asn Asp  Leu Gln Phe Gly Phe  Gly Trp Phe
    1895                 1900                 1905

Ser Tyr  Arg Met Gly Asp Val  Val Cys Asn Ala Ala  Met Leu Ile
    1910                 1915                 1920

Arg Gln  Gly Leu Thr Asn Pro  Lys Ala Phe Lys Ser  Leu Lys Asp
    1925                 1930                 1935

Leu Trp  Asp Tyr Met Leu Asn  Tyr Thr Lys Gly Val  Leu Glu Phe
    1940                 1945                 1950

Ser Ile  Ser Val Asp Phe Thr  His Asn Gln Asn Asn  Thr Asp Cys
    1955                 1960                 1965

Leu Arg  Lys Phe Ser Leu Ile  Phe Leu Val Arg Cys  Gln Leu Gln
    1970                 1975                 1980

Asn Pro  Gly Val Ala Glu Leu  Leu Ser Cys Ser His  Leu Phe Lys
    1985                 1990                 1995

Gly Glu  Ile Asp Arg Arg Met  Leu Asp Glu Cys Leu  His Leu Leu
    2000                 2005                 2010

Arg Thr  Asp Ser Val Phe Lys  Val Asn Asp Gly Val  Phe Asp Ile
    2015                 2020                 2025

Arg Ser  Glu Glu Phe Glu Asp  Tyr Met Glu Asp Pro  Leu Ile Leu
    2030                 2035                 2040

Gly Asp  Ser Leu Glu Leu Glu  Leu Leu Gly Ser Lys  Arg Ile Leu
    2045                 2050                 2055

Asp Gly  Ile Arg Ser Ile Asp  Phe Glu Arg Val Gly  Pro Glu Trp
    2060                 2065                 2070

Glu Pro  Val Pro Leu Thr Val  Lys Met Gly Ala Leu  Phe Glu Gly
    2075                 2080                 2085

Arg Asn  Leu Val Gln Asn Ile  Ile Val Lys Leu Glu  Thr Lys Asp
    2090                 2095                 2100

Met Lys  Val Phe Leu Ala Gly  Leu Glu Gly Tyr Glu  Lys Ile Ser
    2105                 2110                 2115

Asp Val  Leu Gly Asn Leu Phe  Leu His Arg Phe Arg  Thr Gly Glu
    2120                 2125                 2130

His Leu  Leu Gly Ser Glu Ile  Ser Val Ile Leu Gln  Glu Leu Cys
    2135                 2140                 2145

Ile Asp  Arg Ser Ile Leu Leu  Ile Pro Leu Ser Leu  Leu Pro Asp
    2150                 2155                 2160

Trp Phe  Ala Phe Lys Asp Cys  Arg Leu Cys Phe Ser  Lys Ser Arg
    2165                 2170                 2175

Ser Thr  Leu Met Tyr Glu Thr  Val Gly Gly Arg Phe  Arg Leu Lys
    2180                 2185                 2190

Gly Arg  Ser Cys Asp Asp Trp  Leu Gly Gly Ser Val  Ala Glu Asp
    2195                 2200                 2205

Ile Asp
    2210
```

<210> SEQ ID NO 31
<211> LENGTH: 3377
<212> TYPE: DNA
<213> ORGANISM: Lymphocytic choriomeningitis virus (LCMV) strain Clone13

<400> SEQUENCE: 31

```
gcgcaccggg gatcctaggc tttttggatt gcgctttcct ctagatcaac tgggtgtcag     60
```

```
gccctatcct acagaaggat gggtcagatt gtgacaatgt ttgaggctct gcctcacatc    120
atcgatgagg tgatcaacat tgtcattatt gtgcttatcg tgatcacggg tatcaaggct    180
gtctacaatt ttgccacctg tgggatattc gcattgatca gtttcctact tctggctggc    240
aggtcctgtg gcatgtacgg tcttaaggga cccgacattt acaaaggagt ttaccaattt    300
aagtcagtgg agtttgatat gtcacatctg aacctgacca tgcccaacgc atgttcagcc    360
aacaactccc accattacat cagtatgggg acttctggac tagaattgac cttcaccaat    420
gattccatca tcagtcacaa cttttgcaat ctgacctctg ccttcaacaa aaagaccttt    480
gaccacacac tcatgagtat agtttcgagc ctacacctca gtatcagagg gaactccaac    540
tataaggcag tatcctgcga cttcaacaat ggcataacca tccaatacaa cttgacattc    600
tcagatgcac aaagtgctca gagccagtgt agaaccttca gaggtagagt cctagatatg    660
tttagaactg ccttcggggg gaaatacatg aggagtggct ggggctggac aggctcagat    720
ggcaagacca cctggtgtag ccagacgagt taccaatacc tgattataca aaatagaacc    780
tgggaaaacc actgcacata tgcaggtcct tttgggatgt ccaggattct cctttcccaa    840
gagaagacta agttcctcac taggagacta gcgggcacat tcacctggac tttgtcagac    900
tcttcagggg tggagaatcc aggtggttat tgcctgacca aatggatgat tcttgctgca    960
gagcttaagt gtttcgggaa cacagcagtt gcgaaatgca atgtaaatca tgatgaagaa   1020
ttctgtgaca tgctgcgact aattgactac aacaaggctg ctttgagtaa gttcaaagag   1080
gacgtagaat ctgccttgca cttattcaaa acaacagtga attctttgat ttcagatcaa   1140
ctactgatga ggaaccactt gagagatctg atgggggtgc catattgcaa ttactcaaag   1200
ttttggtacc tagaacatgc aaagaccggc gaaactagtg tccccaagtg ctggcttgtc   1260
accaatggtt cttacttaaa tgagacccac ttcagtgacc aaatcgaaca ggaagccgat   1320
aacatgatta cagagatgtt gaggaaggat tacataaaga ggcaggggag taccccccta   1380
gcattgatgg accttctgat gttttccaca tctgcatatc tagtcagcat cttcctgcac   1440
cttgtcaaaa taccaacaca caggcacata aaaggtggct catgtccaaa gccacaccga   1500
ttaaccaaca aaggaatttg tagttgtggt gcatttaagg tgcctggtgt aaaaaccgtc   1560
tggaaaagac gctgaagaac agcgcctccc tgactctcca cctcgaaaga ggtggagagt   1620
cagggaggcc cagagggtct tagagtgtca caacatttgg gcctctaaaa attaggtcat   1680
gtggcagaat gttgtgaaca gttttcagat ctgggagcct tgctttggag gcgctttcaa   1740
aaatgatgca gtccatgagt gcacagtgcg ggtgatctc tttcttcttt ttgtccctta   1800
ctattccagt atgcatctta cacaaccagc catatttgtc ccacactttg tcttcatact   1860
ccctcgaagc ttccctggtc atttcaacat cgataagctt aatgtccttc ctattctgtg   1920
agtccagaag ctttctgatg tcatcggagc cttgacagct tagaaccatc ccctgcggaa   1980
gagcacctat aactgacgag gtcaacccgg gttgcgcatt gaagaggtcg gcaagatcca   2040
tgccgtgtga gtacttggaa tcttgcttga attgtttttg atcaacgggt tccctgtaaa   2100
agtgtatgaa ctgcccgttc tgtggttgga aaattgctat ttccactgga tcattaaatc   2160
taccctcaat gtcaatccat gtaggagcgt tggggtcaat tcctcccatg aggtctttta   2220
aaagcattgt ctggctgtag cttaagccca cctgaggtgg acctgctgct ccaggcgctg   2280
gcctgggtga attgactgca ggtttctcgc ttgtgagatc aattgttgtg ttttcccatg   2340
ctctccccac aatcgatgtt ctacaagcta tgtatggcca tccttcacct gaaaggcaaa   2400
ctttatagag gatgttttca taagggttcc tgtccccaac ttggtctgaa acaaacatgt   2460
```

```
tgagttttct cttggccccg agaactgcct tcaagaggtc ctcgctgttg cttggcttga   2520

tcaaaattga ctctaacatg ttacccccat ccaacagggc tgcccctgcc ttcacggcag   2580

caccaagact aaagttatag ccagaaatgt tgatgctgga ctgctgttca gtgatgaccc   2640

ccagaactgg gtgcttgtct ttcagccttt caagatcatt aagatttgga tacttgactg   2700

tgtaaagcaa gccaaggtct gtgagcgctt gtacaacgtc attgagcgga gtctgtgact   2760

gtttggccat acaagccata gttagacttg gcattgtgcc aaattgattg ttcaaaagtg   2820

atgagtcttt cacatcccaa actcttacca caccacttgc accctgctga ggctttctca   2880

tcccaactat ctgtaggatc tgagatcttt ggtctagttg ctgtgttgtt aagttcccca   2940

tatatacccc tgaagcctgg ggcctttcag acctcatgat cttggccttc agcttctcaa   3000

ggtcagccgc aagagacatc agttcttctg cactgagcct ccccactttc aaaacattct   3060

tctttgatgt tgactttaaa tccacaagag aatgtacagt ctggttgaga cttctgagtc   3120

tctgtaggtc tttgtcatct ctcttttcct tcctcatgat cctctgaaca ttgctgacct   3180

cagagaagtc caacccattc agaaggttgg ttgcatcctt aatgacagca gccttcacat   3240

ctgatgtgaa gctctgcaat tctcttctca atgcttgcgt ccattggaag ctcttaactt   3300

ccttagacaa ggacatcttg ttgctcaatg gtttctcaag acaaatgcgc aatcaaatgc   3360

ctaggatcca ctgtgcg                                                  3377
```

<210> SEQ ID NO 32
<211> LENGTH: 7229
<212> TYPE: DNA
<213> ORGANISM: Lymphocytic choriomeningitis virus (LCMV) strain Clone13

<400> SEQUENCE: 32

```
gcgcaccggg gatcctaggc gtttagttgc gctgtttggt tgcacaactt tcttcgtgag     60

gctgtcagaa gtggacctgg ctgatagcga tgggtcaagg caagtccaga gaggagaaag    120

gcaccaatag tacaaacagg gccgaaatcc taccagatac cacctatctt ggccctttaa    180

gctgcaaatc ttgctggcag aaatttgaca gcttggtaag atgccatgac cactaccttt    240

gcaggcactg tttaaacctt ctgctgtcag tatccgacag gtgtcctctt tgtaaatatc    300

cattaccaac cagattgaag atatcaacag ccccaagctc tccacctccc tacgaagagt    360

aacaccgtcc ggccccggcc ccgacaaaca gcccagcaca agggaaccgc acgtcaccca    420

acgcacacag acacagcacc caacacagaa cacgcacaca cacacacaca cacacccaca    480

cgcacgcgcc cccaccaccg gggggcgccc ccccccgggg ggcggccccc cgggagcccg    540

ggcggagccc cacggagatg cccatcagtc gatgtcctcg gccaccgacc cgcccagcca    600

atcgtcgcag gacctcccct tgagtctaaa cctgcccccc actgtttcat acatcaaagt    660

gctcctagat ttgctaaaac aaagtctgca atccttaaag gcgaaccagt ctggcaaaag    720

cgacagtgga atcagcagaa tagatctgtc tatacatagt tcctggagga ttacacttat    780

ctctgaaccc aacaaatgtt caccagttct gaatcgatgc aggaagaggt tcccaaggac    840

atcactaatc ttttcatagc cctcaagtcc tgctagaaag actttcatgt ccttggtctc    900

cagcttcaca atgatatttt ggacaaggtt tcttccttca aaaagggcac ccatctttac    960

agtcagtggc acaggctccc actcaggtcc aactctctca aagtcaatag atctaatccc   1020

atccagtatt cttttggagc ccaacaactc aagctcaaga gaatcaccaa gtatcaaggg   1080

atcttccatg taatcctcaa actcttcaga tctgatatca aagacaccat cgttcacctt   1140
```

```
gaagacagag tctgtcctca gtaagtggag gcattcatcc aacattcttc tatctatctc   1200
acccttaaag aggtgagagc atgataaaag ttcagccaca cctggattct gtaattggca   1260
cctaaccaag aatatcaatg aaaatttcct taaacagtca gtattattct gattgtgcgt   1320
aaagtccact gaaattgaaa actccaatac cccttttgtg tagttgagca tgtagtccca   1380
cagatccttt aaggatttaa atgcctttgg gtttgtcagg ccctgcctaa tcaacatggc   1440
agcattacac acaacatctc ccattcggta agagaaccac ccaaaaccaa actgcaaatc   1500
attcctaaac ataggcctct ccacattttt gttcaccacc tttgagacaa atgattgaaa   1560
ggggcccagt gcctcagcac catcttcaga tggcatcatt tctttatgag ggaaccatga   1620
aaaattgcct aatgtcctgg ttgttgcaac aaattctcga acaaatgatt caaaatacac   1680
ctgttttaag aagttcttgc agacatccct cgtgctaaca acaaattcat caaccagact   1740
ggagtcagat cgctgatgag aattggcaag gtcagaaaac agaacagtgt aatgttcatc   1800
ccttttccac ttaacaacat gagaaatgag tgacaaggat tctgagttaa tatcaattaa   1860
aacacagagg tcaaggaatt taattctggg actccacctc atgtttttg agctcatgtc   1920
agacataaat ggaagaagct gatcctcaaa gatcttggga tatagccgcc tcacagattg   1980
aatcacttgg ttcaaattca ctttgtcctc cagtagcctt gagctctcag gctttcttgc   2040
tacataatca catgggttta agtgcttaag agttaggttc tcactgttat tcttcccttt   2100
ggtcggttct gctaggaccc aaacacccaa ctcaaaagag ttgctcaatg aaatacaaat   2160
gtagtcccaa agaagaggcc ttaaaaggca tatatgatca cggtgggctt ctggatgaga   2220
ctgtttgtca caaatgtaca gcgttatacc atcccgattg caaactcttg tcacatgatc   2280
atctgtggtt agatcctcaa gcagcttttt gatatacaga ttttccctat ttttgtttct   2340
cacacacctg cttcctagag ttttgcaaag gcctataaag ccagatgaga tacaactctg   2400
gaaagctgac ttgttgattg cttctgacag cagcttctgt gcaccccttg tgaatttact   2460
acaaagtttg ttctggagtg tcttgatcaa tgatgggatt ctttcctctt ggaaagtcat   2520
cactgatgga taaaccacct tttgtcttaa aaccatcctt aatgggaaca tttcattcaa   2580
attcaaccag ttaacatctg ctaactgatt cagatcttct tcaagaccga ggaggtctcc   2640
caattgaaga atggcctcct ttttatctct gttaaatagg tctaagaaaa attcttcatt   2700
aaattcacca tttttgagct tatgatgcag tttccttaca agctttctta caacctttgt   2760
ttcattagga cacagttcct caatgagtct ttgtattctg taacctctag aaccatccag   2820
ccaatctttc acatcagtgt tggtattcag tagaaatgga tccaaaggga aattggcata   2880
ctttaggagg tccagtgttc tcctttggat actattaact agggagactg ggacgccatt   2940
tgcgatggct tgatctgcaa ttgtatctat tgtttcacaa agttgatgtg gctctttaca   3000
cttgacattg tgtagcgctg cagatacaaa ctttgtgaga agagggactt cctcccccca   3060
tacatagaat ctagatttaa attctgcagc gaacctccca gccacacttt ttgggctgat   3120
aaatttgttt aacaagccgc tcagatgaga ttggaattcc aacaggacaa ggacttcctc   3180
cggatcactt acaaccaggt cactcagcct cctatcaaat aaagtgatct gatcatcact   3240
tgatgtgtaa gcctctggtc tttcgccaaa gataacacca atgcagtagt tgatgaacct   3300
ctcgctaagc aaaccataga agtcagaagc attatgcaag attccctgcc ccatatcaat   3360
aaggctggat atatgggatg gcactatccc catttcaaaa tattgtctga aaattctctc   3420
agtaacagtt gtttctgaac ccctgagaag ttttagcttc gacttgacat atgatttcat   3480
cattgcattc acaacaggaa aggggacctc gacaagctta tgcatgtgcc aagttaacaa   3540
```

```
agtgctaaca tgatctttcc cggaacgcac atactggtca tcacctagtt tgagattttg   3600
tagaaacatt aagaacaaaa atgggcacat cattggtccc catttgctgt gatccatact   3660
atagtttaag aacccttccc gcacattgat agtcattgac aagattgcat tttcaaattc   3720
cttatcattg tttaaacagg agcctgaaaa gaaacttgaa aaagactcaa aataatcttc   3780
tattaacctt gtgaacattt ttgtcctcaa atctccaata tagagttctc tatttccccc   3840
aacctgctct ttataagata gtgcaaattt cagccttcca gagtcaggac ctactgaggt   3900
gtatgatgtt ggtgattctt ctgagtagaa gcacagattt ttcaaagcag cactcataca   3960
ttgtgtcaac gacagagctt tactaaggga ctcagaatta ctttccctct cactgattct   4020
cacgtcttct tccagtttgt cccagtcaaa tttgaaattc aagccttgcc tttgcatatg   4080
cctgtatttc cctgagtacg catttgcatt catttgcaac agaatcatct tcatgcaaga   4140
aaaccaatca ttctcagaaa agaactttct acaaaggttt tttgccatct catcgaggcc   4200
acactgatct ttaatgactg aggtgaaata caaaggtgac agctctgtgg aaccctcaac   4260
agcctcacag ataaatttca tgtcatcatt ggttagacat gatgggtcaa agtcttctac   4320
taaatggaaa gatatttctg acaagataac ttttcttaag tgagccatct tccctgttag   4380
aataagctgt aaatgatgta gtccttttgt atttgtaagt tttctccat ctcctttgtc    4440
attggccctc ctacctcttc tgtaccgtgc tattgtggtg ttgacctttt cttcgagact   4500
tttgaagaag cttgtctctt cttctccatc aaaacatatt tctgccaggt tgtcttccga   4560
tctccctgtc tcttctccct tggaaccgat gaccaatcta gagactaact tggaaacttt   4620
atattcatag tctgagtggc tcaacttata cttttgtttt cttacgaaac tctccgtaat   4680
ttgactcaca gcactaacaa gcaatttgtt aaagtcatat tccagaagtc gttctccatt   4740
tagatgctta ttaaccacca cacttttgtt actagcaaga tctaatgctg tcgcacatcc   4800
agagttagtc atgggatcta ggctgtttag cttcttctct cctttgaaaa ttaaagtgcc   4860
gttgttaaat gaagacacca ttaggctaaa ggcttccaga ttaacacctg gagttgtatg   4920
ctgacagtca atttctttac tagtgaatct cttcatttgc tcatagaaca cacattcttc   4980
ctcaggagtg attgcttcct tggggttgac aaaaaaacca aattgacttt tgggctcaaa   5040
gaacttttca aaacatttta tctgatctgt tagcctgtca ggggtctcct ttgtgatcaa   5100
atgacacagg tatgacacat tcaacataaa tttaaatttt gcactcaaca acaccttctc   5160
accagtacca aaaatagttt ttattaggaa tctaagcagc ttatacacca ccttctcagc   5220
aggtgtgatc agatcctccc tcaacttatc cattaatgat gtagatgaaa aatctgacac   5280
tattgccatc accaaatatc tgacactctg tacctgcttt tgatttctct ttgttgggtt   5340
ggtgagcatt agcaacaata gggtcctcag tgcaacctca atgtcggtga gacagtcttt   5400
caaatcagga catgatctaa tccatgaaat catgatgtct atcatattgt ataagacctc   5460
atctgaaaaa attggtaaaa agaacctttt aggatctgca tagaaggaaa ttaaatgacc   5520
atccgggcct tgtatggagt agcaccttga agattctcca gtcttctggt ataataggtg   5580
gtattcttca gagtccagtt ttattacttg gcaaaacact tctttgcatt ctaccacttg   5640
atatctcaca gaccctattt gattttgcct tagtctagca actgagctag ttttcatact   5700
gtttgttaag gccagacaaa cagatgataa tcttctcagg ctctgtatgt tcttcagctg   5760
ctctgtgctg ggttggaaat tgtaatcttc aaacttcgta taatacatta tcgggtgagc   5820
tccaattttc ataaagttct caaattcagt gaatggtatg tggcattctt gctcaaggtg   5880
```

```
ttcagacagt ccgtaatgct cgaaactcag tcccaccact aacaggcatt tttgaatttt   5940
tgcaatgaac tcactaatag atgccctaaa caattcctca aaagacacct ttctaaacac   6000
ctttgacttt tttctattcc tcaaaagtct aatgaactcc tctttagtgc tgtgaaagct   6060
taccagccta tcattcacac tactatagca acaacccacc cagtgtttat catttttttaa  6120
ccctttgaat ttcgactgtt ttatcaatga ggaaagacac aaaacatcca gatttaacaa   6180
ctgtctcctt ctagtattca acagtttcaa actcttgact ttgtttaaca tagagaggag   6240
cctctcatat tcagtgctag tctcacttcc cctttcgtgc ccatgggtct ctgcagttat   6300
gaatctcatc aaaggacagg attcgactgc ctccctgctt aatgttaaga tatcatcact   6360
atcagcaagg ttttcataga gctcagagaa ttccttgatc aagccttcag ggtttacttt   6420
ctgaaagttt ctctttaatt tcccactttc taaatctctt ctaaacctgc tgaaaagaga   6480
gtttattcca aaaaccacat catcacagct catgttgggg ttgatgcctt cgtggcacat   6540
cctcataatt tcatcattgt gagttgacct cgcatctttc agaattttca tagagtccat   6600
accggagcgc ttgtcgatag tagtcttcag ggactcacag agtctaaaat attcagactc   6660
ttcaaagact ttctcatttt ggttagaata ctccaaaagt ttgaataaaa ggtctctaaa   6720
tttgaagttt gcccactctg gcataaaact attatcataa tcacaacgac catctactat   6780
tggaactaat gtgacacccg caacagcaag gtcttccctg atgcatgcca atttgttagt   6840
gtcctctata aatttcttct caaaactggc tggagtgctc ctaacaaaac actcaagaag   6900
aatgagagaa ttgtctatca gcttgtaacc atcaggaatg ataagtggta gtcctgggca   6960
tacaattcca gactccacca aaattgtttc cacagactta tcgtcgtggt tgtgtgtgca   7020
gccactcttg tctgcactgt ctatttcaat gcagcgtgac agcaacttga gtccctcaat   7080
cagaaccatt ctgggttccc tttgtcccag aaagttgagt ttctgccttg acaacctctc   7140
atcctgttct atatagttta aacataactc tctcaattct gagatgattt catccattgc   7200
gcatcaaaaa gcctaggatc ctcggtgcg                                     7229
```

<210> SEQ ID NO 33
<211> LENGTH: 1497
<212> TYPE: DNA
<213> ORGANISM: Lymphocytic choriomeningitis virus (LCMV) strain Clone13

<400> SEQUENCE: 33

```
atgggtcaga ttgtgacaat gtttgaggct ctgcctcaca tcatcgatga ggtgatcaac     60
attgtcatta ttgtgcttat cgtgatcacg ggtatcaagg ctgtctacaa ttttgccacc    120
tgtgggatat tcgcattgat cagtttccta cttctggctg gcaggtcctg tggcatgtac    180
ggtcttaagg gacccgacat ttacaaagga gtttaccaat ttaagtcagt ggagtttgat    240
atgtcacatc tgaacctgac catgcccaac gcatgttcag ccaacaactc ccaccattac    300
atcagtatgg ggacttctgg actagaattg accttcacca atgattccat catcagtcac    360
aacttttgca atctgacctc tgccttcaac aaaaagacct ttgaccacac actcatgagt    420
atagtttcga gcctacacct cagtatcaga gggaactcca actataaggc agtatcctgc    480
gacttcaaca atggcataac catccaatac aacttgacat tctcagatgc acaaagtgct    540
cagagccagt gtagaacctt cagaggtaga gtcctagata tgtttagaac tgccttcggg    600
gggaaataca tgaggagtgg ctggggctgg acaggctcag atggcaagac cacctggtgt    660
agccagacga gttaccaata cctgattata caaaatagaa cctgggaaaa ccactgcaca    720
tatgcaggtc cttttgggat gtccaggatt ctcctttccc aagagaagac taagttcctc    780
```

```
actaggagac tagcgggcac attcacctgg actttgtcag actcttcagg ggtggagaat    840
ccaggtggtt attgcctgac caaatggatg attcttgctg cagagcttaa gtgtttcggg    900
aacacagcag ttgcgaaatg caatgtaaat catgatgaag aattctgtga catgctgcga    960
ctaattgact acaacaaggc tgctttgagt aagttcaaag aggacgtaga atctgccttg   1020
cacttattca aaacaacagt gaattctttg atttcagatc aactactgat gaggaaccac   1080
ttgagagatc tgatgggggt gccatattgc aattactcaa agttttggta cctagaacat   1140
gcaaagaccg gcgaaactag tgtccccaag tgctggcttg tcaccaatgg ttcttactta   1200
aatgagaccc acttcagtga ccaaatcgaa caggaagccg ataacatgat tacagagatg   1260
ttgaggaagg attacataaa gaggcagggg agtacccccc tagcattgat ggaccttctg   1320
atgttttcca catctgcata tctagtcagc atcttcctgc accttgtcaa aataccaaca   1380
cacaggcaca taaaaggtgg ctcatgtcca aagccacacc gattaaccaa caaaggaatt   1440
tgtagttgtg gtgcatttaa ggtgcctggt gtaaaaaccg tctggaaaag acgctga      1497
```

<210> SEQ ID NO 34
<211> LENGTH: 498
<212> TYPE: PRT
<213> ORGANISM: Lymphocytic choriomeningitis virus (LCMV) strain Clone13

<400> SEQUENCE: 34

```
Met Gly Gln Ile Val Thr Met Phe Glu Ala Leu Pro His Ile Ile Asp
1               5                   10                  15

Glu Val Ile Asn Ile Val Ile Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
```

```
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Val Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg


<210> SEQ ID NO 35
<211> LENGTH: 1677
<212> TYPE: DNA
<213> ORGANISM: Lymphocytic choriomeningitis virus (LCMV) strain Clone13

<400> SEQUENCE: 35

atgtccttgt ctaaggaagt taagagcttc caatggacgc aagcattgag aagagaattg     60

cagagcttca catcagatgt gaaggctgct gtcattaagg atgcaaccaa ccttctgaat    120

gggttggact tctctgaggt cagcaatgtt cagaggatca tgaggaagga aaagagagat    180

gacaaagacc tacagagact cagaagtctc aaccagactg tacattctct tgtggattta    240

aagtcaacat caaagaagaa tgttttgaaa gtggggaggc tcagtgcaga agaactgatg    300

tctcttgcgg ctgaccttga gaagctgaag gccaagatca tgaggtctga aaggccccag    360

gcttcagggg tatatatggg gaacttaaca acacagcaac tagaccaaag atctcagatc    420

ctacagatag ttgggatgag aaagcctcag cagggtgcaa gtggtgtggt aagagtttgg    480

gatgtgaaag actcatcact tttgaacaat caatttggca caatgccaag tctaactatg    540

gcttgtatgg ccaaacagtc acagactccg ctcaatgacg ttgtacaagc gctcacagac    600

cttggcttgc tttacacagt caagtatcca aatcttaatg atcttgaaag gctgaaagac    660
```

```
aagcacccag ttctgggggt catcactgaa cagcagtcca gcatcaacat ttctggctat    720

aactttagtc ttggtgctgc cgtgaaggca ggggcagccc tgttggatgg gggtaacatg    780

ttagagtcaa ttttgatcaa gccaagcaac agcgaggacc tcttgaaggc agttctcggg    840

gccaagagaa aactcaacat gtttgtttca gaccaagttg gggacaggaa cccttatgaa    900

aacatcctct ataaagtttg cctttcaggt gaaggatggc catacatagc ttgtagaaca    960

tcgattgtgg ggagagcatg ggaaaacaca acaattgatc tcacaagcga gaaacctgca   1020

gtcaattcac ccaggccagc gcctggagca gcaggtccac ctcaggtggg cttaagctac   1080

agccagacaa tgcttttaaa agacctcatg ggaggaattg accccaacgc tcctacatgg   1140

attgacattg agggtagatt taatgatcca gtggaaatag caatttttcca accacagaac  1200

gggcagttca tacactttta cagggaaccc gttgatcaaa aacaattcaa gcaagattcc   1260

aagtactcac acggcatgga tcttgccgac ctcttcaatg cgcaacccgg gttgacctcg   1320

tcagttatag gtgctcttcc gcaggggatg gttctaagct gtcaaggctc cgatgacatc   1380

agaaagcttc tggactcaca gaataggaag gacattaagc ttatcgatgt tgaaatgacc   1440

agggaagctt cgagggagta tgaagacaaa gtgtgggaca aatatggctg gttgtgtaag   1500

atgcatactg gaatagtaag ggacaaaaag aagaaagaga tcaccccgca ctgtgcactc   1560

atggactgca tcatttttga aagcgcctcc aaagcaaggc tcccagatct gaaaactgtt   1620

cacaacattc tgccacatga cctaattttt agaggcccaa atgttgtgac actctaa      1677
```

<210> SEQ ID NO 36
<211> LENGTH: 558
<212> TYPE: PRT
<213> ORGANISM: Lymphocytic choriomeningitis virus (LCMV) strain Clone13

<400> SEQUENCE: 36

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125

Leu Thr Thr Gln Gln Leu Asp Gln Arg Ser Gln Ile Leu Gln Ile Val
    130                 135                 140

Gly Met Arg Lys Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
```

```
        195                 200                 205

Tyr Pro Asn Leu Asn Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Pro Ala Val Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555
```

<210> SEQ ID NO 37
<211> LENGTH: 273
<212> TYPE: DNA
<213> ORGANISM: Lymphocytic choriomeningitis virus (LCMV) strain Clone13

<400> SEQUENCE: 37

```
atgggtcaag gcaagtccag agaggagaaa ggcaccaata gtacaaacag ggccgaaatc     60

ctaccagata ccacctatct tggccccttta agctgcaaat cttgctggca gaaatttgac    120
```

agcttggtaa gatgccatga ccactacctt tgcaggcact gtttaaacct tctgctgtca 180
gtatccgaca ggtgtcctct ttgtaaatat ccattaccaa ccagattgaa gatatcaaca 240
gccccaagct ctccacctcc ctacgaagag taa 273

<210> SEQ ID NO 38
<211> LENGTH: 90
<212> TYPE: PRT
<213> ORGANISM: Lymphocytic choriomeningitis virus (LCMV) strain Clone13

<400> SEQUENCE: 38

Met Gly Gln Gly Lys Ser Arg Glu Glu Lys Gly Thr Asn Ser Thr Asn
1 5 10 15

Arg Ala Glu Ile Leu Pro Asp Thr Thr Tyr Leu Gly Pro Leu Ser Cys
20 25 30

Lys Ser Cys Trp Gln Lys Phe Asp Ser Leu Val Arg Cys His Asp His
35 40 45

Tyr Leu Cys Arg His Cys Leu Asn Leu Leu Leu Ser Val Ser Asp Arg
50 55 60

Cys Pro Leu Cys Lys Tyr Pro Leu Pro Thr Arg Leu Lys Ile Ser Thr
65 70 75 80

Ala Pro Ser Ser Pro Pro Pro Tyr Glu Glu
85 90

<210> SEQ ID NO 39
<211> LENGTH: 6633
<212> TYPE: DNA
<213> ORGANISM: Lymphocytic choriomeningitis virus (LCMV) strain Clone13

<400> SEQUENCE: 39
atggatgaaa tcatctcaga attgagagag ttatgtttaa actatataga acaggatgag 60
aggttgtcaa ggcagaaact caactttctg ggacaaaggg aacccagaat ggttctgatt 120
gagggactca agttgctgtc acgctgcatt gaaatagaca gtgcagacaa gagtggctgc 180
acacacaacc acgacgataa gtctgtggaa acaattttgg tggagtctgg aattgtatgc 240
ccaggactac cacttatcat tcctgatggt tacaagctga tagacaattc tctcattctt 300
cttgagtgtt ttgttaggag cactccagcc agttttgaga agaaatttat agaggacact 360
aacaaattgg catgcatcag ggaagacctt gctgttgcgg gtgtcacatt agttccaata 420
gtagatggtc gttgtgatta tgataatagt tttatgccag agtgggcaaa cttcaaattt 480
agagaccttt tattcaaact tttggagtat tctaaccaaa atgagaaagt ctttgaagag 540
tctgaatatt ttagactctg tgagtccctg aagactacta tcgacaagcg ctccggtatg 600
gactctatga aaattctgaa agatgcgagg tcaactcaca atgatgaaat tatgaggatg 660
tgccacgaag gcatcaaccc caacatgagc tgtgatgatg tggtttttgg aataaactct 720
cttttcagca ggtttagaag agatttagaa agtgggaaat taaagagaaa ctttcagaaa 780
gtaaaccctg aaggcttgat caaggaattc tctgagctct atgaaaacct tgctgatagt 840
gatgatatct taacattaag cagggaggca gtcgaatcct gtcctttgat gagattcata 900
actgcagaga cccatgggca cgaaagggga agtgagacta gcactgaata tgagaggctc 960
ctctctatgt taaacaaagt caagagtttg aaactgttga atactagaag gagacagttg 1020
ttaaatctgg atgttttgtg tctttcctca ttgataaaac agtcgaaatt caaagggtta 1080
aaaaatgata aacactgggt gggttgttgc tatagtagtg tgaatgatag gctggtaagc 1140

```
tttcacagca ctaaagagga gttcattaga cttttgagga atagaaaaaa gtcaaaggtg   1200
tttagaaagg tgtcttttga ggaattgttt agggcatcta ttagtgagtt cattgcaaaa   1260
attcaaaaat gcctgttagt ggtgggactg agtttcgagc attacggact gtctgaacac   1320
cttgagcaag aatgccacat accattcact gaatttgaga actttatgaa aattggagct   1380
cacccgataa tgtattatac gaagtttgaa gattacaatt tccaacccag cacagagcag   1440
ctgaagaaca tacagagcct gagaagatta tcatctgttt gtctggcctt aacaaacagt   1500
atgaaaacta gctcagttgc tagactaagg caaaatcaaa tagggtctgt gagatatcaa   1560
gtggtagaat gcaaagaagt gttttgccaa gtaataaaac tggactctga agaataccac   1620
ctattatacc agaagactgg agaatcttca aggtgctact ccatacaagg cccggatggt   1680
catttaattt ccttctatgc agatcctaaa aggttctttt taccaatttt ttcagatgag   1740
gtcttataca atatgataga catcatgatt tcatggatta gatcatgtcc tgatttgaaa   1800
gactgtctca ccgacattga ggttgcactg aggaccctat tgttgctaat gctcaccaac   1860
ccaacaaaga gaaatcaaaa gcaggtacag agtgtcagat atttggtgat ggcaatagtg   1920
tcagattttt catctacatc attaatggat aagttgaggg aggatctgat cacacctgct   1980
gagaaggtgg tgtataagct gcttagattc ctaataaaaa ctatttttgg tactggtgag   2040
aaggtgttgt tgagtgcaaa atttaaattt atgttgaatg tgtcatacct gtgtcatttg   2100
atcacaaagg agacccctga caggctaaca gatcagataa aatgttttga aaagttcttt   2160
gagcccaaaa gtcaatttgg tttttttgtc aaccccaagg aagcaatcac tcctgaggaa   2220
gaatgtgtgt tctatgagca aatgaagaga ttcactagta aagaaattga ctgtcagcat   2280
acaactccag gtgttaatct ggaagccttt agcctaatgg tgtcttcatt taacaacggc   2340
actttaattt tcaaaggaga gaagaagcta aacagcctag atcccatgac taactctgga   2400
tgtgcgacag cattagatct tgctagtaac aaaagtgtgg tggttaataa gcatctaaat   2460
ggagaacgac ttctggaata tgactttaac aaattgcttg ttagtgctgt gagtcaaatt   2520
acggagagtt tcgtaagaaa acaaaagtat aagttgagcc actcagacta tgaatataaa   2580
gtttccaagt tagtctctag attggtcatc ggttccaagg gagaagagac agggagatcg   2640
gaagacaacc tggcagaaat atgttttgat ggagaagaag agacaagctt cttcaaaagt   2700
ctcgaagaaa aggtcaacac cacaatagca cggtacagaa gaggtaggag ggccaatgac   2760
aaaggagatg gagaaaaact tacaaataca aaaggactac atcatttaca gcttattcta   2820
acagggaaga tggctcactt aagaaaagtt atcttgtcag aaatatcttt ccatttagta   2880
gaagactttg acccatcatg tctaaccaat gatgacatga aatttatctg tgaggctgtt   2940
gagggttcca cagagctgtc acctttgtat ttcacctcag tcattaaaga tcagtgtggc   3000
ctcgatgaga tggcaaaaaa cctttgtaga aagttctttt ctgagaatga ttggtttttct   3060
tgcatgaaga tgattctgtt gcaaatgaat gcaaatgcgt actcagggaa atacaggcat   3120
atgcaaaggc aaggcttgaa tttcaaattt gactgggaca aactggaaga agacgtgaga   3180
atcagtgaga gggaaagtaa ttctgagtcc cttagtaaag ctctgtcgtt gacacaatgt   3240
atgagtgctg ctttgaaaaa tctgtgcttc tactcagaag aatcaccaac atcatacacc   3300
tcagtaggtc ctgactctgg aaggctgaaa tttgcactat cttataaaga gcaggttggg   3360
ggaaatagag aactctatat tggagatttg aggacaaaaa tgttcacaag gttaatagaa   3420
gattattttg agtctttttc aagtttcttt tcaggctcct gtttaaacaa tgataaggaa   3480
tttgaaaatg caatcttgtc aatgactatc aatgtgcggg aagggttctt aaactatagt   3540
```

```
atggatcaca gcaaatgggg accaatgatg tgcccatttt tgttcttaat gtttctacaa   3600
aatctcaaac taggtgatga ccagtatgtg cgttccggga aagatcatgt tagcactttg   3660
ttaacttggc acatgcataa gcttgtcgag gtccccttc ctgttgtgaa tgcaatgatg   3720
aaatcatatg tcaagtcgaa gctaaaactt ctcaggggtt cagaaacaac tgttactgag   3780
agaattttca gacaatattt tgaaatgggg atagtgccat cccatatatc cagccttatt   3840
gatatggggc agggaatctt gcataatgct tctgacttct atggtttgct tagcgagagg   3900
ttcatcaact actgcattgg tgttatcttt ggcgaaagac cagaggctta cacatcaagt   3960
gatgatcaga tcactttatt tgataggagg ctgagtgacc tggttgtaag tgatccggag   4020
gaagtccttg tcctgttgga attccaatct catctgagcg gcttgttaaa caaatttatc   4080
agcccaaaaa gtgtggctgg gaggttcgct gcagaattta aatctagatt ctatgtatgg   4140
ggggaggaag tccctcttct cacaaagttt gtatctgcag cgctacacaa tgtcaagtgt   4200
aaagagccac atcaactttg tgaaacaata gatacaattg cagatcaagc catcgcaaat   4260
ggcgtcccag tctccctagt taatagtatc caaaggagaa cactggacct cctaaagtat   4320
gccaatttcc ctttggatcc atttctactg aataccaaca ctgatgtgaa agattggctg   4380
gatggttcta gaggttacag aatacaaaga ctcattgagg aactgtgtcc taatgaaaca   4440
aaggttgtaa gaaagcttgt aaggaaactg catcataagc tcaaaaatgg tgaatttaat   4500
gaagaatttt tcttagacct atttaacaga gataaaaagg aggccattct tcaattggga   4560
gacctcctcg gtcttgaaga agatctgaat cagttagcag atgttaactg gttgaatttg   4620
aatgaaatgt tcccattaag gatggtttta agacaaaagg tggtttatcc atcagtgatg   4680
actttccaag aggaaagaat cccatcattg atcaagacac tccagaacaa actttgtagt   4740
aaattcacaa ggggtgcaca gaagctgctg tcagaagcaa tcaacaagtc agctttccag   4800
agttgtatct catctggctt tataggcctt tgcaaaactc taggaagcag gtgtgtgaga   4860
aacaaaaata gggaaaatct gtatatcaaa aagctgcttg aggatctaac cacagatgat   4920
catgtgacaa gagtttgcaa tcgggatggt ataacgctgt acatttgtga caaacagtct   4980
catccagaag cccaccgtga tcatatatgc cttttaaggc ctcttctttg ggactacatt   5040
tgtatttcat tgagcaactc ttttgagttg ggtgtttggg tcctagcaga accgaccaaa   5100
gggaagaata acagtgagaa cctaactctt aagcacttaa acccatgtga ttatgtagca   5160
agaaagcctg agagctcaag gctactggag gacaaagtga atttgaacca agtgattcaa   5220
tctgtgaggc ggctatatcc caagatcttt gaggatcagc ttcttccatt tatgtctgac   5280
atgagctcaa aaaacatgag gtggagtccc agaattaaat tccttgacct ctgtgtttta   5340
attgatatta actcagaatc cttgtcactc atttctcatg ttgttaagtg gaaaagggat   5400
gaacattaca ctgttctgtt ttctgacctt gccaattctc atcagcgatc tgactccagt   5460
ctggttgatg aatttgttgt tagcacgagg gatgtctgca agaacttctt aaaacaggtg   5520
tattttgaat catttgttcg agaatttgtt gcaacaacca ggacattagg caatttttca   5580
tggttccctc ataaagaaat gatgccatct gaagatggtg ctgaggcact gggccccttt   5640
caatcatttg tctcaaaggt ggtgaacaaa aatgtggaga ggcctatgtt taggaatgat   5700
ttgcagtttg gttttgggtg gttctcttac cgaatgggag atgttgtgtg taatgctgcc   5760
atgttgatta ggcagggcct gacaaaccca aaggcattta aatccttaaa ggatctgtgg   5820
gactacatgc tcaactacac aaaagggggta ttggagtttt caatttcagt ggactttacg   5880
```

```
cacaatcaga ataatactga ctgtttaagg aaattttcat tgatattctt ggttaggtgc   5940

caattacaga atccaggtgt ggctgaactt ttatcatgct ctcacctctt taagggtgag   6000

atagatagaa gaatgttgga tgaatgcctc cacttactga ggacagactc tgtcttcaag   6060

gtgaacgatg gtgtctttga tatcagatct gaagagtttg aggattacat ggaagatccc   6120

ttgatacttg gtgattctct tgagcttgag ttgttgggct ccaaaagaat actggatggg   6180

attagatcta ttgactttga gagagttgga cctgagtggg agcctgtgcc actgactgta   6240

aagatgggtg cccttttga aggaagaaac cttgtccaaa atatcattgt gaagctggag    6300

accaaggaca tgaaagtctt tctagcagga cttgagggct atgaaaagat tagtgatgtc   6360

cttgggaacc tcttcctgca tcgattcaga actggtgaac atttgttggg ttcagagata   6420

agtgtaatcc tccaggaact atgtatagac agatctattc tgctgattcc actgtcgctt   6480

ttgccagact ggttcgcctt taaggattgc agactttgtt ttagcaaatc taggagcact   6540

ttgatgtatg aaacagtggg gggcaggttt agactcaagg ggaggtcctg cgacgattgg   6600

ctgggcgggt cggtggccga ggacatcgac tga                                6633
```

<210> SEQ ID NO 40
<211> LENGTH: 2210
<212> TYPE: PRT
<213> ORGANISM: Lymphocytic choriomeningitis virus (LCMV) strain Clone13

<400> SEQUENCE: 40

```
Met Asp Glu Ile Ile Ser Glu Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Thr His Asn His
    50                  55                  60

Asp Asp Lys Ser Val Glu Thr Ile Leu Val Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Arg Glu
        115                 120                 125

Asp Leu Ala Val Ala Gly Val Thr Leu Val Pro Ile Val Asp Gly Arg
    130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205

Ala Arg Ser Thr His Asn Asp Glu Ile Met Arg Met Cys His Glu Gly
    210                 215                 220

Ile Asn Pro Asn Met Ser Cys Asp Asp Val Val Phe Gly Ile Asn Ser
225                 230                 235                 240
```

```
Leu Phe Ser Arg Phe Arg Arg Asp Leu Glu Ser Gly Lys Leu Lys Arg
                245                 250                 255

Asn Phe Gln Lys Val Asn Pro Glu Gly Leu Ile Lys Glu Phe Ser Glu
            260                 265                 270

Leu Tyr Glu Asn Leu Ala Asp Ser Asp Asp Ile Leu Thr Leu Ser Arg
        275                 280                 285

Glu Ala Val Glu Ser Cys Pro Leu Met Arg Phe Ile Thr Ala Glu Thr
    290                 295                 300

His Gly His Glu Arg Gly Ser Glu Thr Ser Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Phe Lys Gly Leu Lys Asn Asp Lys His Trp Val Gly
        355                 360                 365

Cys Cys Tyr Ser Ser Val Asn Asp Arg Leu Val Ser Phe His Ser Thr
    370                 375                 380

Lys Glu Glu Phe Ile Arg Leu Leu Arg Asn Arg Lys Lys Ser Lys Val
385                 390                 395                 400

Phe Arg Lys Val Ser Phe Glu Glu Leu Phe Arg Ala Ser Ile Ser Glu
                405                 410                 415

Phe Ile Ala Lys Ile Gln Lys Cys Leu Leu Val Val Gly Leu Ser Phe
            420                 425                 430

Glu His Tyr Gly Leu Ser Glu His Leu Glu Gln Glu Cys His Ile Pro
        435                 440                 445

Phe Thr Glu Phe Glu Asn Phe Met Lys Ile Gly Ala His Pro Ile Met
    450                 455                 460

Tyr Tyr Thr Lys Phe Glu Asp Tyr Asn Phe Gln Pro Ser Thr Glu Gln
465                 470                 475                 480

Leu Lys Asn Ile Gln Ser Leu Arg Arg Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Ile Gly Ser Val Arg Tyr Gln Val Val Glu Cys Lys Glu Val Phe
        515                 520                 525

Cys Gln Val Ile Lys Leu Asp Ser Glu Glu Tyr His Leu Leu Tyr Gln
    530                 535                 540

Lys Thr Gly Glu Ser Ser Arg Cys Tyr Ser Ile Gln Gly Pro Asp Gly
545                 550                 555                 560

His Leu Ile Ser Phe Tyr Ala Asp Pro Lys Arg Phe Phe Leu Pro Ile
                565                 570                 575

Phe Ser Asp Glu Val Leu Tyr Asn Met Ile Asp Ile Met Ile Ser Trp
            580                 585                 590

Ile Arg Ser Cys Pro Asp Leu Lys Asp Cys Leu Thr Asp Ile Glu Val
        595                 600                 605

Ala Leu Arg Thr Leu Leu Leu Leu Met Leu Thr Asn Pro Thr Lys Arg
    610                 615                 620

Asn Gln Lys Gln Val Gln Ser Val Arg Tyr Leu Val Met Ala Ile Val
625                 630                 635                 640

Ser Asp Phe Ser Ser Thr Ser Leu Met Asp Lys Leu Arg Glu Asp Leu
                645                 650                 655

Ile Thr Pro Ala Glu Lys Val Val Tyr Lys Leu Leu Arg Phe Leu Ile
```

```
            660                 665                 670

Lys Thr Ile Phe Gly Thr Gly Glu Lys Val Leu Leu Ser Ala Lys Phe
        675                 680                 685

Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Gln Phe Gly Phe Phe Val Asn Pro Lys Glu Ala Ile
                725                 730                 735

Thr Pro Glu Glu Glu Cys Val Phe Tyr Glu Gln Met Lys Arg Phe Thr
            740                 745                 750

Ser Lys Glu Ile Asp Cys Gln His Thr Thr Pro Gly Val Asn Leu Glu
        755                 760                 765

Ala Phe Ser Leu Met Val Ser Ser Phe Asn Asn Gly Thr Leu Ile Phe
    770                 775                 780

Lys Gly Glu Lys Lys Leu Asn Ser Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Ser Phe Val Arg Lys Gln
        835                 840                 845

Lys Tyr Lys Leu Ser His Ser Asp Tyr Glu Tyr Lys Val Ser Lys Leu
    850                 855                 860

Val Ser Arg Leu Val Ile Gly Ser Lys Gly Glu Glu Thr Gly Arg Ser
865                 870                 875                 880

Glu Asp Asn Leu Ala Glu Ile Cys Phe Asp Gly Glu Glu Glu Thr Ser
                885                 890                 895

Phe Phe Lys Ser Leu Glu Glu Lys Val Asn Thr Thr Ile Ala Arg Tyr
            900                 905                 910

Arg Arg Gly Arg Arg Ala Asn Asp Lys Gly Asp Gly Glu Lys Leu Thr
        915                 920                 925

Asn Thr Lys Gly Leu His His Leu Gln Leu Ile Leu Thr Gly Lys Met
    930                 935                 940

Ala His Leu Arg Lys Val Ile Leu Ser Glu Ile Ser Phe His Leu Val
945                 950                 955                 960

Glu Asp Phe Asp Pro Ser Cys Leu Thr Asn Asp Asp Met Lys Phe Ile
                965                 970                 975

Cys Glu Ala Val Glu Gly Ser Thr Glu Leu Ser Pro Leu Tyr Phe Thr
            980                 985                 990

Ser Val Ile Lys Asp Gln Cys Gly  Leu Asp Glu Met Ala  Lys Asn Leu
        995                 1000                1005

Cys Arg  Lys Phe Phe Ser Glu  Asn Asp Trp Phe Ser  Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Gly  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Gln Cys  Met Ser Ala
    1070                1075                1080
```

```
Ala Leu  Lys Asn Leu Cys Phe  Tyr Ser Glu Glu Ser  Pro Thr Ser
    1085                 1090                 1095

Tyr Thr  Ser Val Gly Pro Asp  Ser Gly Arg Leu Lys  Phe Ala Leu
    1100                 1105                 1110

Ser Tyr  Lys Glu Gln Val Gly  Gly Asn Arg Glu Leu  Tyr Ile Gly
    1115                 1120                 1125

Asp Leu  Arg Thr Lys Met Phe  Thr Arg Leu Ile Glu  Asp Tyr Phe
    1130                 1135                 1140

Glu Ser  Phe Ser Ser Phe Phe  Ser Gly Ser Cys Leu  Asn Asn Asp
    1145                 1150                 1155

Lys Glu  Phe Glu Asn Ala Ile  Leu Ser Met Thr Ile  Asn Val Arg
    1160                 1165                 1170

Glu Gly  Phe Leu Asn Tyr Ser  Met Asp His Ser Lys  Trp Gly Pro
    1175                 1180                 1185

Met Met  Cys Pro Phe Leu Phe  Leu Met Phe Leu Gln  Asn Leu Lys
    1190                 1195                 1200

Leu Gly  Asp Asp Gln Tyr Val  Arg Ser Gly Lys Asp  His Val Ser
    1205                 1210                 1215

Thr Leu  Leu Thr Trp His Met  His Lys Leu Val Glu  Val Pro Phe
    1220                 1225                 1230

Pro Val  Val Asn Ala Met Met  Lys Ser Tyr Val Lys  Ser Lys Leu
    1235                 1240                 1245

Lys Leu  Leu Arg Gly Ser Glu  Thr Thr Val Thr Glu  Arg Ile Phe
    1250                 1255                 1260

Arg Gln  Tyr Phe Glu Met Gly  Ile Val Pro Ser His  Ile Ser Ser
    1265                 1270                 1275

Leu Ile  Asp Met Gly Gln Gly  Ile Leu His Asn Ala  Ser Asp Phe
    1280                 1285                 1290

Tyr Gly  Leu Leu Ser Glu Arg  Phe Ile Asn Tyr Cys  Ile Gly Val
    1295                 1300                 1305

Ile Phe  Gly Glu Arg Pro Glu  Ala Tyr Thr Ser Ser  Asp Asp Gln
    1310                 1315                 1320

Ile Thr  Leu Phe Asp Arg Arg  Leu Ser Asp Leu Val  Val Ser Asp
    1325                 1330                 1335

Pro Glu  Glu Val Leu Val Leu  Leu Glu Phe Gln Ser  His Leu Ser
    1340                 1345                 1350

Gly Leu  Leu Asn Lys Phe Ile  Ser Pro Lys Ser Val  Ala Gly Arg
    1355                 1360                 1365

Phe Ala  Ala Glu Phe Lys Ser  Arg Phe Tyr Val Trp  Gly Glu Glu
    1370                 1375                 1380

Val Pro  Leu Leu Thr Lys Phe  Val Ser Ala Ala Leu  His Asn Val
    1385                 1390                 1395

Lys Cys  Lys Glu Pro His Gln  Leu Cys Glu Thr Ile  Asp Thr Ile
    1400                 1405                 1410

Ala Asp  Gln Ala Ile Ala Asn  Gly Val Pro Val Ser  Leu Val Asn
    1415                 1420                 1425

Ser Ile  Gln Arg Arg Thr Leu  Asp Leu Leu Lys Tyr  Ala Asn Phe
    1430                 1435                 1440

Pro Leu  Asp Pro Phe Leu Leu  Asn Thr Asn Thr Asp  Val Lys Asp
    1445                 1450                 1455

Trp Leu  Asp Gly Ser Arg Gly  Tyr Arg Ile Gln Arg  Leu Ile Glu
    1460                 1465                 1470
```

```
Glu Leu  Cys Pro Asn Glu Thr  Lys Val Val Arg Lys  Leu Val Arg
    1475                 1480                 1485

Lys Leu  His His Lys Leu Lys  Asn Gly Glu Phe Asn  Glu Glu Phe
    1490                 1495                 1500

Phe Leu  Asp Leu Phe Asn Arg  Asp Lys Lys Glu Ala  Ile Leu Gln
    1505                 1510                 1515

Leu Gly  Asp Leu Leu Gly Leu  Glu Glu Asp Leu Asn  Gln Leu Ala
    1520                 1525                 1530

Asp Val  Asn Trp Leu Asn Leu  Asn Glu Met Phe Pro  Leu Arg Met
    1535                 1540                 1545

Val Leu  Arg Gln Lys Val Val  Tyr Pro Ser Val Met  Thr Phe Gln
    1550                 1555                 1560

Glu Glu  Arg Ile Pro Ser Leu  Ile Lys Thr Leu Gln  Asn Lys Leu
    1565                 1570                 1575

Cys Ser  Lys Phe Thr Arg Gly  Ala Gln Lys Leu Leu  Ser Glu Ala
    1580                 1585                 1590

Ile Asn  Lys Ser Ala Phe Gln  Ser Cys Ile Ser Ser  Gly Phe Ile
    1595                 1600                 1605

Gly Leu  Cys Lys Thr Leu Gly  Ser Arg Cys Val Arg  Asn Lys Asn
    1610                 1615                 1620

Arg Glu  Asn Leu Tyr Ile Lys  Lys Leu Leu Glu Asp  Leu Thr Thr
    1625                 1630                 1635

Asp Asp  His Val Thr Arg Val  Cys Asn Arg Asp Gly  Ile Thr Leu
    1640                 1645                 1650

Tyr Ile  Cys Asp Lys Gln Ser  His Pro Glu Ala His  Arg Asp His
    1655                 1660                 1665

Ile Cys  Leu Leu Arg Pro Leu  Leu Trp Asp Tyr Ile  Cys Ile Ser
    1670                 1675                 1680

Leu Ser  Asn Ser Phe Glu Leu  Gly Val Trp Val Leu  Ala Glu Pro
    1685                 1690                 1695

Thr Lys  Gly Lys Asn Asn Ser  Glu Asn Leu Thr Leu  Lys His Leu
    1700                 1705                 1710

Asn Pro  Cys Asp Tyr Val Ala  Arg Lys Pro Glu Ser  Ser Arg Leu
    1715                 1720                 1725

Leu Glu  Asp Lys Val Asn Leu  Asn Gln Val Ile Gln  Ser Val Arg
    1730                 1735                 1740

Arg Leu  Tyr Pro Lys Ile Phe  Glu Asp Gln Leu Leu  Pro Phe Met
    1745                 1750                 1755

Ser Asp  Met Ser Ser Lys Asn  Met Arg Trp Ser Pro  Arg Ile Lys
    1760                 1765                 1770

Phe Leu  Asp Leu Cys Val Leu  Ile Asp Ile Asn Ser  Glu Ser Leu
    1775                 1780                 1785

Ser Leu  Ile Ser His Val Val  Lys Trp Lys Arg Asp  Glu His Tyr
    1790                 1795                 1800

Thr Val  Leu Phe Ser Asp Leu  Ala Asn Ser His Gln  Arg Ser Asp
    1805                 1810                 1815

Ser Ser  Leu Val Asp Glu Phe  Val Val Ser Thr Arg  Asp Val Cys
    1820                 1825                 1830

Lys Asn  Phe Leu Lys Gln Val  Tyr Phe Glu Ser Phe  Val Arg Glu
    1835                 1840                 1845

Phe Val  Ala Thr Thr Arg Thr  Leu Gly Asn Phe Ser  Trp Phe Pro
    1850                 1855                 1860

His Lys  Glu Met Met Pro Ser  Glu Asp Gly Ala Glu  Ala Leu Gly
```

```
    1865                1870                1875

Pro Phe  Gln Ser Phe Val Ser  Lys Val Val Asn Lys  Asn Val Glu
    1880                1885                1890

Arg Pro  Met Phe Arg Asn Asp  Leu Gln Phe Gly Phe  Gly Trp Phe
    1895                1900                1905

Ser Tyr  Arg Met Gly Asp Val  Val Cys Asn Ala Ala  Met Leu Ile
    1910                1915                1920

Arg Gln  Gly Leu Thr Asn Pro  Lys Ala Phe Lys Ser  Leu Lys Asp
    1925                1930                1935

Leu Trp  Asp Tyr Met Leu Asn  Tyr Thr Lys Gly Val  Leu Glu Phe
    1940                1945                1950

Ser Ile  Ser Val Asp Phe Thr  His Asn Gln Asn Asn  Thr Asp Cys
    1955                1960                1965

Leu Arg  Lys Phe Ser Leu Ile  Phe Leu Val Arg Cys  Gln Leu Gln
    1970                1975                1980

Asn Pro  Gly Val Ala Glu Leu  Leu Ser Cys Ser His  Leu Phe Lys
    1985                1990                1995

Gly Glu  Ile Asp Arg Arg Met  Leu Asp Glu Cys Leu  His Leu Leu
    2000                2005                2010

Arg Thr  Asp Ser Val Phe Lys  Val Asn Asp Gly Val  Phe Asp Ile
    2015                2020                2025

Arg Ser  Glu Glu Phe Glu Asp  Tyr Met Glu Asp Pro  Leu Ile Leu
    2030                2035                2040

Gly Asp  Ser Leu Glu Leu Glu  Leu Leu Gly Ser Lys  Arg Ile Leu
    2045                2050                2055

Asp Gly  Ile Arg Ser Ile Asp  Phe Glu Arg Val Gly  Pro Glu Trp
    2060                2065                2070

Glu Pro  Val Pro Leu Thr Val  Lys Met Gly Ala Leu  Phe Glu Gly
    2075                2080                2085

Arg Asn  Leu Val Gln Asn Ile  Ile Val Lys Leu Glu  Thr Lys Asp
    2090                2095                2100

Met Lys  Val Phe Leu Ala Gly  Leu Glu Gly Tyr Glu  Lys Ile Ser
    2105                2110                2115

Asp Val  Leu Gly Asn Leu Phe  Leu His Arg Phe Arg  Thr Gly Glu
    2120                2125                2130

His Leu  Leu Gly Ser Glu Ile  Ser Val Ile Leu Gln  Glu Leu Cys
    2135                2140                2145

Ile Asp  Arg Ser Ile Leu Leu  Ile Pro Leu Ser Leu  Leu Pro Asp
    2150                2155                2160

Trp Phe  Ala Phe Lys Asp Cys  Arg Leu Cys Phe Ser  Lys Ser Arg
    2165                2170                2175

Ser Thr  Leu Met Tyr Glu Thr  Val Gly Gly Arg Phe  Arg Leu Lys
    2180                2185                2190

Gly Arg  Ser Cys Asp Asp Trp  Leu Gly Gly Ser Val  Ala Glu Asp
    2195                2200                2205

Ile Asp
    2210
```